(12) United States Patent
Fuji et al.

(10) Patent No.: US 7,148,237 B2
(45) Date of Patent: Dec. 12, 2006

(54) NITROGEN-CONTAINING HETEROARYL COMPOUNDS HAVING HIV INTEGRASE INHIBITORY ACTIVITY

(75) Inventors: Masahiro Fuji, Osaka (JP); Hidenori Mikamiyama, Osaka (JP); Hitoshi Murai, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/469,364

(22) PCT Filed: Feb. 27, 2002

(86) PCT No.: PCT/JP02/01778

§ 371 (c)(1),
(2), (4) Date: Aug. 18, 2003

(87) PCT Pub. No.: WO02/070486

PCT Pub. Date: Sep. 12, 2002

(65) Prior Publication Data

US 2004/0127708 A1    Jul. 1, 2004

(30) Foreign Application Priority Data

| Mar. 1, 2001 | (JP) | ............... 2001-057037 |
| Aug. 10, 2001 | (JP) | ............... 2001-243530 |
| Dec. 26, 2001 | (JP) | ............... 2001-395022 |

(51) Int. Cl.
  *C07D 215/28*    (2006.01)
  *C07D 215/26*    (2006.01)
  *A61K 31/47*    (2006.01)
  *C07D 471/04*    (2006.01)

(52) U.S. Cl. ............ 514/311; 546/168; 546/169; 546/170

(58) Field of Classification Search ............ 546/168, 546/169, 170; 514/311
See application file for complete search history.

(56) References Cited

U.S. PATENT DOCUMENTS

| 3,954,733 A | 5/1976 | Tobiki et al. ............ 260/239.1 |
| 3,992,371 A | 11/1976 | Tobiki et al. ............ 260/239.1 |
| 4,125,611 A | 11/1978 | Yamade et al. ............ 424/246 |
| 5,681,832 A | 10/1997 | Haugwitz et al. ............ 514/150 |

FOREIGN PATENT DOCUMENTS

| CH | 370082 | * 8/1963 |
| JP | 52-27794 | 3/1977 |
| JP | 52-93790 | 8/1977 |
| JP | 5-27385 | 2/1993 |
| WO | 98/11073 | 3/1998 |
| WO | 98/45269 | 10/1998 |
| WO | 02/04443 | 1/2002 |
| WO | 02/30426 | 4/2002 |
| WO | 02/30930 | 4/2002 |
| WO | 02/30931 | 4/2002 |
| WO | 02/36734 | 5/2002 |
| WO | 02/055079 | 7/2002 |

OTHER PUBLICATIONS

Schindler et al., CAPLUS Abstract 60:30870, 1963.*
Marcus et al., PubMed Abstract (Intervirology 45(4-6):260-6), 2002.*
van Heeswijk et al., PubMed Abstract (Antivir Ther. 6(4):201-29), 2001.*
M. Quali et al., "Modeling of the Inhibition of Retroviral Integrases by Styrylquinoline Derivatives", J. Med. Chem., vol. 43, No. 10, pp. 1949-1957, 2000.
F. Zouhiri et al., "Structure-Activity Relationships and Binding Mode of Styrylquinolines as Potent Inhibitors of HIV-1 Integrase and Replication of HIV-1 in Cell Culture", J. MEd. Chem., vol. 43, No. 8, pp. 1533-1540.
K. Mekouar et al., "Styrylquinoline Derivatives: A New Class of Potent HIV-1 Integrase Inhibitors that Block HIV-1 Replication in Cem Cells", J. Med. Chem., vol. 41, No. 15, pp. 2846-2857, 1998.
I.S. Haworth et al., "A Prototype Bioreductive DNA groove Binding Ligand", Anti-Cancer Drug Design, vol. 6, No. 1, pp. 59-70, 1991.
M.S. Shankar et al., "Synthesis of Substituted 6-Pyrazolo and 6-Isoxazolo-Benzoxazoles and Their Physiological Activity", J. Indian Chem. Society, vol. 59, No. 9, pp. 1104-1105, 1982.
F. Zouhiri et al., "HIV-1 Replication Inhibitors of the Styrylquinoline Class: Incorporation of a Masked Diketo Acid Pharmacophore", vol. 42, No. 46, pp. 8189-8192, 2001.

* cited by examiner

*Primary Examiner*—Deepak Rao
(74) *Attorney, Agent, or Firm*—Wenderoth, Lind & Ponack, L.L.P.

(57) ABSTRACT

A compound of the formula (I):

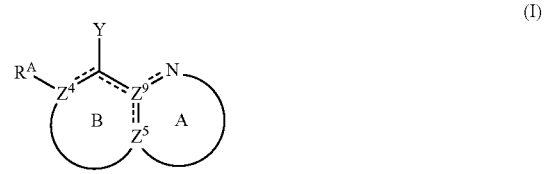

wherein $Z^4$, $Z^5$ and $Z^9$ each is independently carbon atom or nitrogen atom; Y is hydroxy, mercapto or amino; $R^4$ is a group of the formula:

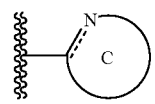

(wherein C ring is nitrogen-containing heteroaryl) has an inhibitory activity against integrase.

14 Claims, No Drawings

NITROGEN-CONTAINING HETEROARYL COMPOUNDS HAVING HIV INTEGRASE INHIBITORY ACTIVITY

This application is a U.S. national stage of International Application No. PCT/JP02/01778 filed Feb. 27, 2002.

TECHNICAL FIELD

The present invention relates to novel compounds having antiviral activities, in detail nitrogen-containing heteroaryl compounds having inhibitory activity against HIV integrase and a pharmaceutical composition containing the same, especially an anti-HIV agent.

BACKGROUND ART

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a combination therapy is reported to be efficient in treatment for AIDS because of the frequent emergence of the resistant mutant by Balzarini, J. et al, Proc. Natl. Acad. Sci. USA 1996, 93, p 13152–13157. Reverse transcriptase inhibitors and protease inhibitors are clinically used as an anti-HIV agent, however agents having the same mechanism of action often exhibit cross-resistance or only an additional activity. Therefore, anti-HIV agents having the other mechanism of action are desired.

Some integrase inhibitors have recently been reported, for example, 1,3-dioxo butenoic acid group or 1,3-propandione group described in WO99/50245, WO99/62520, WO99/62897, WO99/62513, WO00/39086 and WO01/00578.

Additionally, benzimidazole derivatives, anti-platelet agents are described in Chem. Pharm. Bull. 42(3) 560–569 (1994). They have similar structures to those of the present invention compounds.

WO98/45269 and J. Med. Chem. 2000, 43, 1533–1540 describe the following compounds with inhibitory activity against HIV integrase.

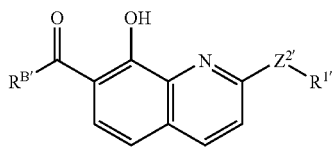

Wherein $R^{B'}$ is hydroxy or alkoxy, $Z^{2'}$ is alkylene or alkenylene, $R^{1'}$ is optionally substituted aryl or optionally substituted heteroaryl.

Furthermore, in U.S. Pat. No. 3,113,135, 5-benzyl-7-acetyl-8-hydroxyquinoline and 5-phenyl-7-acetyl-8-hydroxyquinoline are described.

Under the above circumstances, the development of a novel integrase inhibitor has been desired.

DISCLOSURE OF THE INVENTION

The present inventors have intensively studied to find that a novel nitrogen-containing heteroaryl compound, namely, a compound of the formula (I):

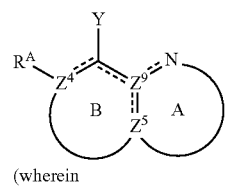

(wherein

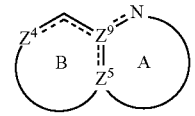

is a condensed nitrogen-containing heterocycle (A ring is nitrogen-containing heterocycle; B ring is carbon ring or heterocycle; $Z^4$, $Z^5$ and $Z^9$ each is independently carbon atom or nitrogen atom);

Y is hydroxy, mercapto or amino;

$R^A$ is a group of the formula:

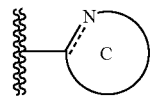

(wherein C ring is nitrogen-containing heteroaryl) or a group of the formula:

(wherein X is oxygen atom, sulfur atom or NH; $R^B$ is hydrogen or a group selected from the substitution group A);

and at least one of A ring, B ring and $R^A$ is substituted with a group of the formula: $-Z^1-Z^2-Z^3-R^1$(wherein $Z^1$ and $Z^3$ each is independently a bond, optionally substituted alkylene or optionally substituted alkenylene; $Z^2$ is a bond, optionally substituted alkylene, optionally substituted alkenylene, —CH(OH)—, —S—, —SO—, —SO$_2$—, —SO$_2$NR$^2$—, —NR$^2$SO$_2$—, —O—, —NR$^2$—, —NR$^2$CO—, —CONR$^2$—, —C(=O)—O—, —O—C(=O)— or —CO—; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle.);

and A ring, B ring or $R^A$ is optionally substituted with one to six group(s) selected from the substitution group A at any position except for the position, at which the group shown by the above-mentioned formula: $-Z^1-Z^2-Z^3-R^1$ (wherein $Z^1$, $Z^2$, $Z^3$ and $R^1$ are the same meanings as above.) is substituted, each broken line shows the presence or absence of a bond, except that each neighboring broken line simultaneously shows the presence of a bond, provided a compound of the formula:

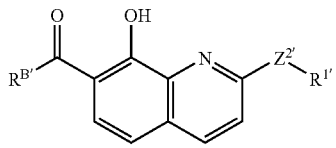

(wherein $R^{B'}$ is hydroxy or alkoxy, $Z^{2'}$ is alkylene or alkenylene, $R^{1'}$ is optionally substituted aryl or optionally substituted heteroaryl.), 5-benzyl-7-acetyl-8-hydroxyquinoline and 5-phenyl-7-acetyl-8-hydroxyquinoline are excluded.), (hereinafter referred to as "a compound of the present invention"), a prodrug, a pharmaceutically acceptable salt or a solvate thereof has inhibitory activity against integrase.

Moreover, the present inventors have discovered that a compound of the present invention and a pharmaceutical composition containing the same are useful as an antiviral agent, an antiretroviral agent, an anti-HIV agent, an anti-HTLV-1 (Human T cell leukemia virus type 1) agent, an anti-FIV (Feline immunodeficiency virus) agent or an anti-SIV (Simian immunodeficiency virus) agent, especially an anti-HIV agent, an integrase inhibitor) agent, to accomplish the present invention.

The present invention provides a compound of the present invention, a prodrug, a pharmaceutically acceptable salt or a solvate thereof, a pharmaceutical composition including them as active ingredients, an antiviral agent, an anti-HIV agent, an integrase inhibitor and a mixture of anti-HIV agents. These are especially useful not only as an anti-HIV agent but also as an anti-AIDS agent for diseases including AIDS and AIDS related clinical symptom, for example, AIDS related complication (ARC), persistent generalized lymphadenopathy(PGL), Kaposi sarcoma, pneumocystis carini pneumonia, sudden thrombocy topenic purpura, AIDS related neurological symptom, for example, AIDS dementia complications, AIDS-associated encephalopathy, multiple sclerosis or tropical spastic paraparesis, and anti-HIV antibody positive and HIV positive symptom in asymptomatic patients.

The present invention is,
(1) a compound of the formula (I):

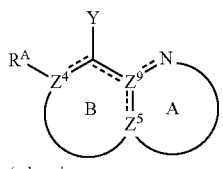

(wherein

is a condensed nitrogen-containing heterocycle (A ring is nitrogen-containing heterocycle; B ring is carbon ring or heterocycle; $Z^4$, $Z^5$ and $Z^9$ each is independently carbon atom or nitrogen atom);

Y is hydroxy, mercapto or amino;
$R^A$ is a group of the formula:

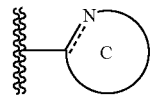

(wherein C ring is nitrogen-containing heteroaryl) or a group of the formula:

(wherein X is oxygen atom, sulfur atom or NH; $R^B$ is hydrogen or a group selected from the substitution group A);

and at least one of A ring, B ring and $R^A$ is substituted with a group of the formula: -$Z^1$-$Z^2$-$Z^3$-$R^1$(wherein $Z^1$ and $Z^3$ each is independently a bond, optionally substituted alkylene or optionally substituted alkenylene; $Z^2$ is a bond, optionally substituted alkylene, optionally substituted alkenylene, —CH(OH)—, —S—, —SO—, —SO$_2$—, —SO$_2$NR$^2$—, —NR$^2$SO$_2$—, —O—, —NR$^2$—, —NR$^2$CO—, —CONR$^2$—, —C(=O)—O—, —O—C(=O)— or —CO—; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle.);

and A ring, B ring or $R^A$ is optionally substituted with one to six group(s) selected from the substitution group A at any position except for the position at which the group shown by the above-mentioned formula: -$Z^1$-$Z^2$-$Z^3$-$R^1$ (wherein $Z^1$, $Z^2$, $Z^3$ and $R^1$ are the same meanings as above.) is substituted, each broken line shows the presence or absence of a bond, except that each neighboring broken line simultaneously shows the presence of a bond, provided a compound of the formula:

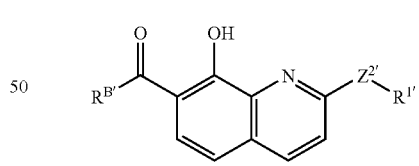

(wherein $R^{B'}$ is hydroxy or alkoxy, $Z^{2'}$ is alkylene or alkenylene, $R^{1'}$ is optionally substituted aryl or optionally substituted heteroaryl), benzyl5-benzyl-7-acetyl-8-hydroxyquinoline and 5-phenyl-7-acetyl-8-hydroxyquinoline are excluded.

The substitution group A is halogen, alkoxycarbonyl, carboxy, optionally substituted alkyl, alkoxy, alkoxyalkyl, nitro, hydroxy, optionally substituted alkenyl, alkynyl, alkylsulfonyl, optionally substituted amino, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl and optionally substituted heteroaralkylsulfonyl), a prodrug, a pharmaceutically acceptable salt or a solvate thereof, (2) a compound according to the above (1) wherein a nitrogen atom neighboring $Z^9$ on A ring binds to a neighboring atom with a double bond and to another neighboring atom with a single bond, a prodrug, a pharmaceutically acceptable salt or a solvate thereof, (3) a compound according to the above (1) wherein

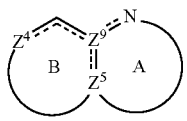

(wherein A ring, B ring, $Z^4$, $Z^5$ and $Z^9$ are the same meanings as above (1)) is a condensed nitrogen-containing heterocycle, a prodrug, a pharmaceutically acceptable salt or a solvate thereof, (4) a compound according to the above (1) (wherein at least one of A ring, B ring and $R^4$ is substituted with a group of the formula: -$Z^1$-$Z^2$-$Z^3$-$R^1$(wherein $Z^1$, $Z^2$, $Z^3$ and $R^1$ are the same meanings as above (1)), and the other parts are optionally substituted with groups selected from the substitution group A), wherein A ring of

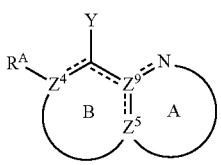 (I)

(wherein $Z^4$, $Z^5$, $Z^9$, Y and $R^4$ are the same meanings as above (1)) is the formula:

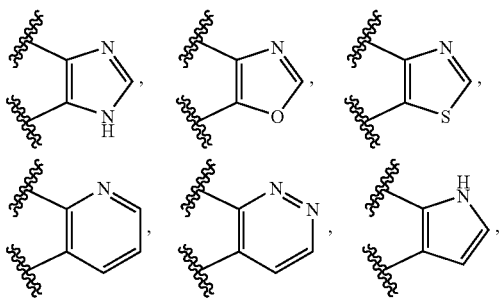

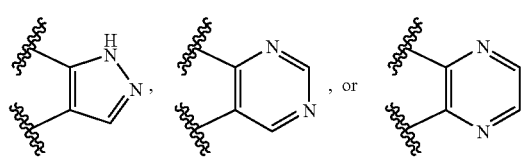

and B ring is the formula:

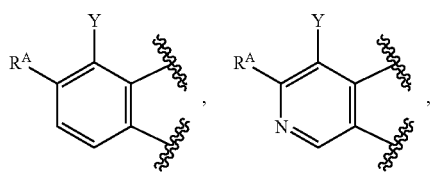

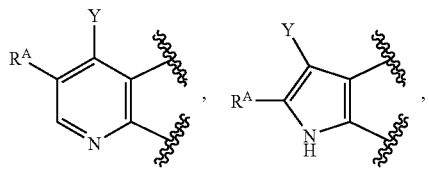

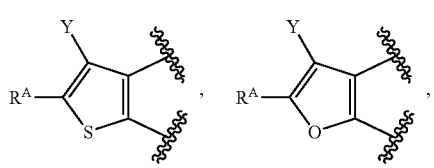

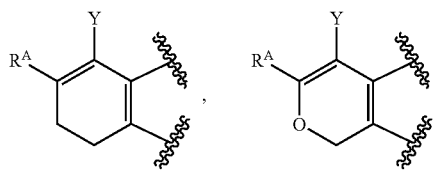

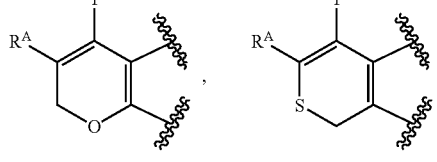

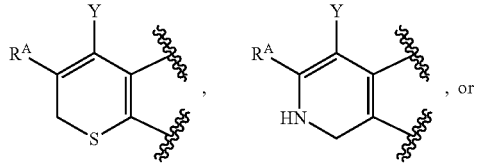

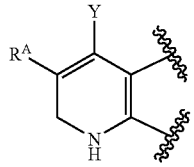

(wherein Y and $R^4$ are the same meanings as above (1)) or A ring is the formula:

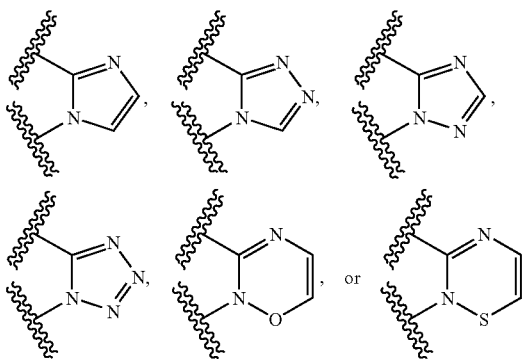

and B ring is the formula:

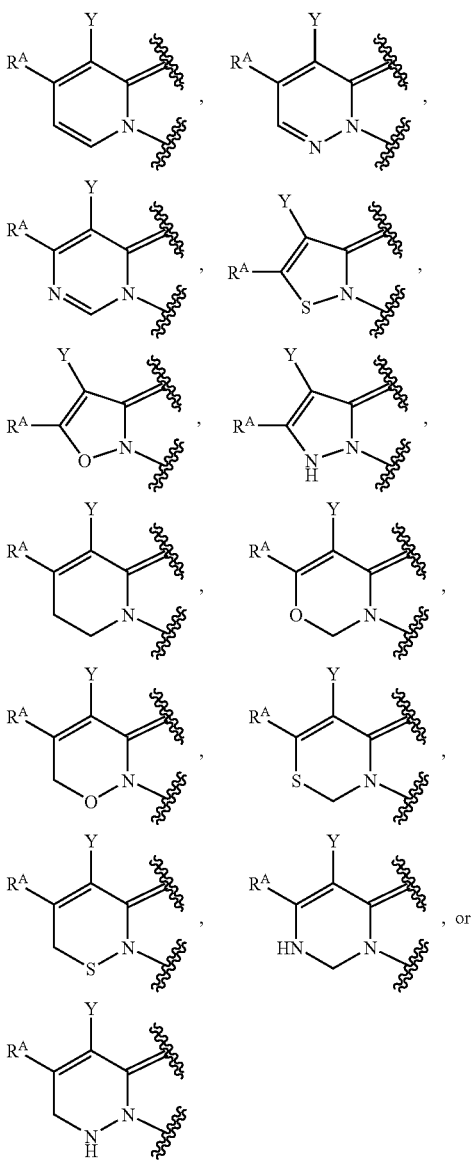

(wherein Y and R^A are the same meanings as above (1)) or A ring is the formula:

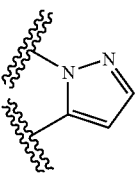

and B ring is the formula:

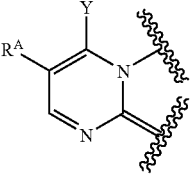

(wherein Y and $R^A$ are the same meanings as above 1), a prodrug, a pharmaceutically acceptable salt or a solvate thereof, (5) a compound according to the above (4) (wherein at least one of A ring, B ring and $R^A$ is substituted with a group of the formula: $-Z^1-Z^2-Z^3-R^1$ (wherein $Z^1$, $Z^2$, $Z^3$ and $R^1$ are the same meanings as above (1)), and the other parts are optionally substituted with groups selected from the substitution group A), wherein

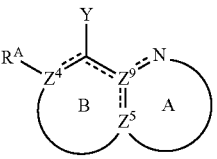
(I)

(wherein $Z^4$, $Z^5$, $Z^9$, Y and $R^A$ are the same meanings as above (1)) is the formula:

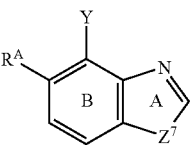

(wherein Y and $R^A$ are the same meanings as above (1)); $Z^7$ is an oxygen atom, a sulfur atom, —CH=CH— or NH), a prodrug, a pharmaceutically acceptable salt or a solvate thereof, (6) a compound according to any one of the above (1) to (5) wherein a group selected from the substitution group A is halogen, alkoxycarbonyl, carboxy, optionally substituted alkyl, alkoxy, alkoxyalkyl, nitro, hydroxy, optionally substituted alkenyl, alkynyl, alkylsulfonyl, optionally substituted amino, alkylthio, alkylthioalkyl, haloalkyl, haloalkoxy, haloalkoxyalkyl, cycloalkyl, cycloalkenyl, oxo, alkylenedioxy, alkylene, alkenylene, azide, cyano, mercapto, optionally substituted carbamoyl, sulfamoyl, sulfoamino, formyl, alkylcarbonyl, alkylcarbonyloxy, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl or optionally substituted heteroaralkylsulfonyl, a prodrug, a pharmaceutically acceptable salt or a solvate thereof, (7) a compound according to the above (6) wherein a group selected from the substitution group A is halogen, optionally substituted alkyl, alkoxy, hydroxy, optionally substituted alkenyl, optionally substituted amino, cyano, optionally substituted carbamoyl, optionally substituted aryl, optionally substituted heteroaryl, optionally substituted heterocycle, optionally substituted aralkyl or optionally substituted aryloxyalkyl, a prodrug, a pharmaceutically acceptable salt or a solvate thereof, (8) a compound according to any one of the above (1) to (7) wherein the formula: $-Z^1-Z^2-Z^3-R^1$ is the formula: $-Z^1-Z^2-Z^3-R^1$ (wherein $Z^1$ is a bond or alkylene; $Z^3$ is a bond; $Z^2$ is optionally substituted alkylene, alkenylene, —S— or —O—; $R^1$ is optionally substituted aryl, optionally substituted heteroaryl or optionally substituted cycloalkyl), a prodrug, a pharmaceutically acceptable salt or a solvate thereof, (9) a compound according to any one of the above (1) to (8) wherein $R^A$ is the formula:

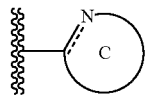

(wherein C ring is the same meaning as above (1)), a prodrug, a pharmaceutically acceptable salt or a solvate thereof,

(10) a compound according to the above (9) wherein an atom neighboring the atom at the bonding position on C ring is nitrogen atom which binds to the neighboring atom with a double bond and to another neighboring atom with a single bond, a prodrug, a pharmaceutically acceptable salt or a solvate thereof,

(11) a compound according to the above (10) wherein an atom neighboring the atom at the bonding position on C ring is nitrogen atom which binds to the neighboring atom with a double bond and to another neighboring atom with a single bond, and another atom neighboring the atom at the bonding position is a heteroatom, a prodrug, a pharmaceutically acceptable salt or a solvate thereof,

(12) a compound according to the above (9) (wherein at least one of A ring, B ring and C ring is substituted with a group of the formula: $-Z^1-Z^2-Z^3-R^1$ (wherein $Z^1$, $Z^2$, $Z^3$ and $R^1$ are the same meanings as above (1)), and the other parts are optionally substituted with groups selected from the substitution group A), wherein the formula:

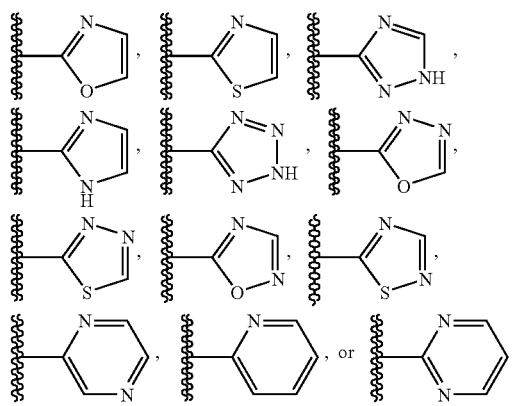

(wherein C ring is the same meaning as above (1)) is the formula:

, a prodrug, a pharmaceutically acceptable salt or a solvate thereof,

(13) a compound according to any one of the above (9) to (12) wherein C ring is substituted with a group of the formula: $-Z^1-Z^2-Z^3-R^1$ (wherein $Z^1$, $Z^2$, $Z^3$ and $R^1$ are the same meanings as above (1)), a prodrug, a pharmaceutically acceptable salt or a solvate thereof,

(14) a compound according to any one of the above (1) to (8) (wherein at least one of A ring, B ring and $R^B$ is substituted with a group of the formula: $-Z^1-Z^2-Z^3-R^1$ (wherein $Z^1$, $Z^2$, $Z^3$ and $R^1$ are the same meanings as above (1)), and the other parts are optionally substituted with groups selected from the substitution group A), wherein $R^A$ is the formula:

(wherein X and $R^B$ are the same meanings as above (1)), a prodrug, a pharmaceutically acceptable salt or a solvate thereof,

(15) a compound according to the above (14) (wherein at least one of A ring, B ring or $R^B$ is substituted with a group of the formula: $-Z^1-Z^2-Z^3-R^1$ (wherein $Z^1$, $Z^2$, $Z^3$ and $R^1$ are the same meanings as above (1)), and the other parts are optionally substituted with groups selected from the substitution group A), wherein X is oxygen atom, $R^B$ is hydroxy, alkoxy, optionally substituted amino, optionally substituted heteroaryl or optionally substituted aryl, a prodrug, a pharmaceutically acceptable salt or a solvate thereof,

(16) a compound according to the above (14) or (15) wherein $R^B$ is substituted with a group of the formula: $-Z^1-Z^2-Z^3-R^1$ (wherein $Z^1$, $Z^2$, $Z^3$ and $R^1$ are the same meanings as above (1)), a prodrug, a pharmaceutically acceptable salt or a solvate thereof,

(17) a compound according to any one of the above (1) to (16) wherein A ring or B ring is substituted with a group of the formula: $-Z^1-Z^2-Z^3-R^1$(wherein $Z^1$, $Z^2$, $Z^3$ and $R^1$ are the same meanings as above (1)), a prodrug, a pharmaceutically acceptable salt or a solvate thereof,

(18) a compound according to the above (1) which is the formula:

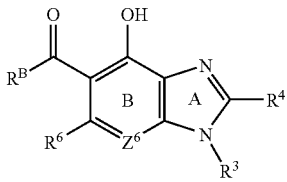

(wherein $R^B$ is hydrogen or a group selected from the substitution group A, $Z^6$ is $=C(-R^5)-$ or $=N-$, at least one of $R^3$ to $R^6$ is the formula: $-Z^1-Z^2-Z^3-R^1$(wherein $Z^1$, $Z^2$, $Z^3$ and $R^1$ are the same meanings as above (1)), the others are hydrogen or groups selected from the substitution group A), a prodrug, a pharmaceutically acceptable salt or a solvate thereof,

(19) a compound according to the above (18) wherein $R^B$ is hydroxy, alkoxy, optionally substituted amino, heterocycle, heteroaryl or aryl, $Z^6$ is $=C(-R^5)-$, at least one of $R^3$ to $R^6$ is the formula: $-Z^1-Z^2-Z^3-R^1$(wherein $Z^1$ and $Z^3$ are bonds, $Z^2$ is a bond, alkylene or alkenylene, $R^1$ is optionally substituted aryl (the substituents are alkyl, halogen, alkoxy, haloalkyl and/or azide)), the others are aralkyl optionally substituted with halogen, hydrogen, halogen or alkyl, a prodrug, a pharmaceutically acceptable salt or a solvate thereof,

(20) a compound according to the above (1) which is the formula:

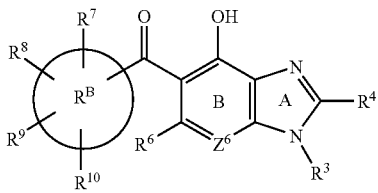

(wherein $R^B$ is aryl, heteroaryl, cycloalkyl, cycloalkenyl or heterocycle, $Z^6$ is $=C(-R^5)-$ or $=N-$, at least one of $R^3$ to $R^{10}$ is the formula: $-Z^1-Z^2-Z^3-R^1$(wherein $Z^1$, $Z^2$, $Z^3$ and $R^1$ are the same meanings as above (1)), the others are hydrogen or groups selected from the substitution group A), a prodrug, a pharmaceutically acceptable salt or a solvate thereof,

(21) a compound according to the above (20) wherein $R^B$ is heteroaryl, $Z^6$ is $=C(-R^5)-$, at least one of $R^3$ to $R^{10}$ is the formula: $-Z^1-Z^2-Z^3-R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, alkyl or halogen, a prodrug, a pharmaceutically acceptable salt or a solvate thereof,

(22) a compound according to the above (1) which is the formula:

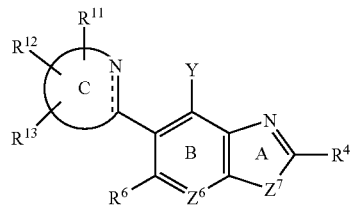

(wherein C ring is nitrogen-containing heteroaryl, Y is hydroxy or mercapto, $Z^6$ is $=C(-R^5)-$, or $=N-$, $Z^7$ is $-N(-R^3)-$, $-S-$ or $-O-$, at least one of $R^3$ to $R^6$ and $R^{11}$ to $R^{13}$ is the formula: $-Z^1-Z^2-Z^3-R^1$(wherein $Z^1$, $Z^2$, $Z^3$ and $R^1$ are the same meanings as above (1)), the others are hydrogen or groups selected from the substitution group A), a prodrug, a pharmaceutically acceptable salt or a solvate thereof,

(23) a compound according to the above (22) wherein C ring is 1,3,4-oxadiazol-2-yl, oxazol-2-yl, thiazol-2-yl, 1,3,4-thiadiazol-2-yl, 1,2,4-triazol-3-yl, imidazol-2-yl or pyrimidin-2-yl, $Z^6$ is $=C(-R^5)-$, or $=N-$, $Z^7$ is $-N(-R^3)-$, $-S-$ or $-O-$, at at least one of $R^3$ to $R^6$ and $R^{11}$ to $R^{13}$ is the formula: $-Z^1-Z^2-Z^3-R^1$ (wherein $Z^1$ is a bond or alkylene, $Z^2$ is a bond, alkylene optionally substituted with aryl, alkenylene, $-O-$ or $-NH-$, $Z^3$ is a bond, $R^1$ is optionally substituted aryl (the substituents are alkyl, halogen, alkoxy, haloalkyl and/or azide ), optionally substituted heteroaryl (the substituents are alkyl, halogen, alkoxy, haloalkyl and/or azide ) or optionally substituted cycloalkyl (the substituents are alkyl, halogen, alkoxy, haloalkyl and/or azide )), the others are hydrogen, halogen, optionally substituted alkyl (the substituents are halogen, alkoxycarbonyl, carboxy, alkoxy, hydroxy, optionally substituted carbamoyl (the substituent is alkyl ), alkenyloxy and/or phthalimide), aralkyl optionally substituted with halogen, aryl optionally substituted with halogen, carbamoyl optionally substituted with alkyl, amino optionally substituted with acyl or alkylthio, a prodrug, a pharmaceutically acceptable salt or a solvate thereof,

(24) a compound according to the above (1) which is the formula:

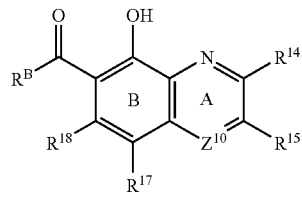

(wherein $R^B$ is hydrogen or a group selected from the substitution group A, $Z^{10}$ is $-C(-R^6)=$ or $-N=$, at least one of $R^{14}$ to $R^{18}$ is the formula: $-Z^1-Z^2-Z^3-R^1$ (wherein $Z^1$, $Z^2$, $Z^3$ and $R^1$ are the same meanings as above (1)), the others are hydrogen or groups selected from the substitution group A), a prodrug, a pharmaceutically acceptable salt or a solvate thereof,

(25) a compound according to the above (24) wherein $R^{15}$ is the formula: $-Z^1-Z^2-Z^3-R^1$(wherein $Z^1$, $Z^2$, $Z^3$ and $R^1$ are the same meanings as above (1)), a prodrug, a pharmaceutically acceptable salt or a solvate thereof,

(26) a compound according to the above (24) wherein $R^{14}$ is hydrogen, alkyl, alkenyl, halogen, haloalkyl, alkoxy, haloalkoxy or optionally substituted amino, a prodrug, a pharmaceutically acceptable salt or a solvate thereof,

(27) a compound according to the above (24) wherein $R^B$ is hydroxy, alkoxy, optionally substituted amino, alkyl, cycloalkyl or aryl, at least one of $R^{14}$ to $R^{18}$ is the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen, optionally substituted alkyl (the substituents are alkoxycarbonyl and/or carboxy), optionally substituted alkenyl (the substituents are alkoxycarbonyl and/or carboxy), aryl, aralkyl optionally substituted with halogen, optionally substituted carbamoyl, cyano or formyl, a prodrug, a pharmaceutically acceptable salt or a solvate thereof,

(28) a compound according to the above (24) wherein $R^B$ is hydroxy, alkoxy, optionally substituted alkyl (the substituents are alkoxy and/or optionally substituted amino), optionally substituted aryl, optionally substituted heteroaryl, cycloalkyl or optionally substituted amino (the substituents are alkyl and/or alkoxy), $R^{14}$ is hydrogen, alkyl, alkenyl, halogen, haloalkyl, alkoxy, haloalkoxy or optionally substituted amino, one of $R^{15}$ and $R^{16}$ is the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), the other is hydrogen, alkyl or halogen, $R^{17}$ is hydrogen, halogen, optionally substituted alkyl (the substituents are alkoxycarbonyl, carboxy, alkoxy, optionally substituted amino and/or optionally substituted carbamoyl (the substituents are alkyl and/or alkylene)), optionally substituted alkenyl (the substituents are alkoxycarbonyl, carboxy and/or optionally substituted carbamoyl), optionally substituted carbamoyl (the substituents are alkyl, alkylene, alkoxyalkyl, aralkyl, aryl and/or heteroaryl), alkoxycarbonyl, carboxy, alkoxy, optionally substituted sulfamoyl, optionally substituted amino, cyano or formyl, $R^{18}$ is hydrogen, alkyl or halogen, a prodrug, a pharmaceutically acceptable salt or a solvate thereof,

(29) a compound according to the above (24) wherein $R^B$ is hydroxy, alkoxy, optionally substituted alkyl (the substituents are alkoxy and/or optionally substituted amino), optionally substituted aryl, optionally substituted heteroaryl, cycloalkyl or optionally substituted amino (the substituents are alkyl and/or alkoxy), $R^{14}$ is hydrogen, alkyl, alkenyl, halogen, haloalkyl, alkoxy, haloalkoxy or optionally substituted amino, $R^{15}$ is the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide )), $R^{16}$, $R^{17}$ and $R^{18}$ each is independently hydrogen, halogen, optionally substituted alkyl (the substituents are alkoxycarbonyl, carboxy, alkoxy, optionally substituted amino and/or optionally substituted carbamoyl (the substituents are alkyl and/or alkylene)), optionally substituted alkenyl (the substituents are alkoxycarbonyl, carboxy and/or optionally substituted carbamoyl), optionally substituted carbamoyl (the substituents are alkyl, alkylene, alkoxyalkyl, aralkyl, aryl and/or heteroaryl), alkoxycarbonyl, carboxy, alkoxy, optionally substituted sulfamoyl, optionally substituted amino, cyano or formyl, a prodrug, a pharmaceutically acceptable salt or a solvate thereof,

(30) a compound according to the above (24) wherein $R^B$ is hydroxy or alkoxy, $R^{14}$ is hydrogen, alkyl, halogen, one of $R^{15}$ and $R^{16}$ is the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide )), the other is hydrogen, alkyl or halogen, $R^{17}$ is hydrogen, halogen, optionally substituted alkyl (the substituents are alkoxycarbonyl, carboxy and/or optionally substituted carbamoyl), optionally substituted alkenyl (the substituents are alkoxycarbonyl, carboxy and/or optionally substituted carbamoyl), optionally substituted carbamoyl, cyano or formyl, $R^{18}$ is hydrogen, alkyl or halogen, a prodrug, a pharmaceutically acceptable salt or a solvate thereof,

(31) a compound according to the above (24) wherein $R^{17}$ is optionally substituted carbamoyl, a prodrug, a pharmaceutically acceptable salt or a solvate thereof,

(32) a compound according to the above (1) which is the formula:

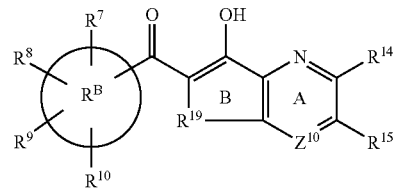

(wherein $R^B$ is aryl, heteroaryl, cycloalkyl, cycloalkenyl or heterocycle, $Z^{10}$ is —C(—$R^{16}$)= or —N=, $R^{19}$ is —O—, —C(—$R^{17}$)=C(—$R^{18}$)— or —CH(—$R^{17}$)—CH(—$R^{18}$)—, at least one of $R^7$ to $R^{10}$ and $R^{14}$ to $R^{18}$ is the formula: -$Z^1$-$Z^2$-$Z^3$-$R^1$(wherein $Z^1$,$Z^2$,$Z^3$ and $R^1$ are the same meanings as above (1)), the others are hydrogen or groups selected from the substitution group A), a prodrug, a pharmaceutically acceptable salt or a solvate thereof,

(33) a compound according to the above (32) wherein $R^B$ is heteroaryl, at least one of $R^7$ to $R^{10}$ and $R^{14}$ to $R^{18}$ is the formula: -$Z^1$-$Z^2$-$Z^3$-$R^1$(wherein $Z^1$ and $Z^3$ are bonds, $Z^2$ is alkylene or —S—, $R^1$ is optionally substituted aryl (the substituents are alkyl, halogen, alkoxy, haloalkyl and/or azide)), the others are hydrogen halogen or alkyl, a prodrug, a pharmaceutically acceptable salt or a solvate thereof,

(34) a compound according to the above (1) which is the formula:

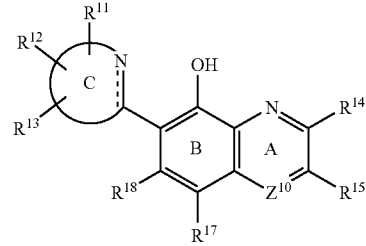

(wherein C ring is nitrogen-containing heteroaryl, $Z^{10}$ is —C(—$R^{16}$)= or —N=, at least one of $R^{11}$ to $R^{18}$ is the formula: -$Z^1$-$Z^2$-$Z^3$-$R^1$(wherein $Z^1$,$Z^2$,$Z^3$ and $R^1$ are the same meanings as above (1)), the others are hydrogen or groups selected from the substitution group A), a prodrug, a pharmaceutically acceptable salt or a solvate thereof,

(35) a compound according to the above (34) wherein C ring is pyrimidin-2-yl, pyridin-2-yl, 1,3,4-oxadiazole-2-yl, 1,3,4-thiadiazol-2-yl, thiazol-2-yl or imidazol-2-yl, at least one of $R^{11}$ to $R^{18}$ is the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl, a prodrug, a pharmaceutically acceptable salt or a solvate thereof,

(36) a compound according to the above (1) which is the formula:

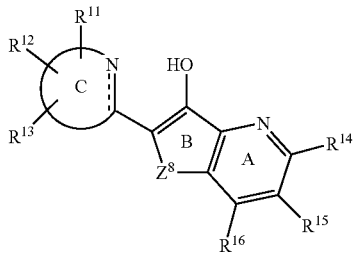

(wherein C ring is nitrogen-containing heteroaryl, $Z^8$ is —O—, —N(—$R^{17}$)— or —S—; at least one of $R^{11}$ to $R^{17}$ is the formula formula: -$Z^1$-$Z^2$-$Z^3$-$R^1$(wherein $Z^1$,$Z^2$,$Z^3$ and $R^1$ are the same meanings as above (1)), the others are hydrogen or groups selected from the substitution group A), a prodrug, a pharmaceutically acceptable salt or a solvate thereof,

(37) a compound according to the above (36) wherein C ring is 1,3,4-oxadiazol-2-yl or 1,3,4-thiadiazol-2-yl, $Z^8$ is —O—, at least one of $R^{11}$ to $R^{17}$ is the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl, a prodrug, a pharmaceutically acceptable salt or a solvate thereof,

(38) a compound according to the above (1) which is the formula:

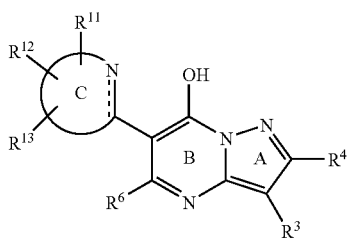

(wherein C ring is nitrogen-containing heteroaryl and at least one of $R^3$, $R^4$, $R^6$ and $R^{11}$ to $R^{13}$ is the formula: -$Z^1$-$Z^2$-$Z^3$-$R^1$ (wherein $Z^1$,$Z^2$,$Z^3$ and $R^1$ are the same meanings as above (1)), the others are hydrogen or groups selected from the substitution group A), a prodrug, a pharmaceutically acceptable salt or a solvate thereof,

(39) a compound according to the above (38) wherein C ring is 1,3,4-oxadiazol-2-yl, at least one of $R^3$,$R^4$,$R^6$ and $R^{11}$ to $R^{13}$ is the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl, a prodrug, a pharmaceutically acceptable salt or a solvate thereof,

(40) a compound according to the above (1) which is the formula:

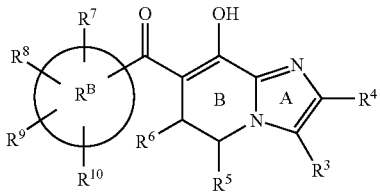

(wherein $R^B$ is aryl, heteroaryl, cycloalkyl, cycloalkenyl or heterocycle, at least one of $R^3$ to $R^{10}$ is the formula: -$Z^1$-$Z^2$-$Z^3$-$R^1$(wherein $Z^1$,$Z^2$,$Z^3$ and $R^1$ are the same meanings as above (1)), the others are hydrogen or groups selected from the substitution group A), a prodrug, a pharmaceutically acceptable salt or a solvate thereof,

(41) a pharmaceutical composition containing the compound according to any one of the above (1) to (40), a prodrug, a pharmaceutically acceptable salt or a solvate thereof as the active ingredient,

(42) a pharmaceutical composition according to the above (41) which is an enzyme inhibitor,

(43) a pharmaceutical composition according to the above (42) which is a nucleic acid related enzyme inhibitor,

(44) a pharmaceutical composition according to the above (43) which is an HIV integrase inhibitor,

(45) a pharmaceutical composition according to the above (41) which is an aniti-HIV agent,

(46) a pharmaceutical composition according to the above (41) which is a critical prevention agent or a therapeutic agent for AIDS or AIDS related complication,

(47) a mixture of anti-HIV agents which comprises a pharmaceutical composition according to the above (44) in combination with a reverse transcriptase inhibitor and/or a protease inhibitor,

(48) a pharmaceutical composition according to the above (44) which has an activity enhancing the anti-HIV activity of a reverse transcriptase inhibitor and/or a protease inhibitor,

(49) a method for the critical prevention or treatment of AIDS or AIDS related complication, which comprises administering a pharmaceutical composition according to the above (41),

(50) use of the compound according to any one of the above (1) to (40) for the manufacture of a pharmaceutical composition for the critical prevention or treatment of AIDS or AIDS related complication.

The present invention is explained in detail blow.

The followings are the character of compound of the formula (I):

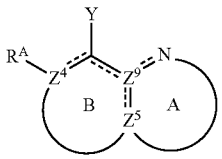

(wherein A ring, B ring, $Z^4$, $Z^5$, $Z^9$, Y and $R^A$ are the same meanings as above (1))

1)

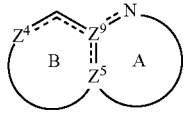

(wherein A ring, B ring, $Z^4$, $Z^5$ and $Z^9$ are the same meanings as above (1)) is a condensed nitrogen-containing heterocycle 2) A ring has the nitrogen atom at the adjacent position of $Z^9$ as a constituent atom of the ring.
3) B ring has Y as a substituent at the adjacent position of $Z^9$.
4) Y is hydroxy, mercapto or amino.
5) B ring has $R^A$ as a substituent at $Z^4$ which is the adjacent position of the atom in which Y is substituted.
6) $R^A$ is a group of the formula:

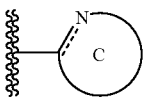

(wherein C ring is the same meaning as above (1)) or the formula:

(wherein X and $R^B$ are the same meanings as above (1))
7) A ring, B ring or $R^A$ is substituted with a group of the formula: $-Z^1-Z^2-Z^3-R^1$ (wherein $Z^1$, $Z^2$, $Z^3$ and $R^1$ are the same meanings as above (1)) at at least one of the substitutable positions (except for the nitrogen atom next to $Z^9$ on A ring and the nitrogen atom next to the bonding position on C ring.)
8) A ring, B ring, C ring or $R^B$ is optionally substituted with one to six group(s) selected from the substitution group A at the other substitutable positions than the position at which a group of the formula: $-Z^1-Z^2-Z^3-R^1$ (wherein $Z^1$, $Z^2$, $Z^3$ and $R^1$ are the same meanings as above (1)) is substituted (except for the nitrogen atom next to $Z^9$ on A ring and the nitrogen atom next to the bonding position on C ring).

The compound of the formula (I) includes a compound of the formula (II):

(II)

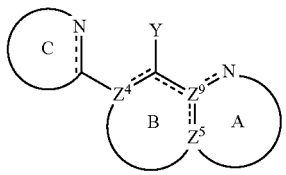

(wherein A ring, B ring, C ring, $Z^4$, $Z^5$, $Z^9$ and Y are the same meanings as above (1)) or a compound of the formula (III):

(III)

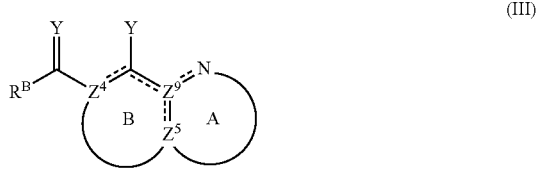

(wherein A ring, B ring, $Z^4$, $Z^5$, $Z^9$, Y, $R^B$ and X are the same meanings as above (1)).

And in the above formula (II) and formula (III), A ring, B ring or $R^A$ (C ring or $R^B$) is substituted a group of the formula: $-Z^1-Z^2-Z^3-R^1$ (wherein $Z^1$, $Z^2$, $Z^3$ and $R^1$ are the same meanings as above (1)) at at least one of the substitutable positions (except for the nitrogen atom next to $Z^9$ on A ring and the nitrogen atom next to the bonding position on C ring.), and A ring, B ring or $R^A$ (C ring or $R^B$) is optionally substituted with one to six group(s) selected from substitution group A at the other substitutable positions than the position at which a group of the formula: $-Z^1-Z^2-Z^3-R^1$ (wherein $Z^1$, $Z^2$, $Z^3$ and $R^1$ are the same meanings as above (1)) is substituted (except for the nitrogen atom next to $Z^9$ on A ring and the nitrogen atom next to the bonding position on C ring).

Among the compound of the formula (II), the preferable embodiments are below. A compound of the formula (II-A):

(II-A)

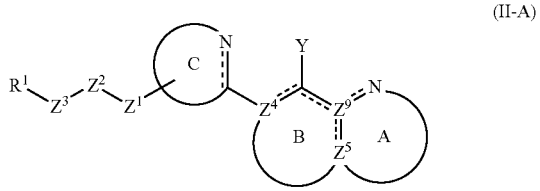

(wherein A ring, B ring, C ring, $Z^4$, $Z^5$, $Z^9$, Y, $Z^1$, $Z^2$, $Z^3$ and $R^1$ are the same meanings as above (1)) and a compound of the formula (II-B):

(II-B)

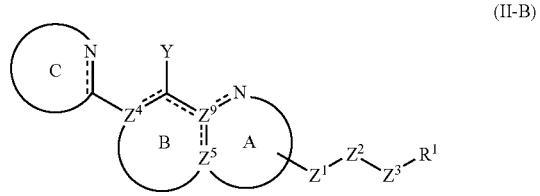

(wherein A ring, B ring, C ring, $Z^4$, $Z^5$, $Z^9$, Y, $Z^1$, $Z^2$, $Z^3$ and $R^1$ are the same meanings as above (1)) are preferable.

Among the compound of the formula (III), the preferable embodiments are below. A compound of the formula (III-A):

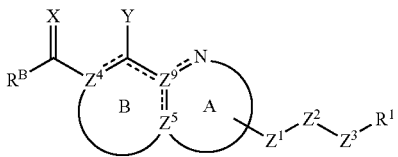
(III-B)

(wherein A ring, B ring, $Z^4$, $Z^5$, $Z^9$, Y, X, $Z^1$, $Z^2$, $Z^3$ $R^1$ and $R^B$ are the same meanings as above (1)) and a compound of the formula (III-B):

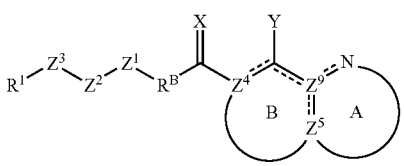
(III-B)

(wherein A ring, B ring, $Z^4$, $Z^5$, $Z^9$, Y, X, $Z^1$, $Z^2$, $Z^3$ $R^1$ and $R^B$ are the same meanings as above (1)) are preferable.

A preferable compound of the formula (III-A) is that wherein $R^B$ is the formula: —OR (R is optionally substituted alkyl.), which is shown by the formula (III-C). A preferable compound of the formula (III-B) is that wherein $R^B$ is optionally substituted aryl or optionally substituted heteroaryl, which is shown by the formula (III-D).

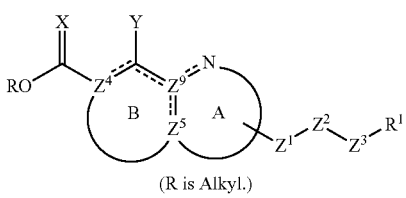
(III-C)

(R is Alkyl.)

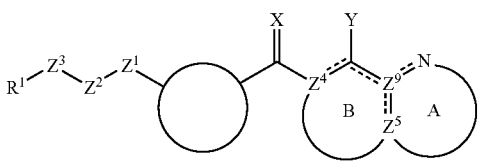
(III-D)

(wherein A ring, B ring, $Z^4$, $Z^5$, $Z^9$, Y, X, $Z^1$, $Z^2$, $Z^3$ $R^1$ and $R^B$ are the same meanings as above (1)).

Then, in the compounds above formula (II-A), formula (II-B), formula (III-A), formula (III-B), formula (III-C) and formula (III-D), A ring, B ring or $R^A$ (C ring or $R^B$) is optionally substituted with one to six group(s) selected from substitution group A at the other substitutable positions than the position at which a group of the formula: $-Z^1-Z^2-Z^3-R^1$ (wherein $Z^1$, $Z^2$, $Z^3$ and $R^1$ are the same meanings as above (1)) is substituted (except for the nitrogen atom next to $Z^9$ on A ring and the nitrogen atom next to the bonding position on C ring.).

The ring of the formula:

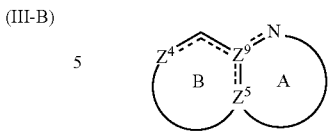

(wherein A ring, B ring, $Z^4$, $Z^5$ and $Z^9$ are the same meanings as above (1)) means a condensed nitrogen-containing heterocycle. Moreover, the broken line shows the presence or absence of a bond, except that each neighboring broken line simultaneously shows the presence of a bond. The part shown as a curved line means atom(s) and bond(s), which constitutes A ring and B ring. Carbon atom, oxygen atom, nitrogen atom and sulfur atom are listed as constituent atoms, and a single bond and a double bond are listed as the bond. Especially, the preferred condensed nitrogen-containing heterocycle is an aromatic ring, thus the atom(s) and the bond(s) which constitutes A ring and B ring should be selected to make the above condensed nitrogen-containing heterocycle aromatic.

Furthermore, preferred is that the number of the heteroatom (oxygen atom, nitrogen atom and sulfur atom) constructing the above nitrogen-containing heterocycle is one to six, especially one to four. A ring and B ring constructing the above nitrogen-containing heterocycle means each 4- to 8-membered ring, especially 5- or 6-membered ring. Then, the heteroatom may not be necessarily included in the atoms constructing B ring.

The preferable embodiments of the condensed nitrogen-containing heterocycle are 1) the case in which the condensed nitrogen-containing heterocycle is

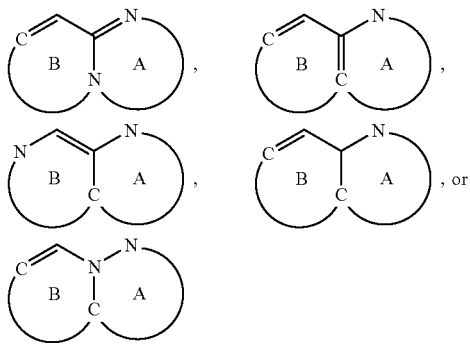

2) the case in which the condensed nitrogen-containing heterocycle is a aromatic ring,
3) the case in which a $Z^4$, $Z^5$ and $Z^9$ are carbon atoms, B ring is a 6-membered aromatic ring and A ring is a 7- or 8-membered nonaromatic ring,
4) the case in which $Z^4$ and $Z^9$ are carbon atoms, $Z^5$ is nitrogen atom, the bond between $Z^9$ and the neighboring nitrogen atom on A ring is a double bond and A ring is a 7- or 8-membered nonaromatic ring,
5) the case in which the nitrogen atom next to $Z^9$ on A ring binds to a neighboring atom with a double bond and binds to another neighboring atom with a single bond shown by the following (S1) and (S2),

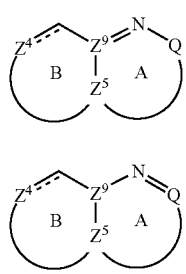
(wherein A ring, B ring, $Z^4$, $Z^5$ and $Z^9$ are the same meanings as above (1); Q is an atom next to the nitrogen atom.).
Especially the followings are preferable as A ring and B ring.
A ring is the formula:
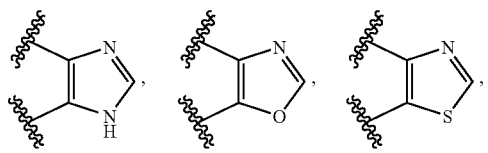
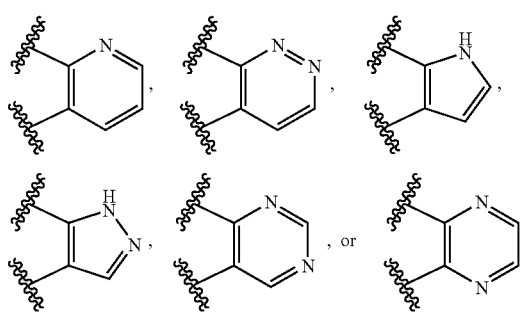
or the formula:
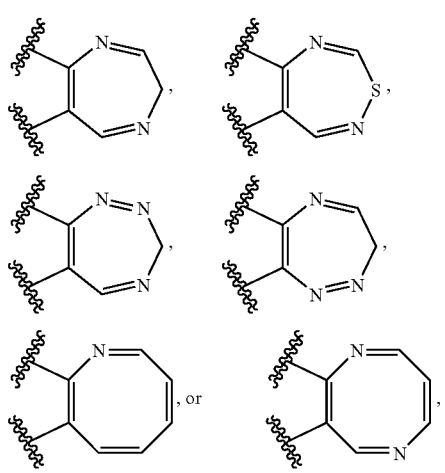
and B ring is the formula:
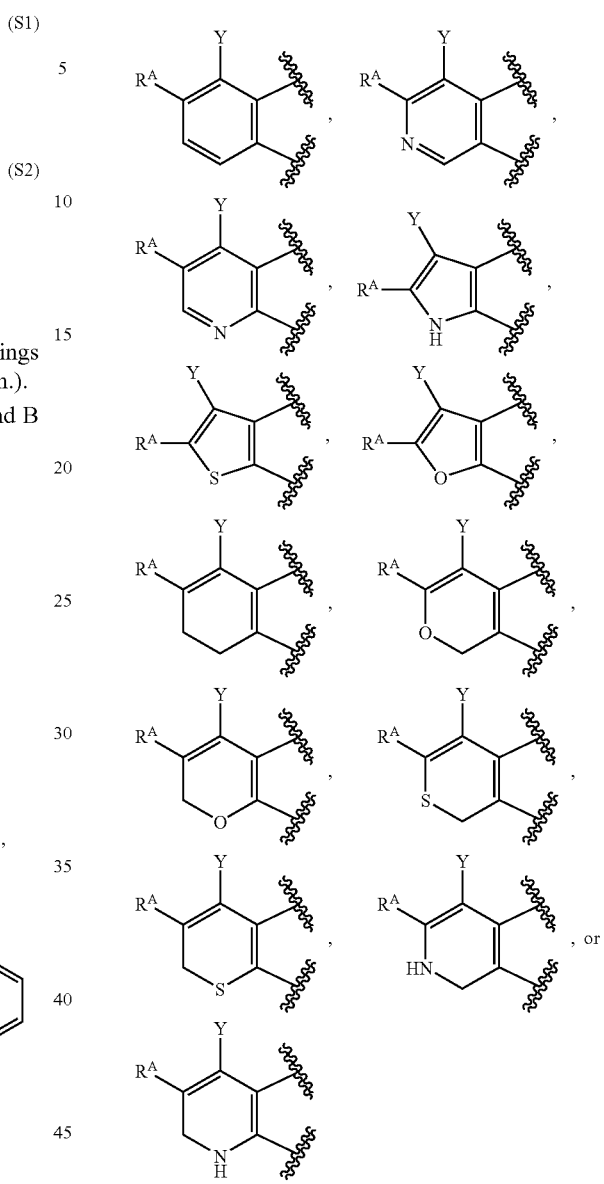
(wherein Y and $R^A$ are the same meanings as above (1)).
And as the other embodiment, preferred is that A ring is the formula:
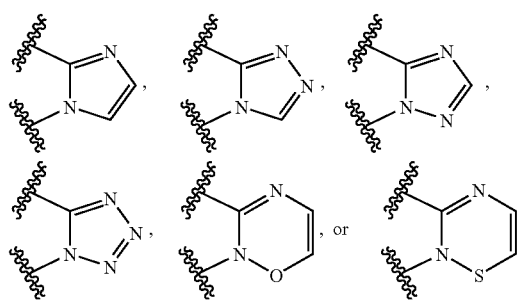

or the formula:
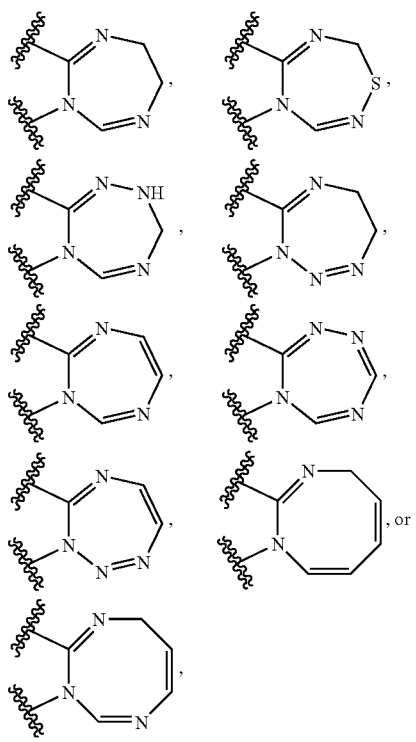
and B ring is the formula:
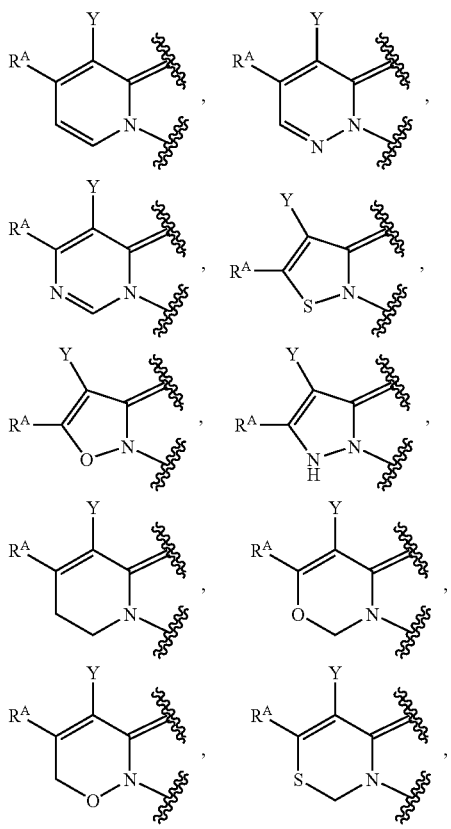
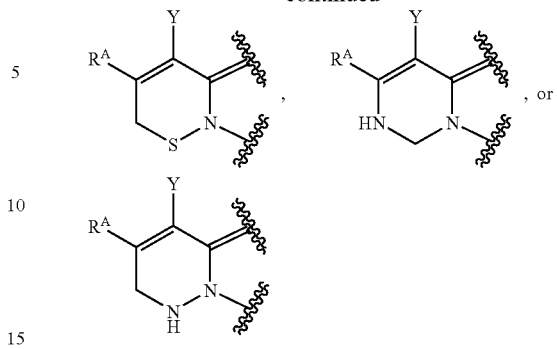
(wherein Y and $R^4$ are the same meanings as above (1)).
Another preferred is that A ring is the formula:
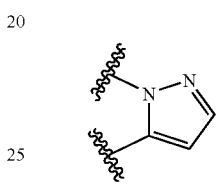
and B ring is the formula:
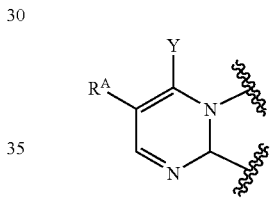
(wherein Y and $R^4$ are the same meanings as above (1)).
When $Z^4$ is nitrogen atom, the following examples are conceived.
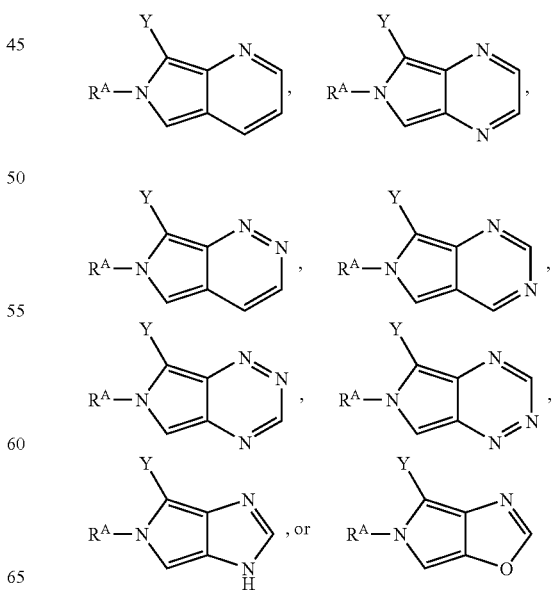

(wherein Y and $R^4$ are the same meanings as above (1))

And the especially preferable combination of A ring and B ring are as follows: 1) both are 6-membered rings, 2) both are 5-membered rings and 3) one is 5-membered ring, the other is 6-membered ring. 1) and 3) are especially preferable. In case of 3), preferable is that A ring is 5-membered ring, B ring is 6-membered ring.

Especially, the ring of the following formula is preferable:

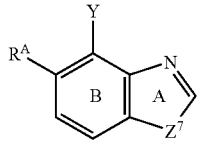

(wherein Y and $R^4$ are the same meanings as above (1), $Z^7$ is the same meaning as above (5)), furthermore, preferred is that $Z^7$ is NH.

Namely, as a compound of the present invention, the followings are preferable, (A-1) a compound of the formula:

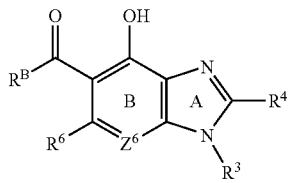

(wherein $R^B$ is hydrogen or a group selected from the substitution group A, $Z^6$ is =C(—$R^5$)— or =N—, at least one of $R^3$ to $R^6$ is a group of the formula: -$Z^1$-$Z^2$-$Z^3$-$R^1$ (wherein $Z^1$, $Z^2$, $Z^3$ and $R^1$ are the same meanings as above (1)), the others are hydrogen or groups selected from the substitution group A), (A-2) a compound of the formula:

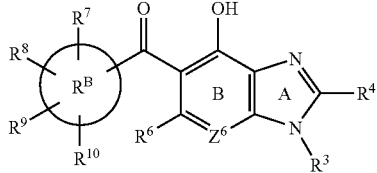

(wherein $R^B$ is aryl, heteroaryl, cycloalkyl, cycloalkenyl or heterocycle, $Z^6$ is =C(—$R^5$)— or =N—, at least one of $R^3$ to $R^{10}$ is a group of the formula: -$Z^1$-$Z^2$-$Z^3$-$R^1$ (wherein $Z^1$, $Z^2$, $Z^3$ and $R^1$ are the same meanings as above (1)), the others are hydrogen or groups selected from the substitution group A), (A-3) a compound of the formula:

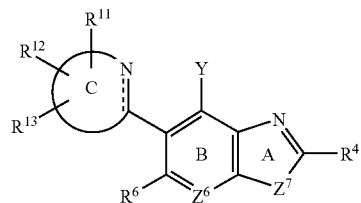

(wherein C ring is nitrogen-containing heteroaryl, Y is hydroxy or mercapto, $Z^6$ is =C(—$R^5$)— or =N—, $Z^7$ is —N(—$R^3$)—, —S— or —O—, at least one of $R^3$ to $R^6$ and $R^{11}$ to $R^{13}$ is a group of the formula: -$Z^1$-$Z^2$-$Z^3$-$R^1$ (wherein $Z^1$, $Z^2$, $Z^3$ and $R^1$ are the same meanings as above (1)), the others are hydrogen or groups selected from the substitution group A)

(A-4) a compound of the formula:

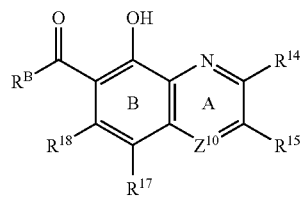

(wherein $R^B$ is hydrogen or a group selected from the substitution group A, $Z^{10}$ is —C(—$R^{16}$)= or —N=, at least one of $R^{14}$ to $R^{18}$ is a group of the formula: -$Z^1$-$Z^2$-$Z^3$-$R^1$ (wherein $Z^1$, $Z^2$, $Z^3$ and $R^1$ are the same meanings as above (1)), the others are hydrogen or groups selected from the substitution group A. However, a compound of the formula:

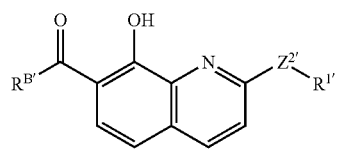

(wherein $R^{B'}$ is hydroxy or alkoxy, $Z^{2'}$ is alkylene or alkenylene, $R^{1'}$ is optionally substituted aryl or optionally substituted heteroaryl), benzyl5-benzyl-7-acetyl-8-hydroxyquinoline and 5-phenyl-7-acetyl-8-hydroxyquinoline are excluded.), (A-5) a compound of the formula:

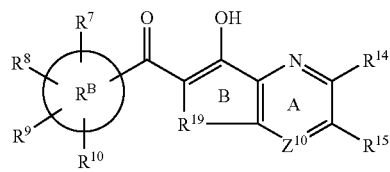

(wherein $R^B$ is aryl, heteroaryl, cycloalkyl, cycloalkenyl or heterocycle, $Z^{10}$ is —C(—$R^{16}$)═ or —N═, $R^{19}$ is —O—, —C(—$R^{17}$)═C(—$R^{18}$)— or —CH(—$R^{17}$)—CH(—$R^{18}$)—, at least one of $R^7$ to $R^{10}$ and $R^{14}$ to $R^{18}$ is a group of the formula: -$Z^1$-$Z^2$-$Z^3$-$R^1$(wherein $Z^1$, $Z^2$, $Z^3$ and $R^1$ are the same meanings as above (1)), the others are hydrogen or groups selected from the substitution group A), (A-6) a compound of the formula:

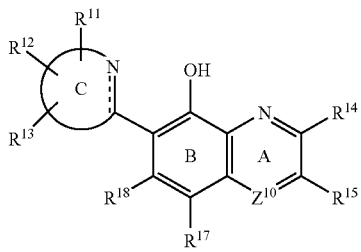

(wherein C ring is nitrogen-containing heteroaryl, $Z^{10}$ is —C(—$R^{16}$)═ or —N═, at least one of $R^{11}$ to $R^{18}$ is a group of the formula: -$Z^1$-$Z^2$-$Z^3$-$R^1$(wherein $Z^1$, $Z^2$, $Z^3$ and $R^1$ are the same meanings as above (1)), the others are hydrogen or groups selected from the substitution group A)

(A-7) a compound of the formula:

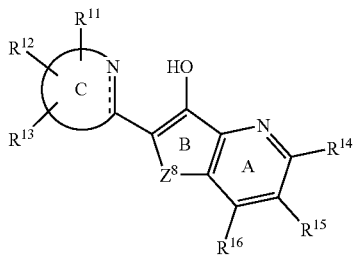

(wherein C ring is nitrogen-containing heteroaryl, $Z^8$ is —O—, —N(—$R^{17}$)— or —S—; at least one of $R^{11}$ to $R^{17}$ is a group of the formula: -$Z^1$-$Z^2$-$Z^3$-$R^1$(wherein $Z^1$, $Z^2$, $Z^3$ and $R^1$ are the same meanings as above (1)), the others are hydrogen or groups selected from the substitution group A)

(A-8) a compound of the formula:

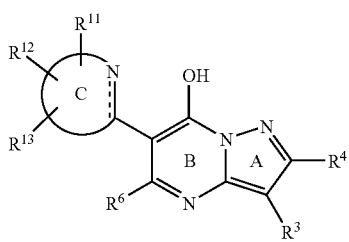

(wherein C ring is nitrogen-containing heteroaryl, at least one of $R^3$, $R^4$, $R^6$ and $R^{11}$ to $R^{13}$ is a group of the formula: -$Z^1$-$Z^2$-$Z^3$-$R^1$(wherein $Z^1$, $Z^2$, $Z^3$ and $R^1$ are the same meanings as above (1)), the others are hydrogen or groups selected from the substitution group A)

(A-9) a compound according to the above (1) which is the formula:

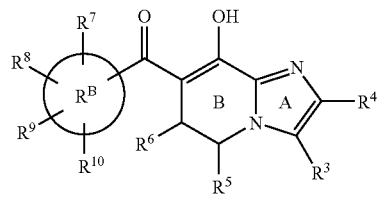

(wherein $R^B$ is aryl, heteroaryl, cycloalkyl, cycloalkenyl or heterocycle, at least one of $R^3$ to $R^{10}$ is a group of the formula: -$Z^1$-$Z^2$-$Z^3$-$R^1$(wherein $Z^1$, $Z^2$, $Z^3$ and $R^1$ are the same meanings as above (1)), the others are hydrogen or groups selected from the substitution group A), a prodrug, a pharmaceutically acceptable salt or a solvate thereof.

Especially, as to (A-1), preferred is the compound wherein $R^B$ is hydroxy, alkoxy, optionally substituted amino, heterocycle, heteroaryl or aryl, $Z^6$ is ═C(—$R^5$)—, at least one of $R^3$ to $R^6$ is a group of the formula: -$Z^1$-$Z^2$-$Z^3$-$R^1$ (wherein $Z^1$ and $Z^3$ are bonds, $Z^2$ is a bond, alkylene or alkenylene, $R^1$ is optionally substituted aryl (the substituents are alkyl, halogen, alkoxy, haloalkyl and/or azide)), the others are aralkyl optionally substituted with halogen, hydrogen, halogen or alkyl.

As to (A-2), preferred is the compound wherein $R^B$ is heteroaryl, $Z^6$ is ═C(—$R^5$)—, at least one of $R^3$ to $R^{10}$ is a group of the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, alkyl or halogen.

As to (A-3), preferred is the compound wherein C ring is 1,3,4-oxadiazol-2-yl, oxazol-2-yl, thiazol-2-yl, 1,3,4-thiadiazol-2-yl, 1,2,4-triazol-3-yl, imidazol-2-yl or pyrimidin-2-yl, $Z^6$ is ═C(—$R^5$)— or ═N—, $Z^7$ is —N(—$R^3$)—, —S— or —O—, at least one of $R^3$ to $R^6$ and $R^{11}$ to $R^{13}$ is a group of the formula: -$Z^1$-$Z^2$-$Z^3$-$R^1$(wherein $Z^1$ is a bond or alkylene, $Z^2$ is a bond, alkylene optionally substituted with aryl, alkenylene, —O— or —NH—, $Z^3$ is a bond, $R^1$ is optionally substituted aryl (the substituents are alkyl, halogen, alkoxy, haloalkyl and/or azide), optionally substituted heteroaryl (the substituents are alkyl, halogen, alkoxy, haloalkyl and/or azide) or optionally substituted cycloalkyl (the substituents are alkyl, halogen, alkoxy, haloalkyl and/or azide)), the others are hydrogen, halogen, optionally substituted alkyl (the substituents are halogen, alkoxycarbonyl, carboxy, alkoxy, hydroxy, optionally substituted carbamoyl (the substituent is alkyl), alkenyloxy and/or phthalimide), aralkyl optionally substituted with halogen, aryl optionally substituted with halogen, carbamoyl optionally substituted with alkyl, amino optionally substituted with acyl, or alkylthio.

As to (A-4), preferred is the compound wherein $R^{15}$ is a group of the formula: -$Z^1$-$Z^2$-$Z^3$-$R^1$(wherein $Z^1$, $Z^2$, $Z^3$ and $R^1$ are the same meaning as above (1)), the compound according to the above (24) wherein $R^{14}$ is hydrogen, alkyl, alkenyl, halogen, haloalkyl, alkoxy, haloalkoxy or optionally substituted amino, the compound wherein $R^B$ is hydroxy, alkoxy, optionally substituted amino, alkyl, cycloalkyl or aryl, at least one of $R^{14}$ to $R^{18}$ is a group of the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen, optionally substituted alkyl (the substituents are alkoxycarbonyl and/or carboxy), optionally substituted alkenyl (the substituents are alkoxycarbonyl and/or carboxy), aryl, aralkyl optionally substituted with halogen, optionally substituted carbamoyl, cyano or formyl, the compound wherein $R^B$ is hydroxy, alkoxy, optionally substituted alkyl (the substituents are alkoxy and/or optionally substituted amino), optionally substituted aryl, optionally substituted heteroaryl, cycloalkyl or optionally substituted amino (the substituents are alkyl and/or alkoxy), $R^{14}$ is hydrogen, alkyl, alkenyl, halogen, haloalkyl, alkoxy, haloalkoxy or optionally substituted amino, one of $R^{15}$ and $R^{16}$ is a group of the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), another is hydrogen, alkyl or halogen, $R^{17}$ is hydrogen, halogen, optionally substituted alkyl (the substituents are alkoxycarbonyl, carboxy, alkoxy, optionally substituted amino and/or optionally substituted carbamoyl (the substituents are alkyl and/or alkylene)), optionally substituted alkenyl (the substituents are alkoxycarbonyl, carboxy and/or optionally substituted carbamoyl), optionally substituted carbamoyl (the substituents are alkyl, alkylene, alkoxyalkyl, aralkyl, aryl and/or heteroaryl), alkoxycarbonyl, carboxy, alkoxy, optionally substituted sulfamoyl, optionally substituted amino, cyano or formyl, $R^{18}$ is hydrogen, alkyl or halogen, the compound wherein $R^B$ is hydroxy, alkoxy, optionally substituted alkyl(the substituent is alkoxy and/or optionally substituted amino), optionally substituted aryl, optionally substituted heteroaryl, cycloalkyl or optionally substituted amino (the substituent is alkyl and/or alkoxy), $R^{14}$ is hydrogen, alkyl, alkenyl, halogen, haloalkyl, alkoxy, haloalkoxy or optionally substituted amino, $R^{15}$ is a group of the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), $R^{16}$, $R^{17}$ and $R^{18}$ each is independently hydrogen, halogen, optionally substituted alkyl (the substituents are alkoxycarbonyl, carboxy, alkoxy, optionally substituted amino and/or optionally substituted carbamoyl (the substituent is alkyl and/or alkylene)), optionally substituted alkenyl (the substituents are alkoxycarbonyl, carboxy and/or optionally substituted carbamoyl), optionally substituted carbamoyl (the substituents are alkyl, alkylene, alkoxyalkyl, aralkyl, aryl and/or heteroaryl), alkoxycarbonyl, carboxy, alkoxy, optionally substituted sulfamoyl, optionally substituted amino, cyano or formyl, and the compound wherein $R^B$ is hydroxy or alkoxy, $R^{14}$ is hydrogen, alkyl, halogen, one of $R^{15}$ and $R^{16}$ is a group of the formula: -$Z^1$-$Z^2$-$Z^3$-$R^1$(wherein $Z^1$ and $Z^3$ are bonds, $Z^2$ is alkylene, $R^1$ is optionally substituted aryl (the substituents are alkyl, halogen, alkoxy, haloalkyl and/or azide)), another is hydrogen, alkyl or halogen, $R^{17}$ is hydrogen, halogen, optionally substituted alkyl (the substituents are alkoxycarbonyl, carboxy and/or optionally substituted carbamoyl), optionally substituted alkenyl(the substituents are alkoxycarbonyl, carboxy and/or optionally substituted carbamoyl), optionally substituted carbamoyl, cyano or formyl, $R^{18}$ is hydrogen, alkyl or halogen.

As to (A-5), preferred is the compound wherein $R^B$ is heteroaryl, at least one of $R^7$ to $R^{10}$ and $R^{14}$ to $R^{18}$ is the formula: -$Z^1$-$Z^2$-$Z^3$-$R^1$ (wherein $Z^1$ and $Z^3$ are bonds, $Z^2$ is —S—, $R^1$ is optionally substituted aryl (the substituents are alkyl, halogen, alkoxy, haloalkyl and/or azide)), the others are hydrogen, halogen or alkyl.

As to (A-6), preferred is the compound wherein C ring is pyrimidin-2-yl, pyridin-2-yl, 1,3,4-oxadiazol-2-yl, 1,3,4-thiadiazol-2-yl, thiazol-2-yl, or imidazol-2-yl, at least one of $R^{11}$ to $R^{18}$ is a group of the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl.

As to (A-7), preferred is the compound wherein C ring is 1,3,4-oxadiazol-2-yl or 1,3,4-thiadiazol-2-yl, $Z^8$ is —O—, at least one of $R^{11}$ to $R^{17}$ is a group of the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl.

As to (A-8), preferred is the compound wherein C ring is 1,3,4-oxadiazol-2-yl, at least one of $R^3$, $R^4$, $R^6$ and $R^{11}$ to $R^{13}$ is a group of the formula: -$Z^1$-$Z^2$-$Z^3$-$R^1$ (wherein $Z^1$ and $Z^3$ are bonds, $Z^2$ is alkylene, $R^1$ is optionally substituted aryl (the substituents are alkyl, halogen, alkoxy, haloalkyl and/or azide)), the others are hydrogen, halogen or alkyl.

Then, as to (A-4), preferred is the compound wherein $R^{14}$ is not substituted alkyl (the substituent is optionally substituted aryl or optionally substituted heteroaryl) and substituted alkenyl (the substituent is optionally substituted aryl or optionally substituted heteroaryl), especially wherein $R^{14}$ is not phenylethenyl substituted with hydroxy. Especially preferred is the compound wherein $R^{14}$ is hydrogen, alkyl or halogen (especially $R^{14}$ is hydrogen). And preferred is the compound wherein a group of the formula: -$Z^1$-$Z^2$-$Z^3$-$R^1$ (wherein $Z^1$, $Z^2$, $Z^3$ and $R^1$ are the same meanings as above (1)) is substituted on any of $R^{15}$ to $R^{18}$ (especially $R^{15}$ or $R^{16}$). And preferred is that $R^{17}$ is hydrogen, halogen, optionally substituted alkyl (the substituents are alkoxycarbonyl, carboxy and/or optionally substituted carbamoyl), optionally substituted alkenyl (the substituents are alkoxycarbonyl, carboxy and/or optionally substituted carbamoyl), optionally substituted carbamoyl or cyano.

The substitution group except for a group of the formula: -$Z^1$-$Z^2$-$Z^3$-$R^1$(wherein $Z^1$, $Z^2$, $Z^3$ and $R^1$ are the same meanings as above (1)), on A ring, B ring, $R^A$, $R^B$ of a compound of the present invention preferably does not interfere with the integrase inhibitory activity. Namely, the present invention is characterized by that the compound of the formula (I), the formula (II) and the formula (III) are substituted with a group of the formula: -$Z^1$-$Z^2$-$Z^3$-$R^1$ (wherein $Z^1$, $Z^2$, $Z^3$ and $R^1$ are the same meanings as above (1)), and the above compounds may include the substitution group interfering with the integrase inhibitory activity. These substitution groups can be selected based on the assay result of the integrase inhibitory activity, and the drug design by the computer, as well as the molecular weight, van der Waals radius and electostatic nature and so on.

Examples of these substitution groups include, not limited thereto, a group selected from the following substitution group A. The substitution group A includes halogen, alkoxycarbonyl, carboxy, optionally substituted alkyl, alkoxy, alkoxyalkyl, nitro, hydroxy, optionally substituted alkenyl, alkynyl, alkylsulfonyl, optionally substituted amino, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitrotho, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl and optionally substituted heteroaralkylsulfonyl. And the compound of the present invention is optionally substituted with a group selected from the substitution group A at one to five position(s).

The divalent group such as alkylenedioxy, alkylene, alkenylene may substitute on the same or different atoms (for example, neighboring atoms).

Among the above substitution groups, especially preferable substitution groups, which substitute on A ring, B ring or $R^4$ at the other substitutable positions than the position at which a group of the formula: $-Z^1-Z^2-Z^3-R^1$ (wherein $Z^1$, $Z^2$, $Z^3$ and $R^1$ are the same meanings as above (1)) is substituted (except for the nitrogen atom next to $Z^9$ on A ring and the nitrogen atom next to the bonding position on C ring.) is halogen, alkoxycarbonyl, carboxy, optionally substituted alkyl, alkoxy, nitro, hydroxy, optionally substituted alkenyl, alkynyl, alkylsulfonyl, optionally substituted amino, alkylthio, haloalkyl, haloalkoxy, cycloalkyl, cycloalkenyl, cyano, mercapto, optionally substituted carbamoyl, alkylcarbonyl, alkylcarbonyloxy, optionally substituted aryl, optionally substituted heteroaryl, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl or optionally substituted heteroaralkylsulfonyl. Moreover, hydrogen, halogen, optionally substituted alkyl, optionally substituted alkenyl, optionally substituted amino, cyano, optionally substituted carbamoyl, optionally substituted aryl or optionally substituted aralkyl is more preferable.

Among the above substitution groups, especially preferable substitution group on $R^B$ is hydroxy, alkyl, alkoxy, optionally substituted amino, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl or optionally substituted heteroaralkylsulfonyl. Moreover, hydroxy, alkyl, alkoxy, optionally substituted amino, optionally substituted aryl, optionally substituted heteroaryl or optionally substituted heterocycle is more preferable.

The substitution group Y on B ring which characterizes the compound of the present invention includes hydroxy, mercapto or amino. Especially, hydroxy is preferable.

$Z^4$ includes carbon atom or nitrogen atom. Especially, carbon atom is preferable.

$Z^5$ includes carbon atom or nitrogen atom.

$Z^9$ includes carbon atom or nitrogen atom. Especially, carbon atom is preferable.

$Z^6$ includes —C(—$R^5$)= or —N=.

$Z^7$ includes oxygen atom, sulfur atom, —CH=CH— or NH. Especially, NH is preferable.

X includes oxygen atom, sulfur atom or NH. Especially, oxygen atom is preferable.

The group of the formula: $-Z^1-Z^2-Z^3-R^1$ (wherein $Z^1$, $Z^2$, $Z^3$ and $R^1$ are the same meanings as above (1)), characteristic of the compound of the present invention, for example, includes the formula: —$R^1$, the formula: —CH$_2$—$R^1$, the formula: —CH=CH—$R^1$, the formula: —CH(OH)—$R^1$, the formula: —S—$R^1$, the formula: —SO—$R^1$, the formula: —SO$_2$—$R^1$, the formula: —SO$_2$NH—$R^1$, the formula: —NHSO$_2$—$R^1$, the formula: —O—$R^1$, the formula: —NH—$R^1$, the formula: —NHCO—$R^1$, the formula: —CONH—$R^1$, the formula: —C(=O)—$R^1$, the formula: —O—C(=O)—$R^1$, the formula: —CO—$R^1$, the formula: —C$_2$H$_4$—$R^1$, the formula: —CH=CH—CH$_2$—$R^1$, the formula: —CH(OH)—CH$_2$—$R^1$, the formula: —S—CH$_2$—$R^1$, the formula: —SO—CH$_2$—$R^1$, the formula: —SO$_2$—CH$_2$—$R^1$, the formula: —SO$_2$NH—CH$_2$—$R^1$, the formula: —NHSO$_2$—CH$_2$—$R^1$, the formula: —O—CH$_2$—$R^1$, the formula: —NH—CH$_2$—$R^1$, the formula: —NHCO—CH$_2$—$R^1$, the formula: —CONH—CH$_2$—$R^1$, the formula: —C(=O)—O—CH$_2$—$R^1$, the formula: —O—C(=O)—CH$_2$—$R^1$, the formula: —CO—CH$_2$—$R^1$, the formula: —CH=CH—CH=CH—$R^1$, the formula: —CH=CH—CH(OH)—$R^1$, the formula: —CH=CH—S—$R^1$, the formula: —CH=CH—SO—$R^1$, the formula: —CH=CH—SO$_2$—$R^1$, the formula: —CH=CH—SO$_2$NH—$R^1$, the formula: —CH=CH—NHSO$_2$—$R^1$, the formula: —CH=CH—O—$R^1$, the formula: —CH=CH—NH—$R^1$, the formula: —CH=CH—NHCO—$R^1$, the formula: —CH=CH—CONH—$R^1$, the formula: —CH=CH—C(=O)—O—$R^1$, the formula: —CH=CH—O—C(=O)—$R^1$, the formula: —CH=CH—CO—$R^1$, the formula: —CH$_2$—CH=CH—$R^1$, the formula: —CH$_2$—CH(OH)—$R^1$, the formula: —CH$_2$—S—$R^1$, the formula: —CH$_2$—SO—$R^1$, the formula: —CH$_2$—SO$_2$—$R^1$, the formula: —CH$_2$—SO$_2$NH—$R^1$, the formula: —CH$_2$—NHSO$_2$—$R^1$, the formula: —CH$_2$—O—$R^1$, the formula: —CH$_2$—NH—$R^1$, the formula: —CH$_2$—NHCO—$R^1$, the formula: —CH$_2$—CONH—$R^1$, the formula: —CH$_2$—C(=O)—O—$R^1$, the formula: —CH$_2$—O—C(=O)—$R^1$, the formula: —CH$_2$—CO—$R^1$, the formula: —CH(OH)—CH=CH—$R^1$, the formula: —S—CH=CH—$R^1$, the formula: —SO—CH=CH—$R^1$, the formula: —SO$_2$—CH=CH—$R^1$, the formula: —SO$_2$NH—CH=CH—$R^1$, the formula: —NHSO$_2$—CH=CH—$R^1$, the formula: —O—CH=CH—$R^1$, the formula: —NH—CH=CH—$R^1$, the formula: —NHCO—CH=CH—$R^1$, the formula: —CONH—CH=CH—$R^1$, the formula: —C(=O)—O—CH=CH—$R^1$, the formula: —O—C(=O)—CH=CH—$R^1$, the formula: —CO—CH=CH—$R^1$, the formula: —C$_3$H$_6$—$R^1$, the formula: —CH$_2$—CH=CH—CH$_2$—$R^1$, the formula: —CH$_2$—CH(OH)—CH$_2$—$R^1$, the formula: —CH$_2$—S—CH$_2$—$R^1$, the formula: —CH$_2$—SO—CH$_2$—$R^1$, the formula: —CH$_2$—SO$_2$—CH$_2$—R$^1$, the formula: —CH$_2$—SO$_2$NH—CH$_2$—R$^1$, the formula: —CH$_2$—NHSO$_2$—CH$_2$—R$^1$, the formula: —CH$_2$—CH$_2$—R$^1$, the formula: —CH$_2$—NH—CH$_2$—R$^1$, the formula: —CH$_2$—NHCO—CH$_2$—R$^1$, the formula: —CH$_2$CONH—CH$_2$—R$^1$, the formula: —CH$_2$—C(=O)—O—CH$_2$—R$^1$, the formula: —CH$_2$—O—C(=O)—CH$_2$—R$^1$, the formula: —CH$_2$—CO—CH$_2$—R$^1$, the formula: —C$_2$H$_4$—CH=CH—R$^1$, —CH$_2$—CH=CH—CH=CH—R$^1$, the formula: —CH$_2$—CH(OH)—CH=CH—R$^1$, the formula: —CH$_2$—S—CH=CH—R$^1$, the formula: —CH$_2$—SO—CH=CH—R$^1$, the formula: —CH$_2$—SO$_2$—CH=CH—R$^1$, the formula: —CH$_2$—SO$_2$NH—CH=CH—R$^1$, the formula: —CH$_2$—NHSO$_2$—CH=CH—R$^1$, the formula: —CH$_2$—O—CH=CH—R$^1$, the formula: —CH$_2$—NH—CH=CH—R$^1$, the formula: —CH$_2$—NHCO—CH=CH—R$^1$, the formula: —CH$_2$—CONH—CH=CH—R$^1$, the formula: —CH$_2$—C(=O)—O—CH=CH—R$^1$, the formula: —CH$_2$—O—C(=O)—CH=CH—R$^1$, the formula: —CH$_2$—CO—CH=CH—R$^1$, the formula: —CH=CH—C$_2$H$_4$—R$^1$, the formula: —CH=CH—CH=CH—CH$_2$—R$^1$, the formula: —CH=CH—CH(OH)—CH$_2$—R$^1$, the formula: —CH=CH—S—CH$_2$—R$^1$, the formula: —CH=CH—SO—CH$_2$—R$^1$, the formula: —CH=CH—SO$_2$—CH$_2$—R$^1$, the formula: —CH=CH—SO$_2$NH—CH$_2$—R$^1$, the formula: —CH=CH—NHSO$_2$—CH$_2$—R$^1$, the formula: —CH=CH—O—CH$_2$—R$^1$, the formula: —CH=CH—NH—CH$_2$—R$^1$, the formula: —CH=CH—NHCO—CH$_2$—R$^1$, the formula: —CH=CH—CONH—CH$_2$—R$^1$, the formula: —CH=CH—C(=O)—O—CH$_2$—R$^1$, the formula: —CH=CH—O—C(=O)—CH$_2$—R$^1$ or the formula: —CH=CH—CO—CH$_2$—R$^1$ (wherein R$^1$ is optionally substituted aryl, optionally substituted heteroaryl, optionally substituted cycloalkyl, optionally substituted cycloalkenyl, or optionally substituted heterocycle.).

Especially, preferred as a group the formula: -Z$^1$-Z$^2$-Z$^3$-R$^1$ (wherein Z$^1$, Z$^2$, Z$^3$ and R$^1$ are the same meanings as above (1)) is 1) the case in which Z$^1$ and Z$^3$ are bonds,
2) the case in which Z$^1$ and Z$^3$ are bonds, Z$^2$ is a bond, —CO—, —O—, —S—, —SO$_2$— or lower alkylene (especially —CH$_2$—, —(CH$_2$)$_2$—),
3) the case in which Z$^1$ and Z$^3$ are bonds, Z$^2$ is a bond, —CO—, —O—, —S—, —SO$_2$— or lower alkylene (especially —CH$_2$—, —(CH$_2$)$_2$—), R$^1$ is optionally substituted aryl or optionally substituted heteroaryl,
4) the case in which Z$^1$ and Z$^3$ are bonds, Z$^2$ is —SO$^2$—, —CH$_2$— or —C$_2$H$_4$—, R$^1$ is optionally substituted aryl (especially phenyl),
5) the case in which Z$^1$ is a bond or alkylene, Z$^3$ is a bond, Z$^2$ is optionally substituted alkylene, alkenylene or —O—, R$^1$ is optionally substituted aryl, optionally substituted heteroaryl or optionally substituted cycloalkyl,
6) the case in which Z$^1$ is a bond or alkylene,
7) the case in which Z$^1$ is a bond,
8) the case in which Z$^2$ is a bond, alkylene, —SO$^2$— or —O—,
9) the case in which Z$^2$ is a bond, alkylene or —O—,
10) the case in which Z$^2$ is alkylene or —O—,
11) the case in which Z$^3$ is a bond or alkylene,
12) the case in which R$^1$ is optionally substituted cycloalkyl, optionally substituted aryl or optionally substituted heteroaryl,
13) the case in which R$^1$ is optionally substituted cycloalkyl, optionally substituted cycloalkenyl, optionally substituted heterocycle or optionally substituted aryl,
14) the case in which R$^1$ is optionally substituted cycloalkyl, optionally substituted aryl, optionally substituted heteroaryl or optionally substituted heterocycle,
15) the case in which R$^1$ is optionally substituted aryl,
16) the case in which Z$^1$ and Z$^3$ are bonds, Z$^2$ is alkylene, R$^1$ is optionally substituted aryl,
17) the case in which Z$^1$ is a bond or alkylene, Z$^3$ is a bond, Z$^2$ is optionally substituted alkylene, alkenylene, —S— or —O—, R$^1$ is optionally substituted aryl, optionally substituted heteroaryl or optionally substituted cycloalkyl.

The preferable example of a group of the formula: -Z$^1$-Z$^2$-Z$^3$-R$^1$ includes phenyl, 2-fluorophenyl, 3-fluorophenyl, 4-fluorophenyl, 2-chlorophenyl, 3-chlorophenyl, 4-chlorophenyl, 2,4-difluorophenyl, 2,6-difluorophenyl, 2,5-difluorophenyl, 3,4-difluorophenyl, 4-methylphenyl, 3-trifluoromethylphenyl, 4-trifluoromethylphenyl, 4-hydroxyphenyl, 4-methoxyphenyl, 4-bromophenyl, 4-biphenylyl, benzyl, 4-fluorobenzyl, 4-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 3,6-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-difluorophenyl)ethyl, 2-(2,6-difluorophenyl)ethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxyphenyl)ethyl, 2-(4-methoxyphenyl)ethyl, 2-(4-bromophenyl)ethyl, 2-(4-biphenylyl)ethyl, benzenesulfonyl, 2-fluorobenzenesulfonyl, 3-fluorobenzenesulfonyl, 4-fluorobenzenesulfonyl, 2-chlorobenzenesulfonyl, 3-chlorobenzenesulfonyl, 4-chlorobenzenesulfonyl, 2,4-difluorobenzenesulfonyl, 2,6-difluorobenzenesulfonyl, 2,5-difluorobenzenesulfonyl, 3,4-difluorobenzenesulfonyl, 4-methylbenzenesulfonyl, 3-trifluoromethylbenzenesulfonyl, 4-trifluoromethylbenzenesulfonyl, 4-hydroxybenzenesulfonyl, 4-methoxybenzenesulfonyl, 4-bromobenzenesulfonyl, 4-phenylbenzenesulfonyl, phenylthio, 2-fluorophenylthio, 3-fluorophenylthio, 4-fluorophenylthio, 2-chlorophenylthio, 3-chlorophenylthio, 4-chlorophenylthio, 2,4-difluorophenylthio, 2,6-difluorophenylthio, 2,5-difluorophenylthio, 3,4-difluorophenylthio, 4-methylphenylthio, 3-trifluoromethylphenylthio, 4-trifluoro methylphenylthio, 4-hydroxyphenylthio, 4-methoxyphenylthio, 4-bromophenylthio, 4-biphenylylthio, phenoxyl, 2-fluorophenoxyl, 3-fluorophenoxyl, 4-fluorophenoxyl, 2-chlorophenoxyl, 3-chlorophenoxyl, 4-chlorophenoxyl, 2,4-difluorophenoxyl, 2,6-difluorophenoxyl, 2,5-difluorophenoxyl, 3,4-difluorophenoxyl, 4-methylphenoxyl, 3-trifluoromethylphenoxyl, 4-trifluoromethylphenoxyl, 4-hydroxyphenoxyl, 4-methoxyphenoxyl, 4-bromophenoxyl, 4-phenylphenoxyl, benzoyl, 2-fluorobenzoyl, 3-fluorobenzoyl, 4-fluorobenzoyl, 2-chlorobenzoyl, 3-chlorobenzoyl, 4-chlorobenzoyl, 2,4-difluorobenzoyl, 2,6-difluorobenzoyl, 2,5-difluorobenzoyl, 3,4-difluorobenzoyl, 4-methylbenzoyl, 3-trifluoromethylbenzoyl, 4-trifluoromethylbenzoyl, 4-hydroxybenzoyl, 4-methoxybenzoyl, 4-bromobenzoyl, 4-phenylbenzoyl, 2-thienyl, 3-thienyl, furfuryl, 3-furylmethyl, (2-chlorothiophene3-yl)methyl, 2-picolyl, 3-picolyl, 4-picolyl, (2-fluoropyridin-3-yl)methyl, (2-fluoropyridin-5-yl)methyl or (5-fluoropyridin-2-yl)methyl.

Characteristics of the compound of the present invention includes that A ring, B ring or R$^A$ is substituted with a group of the formula: -$Z^1$-$Z^2$-$Z^3$-$R^1$ (wherein $Z^1$, $Z^2$, $Z^3$ and $R^1$ are the same meanings as above (1)) at at least one of the substitutable positions except for the nitrogen atom next to $Z^9$ on A ring and the nitrogen atom next to the bonding position on C ring. Especially, the case in which A ring, C ring or $R^B$ is substituted is preferable.

The above substitutable positions mean any atoms binding to hydrogen atom on A ring, B ring or $R^A$. The compound of the present invention means a compound wherein such a hydrogen atom(s) is substituted with a group of the formula: -$Z^1$-$Z^2$-$Z^3$-$R^1$ (wherein $Z^1$, $Z^2$, $Z^3$ and $R^1$ are the same meanings as above (1)).

A group of the formula:

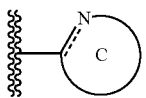

(C ring is the same meaning as above (1)) means heteroaryl wherein an atom next to the atom at the bonding position is nitrogen atom.

Especially, preferred is heteroaryl shown by (T1) and (T2) wherein an atom next to the atom at the bonding position on C ring is nitrogen atom, which binds to a neighboring atom with a double bond and binds to another neighboring atom with a single bond. More preferred is heteroaryl shown by (T3) and (T4) wherein an atom next to the atom at the bonding position on C ring is nitrogen atom, which binds to a neighboring atom with a double bond and binds to another neighboring atom with a single bond and another atom next to the atom at the bonding position is a heteroatom.

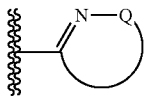 (T1)

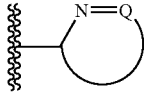 (T2)

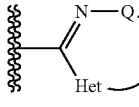 (T3)

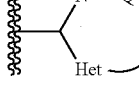 (T4)

(wherein a group of T1 to T4 is heteroaryl wherein an atom next to the atom at the bonding position is nitrogen atom. N is nitrogen atom, Q is an atom next to nitrogen atom; Het is heteroatom.)

Moreover, the broken line shows the presence or absence of a bond. The part shown as a curved line means an atom(s) and a bond(s), which constitute C ring and can be selected to make a C ring aromatic. C ring may include a heteroatom(s) other than the nitrogen atom shown in the above formula and the constituent atom of C ring includes carbon atom, oxygen atom, nitrogen atom and sulfur atom. The bond constructing C ring includes a single bond and a double bond. C ring is not only a monocycle but also a condensed ring (2 to 5 condensed rings), and especially a monocycle or a bicycle is preferable, and a monocycle is more preferable.

Heteroaryl of C ring being a monocycle means 5- to 8-membered heteroaryl wherein an atom next to the atom at the bonding position is nitrogen atom and one to four of oxygen atom, sulfur atom, and/or nitrogen atom may be included. Especially 5- or 6-membered heteroaryl is preferable. For example, it is pyrrol-2-yl, imidazol-2-yl, imidazol-4-yl, pyrazol-3-yl, triazol-3-yl, tetrazol-5-yl, oxazol-2-yl, oxazol-4-yl, isoxazol-3-yl, thiazol-2-yl, thiazol-4-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl, isothiazol-3-yl, pyridin-2-yl, pyridazin-3-yl, pyrazin-2-yl, pyrimidin-2-yl, pyrimidin-4-yl or frazan 3-yl.

Especially preferred is heteroaryl wherein an atom next to the atom at the bonding position is nitrogen atom, which binds to the neighboring atom with a double bond and binds to another neighboring atom with a single bond. For example, it is imidazol-2-yl, imidazol-4-yl, pyrazol-3-yl, triazol-3-yl, tetrazol-5-yl, oxazol-2-yl, oxazol-4-yl, isoxazol-3-yl, thiazol-2-yl, thiazol-4-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl, isothiazol-3-yl, pyridin-2-yl, pyridazin-3-yl, pyrazin-2-yl, pyrimidin-2-yl, pyrimidin-4-yl or frazan 3-yl.

Furthermore, preferred is heteroaryl wherein an atom next to the atom at the bonding position is nitrogen atom, which binds to the neighboring atom with a double bond and binds to another neighboring atom with a single bond and another atom next to the atom at the bonding position is a heteroatom. For example, it is imidazol-2-yl, triazol-3-yl, tetrazol-5-yl, oxazol-2-yl, thiazol-2-yl, 1,3,4-thiadiazol-2-yl, 1,2,4-thiadiazol-5-yl, 1,2,4-thiadiazol-3-yl, 1,3,4-oxadiazol-2-yl, 1,2,4-oxadiazol-5-yl, 1,2,4-oxadiazol-3-yl or pyrimidin-2-yl.

Heteroaryl of C ring being a condensed ring is heteroaryl wherein 1 to 4 of 5- to 8-membered aromatic carbocycle (e.g., 5- to 8-membered aromatic carbocycle) and/or the other 5- to 8-membered heteroaryl (e.g., 5- to 8-membered heteroaryl which may include 1 to 4 of oxygen atoms, sulfur atoms and/or nitrogen atoms in the ring) are condensed with the above monocycle. As a condensed aromatic ring, 5- or 6-membered ring is preferable. For example, it is benzimidazol-2-yl, benzooxazol-2-yl, quinaoxalin-2-yl, cinnolin3-yl, quinazoln-2-yl, quinazolin-4-yl, quinolin-2-yl, phthalazin1-yl, isoquinolin-1-yl, isoquinolin-3-yl, purine-2-yl, purine-6-yl, purine-8-yl, pteridin-2-yl, pteridin-4-yl, pteridin-6-yl, pteridin-7-yl, carbazol-1-yl, phenantridin-6-yl, indol-2-yl or isoindol-1-yl.

Especially, preferred is heteroaryl wherein an atom next to the atom at the bonding position is nitrogen atom, which binds to the neighboring atom with a double bond and binds to another neighboring atom with a single bond. For example, benzimidazol-2-yl, benzooxazol-2-yl, quinoxalin-2-yl, cinnoline3-yl, quinazolin-2-yl, quinazolin-4-yl, quinolin-2-yl, phthalazin1-yl, isoquinolin-1-yl, isoquinolin-3-yl, purine-2-yl, purine-6-yl, purine-8-yl, pteridin-2-yl, pteridin-4-yl, pteridin-6-yl, pteridin-7-yl or phenantridin6-yl is preferred.

Furthermore, preferred is heteroaryl wherein an atom next to the atom at the bonding position is nitrogen atom, which binds to the neighboring atom with a double bond and binds to another neighboring atom with a single bond and another atom next to the atom at the bonding position is a heteroatom. For example, it is benzimidazol-2-yl, benzooxazol-2-yl, quinazolin-2-yl, purine-2-yl, purine-8-yl or pteridin-2-yl is preferred.

Especially preferred is a group of the formula:

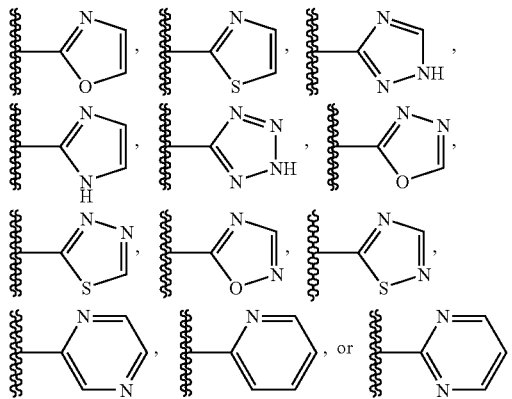

In the above cases, C ring is optionally substituted with a group of the formula: —$Z^1$-$Z^2$-$Z^3$-$R^1$ (wherein $Z^1$, $Z^2$, $Z^3$ and $R^1$ are the same meanings as above (1)) or a group selected from the substitution group A.

The terms used in the present specification are explained as follows. Each term by itself or as part of another has the following meaning.

The term "alkylene" means a C1–C6 straight or branched alkylene group, for example, methylene, ethylene, trimethylene, propylene, tetramethylene, ethylethylene, pentamethylene or hexamethylene. Preferred is a C1–C4 straight alkylene group such as methylene, ethylene, trimethylene or tetramethylene.

The term "alkenylene" means a C2–C6 straight or branched alkenylene group, which is the above "alkylene" having one or more double bonds, for example, vinylene, propenylene or butenylene. Preferred is a C2–C3 straight alkenylene group such as vinylene or propenylene.

The term "alkyl" means a C1–C10 straight or branched alkyl group, for example, methyl, ethyl, n-propyl, isopropyl, n-butyl, isobutyl, sec-buthyl, tert-butyl, n-pentyl, isopentyl, neopentyl, tert-pentyl, n-hexyl, isohexyl, n-heptyl, n-octyl, n-nonyl or n-decyl. Preferred is a C1–C6 alkyl group such as methyl, ethyl, n-propyl, isopropyl, n-butyl, isobutyl, sec-buthyl, tert-butyl n-pentyl, isopentyl, neopentyl, tert-pentyl, n-hexyl or isohexyl.

The term "alkenyl" means a C2–C8 straight or branched alkenyl group which is the above "alkyl" having one or more double bonds, for example, vinyl, 1-propenyl, 2-propenyl, 1-butenyl, 2-butenyl, 3-butenyl, 1,3-butadienyl or 3-methyl-2-butenyl.

The term "aryl" means a monocyclic aromatic hydrocarbon group (e.g., phenyl) or a polycyclic aromatic hydrocarbon group (e.g., 1-naphthyl, 2-naphthyl, 1-antolyl, 2-antolyl, 9-antolyl, 1-phenantolyl, 2-phenantolyl, 3-phenantolyl, 4-phenantolyl or 9-phenantolyl). Preferred is phenyl or naphthyl (e.g., 1-naphthyl or 2-naphthyl).

The term "heteroaryl" means a monocyclic heteroaryl and a condensed heteroaryl.

A monocycle heteroaryl means a group, which is derived from a 5 to 8-membered aromatic ring which may contain 1 to 4 of oxygen atom, sulfur atom, and/or nitrogen atom and have a bonding position at any substitutable position.

A condensed heteroaryl means a group, wherein a 5 to 8-membered aromatic ring which may contain 1 to 4 of oxygen atom, sulfur atom, and/or nitrogen atom is condensed with 1 to 4 of 5 to 8-membered aromatic carboncycle or the other 5 to 8-membered aromatic hetetrocycle and may have a bonding position at the any substitutable position.

The term "heteroaryl" means the following groups, for example, furyl (e.g., 2-furyl or 3-furyl), thienyl (e.g., 2-thienyl or 3-thienyl), pyrrolyl (e.g., 1-pyrrolyl, 2-pyrrolyl or 3-pyrrolyl), imidazolyl (e.g., 1-imidazolyl, 2-imidazolyl or 4-imidazolyl), pyrazolyl (e.g., 1-pyrazolyl, 3-pyrazolyl or 4-pyrazolyl), triazolyl (e.g., 1,2,4-triazol-1-yl, 1,2,4-triazolyl-3-yl or 1,2,4-triazol-4-yl), tetrazolyl (e.g., 1-tetrazolyl, 2-tetrazolyl or 5-tetrazolyl), oxazolyl (e.g., 2-oxazolyl, 4-oxazolyl or 5-oxazolyl), isoxazolyl (e.g., 3-isoxazolyl, 4-isoxazolyl or 5-isoxazolyl), thiazolyl (e.g., 2-thiazolyl, 4-thiazolyl or 5-thiazolyl), thiadiazolyl, isothiazolyl (e.g., 3-isothiazolyl, 4-isothiazolyl or 5-isothiazolyl), pyridyl (e.g., 2-pyridyl, 3-pyridyl or 4-pyridyl), pyridazinyl (e.g., 3-pyridazinyl or 4-pyridazinyl), pyrimidinyl (e.g., 2-pyrimidinyl, 4-pyrimidinyl or 5-pyrimidinyl), furazanyl (e.g., 3-furazanyl), pyrazinyl(e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl or 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g., 1-benzoimidazolyl, 2-benzoimidazolyl, 4-benzoimidazolyl or 5-benzoimidazolyl), dibenzofuryl, benzoxazolyl, quinoxalyl (e.g., 2-quinoxalinyl, 5-quinoxalinyl or 6-quinoxalinyl), cinnolinyl (e.g., 3-cinnolinyl, 4-cinnolinyl, 5-cinnolinyl, 6-cinnolinyl, 7-cinnolinyl or 8-cinnolinyl), quinazolyl (e.g., 2-quinazolinyl, 4-quinazolinyl, 5-quinazolinyl, 6-quinazolinyl, 7-quinazolinyl or 8-quinazolinyl), quiinolyl (e.g., 2-quinolyl, 3-quinolyl, 4-quinolyl, 5-quinolyl, 6-quinolyl, 7-quinolyl or 8-quinolyl), phthalazinyl (e.g., 1-phthalazinyl, 5-phthalazinyl or 6-phthalazinyl), isoquinolyl (e.g., 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g., 2-pteridinyl, 4-pteridinyl, 6-pteridinyl or 7-pteridinyl), carbazolyl, phenantridinyl, acridinyl (e.g., 1-acridinyl, 2-acridinyl, 3-acridinyl, 4-acridinyl or 9-acridinyl), indolyl (e.g., 1-indolyl, 2-indolyl, 3-indolyl, 4-indolyl, 5-indolyl, 6-indolyl or 7-indolyl), isoindolyl, phenazinyl (e.g., 1-phenazinyl or 2-phenazinyl) or phenothiazinyl (e.g., 1-phenothiazinyl, 2-phenothiazinyl, 3-phenothiazinyl or 4-phenothiazinyl).

The term "cycloalkyl" means a C3–C10 cyclic saturated hydrocarbon group, for example, cyclopropyl, cyclobutyl, cyclopentyl, cyclohexyl, cycloheptyl, or cyclooctyl. Preferred is a C3–C6 cycloalkyl group such as cyclopentyl or cyclohexyl.

The term "cycloalkenyl" means a C3–C10 cyclic non-aromatic hydrocarbonyl group, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl or 3-cyclopenten-1-yl), cyclohexenyl (e.g., 1-cyclohexen-1-yl, 2-cyclohexen-1-yl or 3-cyclohexen-1-yl), cycloheptenyl (e.g., 1-cycloheptenyl) or cyclooctenyl (e.g., 1-cyclooctenyl). Especially preferable is 1-cyclohexen-1-yl, 2-cyclohexen-1-yl or 3-cyclohexen-1-yl.

The term "heterocycle" means a non-aromatic heterocyclic group which contains at least one of nitrogen atom, oxygen atom and sulfur atom, and which has a bonding position at any substitutable position, for example, 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino or tetrahydropyranyl. Then, "a non-aromatic heterocyclic group" can be saturated or unsaturated.

Alkyl of "alkoxy" is the same meaning as above "alkyl". "Alkoxy" is, for example, methoxy, ethoxy, n-propoxy, isopropoxy, n-butoxy, isobutoxy, tert-butoxy. Especially preferable is methoxy or ethoxy.

The term "alkoxycarbonyl" means a carbonyl substituted with above "alkoxy", for example, methoxycarbonyl, ethoxycarbonyl, n-propoxycarbonyl, isopropoxycarbonyl, n-butoxycarbonyl, isobutoxycarbonyl, or tert-butoxycarbonyl.

The term "alkoxyalkyl" means the above "alkyl" substituted with above "alkoxy", for example, methoxymethyl, ethoxymethyl, n-propoxymethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl or tert-butoxyethyl.

The term "alkynyl" means a C2–C8 alkynyl group, which is the above "alkyl" having one or more triple bond, for example, ethynyl, 1-propynyl, 2-propynyl, 1-butynyl, 2-butynyl or 3-butynyl.

The term "alkylsulfonyl" means a sulfonyl substituted with the above "alkyl", for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, n-heptylsulfonyl, n-octylsulfonyl, n-nonylsulfonyl or n-decylsulfonyl.

The term "optionally substituted amino" means a substituted or unsubstituted amino.

The term "optionally substituted carbamoyl" means a substituted or unsubstituted carbamoyl.

The substituent of "optionally substituted amino" and "optionally substituted carbamoyl" is alkyl (e.g., methyl, ethyl or dimethyl), alkoxyalkyl (e.g., ethoxymethyl or ethoxyethyl), acyl (e.g., formyl, acetyl, benzoyl or toluoyl), aralkyl (e.g., benzyl), hydroxy, alkylsulfonyl (e.g., methanesulfonyl or ethanesulfonyl), arylsulfonyl optionally substituted with alkyl (e.g., benzenesulfonyl or toluenesulfonyl), cycloalkyl (e.g., cyclopropyl), alkylene (e.g., trimethylene, tetramethylene or pentamethylene) or aryl optionally substituted with alkyl (e.g., phenyl or trityl).

The term "alkylthio" means sulfur atom substituted with the above "alkyl", for example, methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio or n-decylthio. A C1–C6 alkylthio is preferable.

The term "alkylthioalkyl" means the above "alkyl" substituted with the above "alkylthio", for example, methylthiomethyl, ethylthiomethyl, n-propylthiomethyl, isopropylthiomethyl, n-butylthiomethyl, isobutylthiomethyl, sec-butylthiomethyl, tert-butylthiomethyl, n-pentylthiomethyl, isopentylthiomethyl, neopentylthiomethyl, tert-pentylthiomethyl, n-hexylthiomethyl, isohexylthiomethyl, n-heptylthiomethyl, n-octylthiomethyl, n-nonylthiomethyl, n-decylthiomethyl, methylthioethyl, ethylthioethyl, n-propylthioethyl, isopropylthioethyl, n-butylthioethyl, isobutylthioethyl, sec-butylthioethyl, tert-butylthioethyl, n-pentylthioethyl, isopentylthioethyl, neopentylthioethyl, tert-pentylthioethyl, n-hexylthioethyl, isohexylthioethyl, n-heptylthioethyl, n-octylthioethyl, n-nonylthioethyl or n-decylthioethyl. A C1–2 alkyl substituted with C1–6 alkylthio is preferable.

The term "haloalkyl" means the above "alkyl" substituted with one or more halogen. A C1–C3 halogenated alkyl is especially preferable, for example, trifluoromethyl, chloromethyl, dichloromethyl, 1,1-dichloroethyl or 2,2,2-trichloroethyl.

The term "haloalkoxy" means oxygen atom substituted with the above "haloalkyl", for example, trifluoromethoxy, chloromethoxy, dichloromethoxy, 1,1-dichloroethoxy or 2,2,2-trichloroethoxy.

The term "haloalkoxyalkyl" means the above "alkyl" substituted with the above "haloalkoxy", for example, trifluoromethoxymethyl, chloromethoxymethyl, dichloromethoxymethyl, 1,1-dichloroethoxymethyl, 2,2,2-trichloroethoxymethyl, trifluoromethoxyethyl, chloromethoxyethyl, dichloromethoxyethyl, 1,1-dichloroethoxyethyl or 2,2,2-trichloroethoxyethyl.

The term "alkyl carbonyl" means a carbonyl substituted with the above "alkyl", for example, acetyl, propionyl, butyryl, isobutyryl, valeryl, isovaleryl, pivaloyl, hexanoyl, octanoyl or lauroyl.

The term "alkylcarbonyloxy" means oxygen atom substituted with the above "alkylcarbonyl", for example, acetyloxy, propionyloxy, butyryloxy, isobutyryloxy, valeryloxy, isovaleryloxy, pivaloyloxy, hexanoyloxy, octanoyloxy or lauroyloxy.

The term "aralkyl" means the above "alkyl" substituted with 1 to 3 above "aryl", for example, benzyl, diphenylmethyl, triphenylmethyl, phenethyl, 1-naphthylmethyl or 2-naphthylmethyl.

The term "heteroaralkyl" means the above "alkyl" substituted with 1 to 3 above "heteroaryl". A heteroaralkyl wherein alkyl is C1–C4 is preferable. A heteroaralkyl wherein alkyl is C1 or C2 is especially preferable, for example, furylmethyl, thienylmethyl, pyrrolylmethyl, imidazolylmethyl, pyrazolylmethyl, triazolylmethyl, tetrazolylmethyl, oxazolylmethyl, isoxazolylmethyl, thiazolylmethyl, thiadiazolylmethyl, isothiazolylmethyl, pyridylmethyl, pyridazinylmethyl, pyrimidinylmethyl, furazanylmethyl, pyrazinylmethyl, oxadiazolylmethyl, benzofurylmethyl, benzothienylmethyl, benzimidazolylmethyl, dibenzofurylmethyl, benzooxazolylmethyl, quinoxalylmethyl, cinnolinylmethyl, quinazolylmethyl, quinolylmethyl, phthalazinylmethyl, isoquinolylmethyl, puriylmethyl, pteridinylmethyl, carbazolylmethyl, phenantridinylmethyl, acridinylmethyl, indolylmethyl, isoindolylmethyl, phenazinylmethyl, phenothiazinylmethyl, furylethyl, thienylethyl, pyrrolylethyl, imidazolylethyl, pyrazolylethyl, triazolylethyl, tetrazolylethyl, oxazolylethyl, isoxazolylethyl, thiazolylethyl, thiadiazolylethyl, isothiazolylethyl, pyridylethyl, pyridazinylethyl, pyrimidinylethyl, furazanylethyl, pyrazinylethyl, oxadiazolylethyl, benzofurylethyl, benzothienylethyl, benzimidazolylethyl, dibenzo furylethyl, benzooxazolylethyl, uinoxalylethyl, cinnolinylethyl, quinazolylethyl, quinolylethyl, phthalazinylethyl, isoquinolylethyl, puriylethyl, pteridinylethyl, carbazolylethyl, phenantridinylethyl, acridinylethyl, indolylethyl, isoindolylethyl, phenazinylethyl or phenothiazinylethyl.

Then, "aryl", "aralkyl", "heteroaryl" "heteroaralkyl" and "alkyl" of "aryloxy", "heteroaryloxy", "arylthio", "heteroarylthio", "aralkyloxy", "heteroaralkyloxy", "aralkylthio", "heteroaralkylthio", "aryloxyalkyl", "heteroaryloxyalkyl", "arylthioalkyl", "heteroarylthioalkyl", "arylsulfonyl", "heteroarylsulfonyl", "aralkylsulfonyl" and "heteroaralkylsulfonyl" are the same meanings as the above.

In the case that "optionally substituted alkylene", "optionally substituted alkenylene", "optionally substituted alkyl", "optionally substituted alkenyl", "optionally substituted aryl", "optionally substituted heteroaryl", "optionally substituted cycloalkyl", "optionally substituted cycloalkenyl", "optionally substituted heterocycle", "optionally substituted aralkyl", "optionally substituted heteroaralkyl", "optionally substituted aryloxy", "optionally substituted heteroaryloxy", "optionally substituted arylthio", "optionally substituted heteroarylthio", "optionally substituted aralkyloxy", "optionally substituted heteroaralkyloxy", "optionally substituted aralkylthio", "optionally substituted heteroaralkylthio", "optionally substituted aryloxyalkyl", "optionally substituted heteroaryl oxyalkyl", "optionally substituted arylthioalkyl", "optionally substituted heteroarylthioalkyl", "optionally substituted arylsulfonyl", "optionally substituted heteroarylsulfonyl", "optionally substituted aralkyl sulfonyl" and "optionally substituted heteroaralkylsulfonyl" have the substitution groups, each of them is optionally substituted at any position with the same or different 1 to 4 substitution groups. And these substitution groups can be selected from the substitution group A as not to interfere with the inhibitory activity against integrase.

The substitution group is, for example, hydroxy, carboxy, halogen (e.g., F, Cl, Br or I), halo alkyl (e.g., $CF_3$, $CH_2CF_3$ and $CH_2CCl_3$), alkyl (e.g., methyl, ethyl, isopropyl and tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy and butoxy), alkenyloxy (e.g., vinyloxy and allyloxy), alkoxycarbonyl (e.g., methoxycarbonyl, ethoxycarbonyl and tert-butoxycarbonyl), nitro, nitroso, optionally substituted amino (e.g., alkylamino, methylamino, ethylamino and dimethylamino), acylamino (e.g., acetylamino and benzoylamino), aralkylamino (e.g., benzylamino, tritylamino and hydroxyamino), azide, aryl (e.g., phenyl), aralkyl (e.g., benzyl), cyano, isocyano, isocyanate, thiocyanate, isothiocyanate, mercapto, alkylthio (e.g., methylthio), alkylsulfonyl (e.g., methanesulfonyl and ethanesulfonyl), optionally substituted carbamoyl (e.g., alkylcarbamoyl methylcarbamoyl, ethylcarbamoyl and dimethylcarbamoyl), sulfamoyl, acyl (e.g., formyl and acetyl), formyloxy, haloformyl, oxal, thioformyl, thiocarboxy, dithiocarboxy, thiocarbamoyl, sulfino, sulfo, sulfoamino, hydrazino, azide, ureide, amidino, guanidino or phthalimide.

As the substituent of "optionally substituted aryl", "optionally substituted heteroaryl", "optionally substituted cycloalkyl", "optionally substituted cycloalkenyl" and "optionally substituted heterocycle" in $R^1$, among the above substituent, especially preferred is hydroxy, carboxy, halogen (e.g., F, Cl, Br or I), haloalkyl (e.g., $CF_3$, $CH_2CF_3$ or $CH_2CCl_3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), nitro, optionally substituted amino (e.g., alkylamino (e.g., methylamino, ethylamino or dimethylamino), acylamino (e.g., acetyl amino or benzoylamino), aralkylamino (e.g., benzylamino, tritylamino) or hydroxyamino), azide, aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl ), formyloxy, thiocarbamoyl, sulfoamino, hydrazino, azide, ureide, amidino or guanidino. Especially, alkyl, haloalkyl, halogen (especially F, Cl or Br) or alkoxy (especially methoxy) is preferable and monosubstitution or disubstitution is preferable.

As the substituent of "optionally substituted alkylene" and "optionally substituted alkenylene" in $Z^1$, $Z^2$ and $Z^3$, among the above substituent, especially preferred is hydroxy, carboxy, halogen (e.g., F, Cl, Br or I), haloalkyl (e.g., $CF_3$, $CH_2CF_3$ or $CH_2CCl_3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), optionally substituted amino (e.g., alkylamino (e.g., methylamino, ethylamino or dimethylamino), acylamino (e.g., acetylamino or benzoylamino), aralkylamino (e.g., benzylamino or tritylamino) or hydroxyamino), aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl), formyloxy, thiocarbamoyl, sulfoamino, hydrazino, azide, ureide, amidino or guanidino.

In the case that a group selected from the substitution group A is "optionally substituted aryl", "optionally substituted heteroaryl", "optionally substituted cycloalkyl", "optionally substituted cycloalkenyl", "optionally substituted heterocycle", "optionally substituted aralkyl", "optionally substituted heteroaralkyl", "optionally substituted aryloxy", "optionally substituted heteroaryloxy", "optionally substituted arylthio", "optionally substituted heteroarylthio", "optionally substituted aralkyloxy", "optionally substituted heteroaralkyloxy", "optionally substituted aralkylthio", "optionally substituted heteroaralkylthio", "optionally substituted aryloxyalkyl", "optionally substituted heteroaryloxyalkyl", "optionally substituted arylthioalkyl", "optionally substituted heteroarylthioalkyl", "optionally substituted arylsulfonyl", "optionally substituted heteroarylsulfonyl", "optionally substituted aralkylsulfonyl" or "optionally substituted heteroaralkylsulfonyl", as the substituent, among the above substituent, especially preferred is hydroxy, carboxy, halogen (e.g., F, Cl, Br or I), haloalkyl (e.g., $CF_3$, $CH_2CF_3$ or $CH_2CCl_3$), alkyl (e.g., methyl, ethyl, isopropyl or tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy or butoxy), alkoxycarbonyl (e.g., methoxycarbonyl, ethoxycarbonyl or tert-butoxycarbonyl), nitro, optionally substituted amino (e.g., alkylamino (e.g., methylamino, ethylamino or dimethylamino), acylamino (e.g., acetylamino or benzoylamino), aralkylamino (e.g., benzylamino or tritylamino) or hydroxyamino), azide, aryl (e.g., phenyl), aralkyl (e.g., benzyl), cyano, mercapto, alkylthio (e.g., methylthio), alkylsulfonyl (e.g., methanesulfonyl or ethanesulfonyl), optionally substituted carbamoyl, sulfamoyl, acyl (e.g., formyl or acetyl), formyloxy, thiocarbamoyl, sulfoamino, hydrazino, azide, ureide, amidino or guanidino. Especially, alkyl, haloalkyl, halogen (especially F, Cl or Br), alkoxy (especially methoxy), is preferable and monosubstitution or disubstitution is preferable.

The present invention includes a compound, its prodrug, a pharmaceutically acceptable salt or a solvate thereof. All of the theoretical possible tautomers and geometrical isomers of a compound of the present invention are also within the scope of the present invention. For example, a compound of the formula (I) (a keto form) wherein Y is oxo, thioxo or imino is also included in the present invention, as far as it is a tautomer of a compound (an enol form) wherein Y is hydroxy, mercapto or amino.

A prodrug is a derivative of a compound of the present invention having a group which can be decomposed chemically or metabolically, and such a prodrug is converted to a pharmaceutically active compound of the present invention by means of solvolysis or by placing the compound in vivo under a physiological condition. Method for selecting and preparing an appropriate prodrug derivative are described in the literature such as Design of Prodrugs, Elsevier, Amsterdam 1985.

It is known that HIV multiplies vigorously in a lymph node even in the asymptomatic term. Thus a prodrug of a compound of the present invention is preferably a lymph-directive one. The diseases caused by HIV include AIDS-associated encephalopathy. Thus a preferable prodrug of a compound of the present invention is a brain-directive one. As these lymph-directive prodrug and brain-directive prodrug, the following prodrugs with high lipophilicity are preferable.

When a compound of the present invention has a carboxyl group, an ester derivative prepared by reacting an original acid compound with a suitable alcohol or an amide derivative prepared by reacting an original acid compound with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester.

When a compound of the present invention has a hydroxy group, an acyloxy derivative prepared by reacting a compound having a hydroxyl group with a suitable acylhalide or a suitable acid anhydride is exemplified as a prodrug. An especially preferred acyloxy derivative as a prodrug is —O(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$.

When a compound of the present invention has an amino group, an amide derivative prepared by reacting a compound having amino with a suitable acid halide or a suitable mixed anhydride is exemplified as a prodrug. An especially preferred amide derivative as a prodrug is —NHC(=O)—(CH$_2$)$_{20}$CH$_3$ or —NHC(=O)—CH(NH$_2$)CH$_3$.

Especially in the case of a compound of the present invention, a prodrug can be produced by the chemical modification of Y, a substituent on B ring. For example, Y is substituted with acyl and it is examined whether the prodrug is converted to a compound of the present invention by means of solvolysis or by placing the compound under a physiological condition or not. Therefore, even if Y is a substituent except for hydroxy, mercapto or amino, a compound wherein Y is converted to hydroxy, mercapto or amino by means of solvolysis or by placing the compound under a physiological condition is the prodrug of the present invention and is contained in the present invention. For example, a compound converted to a compound of the present invention in phosphate buffer (pH7.4)-ethanol or plasma is a compound of the present invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N, N-dibenzylethylenediamine salts; heterocyclic aromatic amine salts such as pyridin salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, or ascorbates; sulfonates such as methanesulfonates, isethionates, benzenesulfonates, or p-toluenesulfonates; and acidic amino acid salts such as aspartates or glutamates.

Furthermore, various solvates of a compound of the present invention, for example, monosolvate, disolvate, monohydrate or dihydrate are also within the scope of the present invention.

The term "inhibit" means that a compound of the present invention suppresses the action of integrase.

The term "pharmaceutically acceptable" means harmless with respect to the prevention and the treatment.

BEST MODE FOR CARRYING OUT THE INVENTION

The general method for the production of a compound of the present invention is explained below.

A compound of the present invention is a novel nitrogen-containing heteroaryl compound having as the main construction a ring of the formula:

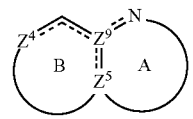

(wherein A ring, B ring, Z$^4$, Z$^5$ and Z$^9$ are the same meanings as above (1)). In the present invention, various kinds of nitrogen-containing heteroaryl compounds can be used.

For example, these nitrogen-containing heteroaryl compounds can be produced by using substituents in a compound having one ring (for example, B ring), followed by constructing the other ring (for example, A ring). The following documents can be referred to as the general organic synthesis of various kinds of nitrogen-containing heteroaryl compounds: (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS. Furthermore, various kinds of functional groups can be introduced by using general reactions for aromatic compounds or specific reactions for each heteroaryl.

Below is described the representative methods for production of a compound of the present invention. A compound of the present invention can be produced by not only the following methods but also the other methods.

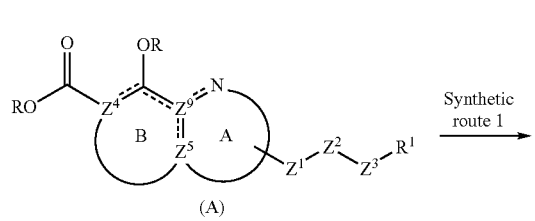

(A)

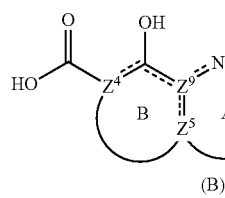

(B)

Synthetic Route 1

This synthetic route is to produce a compound of the formula (B) from a compound of the formula (A). Namely, it is deprotection of the carboxyl group and the phenolic hydroxyl group.

This synthetic route can be performed in a reaction solvent under heating in the presence of trialkylsilylhalide and alkalimetal iodide.

As trialkylsilylhalide, trimethylsilylchloride can be used.

As alkalimetal iodide, for example, NaI or KI can be used.

The reaction temperature is room temperature to 100° C. 70 to 90° C. is preferable.

As a reaction solvent, polar solvents are preferable. For example, acetonitrile can be used.

And this synthetic route can be performed, under heating, using hydrobromic acid/acetic acid. As hydrobromic acid/acetic acid, 47% hydrobromic acid/acetic acid is preferable.

And this synthetic route can be performed by using $BBr_3$ at 0° C. to room temperature or by using pyridiniumchloride at 150 to 220° C.

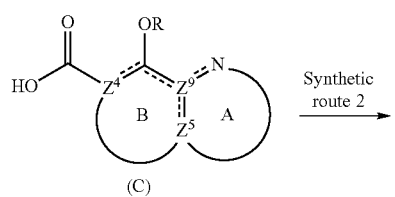

(C)

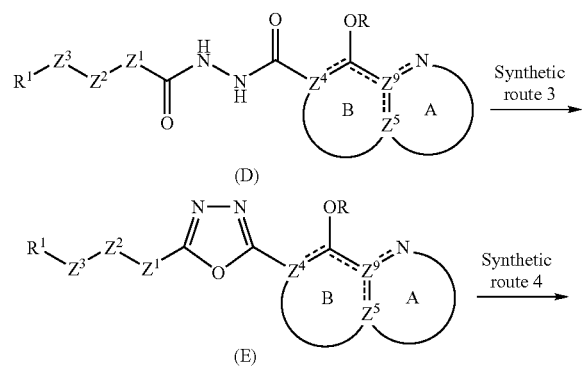

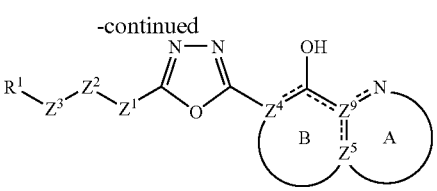

(F)

Synthetic route 5

(C) →

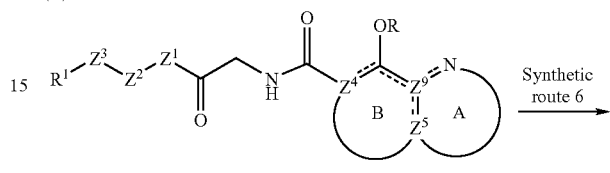

(G)

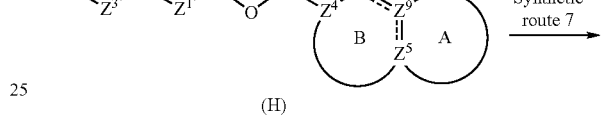

(H)

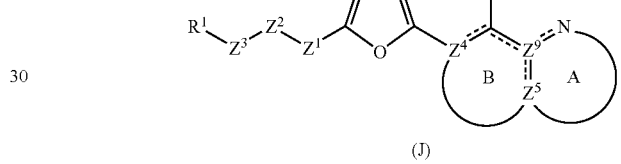

(J)

Synthetic Route 2

This synthetic route is to produce a compound of the formula (D) from a compound of the formula (C). Namely, it is a transformation reaction from a carboxylic acid to diacylhydrazine.

This synthetic route can be performed by reacting carboxylic acid and monoacyl hydrazine in a suitable solvent in presence of a condensing agent.

As a condensing agent, dicyclohexylcarbodiimide or 1-ethyl-3-(3-dimethylaminopropyl)carbodiimide hydrochloride can be used. If necessary, another reagent such as 1-hydroxybenzotriazole or N-hydroxysuccinimide is added.

The reaction temperature is 0 to 100° C. 20 to 30° C. is preferable.

As a reaction solvent, various aprotic solvents can be used. Tetrahydrofuran or N,N-dimethylformamide is preferable.

Synthetic Route 3

This synthetic route is to produce a compound of the formula (E) from a compound of the formula (D). Namely, it is a formation reaction from diacylhydrazine to oxadiazole.

This synthetic route can be performed by heating diacylhydrazine with phosphorus oxychloride or thionylchloride. The reaction temperature is 50 to 100° C. 80 to 100° C. is preferable.

And this synthetic route can be performed by using dibromotriphenylphophorane in the presence of the base of triethylamine. The reaction temperature is 0 to 100° C. 0 to 30° C. is preferable. As a reaction solvent, dichloromethane or tetrahydrofuran is preferable.

Synthetic Route 4

This synthetic route is to produce a compound of the formula (F) from a compound of the formula (E). It is performed as well as synthetic route 1.

Synthetic Route 5

This synthetic route is to produce a compound of the formula (G) from a compound of the formula (C). Namely, it is a process to synthesize amide by condensating a carboxylic acid and α-aminoketone.

This synthetic route can be performed by reacting a carboxylic acid and α-aminoketone in a suitable solvent in the presence of a condensing agent.

As a condensing agent, dicyclohexylcarbodiimide or 1-ethyl-3-(3-dimethylaminopropyl)carbodiimide hydrochloride can be used. If necessary, another reagent such as 1-hydroxybenzotriazole or N-hydroxysuccinimide is added.

The reaction temperature is 0 to 100° C. 20 to 30° C. is preferable.

As a reaction solvent, various aprotic solvents can be used. Tetrahydrofuran or N,N-dimethylformamide is preferable.

Synthetic Route 6

This synthetic route is to produce a compound of the formula (H) from a compound of the formula (G). It is performed as well as synthetic route 3.

Synthetic Route 7

This synthetic route is to produce a compound of the formula (J) from a compound of the formula (H). It is performed as well as synthetic route 1.

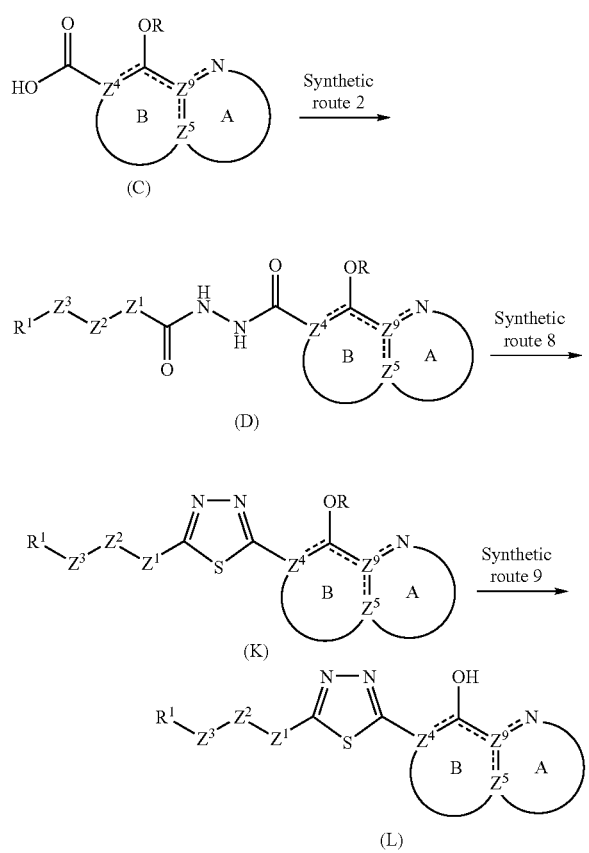

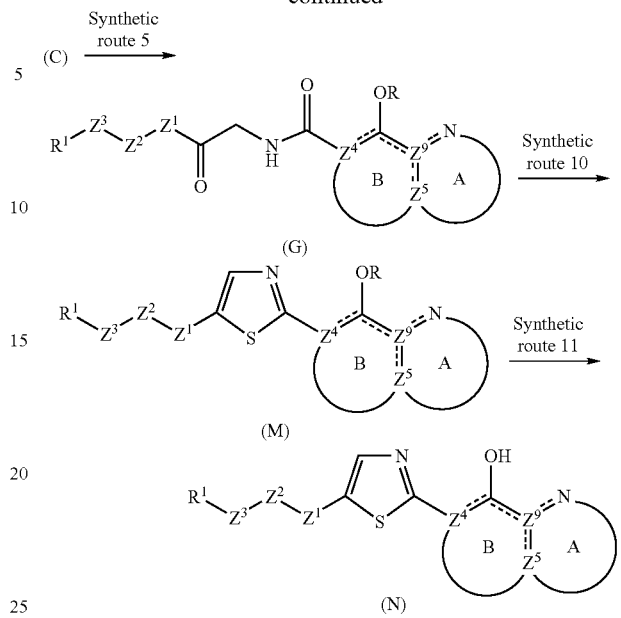

Synthetic Route 8

This synthetic route is to produce a compound of the formula (K) from a compound of the formula (D). Namely, it is a formation reaction from diacylhydrazine to thiadiazole.

This synthetic route can be performed by heating diacylhydrazine with phosphorus pentasulfide or Lawesson's reagent.

The reaction temperature is 50 to 150° C. 80 to 100° C. is preferable.

As a reaction solvent, toluene or tetrahydrofuran is preferable.

Synthetic Route 9

This synthetic route is to produce a compound of the formula (L) from a compound of the formula (K). It is performed as well as synthetic route 1.

Synthetic Route 10

This synthetic route is to produce a compound of the formula (M) from a compound of the formula (G). It is performed as well as synthetic route 8.

Synthetic Route 11

This synthetic route is to produce a compound of the formula (N) from a compound of the formula (M). It is performed as well as synthetic route 1.

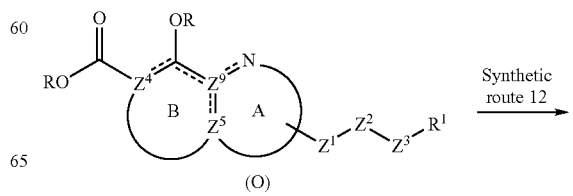

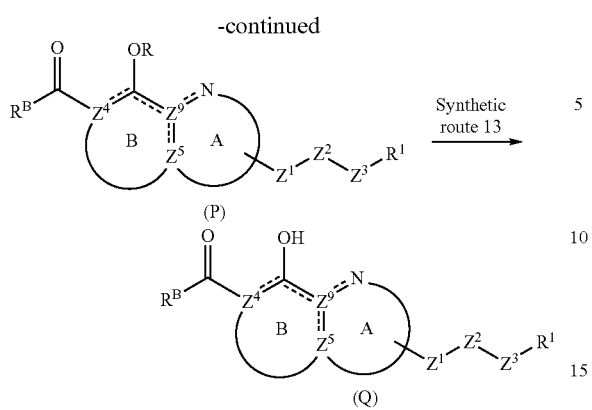

Synthetic Route 12

This synthetic route is to produce a compound of the formula (P) from a compound of the formula (O). Namely, it is a process to synthesize ketone from ester.

This synthetic route is performed by reacting ester and an organometallic reagent in a suitable solvent.

As an organometallic reagent, alkyllithium, aryllithium, heteroaryllithium or Grignard reagent can be used.

The reaction temperature is $-70°$ C. to room temperature. $-70$ to $0°$ C. is preferable.

As a reaction solvent, ethereal solvents can be used. Tetrahydrofuran or diethylether is preferable.

Synthetic Route 13

This synthetic route is to produce a compound of the formula (Q) from a compound of the formula (P). It is performed as well as synthetic route 1.

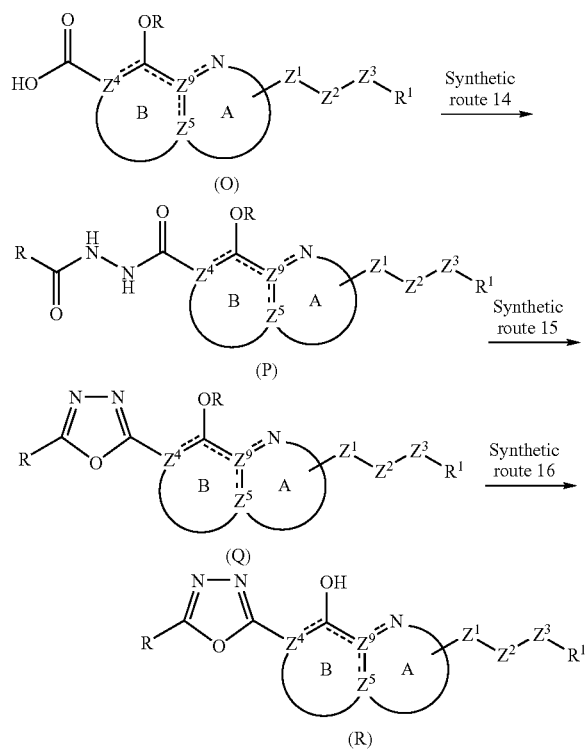

Synthetic Route 14

This synthetic route is to produce a compound of the formula (S) from a compound of the formula (R). It is performed as well as synthetic route 2.

Synthetic Route 15

This synthetic route is to produce a compound of the formula (T) from a compound of the formula (S). It is performed as well as synthetic route 3.

Synthetic Route 16

This synthetic route is to produce a compound of the formula (U) from a compound of the formula (T). It is performed as well as synthetic route 1.

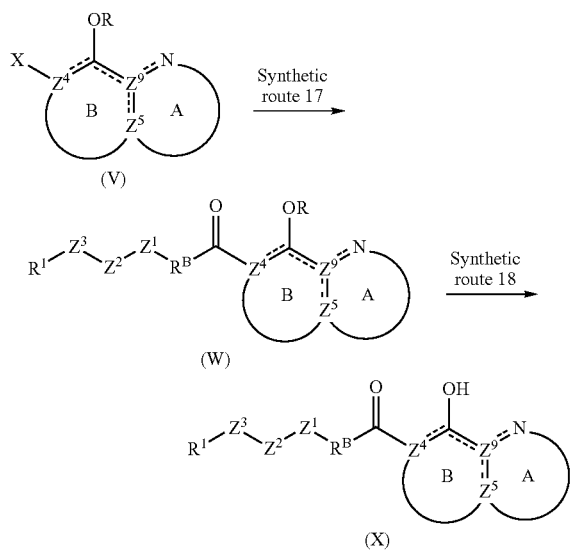

Synthetic Route 17

This synthetic route is to produce a compound of the formula (W) from a compound of the formula (V). Namely, it is a transformation reaction from a halogen compound (X=Cl, Br or I) to a ketone compound.

This synthetic route is performed by converting a halogen compound (X=Cl, Br or I) to an organometallic compound (X=Metal) with an organometallic reagent, followed by reacting with a carboxylic acid chloride or an active ester in a suitable solvent.

As an organometallic reagent, alkyllithium or aryllithium can be used.

The reaction temperature is $-70°$ C. to room temperature. $-70$ to $0°$ C. is preferable.

As a reaction solvent, ethereal solvents can be used. Tetrahydrofuran or diethylether is preferable.

Synthetic Route 18

This synthetic route is to produce a compound of the formula (X) from a compound of the formula (W). It is performed as well as synthetic route 1.

Method for use of the compound of the present invention is explained below.

The compound of the present invention is useful as a pharmaceutical composition such as an antiviral agent. The compound of the present invention has an outstanding inhibitory activity against integrase of viruses. Therefore, the compound of the present invention is expected to prevent or treat various diseases caused by viruses producing integrase to grow in animal cells upon infection, and is useful as, for example, an integrase inhibitor against retroviruses (e.g., HIV-1, HIV-2, HTLV-1, SIV or FIV), especially, an anti-HIV agent.

The compound of the present invention can be used in a combination therapy with an anti-HIV agent possessing other inhibitory mechanism such as a reverse transcriptase inhibitory agent and/or a protease inhibitory agent. Since any integrase inhibitor has not been on sale yet, it is useful to use the compound of the present invention in combination therapy with a reverse transcriptase inhibitory agent and/or a protease inhibitory agent.

And the compound of the present invention can be used not only as an anti-HIV mixture but also as a concomitant agent enhancing the activity of the other anti-HIV agent in a cocktail therapy.

The compound of the present invention can be used so as in the gene therapy using a retrovirus vector derived from HIV or MLV to suppress the spread of the retrovirus infection over non-target tissues. Especially, in the case that cells infected with such a vector in vitro are put back in a body, a previous administration of the compound of the present invention prevents an unnecessary infection.

The compounds of the present invention can be administered orally or parenterally. For oral administration, the compound of the present invention can be used in any form of usual formulations, for example, solid formulations such as tablets, powders, granules, capsules; aqueous formulations; oleaginous suspensions; or solutions such as syrup or elixir. For parenteral administration, the compound of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives or stabilizers can be optionally used. And as an anti-HIV agent, oral agents are especially preferable.

The formulation according to the present invention may be manufactured by combining (for example, admixing) a curatively effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In case a carrier functions as a diluent, the carrier is a solid, semi-solid, or liquid material, which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid or a mixture thereof. For instance, a compound of the present invention is dissolved in 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator or capsule. A tablet for oral administration contains a suitable excipient such as calcium carbonate, sodium carbonate and lactose, calcium phosphate together with a disintegrator such as corn starch and alginic acid and/or a binder such as gelatin and acacia, and a lubricant such as magnesium stearate, stearic acid and talc.

In a powder medicine, a carrier is a finely pulverized solid, which is blended with finely pulverized active ingredients. In a tablet, active ingredients are admixed with a carrier having required binding power in a suitable ratio, and it is solidified in a desired shape and size. Powder medicine and tablet contain as the active ingredient about 1 to about 99% by weight of novel compounds of the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent or elixir agent. Active ingredients may be dissolved or suspended into a pharmaceutically acceptable carrier such as sterile water, a sterile organic solvent or a mixture thereof. Active ingredients may be dissolved frequently into a suitable organic solvent such as propylene glycol aqueous solution. When finely pulverized active ingredients are dispersed into aqueous starch, sodium carboxylmethylcellulose solution or suitable oil, the other compositions can be prepared.

Although an appropriate dosage of the compound of the present invention varies depending on the administration route, age, body weight, conditions of the patient, and kind of disease, in the case of oral administration, the daily dosage for an adult can be between approximately 0.05–3000 mg, preferably approximately 0.1–1000 mg, if necessary, in divisions. In the case of parenteral administration, the daily dosage for an adult can be between approximately 0.01–1000 mg, preferably approximately 0.05–500 mg.

EXAMPLE

Examples of the present invention are shown below. Reactions were usually carried out under nitrogen atmosphere, and reaction solvents dried over molecular sieves were used. Extracts were dried over sodium sulfate or magnesium sulfate.

(Reagent)
n-butyllithium=1.5 mol/l hexan solution
sodium hydride=60% oil suspension (Abbreviation)
Et=ethyl; MeOH=methanol; EtOH=ethanol; DMF=N,N-dimethylformamide;
THF=tetrahydrofuran; DMSO=dimethylsulfoxide; HOBt=1-hydroxybenzotriazole;
WSCD=1-ethyl-3-(3-dimethylaminopropyl)carbodiimide hydrochloride

Example 1

Compound I-1

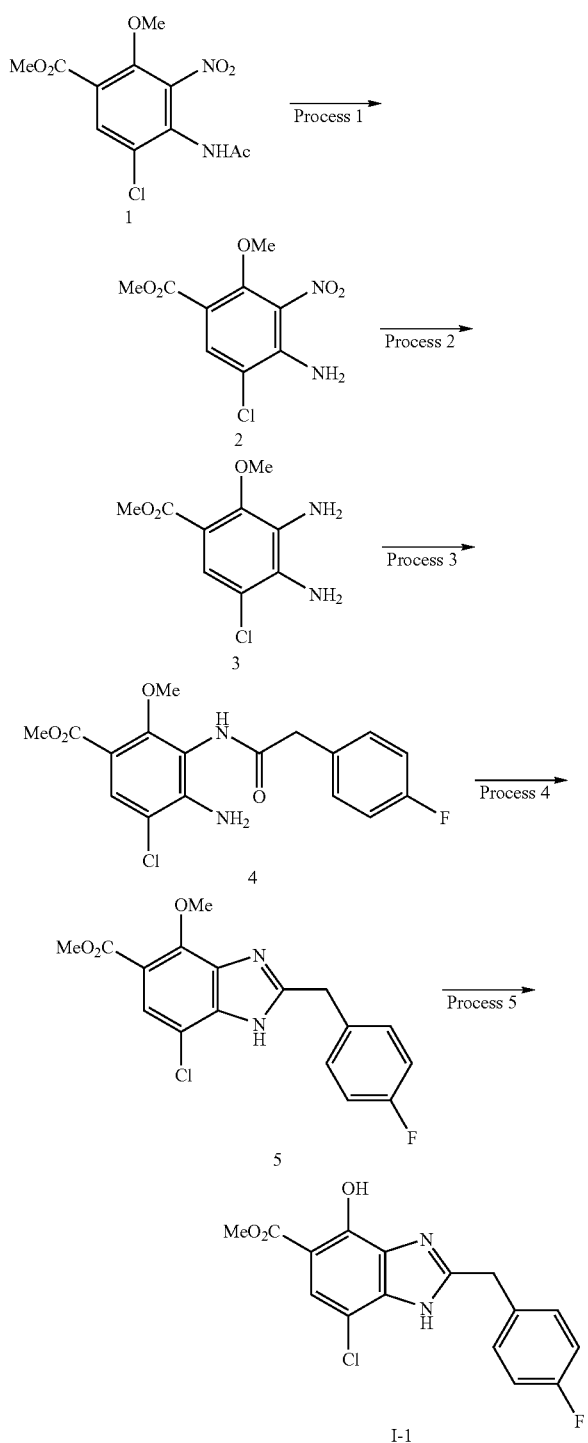

Process 1

To a methanol (200 ml) solution of 4-acetylamino-5-chloro-2-methoxy-3-nitrobenzoic acid 1 (20.6 g, 67.9 mmol) described in the literature (Chem. Pharm. Bull. 42, 560–569, (1994)) was added 5 N hydrochloric acid (60 ml) at room temperature, and the mixture was refluxed for 14 hours. After the reaction solution was neutralized with 2 N sodium hydroxide solution under ice-cooling, water (100 ml) was added and stirred for 30 minutes. Precipitated crystals were collected and washed with water (100 ml) to give compound 2 (11.9 g) as wet yellow crystals.

Process 2

A suspension of compound 2 (11.9 g) obtained by the process 1, ammonium chloride (1.22 g, 22.8 mmol) and iron (10.2 g, 183 mmol) in ethanol (450 ml)-water (90 ml) was refluxed for 3 hours. The reaction mixture was filtered through Celite and the remained residue was washed with chloroform-methanol (1:1 v/v, 500 ml). After the filtrate was concentrated under reduced pressure, water (100 ml) was added to the residue and the whole was extracted with ethyl acetate. The organic layer was washed with brine (100 ml) and dried over sodium sulfate. Removal of solvent under reduced pressure gave crude compound 3 (11.6 g) as a dark brown oil.

Process 3

A solution of 4-fluorophenylacetyl chloride (10.9 g, 63.4 mmol) in THF (100 ml) was added dropwise over 20 minutes to a solution of compound 3 (11.6 g) obtained by the process 2 and triethylamine (9.20 ml, 66.0 mmol) in THF (400 ml) under ice-cooling. The reaction mixture was stirred for 1.5 hours under ice-cooling and further 1.5 hours at room temperature. After water (500 ml) was added dropwise to the reaction mixture under ice-cooling, precipitated crystals were collected and washed with water to give compound 4 (18.9 g) as wet colorless crystals.

Process 4

A solution of compound 4 (18.9 g) obtained by the process 3 in acetic acid (180 ml) was refluxed for 1.5 hours. Removal of solvent under reduced pressure gave a crystalline residue, which was recrystallized from ethyl acetate-hexane to give compound 5 (12.4 g, 35.6 mmol, 52% overall yield) as pale brown crystals.

M.p.: 151–153° C.

NMR (CDCl$_3$) δ: 3.92 (3H, s), 4.23 (3H, brs), 4.29 (2H, s), 7.05 (2H, m), 7.74 (2H, m).

Process 5

Boron trichloride (2 M in toluene, 0.625 ml, 1.25 mmol) was added dropwise to a solution of compound 5 (174 mg, 0.500 mmol) in dichloromethane (5 ml) under ice-cooling, and the mixture was stirred for 1.5 hours. The reaction was quenched with water (5 ml), and the whole was neutralized with 28% ammonia. The mixture was extracted with chloroform, and the organic layer was dried over sodium sulfate. Removal of solvent under reduced pressure gave a crystalline residue, which was recrystallized from ethanol-hexane to give compound I-1 (36.0 mg, 22%) as colorless crystals.

M.p.: 257–260° C. Recrystallization solvent: ethanol-hexane

Elemental analysis for $C_{16}H_{12}ClFN_2O_3$ Calcd. (%): C, 57.41; H, 3.61; N, 8.37; Cl, 10.59; F, 5.57. Found. (%): C, 57.20; H, 3.50; N, 8.31; Cl, 10.50; F, 5.57.

NMR (DMSO-d$_6$) δ: 3.91 (3H, s), 4.20 (2H, s), 7.15 (2H, m), 7.39 (2H, m), 7.56 (1H, s).

IR (KBr): 3431, 1672 cm$^{-1}$.

Compounds I-2–I-5 were synthesized in a same manner similar to Example 1.

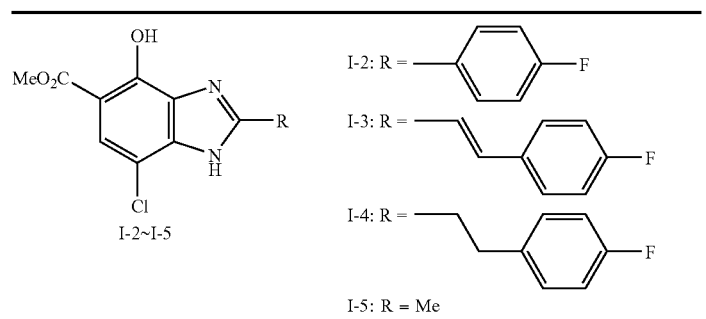

Compound I-2

M.p.: 250–251° C. Recrystallization solvent: ethanol

Elemental analysis for $C_{15}H_{10}ClFN_2O_3(H_2O)_{0.5}$(ethanol)$_{0.6}$ Calcd. (%): C, 54.45; H, 4.12; N, 7.84; Cl, 9.92; F, 5.32. Found. (%): C, 54.45; H, 3.94; N, 7.92; Cl, 9.83; F, 5.21.
NMR (DMSO-$d_6$) δ: 3.94 (3H, s), 7.42 (2H, m), 7.61 (1H, s), 8.36 (2H, m), 11.18 (1H, brs), 13.86 (1H, brs).
IR (KBr): 3408, 1672 cm$^{-1}$.

Compound I-3

M.p.: 203–206° C. Recrystallization solvent: ethanol

Elemental analysis for $C_{17}H_{12}ClFN_2O_3(H_2O)_{0.3}$(ethanol)$_{0.4}$ Calcd. (%): C, 57.69; H, 4.08; N, 7.56; Cl, 9.57; F, 5.13. Found. (%): C, 57.72; H, 3.80; N, 7.66; Cl, 9.40; F, 4.98.
NMR (DMSO-$d_6$) δ: 3.93 (3H, s), 7.18 (1H, d, J=16.5 Hz), 7.29 (2H, m), 7.59 (1H, s), 7.75 (2H, m), 7.88 (1H, d, J=16.5 Hz).
IR (KBr): 3323, 1672 cm$^{-1}$.

Compound I-4

M.p.: 192–194° C. Recrystallization solvent: ethanol

Elemental analysis for $C_{17}H_{14}ClFN_2O_3(HCl)_{1.0}$ Calcd. (%): C, 53.00; H, 3.92; N, 7.27; Cl, 18.41; F, 4.93. Found. (%): C, 52.96; H, 3.83; N, 7.33; Cl, 17.76; F, 4.68.
NMR (DMSO-$d_6$) δ: 3.10–3.28 (4H, m), 3.93 (3H, s), 7.12 (2H, m), 7.30 (2H, m), 11.14 (1H, brs).
IR (KBr): 3421, 1685 cm$^{-1}$.

Compound I-5

M.p.: 259–261° C. (dec.) Recrystallization solvent: methanol

Elemental analysis for $C_{10}H_9ClN_2O_3(H_2O)_{0.1}$ Calcd. (%): C, 49.54; H, 3.82; N, 11.55; Cl, 14.62. Found. (%): C, 49.67; H, 3.74; N, 11.56; Cl, 14.32.
NMR (DMSO-$d_6$) δ: 2.52 (3H, s), 3.91 (3H, s), 7.53 (1H, s), 11.02 (1H, brs), 13.24 (1H, brs).
IR (KBr): 3419, 1672 cm$^{-1}$.

Example 2

Compound I-6

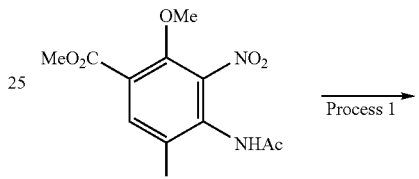

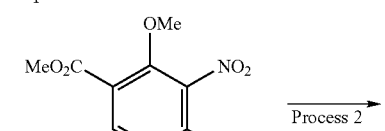

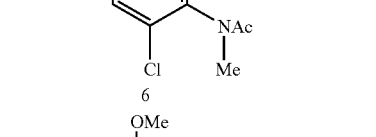

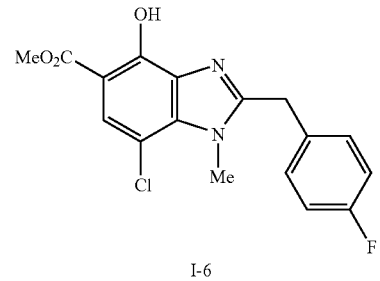

Process 1

Sodium hydride (60%, 0.42 g, 10.5 mmol) was added over 5 minutes to a solution of compound 1 (3.03 g, 10.0 mmol) in DMF (40 ml) under ice-cooling, and the mixture was stirred for 1 hour at room temperature. Methyl iodide (0.685 ml, 11.0 mmol) was added to the reaction mixture under ice-cooling and the whole was stirred for 3 hours at room temperature. The reaction mixture was acidified to pH 3 with 10% hydrochloric acid under ice-cooling. The whole was added water (50 ml) and extracted with ethyl acetate. The organic layer was washed with water (50 ml) and brine (50 ml), and dried over sodium sulfate. The solvent was evaporated under reduced pressure to give crude compound 6 as a dark brown oil.

Process 2

Sodium methoxide (28% methanol solution, 3 ml) was added to a solution of the crude compound 6 obtained by the process 1 in methanol (3 ml), and the mixture was refluxed for 2 hours. The reaction mixture was poured into 1 N hydrochloric acid (20 ml) under ice-cooling, and the whole was extracted with ethyl acetate. The organic layer was washed with water and brine, and dried over sodium sulfate. A crude product obtained by evaporation under reduced pressure was subjected to silica gel column chromatography. The fractions containing desired compound eluted with hexane-ethyl acetate (2:1 v/v) were concentrated under reduced pressure. The crystalline residue was recrystallized from ethyl acetate-hexane. Compound 7 (1.02 g, 3.71 mmol, 37%) was obtained as yellow crystals.

Process 3–6

Compound I-6 was synthesized in a same manner similar to the processes 2–5 of Example 1.

M.p.: 198–201° C. Recrystallization solvent: ethanol-diisopropyl ether

Elemental analysis for $C_{17}H_{14}ClFN_2O_3$ Calcd. (%): C, 58.55; H, 4.05; N, 8.03; Cl, 10.17; F, 5.45. Found. (%): C, 58.29; H, 4.03; N, 7.98; Cl, 10.02; F, 5.21.

NMR (DMSO-$d_6$) δ: 3.91 (3H, s), 3.96 (3H, s), 4.33 (2H, s), 7.16 (2H, m), 7.32 (2H, m), 11.10 (1H, brs).

IR (KBr): 3419, 1670 cm$^{-1}$.

Compounds I-7–I-9 were synthesized in a same manner similar to the processes 2–5 of Example 2.

Compound I-7

M.p.: 192–195° C. Recrystallization solvent: ethyl acetate-hexane

Elemental analysis for $C_{23}H_{17}ClF_2N_2O_3$ Calcd. (%): C, 62.38; H, 3.87; N, 6.33; Cl, 8.01; F, 8.58. Found. (%): C, 62.32; H, 4.05; N, 6.23; Cl, 7.80; F, 8.35.

NMR (DMSO-$d_6$) δ: 3.91 (3H, s), 4.26 (2H, s), 5.77 (2H, s), 6.88 (2H, m), 7.03 (2H, m), 7.07 (2H, m), 7.23 (2H, m), 7.55 (1H, s), 11.10 (1H, brs).

IR (KBr): 3431, 1691 cm$^{-1}$.

Compound I-8

M.p.: 156–159° C. Recrystallization solvent: methanol

Elemental analysis for $C_{16}H_{12}ClFN_2O_3(H_2O)_{0.3}$ Calcd. (%): C, 56.50; H, 3.73; N, 8.24; Cl, 10.42; F, 5.59. Found. (%): C, 56.75; H, 3.83; N, 8.27; Cl, 10.11; F, 5.35.

NMR (DMSO-$d_6$) δ: 3.90 (3H, s), 5.75 (2H, s), 7.17 (4H, d, J=7.2 Hz), 7.57 (1H, s), 8.49 (1H, s), 11.20 (1H, brs).

IR (KBr): 3410, 1674 cm$^{-1}$.

Compound I-9

M.p.: 205–207° C. Recrystallization solvent: methanol

Elemental analysis for $C_{17}H_{14}ClFN_2O_3$ Calcd. (%): C, 58.55; H, 4.05; N, 8.03; Cl, 10.17; F, 5.45. Found. (%): C, 58.42; H, 4.15; N, 8.05; Cl, 9.76; F, 5.21.

NMR (DMSO-$d_6$) δ: 3.12 (2H, t, J=7.4 Hz), 3.92 (3H, s), 4.70 (2H, t, J=7.4 Hz), 7.10 (2H, m), 7.15 (2H, m), 7.62 (1H, s), 8.08 (1H, s), 11.18 (1H, brs).

IR (KBr): 3423, 1674 cm$^{-1}$.

Example 3

Compound I-10

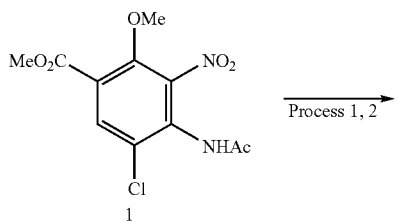

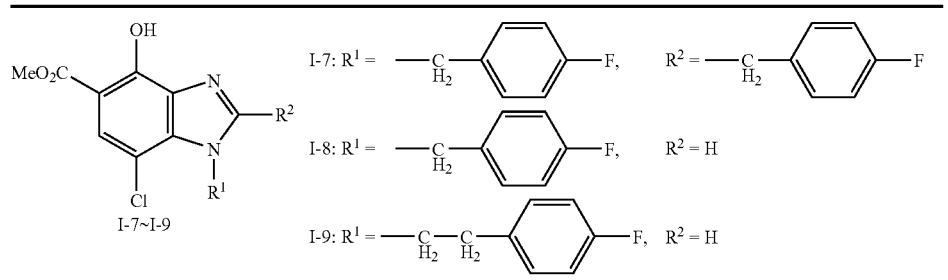

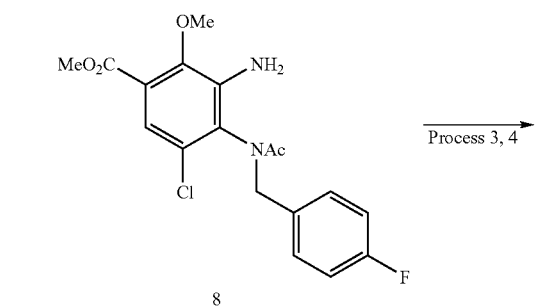

-continued

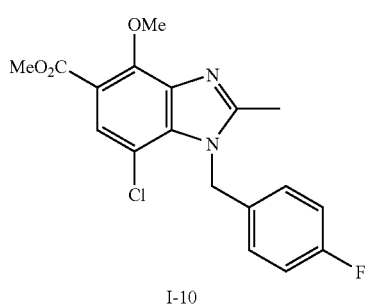

I-10

Example 4

Compound I-12

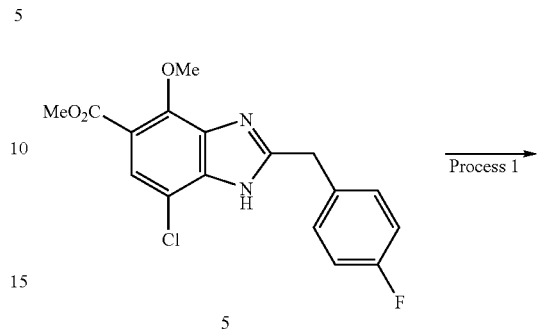

Process 1–4

Compound I-10 was synthesized in a same manner similar to the process 1 of Example 2 and the processes 2, 4, 5 of Example 1.

M.p.: 168–170° C. Recrystallization solvent: methanol-isopropanol

Elemental analysis for $C_{17}H_{14}ClFN_2O_3$ Calcd. (%): C, 58.55; H, 4.05; N, 8.03; Cl, 10.17; F, 5.45. Found. (%): C, 58.47; H, 3.97; N, 8.08; Cl, 9.90; F, 5.19.

NMR (DMSO-$d_6$) δ: 2.49 (3H, s), 3.90 (3H, s), 5.74 (2H, s), 7.05 (2H, m), 7.18 (2H, m), 7.54 (1H, s), 11.10 (1H, brs).

IR (KBr): 3417, 1699 cm$^{-1}$.

Compound I-11 was synthesized in a same manner similar to Example 3.

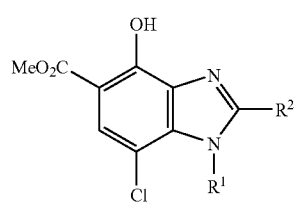

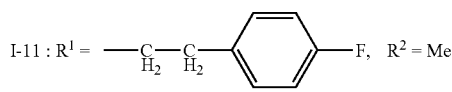

Compound I-11

M.p.: 185–187° C. Recrystallization solvent: ethyl acetate-hexane

Elemental analysis for $C_{18}H_{16}ClFN_2O_3$ Calcd. (%): C, 59.59; H, 4.45; N, 7.72; Cl, 9.77; F, 5.24. Found. (%): C, 59.59; H, 4.40; N, 7.70; Cl, 9.43; F, 5.06.

NMR (CDCl$_3$) δ: 2.25 (3H, s), 3.10 (2H, t, J=7.3 Hz), 3.98 (3H, s), 4.59 (2H, t, J=7.3 Hz), 6.98 (4H, d, J=6.9 Hz), 7.69 (1H, s), 11.26 (1H, brs)

IR (KBr): 3419, 1674 cm$^{-1}$.

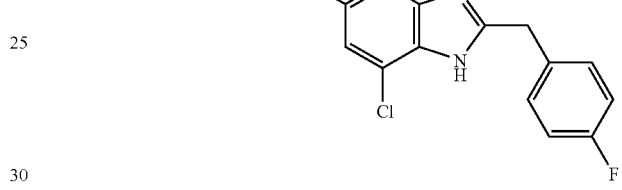

I-12

Process 1

Chlorotrimethylsilane (0.295 ml, 2.32 mmol) was added to a suspension of compound 5 (101 mg, 0.289 mmol) and sodium iodide (351 mg, 2.34 mmol) in acetonitrile (1.5 ml) at room temperature, and the mixture was refluxed for 48 hours. Water (5 ml) was added to the reaction mixture at room temperature, and the whole was extracted with diethyl ether. The organic layer was washed with water (5 ml), 10% sodium thiosulfate solution (10 ml) and brine (10 ml), and dried over sodium sulfate. A residue obtained by evaporation under reduced pressure was dissolved in 1 N sodium hydroxide solution, the mixture was neutralized with 1 N hydrochloric acid and added water (100 ml). Precipitated crystals were collected, washed with water and dried under vacuum to give compound I-12 (74.9 mg, 0.234 mmol, 81%) as a pale brown powder.

Elemental analysis for $C_{15}H_{10}ClFN_2O_3(H_2O)_{0.4}$ Calcd. (%): C, 54.94; H, 3.32; N, 8.54; Cl, 10.81; F, 5.79. Found. (%): C, 54.69; H, 3.32; N, 8.94; Cl, 11.15; F, 5.57.

NMR (DMSO-$_6$) δ: 4.20 (2H, s), 7.16 (2H, m), 7.38 (2H, m), 7.55 (1H, s).

IR (KBr): 3427, 1630 cm$^{-1}$.

Compounds I-13–I-16 were synthesized in a same manner similar to Example 4.

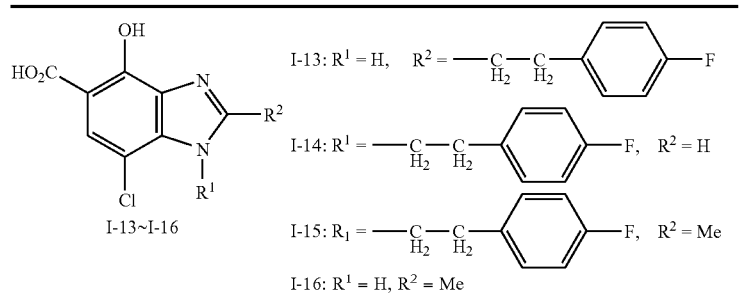

Compound I-13

Elemental analysis for $C_{16}H_{12}ClFN_2O_3(H_2O)_{0.3}$ Calcd. (%): C, 56.50; H, 3.73; N, 8.24; Cl, 10.42; F, 5.59. Found. (%): C, 56.42; H, 3.68; N, 8.33; Cl, 10.63; F, 5.41.

NMR (DMSO-$d_6$) δ: 3.13 (4H, s), 7.11 (2H, m), 7.29 (2H, m), 7.55 (1H, s).

IR (KBr): 3423, 1631 cm$^{-1}$.

Compound I-14

M.p.: 237–239° C.

Elemental analysis for $C_{16}H_{12}ClFN_2O_3(H_2O)_{0.2}$ Calcd. (%): C, 56.80; H, 3.69; N, 8.28; Cl, 10.48; F, 5.62. Found. (%): C, 56.74; H, 3.62; N, 8.33; Cl, 10.11; F, 5.40.

NMR (DMSO-$d_6$) δ: 3.12 (2H, t, J=7.5 Hz), 4.70 (2H, t, J=7.5 Hz), 7.10 (2H, m), 7.17 (2H, m), 7.62 (1H, s), 8.08 (1H, s).

IR (KBr): 3421, 1697 cm$^{-1}$.

Compound I-15

M.p.: 244–245° C.

Elemental analysis for $C_{17}H_{14}ClFN_2O_3(H_2O)_{1.4}$ Calcd. (%): C, 54.60; H, 4.53; N, 7.49; Cl, 9.48; F, 5.08. Found. (%): C, 54.66; H, 4.14; N, 7.54; Cl, 9.23; F, 4.96.

NMR (DMSO-$d_6$) δ: 2.26 (3H, s), 3.06 (2H, t, J=7.2 Hz), 4.55 (2H, t, J=7.2 Hz), 7.07–7.20 (4H, m), 7.53 (1H, s).

IR (KBr): 3421, 1660 cm$^{-1}$.

Compound I-16

M.p.: 267–270° C. Recrystallization solvent: ethanol

Elemental analysis for $C_9H_7ClN_2O_3(NH_3)(H_2O)_{0.15}$ Calcd. (%): C, 43.88; H, 4.21; N, 17.06; Cl, 14.39. Found. (%): C, 44.15; H, 4.05; N, 16.70; Cl, 14.12.

NMR (DMSO-$d_6$) δ: 2.44 (3H, s), 7.40 (1H, s).

IR (KBr): 1645 cm$^{-1}$.

Example 5

Compound I-17

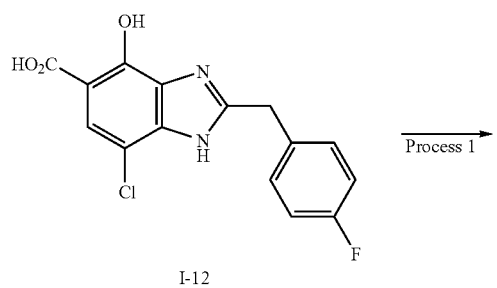

Process 1

1-Ethyl-3-(3-dimethylaminopropyl)carbodiimide hydrochloride (49.4 mg, 0.258 mmol) was added to a suspension of compound I-12 (67.2 mg, 0.210 mmol), 1-hydroxybenzotriazole (35.4 mg, 0.262 mmol), N-methylmorpholine (0.070 ml, 0.64 mmol) and dimethylamine hydrochloride (53.6 mg, 0.657 mmol) in DMF (2 ml) at room temperature, and the mixture was stirred for 4 hours. Water (5 ml) was added to the reaction mixture under ice-cooling and the whole was extracted with diethyl ether. The organic layer was washed with water and brine, and dried over sodium sulfate. The crystalline residue obtained by evaporation under reduced pressure was recrystallized from ethanol-diisopropyl ether to give compound I-17 (19.4 mg, 0.0558 mmol, 27%) as colorless crystals.

M.p.: 253–257° C. Recrystallization solvent: ethanol-diisopropyl ether

Elemental analysis for $C_{17}H_{15}ClFN_3O_2(H_2O)_{0.1}$ Calcd. (%): C, 58.41; H, 4.38; N, 12.02; Cl, 10.14; F, 5.43. Found. (%): C, 58.25; H, 4.28; N, 11.98; Cl, 10.08; F, 5.18.

NMR (DMSO-$d_6$) δ: 2.90 (3H, s), 2.93 (3H, s), 4.19 (2H, s), 6.95 (1H, s), 7.16 (2H, m), 7.37 (2H, m).

IR (KBr): 3425, 1603 cm$^{-1}$.

Compounds I-18–I-20 were synthesized in a same manner similar to the Example 5.

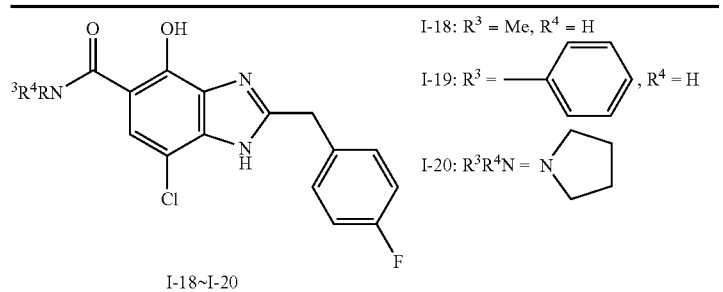

I-18~I-20

Compound I-18

M.p.: 287–291° C. (dec.) Recrystallization solvent: methanol

Elemental analysis for $C_{16}H_{13}ClFN_3O_2(H_2O)_{0.1}$ Calcd. (%): C, 57.27; H, 3.97; N, 12.52; Cl, 10.57; F, 5.66. Found. (%): C, 57.19; H, 3.89; N, 12.35; Cl, 10.28; F, 5.38.

NMR (DMSO-$d_6$) δ: 2.82 (3H, d, J=4.8 Hz), 4.17 (2H, s), 7.15 (2H, m), 7.38 (2H, m), 7.72 (1H, s).

IR (KBr): 3386, 1604 cm$^{-1}$.

Compound I-19

M.p.: 184–186° C. Recrystallization solvent: methanol-diisopropyl ether

Elemental analysis for $C_{21}H_{15}ClFN_3O_2(HCl)_{1.0}(H_2O)_{0.3}$ Calcd. (%): C, 57.63; H, 3.82; N, 9.60; Cl, 16.20; F, 4.34. Found. (%): C, 57.60; H, 3.81; N, 9.89; Cl, 15.95; F, 4.29.

NMR (DMSO-$d_6$) δ: 4.32 (2H, s), 7.14–7.24 (3H, m), 7.39 (2H, d, J=7.8 Hz), 7.46 (2H, m), 7.3972 (2H, d, J=7.8 Hz), 8.17 (1H, s), 10.53 (1H, brs).

IR (KBr): 3423, 1601 cm$^{-1}$.

Compound I-20

M.p.: 268–272° C. (dec.) Recrystallization solvent: methanol-THF-diisopropyl ether Elemental analysis for $C_{19}H_{17}ClFN_3O_2$ Calcd. (%): C, 61.05; H, 4.58; N, 11.24; Cl, 9.48; F, 5.08. Found. (%): C, 60.82; H, 4.49; N, 11.23; Cl, 9.36; F, 4.84.

NMR (DMSO-$d_6$) δ: 1.80–1.87 (4H, m), 3.25–3.56 (4H, m), 4.19 (2H, s), 6.95 (1H, s), 7.07–7.22 (3H, m), 7.38 (2H, m), 12.90 (1H, brs).

IR (KBr): 3425, 1591 cm$^{-1}$.

Example 6

Compound I-21

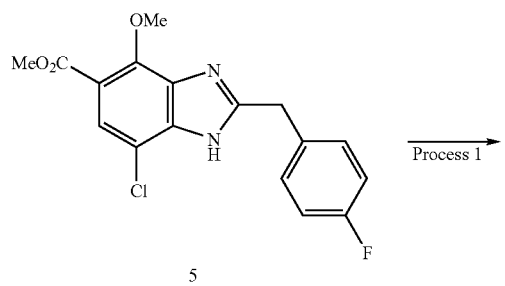

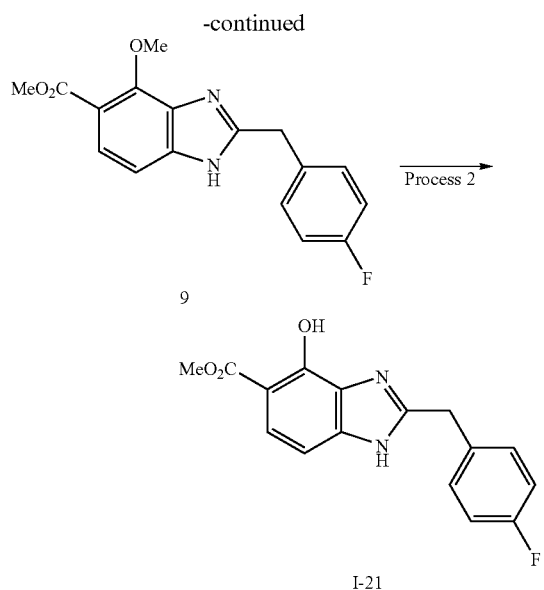

Process 1

A suspension of compound 5 (2.50 g, 7.17 mmol), 10% palladium carbon (499 mg) and triethylamine (10 ml) in methanol was stirred under 4 atm of hydrogen atmosphere for 15 hours at room temperature. The reaction mixture was filtered, evaporated under reduced pressure, and subjected to silica gel column chromatography. The fractions containing desired compound eluted with hexane-ethyl acetate (1:1 v/v) were concentrated under reduced pressure. The crystalline residue was recrystallized from ethyl acetate-hexane-diisopropyl ether to give compound 9 (2.18 g, 6.93 mmol, 97%) as colorless crystals.

Process 2

Compound I-21 was synthesized in a same manner similar to the process 5 of Example 1.

M.p.: 199–201° C. Recrystallization solvent: ethanol-diisopropyl ether

Elemental analysis for $C_{16}H_{13}FN_2O_3(HCl)_{1.0}$ Calcd. (%): C, 57.07; H, 4.19; N, 8.32; Cl, 10.53; F, 5.64. Found. (%): C, 56.90; H, 4.21; N, 8.45; Cl, 10.29; F, 5.68.

NMR (DMSO-$d_6$) δ: 3.94 (3H, s), 4.45 (2H, s), 7.22 (2H, m), 7.24 (1H, d, J=8.7 Hz), 7.51 (2H, m), 7.81 (1H, d, J=8.7 Hz), 11.29 (1H, brs).

IR (KBr): 3417, 1678 cm$^{-1}$.

Compounds I-22 and I-23 were synthesized in a same manner similar to Example 6.

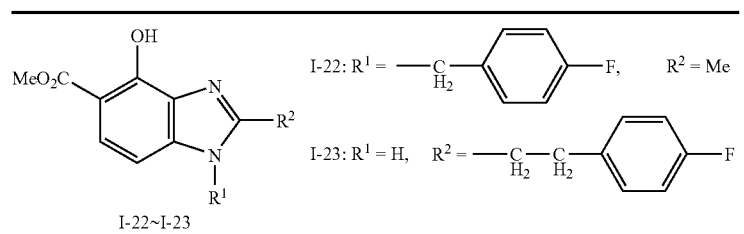

I-22~I-23

Compound I-22
 M.p.: 202–204° C.
 Elemental analysis for $C_{17}H_{15}FN_2O_3(HCl)_{0.1}$ Calcd. (%): C, 64.22; H, 4.79; N, 8.81; Cl, 1.11; F, 5.98. Found. (%): C, 64.53; H, 4.72; N, 8.80; Cl, 1.09; F, 5.75.
 NMR (DMSO-$d_6$) δ: 2.51 (3H, s), 3.90 (3H, s), 5.46 (2H, s), 7.08 (1H, d, J=8.7 Hz), 7.17 (4H, d, J=7.2 Hz), 7.60 (1H, d, J=8.7 Hz), 11.27 (1H, brs).
 IR (KBr): 3417, 1666 cm$^{-1}$.

Compound I-23
 M.p.: 222–225° C. Recrystallization solvent: ethanol
 Elemental analysis for $C_{17}H_{15}FN_2O_3(HCl)_{1.0}$ Calcd. (%): C, 58.21; H, 4.60; N, 7.99; Cl, 10.11; F, 5.42. Found. (%): C, 58.03; H, 4.49; N, 8.02; Cl, 9.83; F, 5.20.
 NMR (DMSO-$d_6$) δ: 3.21 (2H, t, J=7.4 Hz), 3.37 (2H, t, J=7.4 Hz), 3.95 (3H, s), 7.13 (2H, m), 7.27 (1H, d, J=8.6 Hz), 7.29 (2H, m), 7.83 (1H, d, J=8.6 Hz), 11.28 (1H, brs).
 IR (KBr): 3423, 1684 cm$^{-1}$.

Example 7

Compound I-24

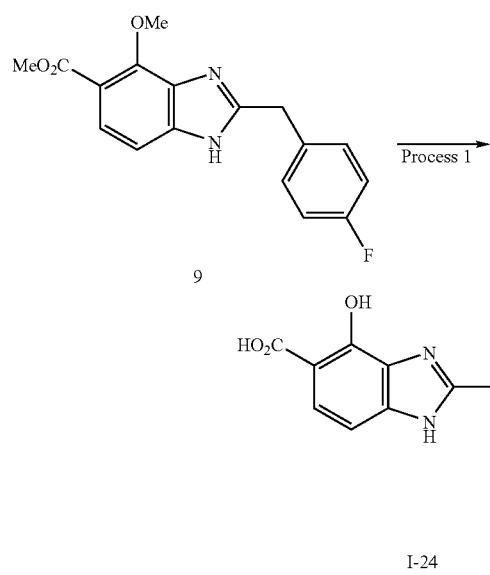

Process 1
 Compound I-24 was synthesized in a same manner similar to the process 1 of Example 4.
 Elemental analysis for $C_{15}H_{11}FN_2O_3(H_2O)_{0.5}$ Calcd. (%): C, 61.02; H, 4.10; N, 9.49; F, 6.43. Found. (%): C, 61.26; H, 3.83; N, 9.56; F, 6.05.
 NMR (DMSO-$d_6$) δ: 4.21 (3H, s), 6.96 (1H, d, J=8.6 Hz), 7.17 (2H, m), 7.39 (2H, m), 7.59 (1H, d, J=8.6 Hz).
 IR (KBr): 3431, 1631 cm$^{-1}$.
 Compound I-25 was synthesized in a same manner similar to Example 7.

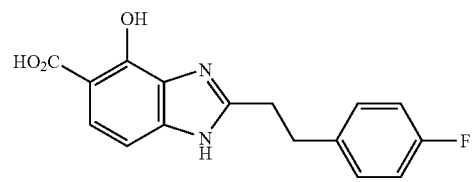

M.p.: 152–155° C.
 Elemental analysis for $C_{16}H_{13}FN_2O_3(HCl)_{0.2}(H_2O)_{0.2}$ Calcd. (%): C, 61.76; H, 4.41; N, 9.00; Cl, 2.28; F, 6.11. Found. (%): C, 61.64; H, 4.38; N, 9.04; Cl, 1.89; F, 5.85.
 NMR DMSO-$d_6$) δ: 3.07–3.23 (4H, m), 6.95 (1H, d, J=8.4 Hz), 7.11 (2H, m), 7.27 (2H, m), 7.63 (1H, d, J=8.4 Hz).
 IR (KBr): 3421, 1631 cm$^{-1}$.

Example 8

Compound I-26

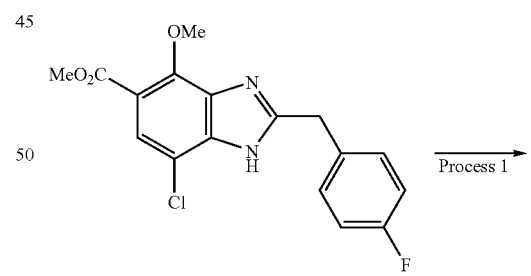

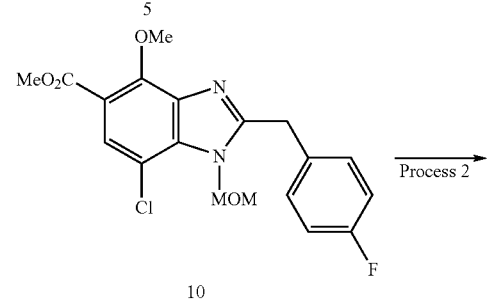

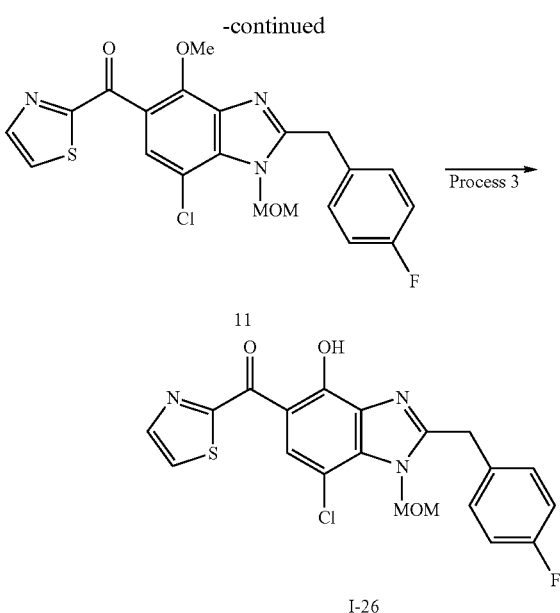

Process 1

A solution of compound 5 (900 mg, 2.58 mmol) in DMF-THF (1:2 v/v, 3 ml) was added dropwise to a suspension of sodium hydride (60%, 130 mg, 3.36 mmol) in THF under ice-cooling, and the mixture was stirred for 45 minutes. Water (10 ml) was added to the reaction mixture under ice-cooling, and the whole was extracted with ethyl acetate. The organic layer was washed with water (20 ml) and brine (20 ml), and dried over sodium sulfate. The crystalline residue obtained by evaporation under reduced pressure was triturated with diisopropyl ether-hexane to give compound 10 as a mixture of regioisomers (894 mg, 2.28 mmol, 88%) as colorless crystals.

Process 2

2-Bromothiazole (0.0413 ml, 0.458 mmol) was added dropwise to a solution of n-butyllithium (1.50 M in hexane, 0.305 ml, 0.458 mmol) in diethyl ether at −78° C., and the mixture was stirred for 20 minutes. A solution of compound 10 (151 mg, 0.383 mmol) in THF-diethyl ether (4:1 v/v, 2.5 ml) was added to the reaction mixture, and the whole was stirred for 30 minutes. The reaction was quenched with saturated ammonium chloride solution (2 ml) and water under ice-cooling, and the whole was extracted with ethyl acetate. The organic layer was washed with water (5 ml) and brine (5 ml), and dried over sodium sulfate. The solvent was evaporated under reduced pressure to give crude compound 11 as a dark brown oil.

Process 3

47% hydrobromic acid (4 ml) was added to a solution of crude 11 in acetic acid (1.5 ml), and the mixture was refluxed for 1.5 hours. After the reaction mixture was neutralized with 5 N sodium hydroxide solution under ice-cooling, water was added to the mixture. Precipitated crystals were collected, washed with water and recrystallized from methanol to give compound I-26 (46.3 mg, 1.19 mmol, 31%) as yellow crystals.

M.p.: 137–139° C. Recrystallization solvent: methanol

Elemental analysis for $C_{18}H_{11}ClFN_3O_2S(H_2O)_{1.3}$ Calcd. (%): C, 52.57; H, 3.33; N, 10.22; Cl, 8.62; F, 4.62; S, 7.80. Found. (%): C, 52.47; H, 3.01; N, 9.96; Cl, 8.72; F, 4.60; S, 7.84.

NMR (DMSO-$d_6$) δ: 4.23 (2H, s), 7.17 (2H, m), 7.40 (2H, m), 8.33 (1H, d, J=2.7 Hz), 8.35 (1H, d, J=2.7 Hz), 8.92 (1H, s), 13.33 (1H, brs).

IR (KBr): 3429, 1631 cm$^{-1}$.

Compounds I-27–I-31 were synthesized in a same manner similar to Example 8.

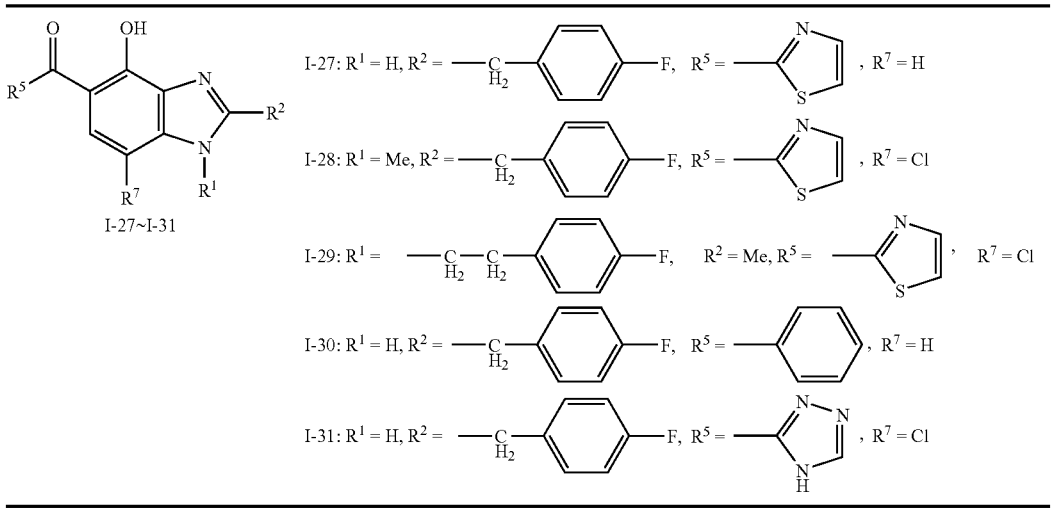

Compound I-27

M.p.: 239–240° C. Recrystallization solvent: ethanol

Elemental analysis for $C_{18}H_{12}FN_3O_2S(H_2O)_{0.1}$ Calcd. (%): C, 60.87; H, 3.46; N, 11.83; F, 5.35; S, 9.03. Found. (%): C, 60.76; H, 3.36; N, 11.77; F, 5.10; S, 9.00.

NMR (DMSO-$d_6$) δ: 4.20 (2H, s), 7.13 (2H, m), 7.18 (1H, d, J=9.0 Hz), 7.39 (2H, m), 8.27 (1H, d, J=2.9 Hz), 8.31 (1H, d, J=2.9 Hz), 8.87 (1H, d, J=2.9 Hz), 13.06 (1H, brs).

IR (KBr): 3440, 1637 cm$^{-1}$.

Compound I-28

M.p.: 258–261° C. Recrystallization solvent: methanol-THF-acetonitrile

Elemental analysis for $C_{19}H_{13}ClFN_3O_2S$ Calcd. (%): C, 56.79; H, 3.26; N, 10.46; Cl, 8.82; F, 4.73; S, 7.98. Found. (%): C, 56.62; H, 3.18; N, 10.37; Cl, 8.77; F, 4.60; S, 7.83.

NMR (DMSO-$d_6$) δ: 3.98 (3H, s), 4.35 (2H, s), 7.13 (2H, m), 7.34 (2H, m), 8.29–8.36 (2H, m), 8.86 (1H, s), 12.90 (1H, brs).

IR (KBr): 3433, 1639 cm$^{-1}$.

Compound I-29

M.p.: 208–211° C. Recrystallization solvent: ethyl acetate-hexane

Elemental analysis for $C_{20}H_{15}ClFN_3O_2S$ Calcd. (%): C, 57.76; H, 3.64; N, 10.10; Cl, 8.52; F, 4.57; S, 7.71. Found. (%): C, 57.61; H, 3.48; N, 10.01; Cl, 8.22; F, 4.39; S, 7.51.

NMR (DMSO-$d_6$) δ: 2.32 (3H, s), 3.10 (2H, d, J=7.4 Hz), 4.62 (2H, d, J=7.4 Hz), 7.08–7.23 (4H, m), 8.31 (1H, d, J=3.0 Hz), 8.34 (1H, d, J=3.0 Hz), 8.83 (1H, s), 12.78 (1H, brs).

IR (KBr): 3433, 1643 cm$^{-1}$.

Compound I-30

M.p.: 189–192° C. Recrystallization solvent: methanol-ethyl acetate

Elemental analysis for $C_{21}H_{15}FN_2O_2(HBr)_{1.0}$ Calcd. (%): C, 59.03; H, 3.77; N, 6.56; Br, 18.70; F, 4.45. Found. (%): C, 58.85; H, 3.65; N, 6.68; Br, 19.09; F, 4.38.

NMR (DMSO-$d_6$) δ: 4.44 (2H, s), 7.20–7.29 (3H, m), 7.43–7.51 (3H, m), 7.54–7.62 (2H, m), 7.65–7.75 (3H, m), 12.19 (1H, brs).

IR (KBr): 3431, 1658 cm$^{-1}$.

Compound I-31

M.p.: 287–289° C. (dec.) Recrystallization solvent: methanol-THF

Elemental analysis for $C_{17}H_{11}ClFN_5O_2(HBr)_{0.15}(H_2O)_{0.5}$ Calcd. (%): C, 51.97; H, 3.12; N, 17.82; Br, 3.05; Cl, 9.02; F, 4.84. Found. (%): C, 52.07; H, 3.24; N, 17.56; Br, 2.94; Cl, 8.78; F, 4.69.

NMR (DMSO-$d_6$) δ: 4.24 (2H, s), 7.17 (2H, m), 7.40 (2H, m), 8.69 (1H, s), 8.76 (1H, brs), 12.19 (1H, brs).

IR (KBr): 3440, 1649 cm$^{-1}$.

Example 9

Compound I-32

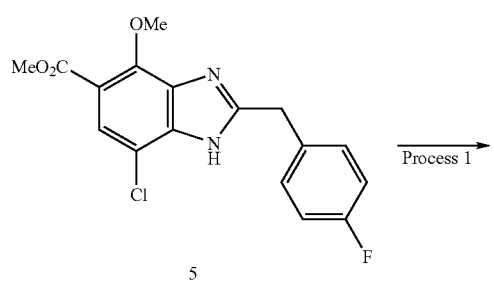

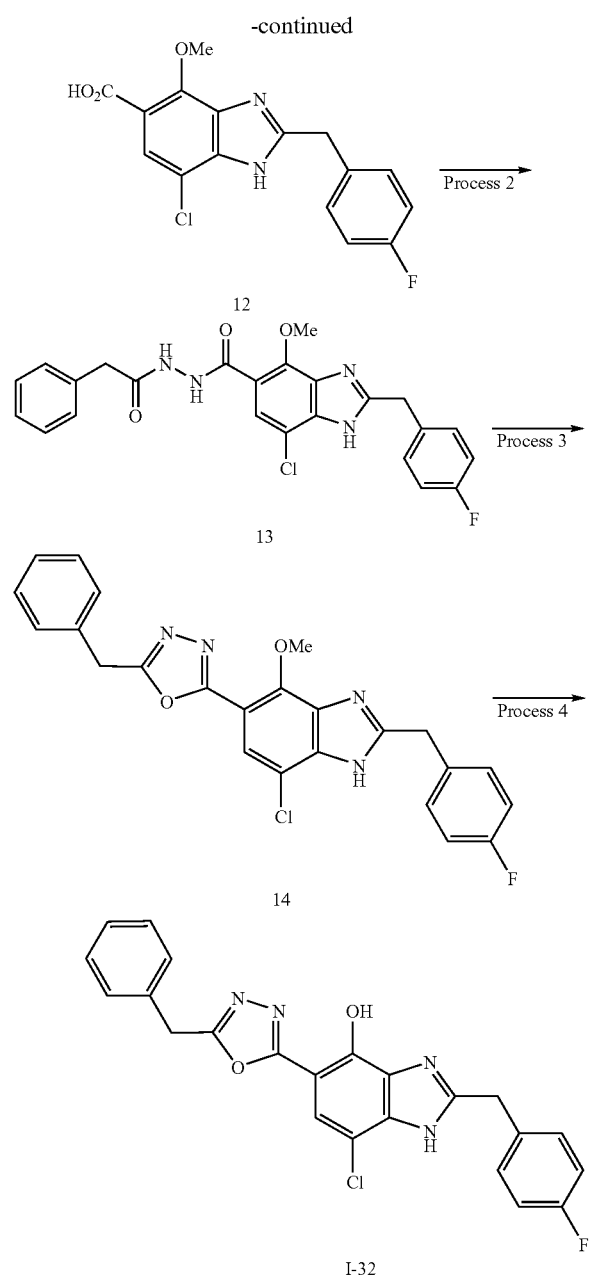

Process 1

1 N sodium hydroxide solution was added to a solution of compound 5 (1.36 g, 3.90 mmol) in ethanol at room temperature, and the mixture was refluxed for 3.5 hours. The reaction mixture was acidified to pH 5 with 2 N hydrochloric acid under ice-cooling, and the whole was extracted with ethyl acetate. The organic layer was washed with brine and dried over sodium sulfate. The crystalline residue obtained by evaporation under reduced pressure was recrystallized from ethyl acetate-methanol-hexane to give compound 12 (1.06 g, 3.17 mmol, 81%) as colorless crystals.

M.p.: 201–205° C.

NMR (CDCl$_3$) δ: 3.93 (3H, brs), 4.22 (2H, s), 7.16 (2H, m), 7.39 (2H, m), 7.53 (1H, s).

Process 2

1-Ethyl-3-(3-dimethylaminopropyl)carbodiimide hydrochloride (291 mg, 1.52 mmol) was added to a suspension of compound 12 (337 mg, 1.01 mmol), 1-hydroxybenzotriazole (207 mg, 1.53 mmol) and phenylacetic hydrazide (234 mg, 1.53 mmol) in THF (3 ml) at room temperature, and the mixture was stirred for 5.5 hours. After the reaction was quenched with water (15 ml) under ice-cooling, precipitated crystals were collected, washed with water and dried under vacuum to give crude compound 13 (470 mg) as colorless crystals.

Process 3

A mixture of crude product 13 (401 mg) and phosphorus oxychloride (4 ml) was refluxed for 2 hours. Removal of an excess of phosphorus oxychloride under reduced pressure gave the residue, which was added ice-water and neutralized with 28% ammonia. Precipitated crystals were collected, washed with water and dried under vacuum to give crude compound 14 (251 mg) as colorless crystals.

Process 4

Compound I-32 was synthesized in a same manner similar to the process 1 of Example 4.

M.p.: 169–172° C. Recrystallization solvent: ethyl acetate-diisopropyl ether

Elemental analysis for $C_{23}H_{16}ClFN_4O_2(H_2O)_{0.3}$ Calcd. (%): C, 62.75; H, 3.80; N, 12.73; Cl, 8.05; F, 4.32. Found. (%): C, 62.72; H, 3.69; N, 12.79; Cl, 7.62; F, 4.16.

NMR (DMSO-$d_6$) δ: 4.22 (2H, s), 4.38 (2H, s), 7.16 (2H, m), 7.26–7.55 (8H, m).

IR (KBr): 3411 cm$^{-1}$.

Compounds I-33–I-50 were synthesized in a same manner similar to Example 9.

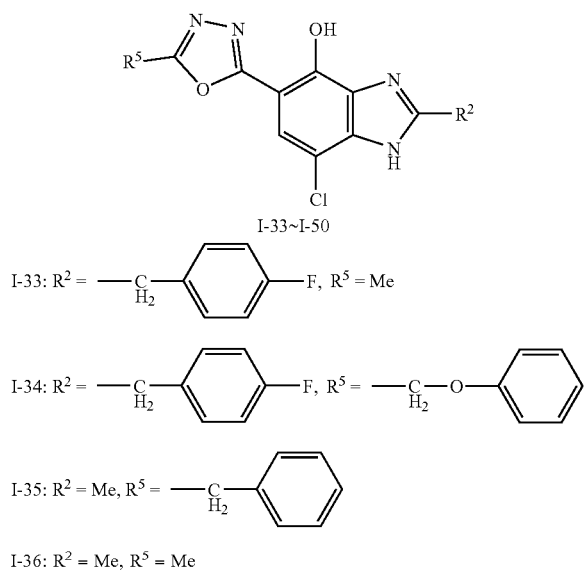

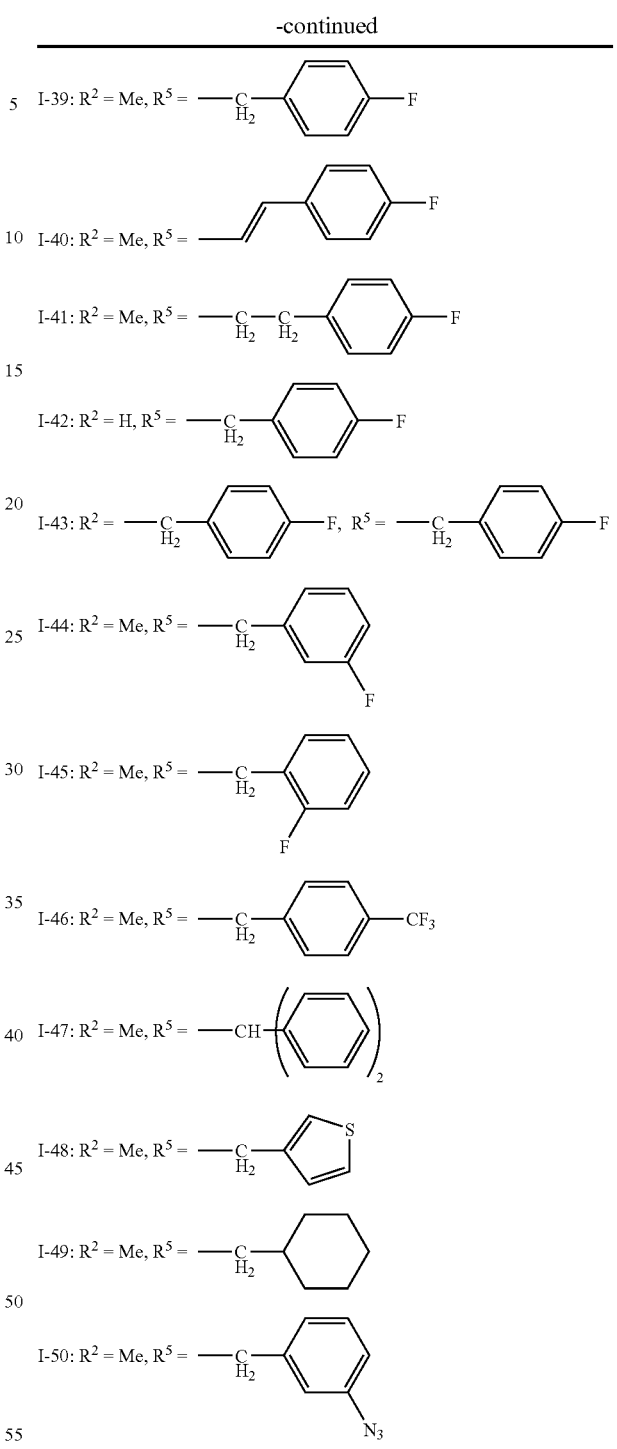

Compound I-33

M.p.: 206–208° C. Recrystallization solvent: isopropanol

Elemental analysis for $C_{17}H_{12}ClFN_4O_2$(isopropanol)$_{0.1}$ $(H2O)_{0.2}$ Calcd. (%): C, 56.41; H, 3.61; N, 15.21; Cl, 9.62; F, 5.16. Found. (%): C, 56.48; H, 3.46; N, 15.13; Cl, 9.28; F, 4.92.

NMR (CDCl$_3$) δ: 2.66 (3H, s), 4.35 (2H, s), 7.05 (2H, m), 7.31 (2H, m), 7.60 (1H, s).

IR (KBr): 3429 cm$^{-1}$.

Compound I-34

M.p.: 180–182° C. Recrystallization solvent: isopropanol

Elemental analysis for $C_{23}H_{16}ClFN_4O_3(HCl)_{0.1}(H_2O)_{0.3}$ Calcd. (%): C, 60.07; H, 3.66; N, 12.18; Cl, 8.48; F, 4.13. Found. (%): C, 60.10; H, 3.36; N, 12.35; Cl, 8.54; F, 3.98.

NMR (CDCl$_3$) δ: 4.35 (2H, s), 5.36 (2H, s), 6.99–7.11 (3H, m), 7.23–7.39 (6H, m), 7.65 (1H, s).

IR (KBr): 3421 cm$^{-1}$.

Compound I-35

M.p.: 255–257° C. Recrystallization solvent: ethanol

Elemental analysis for $C_{17}H_{13}ClN_4O_2$(ethanol)$_{0.2}$ Calcd. (%): C, 59.71; H, 4.09; N, 16.01; Cl, 10.13. Found. (%): C, 59.44; H, 3.96; N, 16.18; Cl, 9.98.

NMR (DMSO-d$_6$) δ: 2.54 (3H, s), 4.38 (2H, s), 7.27–7.50 (6H, m), 10.55 (1H, brs), 12.96 (1H, brs).

IR (KBr): 3410 cm$^{-1}$.

Compound I-36

M.p.: 262–265° C. Recrystallization solvent: methanol

Elemental analysis for $C_{11}H_9ClN_4O_2$ Calcd. (%): C, 49.92; H, 3.43; N, 21.17; Cl, 13.40. Found. (%): C, 49.68; H, 3.38; N, 21.00; Cl, 13.32.

NMR (DMSO-d$_6$) δ: 2.54 (3H, s), 2.60 (3H, s), 7.50 (1H, s), 10.50 (1H, brs), 12.94 (1H, brs).

IR (KBr): 3421 cm$^{-1}$.

Compound I-37

M.p.: 266–268° C. Recrystallization solvent: ethanol

Elemental analysis for $C_{17}H_{13}ClN_4O_3(H_2O)_{0.6}$ Calcd. (%): C, 55.55; H, 3.89; N, 15.24; Cl, 9.64. Found. (%): C, 55.63; H, 3.77; N, 15.08; Cl, 9.60.

NMR (DMSO-d$_6$) δ: 2.55 (3H, s), 5.49 (2H, s), 7.03 (1H, m), 7.14 (2H, m), 7.35 (2H, m), 7.54 (1H, brs), 10.48 (1H, brs), 12.99 (1H, brs).

IR (KBr): 3384 cm$^{-1}$.

Compound I-38

M.p.: >300° C. Recrystallization solvent: chloroform-methanol

Elemental analysis for $C_{16}H_{11}ClN_4O_2(H_2O)_{0.4}$ Calcd. (%): C, 57.55; H, 3.56; N, 16.78; Cl, 10.62. Found. (%): C, 57.30; H, 3.76; N, 16.67; Cl, 10.86.

NMR (DMSO-d$_6$) δ: 2.56 (3H, s), 7.60–7.71 (3H, m), 7.78 (1H, s), 8.13–8.24 (2H, m), 10.59 (1H, brs), 12.98 (1H, brs).

IR (KBr): 3415 cm$^{-1}$.

Compound I-39

M.p.: 247–249° C. Recrystallization solvent: isopropanol

Elemental analysis for $C_{17}H_{12}ClFN_4O_2$ Calcd. (%): C, 56.91; H, 3.37; N, 15.62; Cl, 9.88; F, 5.30. Found. (%): C, 56.76; H, 3.42; N, 15.58; Cl, 10.16; F, 5.08.

NMR (DMSO-d$_6$) δ: 2.54 (3H, s), 4.38 (2H, s), 7.21 (2H, m), 7.42–7.53 (3H, m), 10.61 (1H, brs), 12.95 (1H, brs).

IR (KBr): 3338 cm$^{-1}$.

Compound I-40

M.p.: >300° C. Recrystallization solvent: chloroform-methanol

Elemental analysis for $C_{18}H_{12}ClFN_4O_2(CHCl_3)_{0.3}(H_2O)_{0.5}$ Calcd. (%): C, 52.89; H, 3.23; N, 13.48; Cl, 16.21; F, 4.57. Found. (%): C, 52.56; H, 3.13; N, 13.41; Cl, 16.54; F, 4.37.

NMR (DMSO-d$_6$) δ: 2.55 (3H, s), 7.31 (2H, m), 7.40 (1H, d, J=16.5 Hz), 7.73 (1H, s), 7.70–7.98 (3H, m), 10.60 (1H, brs), 13.01 (1H, brs).

IR (KBr): 3367 cm$^{-1}$.

Compound I-41

M.p.: 175–177° C. Recrystallization solvent: ethyl acetate

Elemental analysis for $C_{18}H_{14}ClFN_4O_2$ Calcd. (%): C, 57.99; H, 3.79; N, 15.03; Cl, 9.51; F, 5.10. Found. (%): C, 57.88; H, 3.76; N, 14.99; Cl, 9.12; F, 5.07.

NMR (DMSO-d$_6$) δ: 2.54 (3H, s), 3.12 (2H, t, J=7.4 Hz), 3.27 (2H, t, J=7.4 Hz), 7.12 (2H, m), 7.36 (2H, m), 7.50 (1H, s), 10.55 (1H, brs), 12.99 (1H, brs).

IR (KBr): 3423 cm$^{-1}$.

Compound I-42

M.p.: 250–253° C. Recrystallization solvent: chloroform-methanol

Elemental analysis for $C_{16}H_{10}ClFN_4O_2(S)_{0.75}(H_2O)_{0.5}$ Calcd. (%): C, 50.87; H, 2.93; N, 14.83; Cl, 9.38; F, 5.03; S, 6.37. Found. (%): C, 50.90; H, 2.63; N, 14.83; Cl, 9.47; F, 4.82; S, 6.32.

NMR (DMSO-d$_6$) δ: 4.39 (2H, s), 7.21 (2H, m), 7.47 (2H, m), 7.57 (1H, s), 8.39 (1H, s), 10.52 (1H, brs), 13.29 (1H, brs).

IR (KBr): 3431 cm$^{-1}$.

Compound I-43

M.p.: 103–105° C. Recrystallization solvent: methanol

Elemental analysis for $C_{16}H_{10}ClFN_4O_2$(methanol)$_{0.5}$ $(H_2O)_{0.5}$ Calcd. (%): C, 59.07; H, 3.80; N, 11.72; Cl, 7.42; F, 7.95. Found. (%): C, 59.09; H, 3.72; N, 11.90; Cl, 7.29; F, 7.82.

NMR (DMSO-d$_6$) δ: 4.22 (2H, s), 4.38 (2H, s), 7.16 (2H, m), 7.21 (2H, m), 7.39 (2H, m), 7.46 (2H, m), 7.51 (1H, s), 10.56 (1H, brs), 13.18 (1H, brs).

IR (KBr): 3423 cm$^{-1}$.

Compound I-44

M.p.: 246–250° C. Recrystallization solvent: isopropanol

Elemental analysis for $C_{17}H_{12}ClFN_4O_2(H_2O)_{0.2}$ Calcd. (%): C, 56.35; H, 3.45; N, 15.46; Cl, 9.78; F, 5.24. Found. (%): C, 56.43; H, 3.19; N, 15.51; Cl, 9.98; F, 5.05.

NMR (DMSO-d$_6$) δ: 2.54 (3H, s), 4.42 (2H, s), 7.15 (1H, m), 7.22–7.33 (2H, m), 7.38–7.53 (2H, m), 10.52 (1H, brs), 12.96 (1H, brs).

IR (KBr): 3429 cm$^{-1}$.

Compound I-45

M.p.: 272–276° C. Recrystallization solvent: methanol-isopropanol

Elemental analysis for $C_{17}H_{12}ClFN_4O_2$(isopropanol)$_{0.1}$ $(H_2O)_{0.2}$ Calcd. (%): C, 56.41; H, 3.61; N, 15.21; Cl, 9.62; F, 5.16. Found. (%): C, 56.28; H, 3.31; N, 15.32; Cl, 9.47; F, 5.03.

NMR (DMSO-d$_6$) δ: 2.54 (3H, s), 4.42 (2H, s), 7.20–7.32 (2H, m), 7.35–7.56 (3H, m), 10.51 (1H, brs), 12.96 (1H, brs).

IR (KBr): 3408 cm$^{-1}$.

Compound I-46

M.p.: 163–166° C. Recrystallization solvent: ethyl acetate

Elemental analysis for $C_{18}H_{12}ClF_3N_4O_2(H_2O)_{0.4}$ Calcd. (%): C, 51.97; H, 3.10; N, 13.47; Cl, 8.52; F, 13.70. Found. (%): C, 51.79; H, 2.81; N, 13.57; Cl, 8.74; F, 13.67.

NMR (DMSO-d$_6$) δ: 2.54 (3H, s), 4.52 (2H, d, J=7.8 Hz), 7.41–7.80 (5H, m), 10.39 (1H, brs), 12.97 (1H, brs).

IR (KBr): 3411 cm$^{-1}$.

Compound I-47

M.p.: 268–270° C. Recrystallization solvent: acetonitrile

Elemental analysis for $C_{23}H_{17}ClN_4O_2(H_2O)_{0.1}$ Calcd. (%): C, 65.98; H, 4.14; N, 13.58; Cl, 8.47. Found. (%): C, 65.86; H, 4.06; N, 13.40; Cl, 8.48.

NMR (DMSO-d$_6$) δ: 2.54 (3H, s), 6.08 (2H, d, J=9.6 Hz), 7.26–7.53 (11H, m), 10.47 (1H, brs), 12.97 (1H, brs).
IR (KBr): 3421 cm$^{-1}$.

Compound I-48

M.p.: 249–252° C. Recrystallization solvent: methanol
Elemental analysis for $C_{15}H_{11}ClN_4O_2S(S)_{0.1}$ Calcd. (%): C, 51.48; H, 3.17; N, 16.01; Cl, 10.13; S, 10.08. Found. (%): C, 51.36; H, 3.08; N, 15.95; Cl, 9.88; S, 10.07.
NMR (DMSO-d$_6$) δ: 2.54 (3H, s), 4.39 (2H, s), 7.17 (1H, m), 7.51 (2H, m), 7.57 (1H, m), 10.57 (1H, brs), 12.96 (1H, brs).
IR (KBr): 3429 cm$^{-1}$.

Compound I-49

M.p.: 263–266° C. Recrystallization solvent: isopropanol
Elemental analysis for: $C_{17}H_{19}ClN_4O_2(H_2O)_{0.2}$ Calcd. (%): C, 58.27; H, 5.58; N, 15.99; Cl, 10.12. Found. (%): C, 58.38; H, 5.50; N, 16.03; Cl, 10.10.
NMR (DMSO-d$_6$) δ: 0.99–1.34 (5H, m), 1.58–1.91 (6H, m), 2.54 (3H, s), 2.84 (1H, d, J=6.6 Hz), 7.51 (1H, s), 10.51 (1H, brs), 12.96 (1H, brs).
IR (KBr): 3419 cm$^{-1}$.

Compound I-50

M.p.: 169–173° C. Recrystallization solvent: methanol-isopropanol
Elemental analysis for $C_{17}H_{12}ClN_7O_2(HBr)_{0.7}(H_2O)_{0.8}$ Calcd. (%): C, 45.09; H, 3.18; N, 21.65; Br, 12.35; Cl, 7.83. Found. (%): C, 45.19; H, 3.20; N, 21.30; Br, 12.38; Cl, 7.64.
NMR (DMSO-d$_6$) δ: 2.64 (3H, s), 4.43 (2H, s), 7.08 (1H, m), 7.18–7.28 (2H, m), 7.43 (1H, m), 7.65 (1H, s).
IR (KBr): 3408, 2114 cm$^{-1}$.

Example 10

Compound I-51

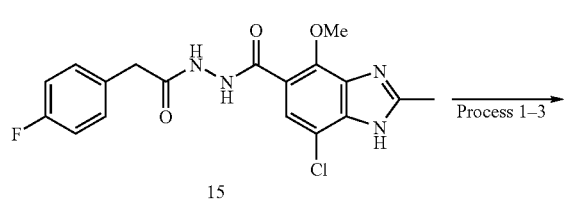

15

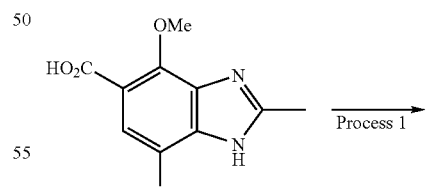

I-51

Processes 1–3

Compound I-51 was synthesized in a same manner similar to the process 1 of Example 6, the process 3 of Example 9 and the process 1 of Example 4.
M.p.: 228–231° C. Recrystallization solvent: ethanol
Elemental analysis for $C_{17}H_{13}FN_4O_2(H_2O)_{0.1}$ Calcd. (%): C, 62.61; H, 4.08; N, 17.18; F, 5.83. Found. (%): C, 62.44; H, 4.07; N, 17.03; F, 5.67.
NMR (DMSO-d$_6$) δ: 2.50 (3H, s), 4.37 (2H, s), 7.05 (1H, d, J=8.4 Hz), 7.21 (2H, m), 7.40–7.51 (3H, m), 10.42 (1H, brs), 12.51 (1H, brs).
IR (KBr): 3408 cm$^{-1}$.

Compound I-52 was synthesized in a same manner similar to Example 10.

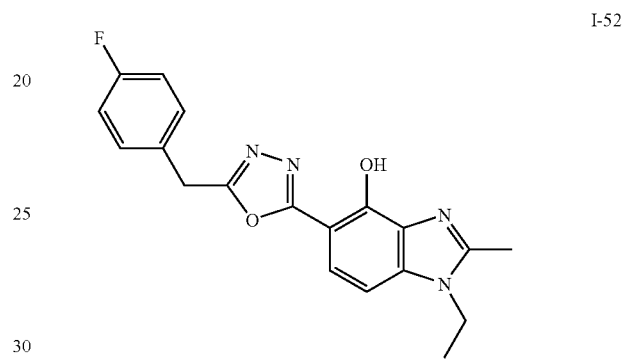

I-52

Compound I-52

M.p.: 172–173° C. Recrystallization solvent: isopropanol
Elemental analysis for $C_{19}H_{17}FN_4O_2$ Calcd. (%): C, 64.76; H, 4.86; N, 15.90; F, 5.39. Found. (%): C, 64.65; H, 4.71; N, 15.78; F, 5.32.
NMR (CDCl$_3$) δ: 1.41 (3H, t, J=7.4 Hz), 2.64 (3H, s), 4.15 (2H, q, J=7.4 Hz), 4.27 (2H, s), 6.89 (1H, d, J=8.6 Hz), 7.06 (2H, m), 7.35 (2H, m), 7.52 (1H, d, J=8.6 Hz), 10.54 (1H, brs).
IR (KBr): 3431 cm$^{-1}$.

Example 11

Compound I-53

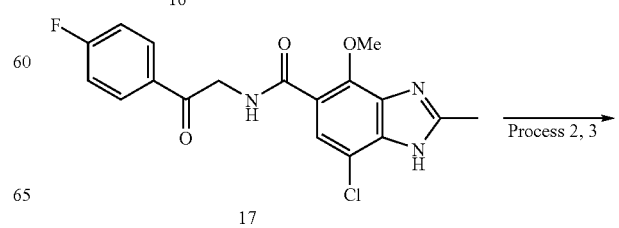

16

17

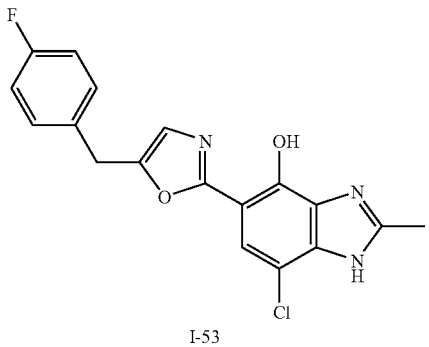

I-53

Process 1

1-Ethyl-3-(3-dimethylaminopropyl)carbodiimide hydrochloride (424 mg, 2.21 mmol) was added to a suspension of compound 16 (502 mg, 2.09 mmol), 1-hydroxybenzotriazole (297 mg, 2.20 mmol) and 1-amino-3-(4-fluorophenyl)propane-2-one hydrochloride (445 mg, 2.19 mmol) in THF-DMF (5:1 v/v, 12 ml) at room temperature, and the mixture was stirred for 50 minutes. N-methylmorpholine (0.455 ml, 4.14 mmol) was added dropwise to the reaction mixture, and the whole was stirred for 2 hours. After the reaction was quenched with water (50 ml) at room temperature, precipitated crystals were collected, washed with water and dried under vacuum to give crude compound 17 (549 mg) as pale brown crystals.

Processes 2 and 3

Compound I-53 was synthesized in a same manner similar to the process 2 of Example 10 and the process 1 of Example 4.

M.p.: 242–245° C. Recrystallization solvent: ethyl acetate

Elemental analysis for $C_{18}H_{13}ClFN_3O_2(HCl)_{0.1}(H_2O)_{0.1}$
Calcd. (%): C, 59.52; H, 3.69; N, 11.57; Cl, 10.74; F, 5.23.
Found. (%): C, 59.40; H, 3.55; N, 11.47; Cl, 10.85; F, 5.31.

NMR (DMSO-$d_6$) δ: 2.52 (3H, s), 4.16 (2H, s), 7.19 (2H, m), 7.41 (2H, m), 7.49 (1H, s), 11.64 (1H, brs), 13.13 (1H, brs).

IR (KBr): 3421 cm$^{-1}$.

Example 12

Compound I-54

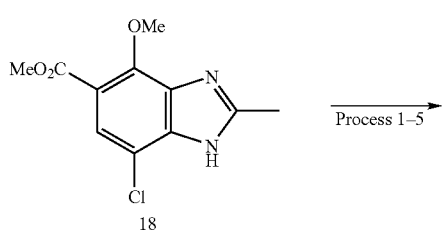

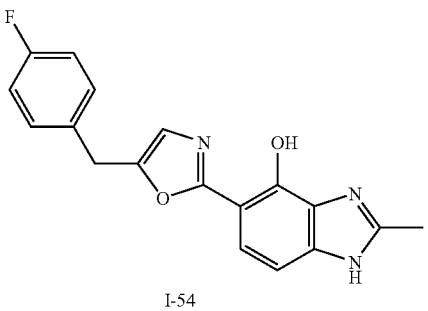

I-54

Processes 1–5

Compound I-54 was synthesized in a same manner similar to the process 1 of Example 6, the process 1 of Example 9, the process 1 of Example 11, the process 2 of Example 10 and the process 1 of Example 4.

M.p.: 208–210° C. Recrystallization solvent: acetonitrile

Elemental analysis for $C_{18}H_{14}FN_3O_2(HCl)_{0.4}(H_2O)_{0.5}$
Calcd. (%): C, 62.32; H, 4.47; N, 12.11; Cl, 4.09; F, 5.48.
Found. (%): C, 62.25; H, 4.14; N, 12.12; Cl, 4.12; F, 5.54.

NMR (DMSO-$d_6$) δ: 2.55 (3H, s), 4.17 (2H, s), 7.13 (1H, d, J=8.6 Hz), 7.18 (2H, m), 7.40 (2H, m), 7.56 (1H, d, J=8.6 Hz), 11.71 (1H, brs).

IR (KBr): 3425 cm$^{-1}$.

Compound I-55 was synthesized in a same manner similar to Example 12.

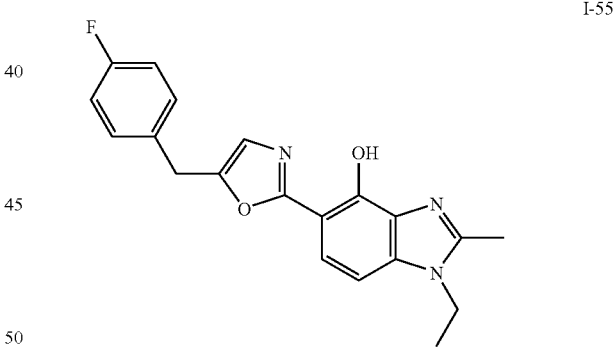

I-55

Compound I-55

M.p.: 150–151° C. Recrystallization solvent: ethyl acetate-hexane

Elemental analysis for $C_{20}H_{18}FN_3O_2$ Calcd. (%): C, 68.36; H, 5.16; N, 11.96; F, 5.41. Found. (%): C, 68.31; H, 5.15; N, 11.90; F, 5.36.

NMR (CDCl$_3$) δ: 1.41 (3H, t, J=7.2 Hz), 2.62 (3H, s), 4.06 (2H, s), 4.14 (2H, q, J=7.2 Hz), 6.84 (1H, m), 6.84 (1H, d, J=8.4 Hz), 7.04 (2H, m), 7.26 (2H, m), 7.62 (1H, d, J=8.4 Hz), 11.76 (1H, brs).

IR (KBr): 3433 cm$^{-1}$.

Example 13

Compound I-56

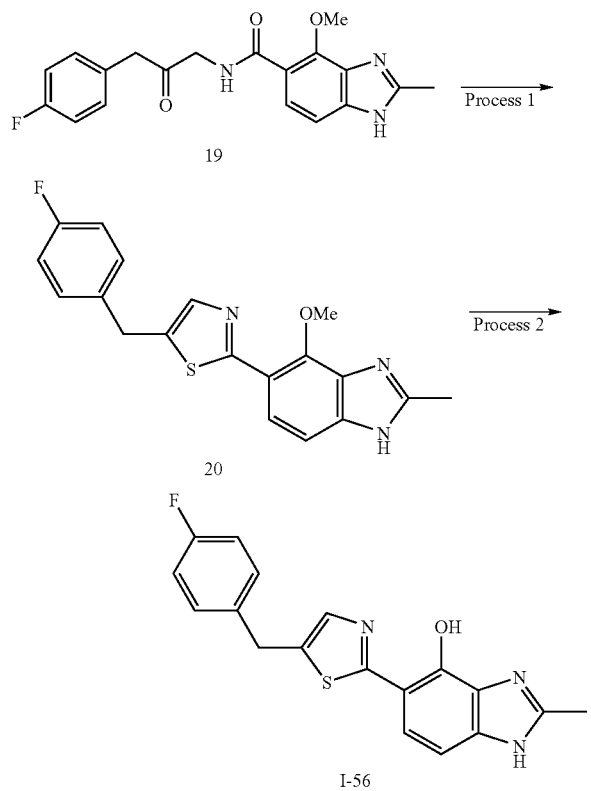

Example 14

Compound I-57

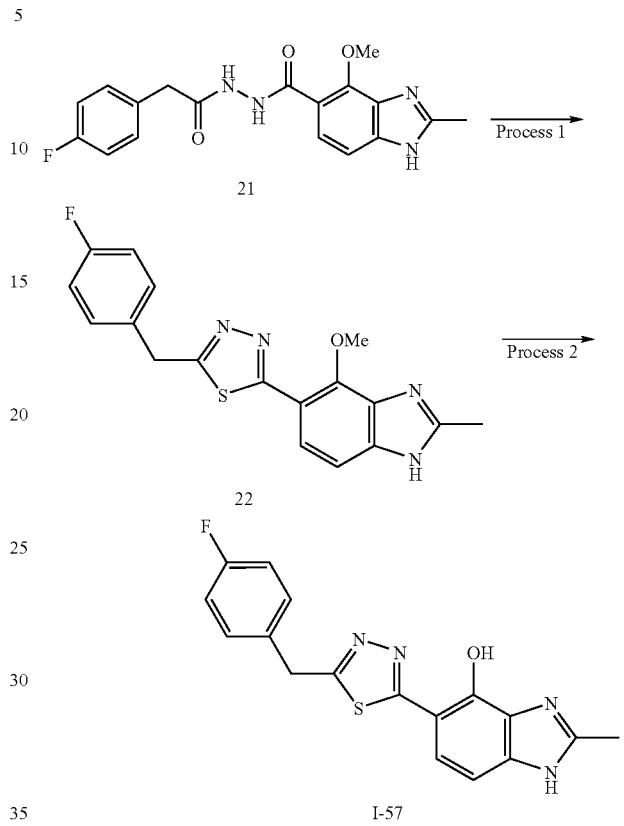

Process 1

A solution of compound 19 (302 mg, 0.850 mmol) and Lawesson's reagent (691 mg, 1.71 mmol) in pyridine (4.5 ml) was stirred at 110° C. for 2 hours. After cooling, the reaction mixture was diluted with ethyl acetate, washed with 0.1 N hydrochloric acid (15 ml×2), water (15 ml) and brine (15 ml), and dried over sodium sulfate. A crude product obtained by evaporation under reduced pressure was subjected to silica gel column chromatography. The fractions containing desired compound eluted with ethyl acetate were concentrated under reduced pressure to give compound 20 (126 mg, 0.357 mmol, 42%) as yellow crystals.

Process 2

Compound I-56 was synthesized in a same manner similar to the process 1 of Example 4.

M.p.: 234–238° C. Recrystallization solvent: methanol-diethyl ether

Elemental analysis for $C_{18}H_{15}ClFN_3OS(HCl)_{1.0}(H_2O)_{0.4}$ Calcd. (%): C, 56.44; H, 4.16; N, 10.97; Cl, 9.26; F, 4.96; S, 8.37. Found. (%): C, 56.52; H, 4.21; N, 10.82; Cl, 9.46; F, 4.85; S, 8.16.

NMR (DMSO-$d_6$) δ: 2.75 (3H, s), 4.29 (2H, s), 7.18 (2H, m), 7.27 (1H, d, J=8.7 Hz), 7.39 (2H, m), 7.81 (1H, d, J=8.7 Hz), 7.83 (1H, s), 13.03 (1H, brs), 14.99 (1H, brs).

IR (KBr): 3423 cm$^{-1}$.

Process 1

Compound I-22 was synthesized in a same manner similar to the process 1 of Example 13.

Process 2

Compound I-57 was synthesized in a same manner similar to the process 1 of Example 4.

M.p.: 249–253° C. Recrystallization solvent: methanol

Elemental analysis for: $C_{17}H_{13}FN_4OS(H_2O)_{0.2}$ Calcd. (%): C, 59.36; H, 3.93; N, 16.29; F, 5.52; S, 9.32. Found. (%): C, 59.32; H, 3.76; N, 16.20; F, 5.46; S, 9.37.

NMR (DMSO-$d_6$) δ: 2.51 (3H, s), 4.46 (2H, s), 7.02 (1H, brd, J=8.7 Hz), 7.19 (2H, m), 7.43 (2H, m), 7.94 (1H, brs), 12.48 (1H, brs).

IR (KBr): 3423 cm$^{-1}$.

Example 15

Compound I-58

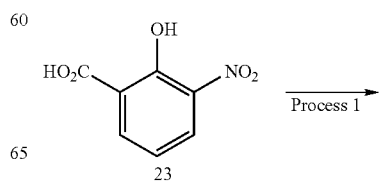

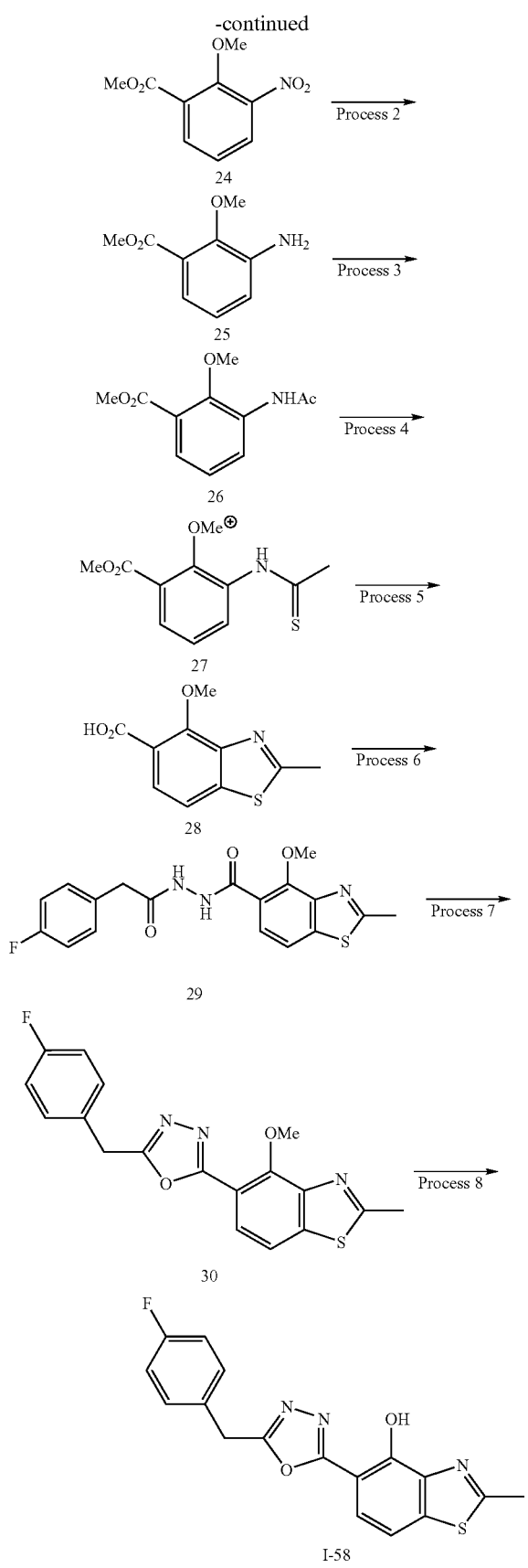

Process 1

Potassium carbonate (31.8 g, 0.230 mol) and dimethyl sulfate (21.8 ml, 0.230 mol) were added to a solution of 3-nitrosalicylic acid 23 (18.3 g, 0.100 mol) in acetone (400 ml) at room temperature and the mixture was stirred at 50° C. for 15 hours. After cooling, the reaction mixture was filtered and a remained inorganic residue was washed with acetone. After the filtrate was concentrated, water and 10% hydrochloric acid (40 ml) were added to the residue and the whole was extracted with ethyl acetate. The organic layer was washed with saturated sodium hydrogencarbonate solution and brine, and dried over sodium sulfate. The solvent was evaporated under reduced pressure to give crude compound 24 (23.3 g, quant.) as a colorless oil.

NMR (CDCl$_3$) δ: 3.97 (3H, s), 4.01 (3H, s), 7.28 (1H, dd, J=8.1, 8.1 Hz), 7.92 (1H, dd, J=8.1, 1.8 Hz), 8.03 (1H, dd, J=8.1, 1.8 Hz).

Process 2

Water (30 ml), iron powder (15.5 g, 0.277 mol) and ammonium chloride (1.85 g, 0.0347 mol) were added to a solution of compound 24 (14.6 g, 0.0693 mol) in 99.5% ethanol (300 ml) at room temperature, and the mixture was refluxed for 4 hours. After cooling, the reaction mixture was filtered and a remained inorganic residue was washed with ethanol. After the filtrate was evaporated, water and saturated sodium hydrogencarbonate solution added to the residue and extracted with ethyl acetate. The organic layer was washed with saturated sodium hydrogencarbonate solution and brine, and dried over sodium sulfate. Removal of solvent under reduced pressure gave crude compound 25 (11.4 g, 91%) as a colorless oil.

NMR (CDCl$_3$) δ: 3.85 (3H, s), 3.91 (3H, s), 6.91 (1H, dd, J=8.1, 2.1 Hz), 6.95 (1H, dd, J=8.1, 8.1 Hz), 7.19 (1H, dd, J=8.1, 2.1 Hz).

Process 3

Pyridine (10.2 ml, 0.126 mol) and acetic anhydride (8.90 ml, 0.0941 mol) were added to a solution of compound 25 (11.4 g, 0.0628 mol) in THF (30 ml) at room temperature, and the mixture was stirred for 1.5 hours under ice-cooling and further 30 minutes at room temperature. The reaction mixture was poured into a mixture of 10% hydrochloric acid (35 ml)-ice-water-ethyl acetate, and the whole was extracted with ethyl acetate. The organic layer was washed with 5% hydrochloric acid, saturated sodium hydrogencarbonate solution and brine, and dried over sodium sulfate. The crystalline residue obtained by evaporation under reduced pressure was washed with hexane-ethyl acetate (4:1) to give crude compound 26 (12.7 g, 90%) as colorless crystals.

NMR (CDCl$_3$) δ: 2.24 (3H, s), 3.89 (3H, s), 3.93 (3H, s), 7.16 (1H, dd, J=8.1, 8.1 Hz), 7.56 (1H, dd, J=8.1, 1.8 Hz), 7.86 (1H, brs), 8.55 (1H, dd, J=8.1, 1.8 Hz).

Process 4

Lawesson's reagent (10.8 g, 0.0267 mol) was added to a suspension of compound 26 (11.9 g, 0.0535 mol) in toluene (150 ml) at room temperature, and the mixture was stirred at 70° C. for 2 hours. The reaction mixture was diluted with ethyl acetate, washed with water and dried over sodium sulfate. A crude product obtained by evaporation under reduced pressure was subjected to silica gel column chromatography. The fractions containing desired compound eluted with hexane-ethyl acetate (2:1 v/v) were concentrated under reduced pressure. The crystalline residue was washed with hexane-ethyl acetate to give compound 27 (12.2 g, 95%) as yellow crystals.

NMR (CDCl₃) δ: 2.79 (3H, s), 3.90 (3H, s), 3.94 (3H, s), 7.22 (1H, dd, J=8.1, 8.1 Hz), 7.72 (1H, dd, J=8.1, 1.8 Hz), 9.01 (1H, dd, J=8.1, 1.8 Hz), 9.14 (1H, brs).

Process 5

6 N Potassium hydroxide solution (9.30 ml, 56.0 mmol) was added to a solution of compound 27 (3.35 g, 14.0 mmol) and potassium ferricyanide (9.22 g, 28.0 mmol) in water (55 ml) at 60° C., and the mixture was stirred at 60° C. for 1 hour. The reaction mixture was poured into a mixture of 10% hydrochloric acid (20 ml)-ice-water-ethyl acetate, and the whole was extracted with ethyl acetate. The organic layer was washed with water and brine, and dried over sodium sulfate. A crude product obtained by evaporation under reduced pressure was subjected to silica gel column chromatography. The fractions containing desired compound eluted with chloroform-methanol (15:1 v/v) were concentrated under reduced pressure. The crystalline residue was washed with diisopropyl ether-ethyl acetate to give compound 28 (1.52 g, 49%) as colorless crystals.

NMR (DMSO-d₆) δ: 2.83 (3H, s), 4.12 (3H, s), 7.64 (1H, d, J=8.4 Hz), 7.79 (1H, d, J=8.4 Hz), 12.91 (1H, brs).

Process 6

Compound 29 (94%) was synthesized as colorless crystals in a same manner similar to the process 2 of Example 9.

NMR (CDCl₃) δ: 2.85 (3H, s), 3.70 (2H, s), 4.49 (3H, s), 7.04 (2H, m), 7.33 (2H, m), 7.59 (1H, d, J=8.4 Hz), 8.09 (1H, d, J=8.4 Hz), 9.30 (1H, d, J=6.9 Hz), 10.93 (1H, d, J=6.9 Hz).

Process 7

Compound 30 (91%) was synthesized as colorless crystals in a same manner similar to the process 3 of Example 9.

NMR (CDCl₃) δ: 2.87 (3H, s), 4.24 (3H, s), 4.29 (2H, s), 7.05 (2H, m), 7.37 (2H, m), 7.60 (1H, d, J=8.4 Hz), 7.86 (1H, d, J=8.4 Hz).

Process 8

Compound I-58 (47%) was synthesized as colorless crystals in a same manner similar to the process 1 of Example 4.

M.p.: 183–184° C. Recrystallization solvent: chloroform-ethyl acetate

Elemental analysis for $C_{17}H_{12}FN_3O_2S$ Calcd. (%): C, 59.81; H, 3.54; N, 12.31; F, 5.57; S, 9.39. Found. (%): C, 59.68; H, 3.43; N, 12.23; F, 5.54; S, 9.46.

NMR (CDCl₃) δ: 2.88 (3H, s), 4.30 (2H, s), 7.07 (2H, m), 7.36 (2H, m), 7.41 (1H, d, J=8.4 Hz), 7.63 (1H, d, J=8.4 Hz), 10.83 (1H, brs).

IR (KBr): 3442, 1626, 1583, 1514, 1460, 1365, 1227, 1165 cm⁻¹.

Compounds I-59–I-61 were synthesized in a same manner similar to Example 15.

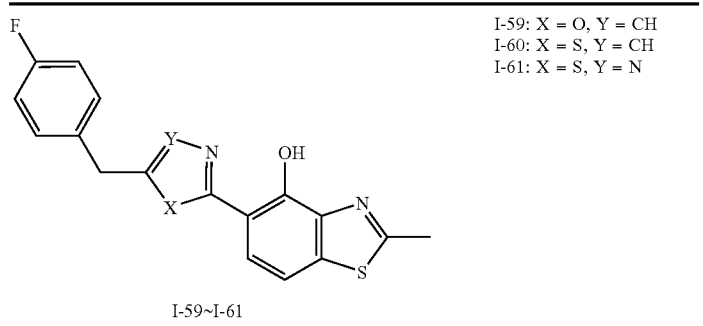

I-59: X = O, Y = CH
I-60: X = S, Y = CH
I-61: X = S, Y = N

I-59~I-61

Compound I-59

M.p.: 168–169° C. Recrystallization solvent: hexane-ethyl acetate

Elemental analysis for $C_{18}H_{13}FN_2O_2S$ Calcd. (%): C, 63.52; H, 3.85; N, 8.23; F, 5.58; S, 9.42. Found. (%): C, 63.45; H, 3.75; N, 8.15; F, 5.46; S, 9.40.

NMR (CDCl₃) δ: 2.87 (3H, s), 4.07 (2H, s), 6.89 (1H, t, J=0.9 Hz), 7.04 (2H, m), 7.22–7.30 (2H, m), 7.35 (1H, d, J=8.4 Hz), 7.73 (1H, d, J=8.4 Hz), 11.96 (1H, brs).

IR (KBr): 1572, 1508, 1466 cm⁻¹.

Compound I-60

M.p.: 197–198° C. Recrystallization solvent: chloroform-ethyl acetate

Elemental analysis for $C_{18}H_{13}FN_2OS_2$ Calcd. (%): C, 60.65; H, 3.68; N, 7.86; F, 5.33; S, 17.99. Found. (%): C, 60.49; H, 3.50; N, 7.75; F, 5.43; S, 17.98.

NMR (CDCl₃) δ: 2.86 (3H, s), 4.17 (2H, s), 7.03 (2H, m), 7.20–7.28 (2H, m), 7.28 (1H, d, J=8.4 Hz), 7.45 (1H, d, J=8.4 Hz), 7.52 (1H, t, J=0.9 Hz), 13.04 (1H, brs).

IR (KBr): 1510, 1452 cm⁻¹.

Compound I-61

M.p.: 195–196° C. Recrystallization solvent: chloroform-ethyl acetate

Elemental analysis for $C_{17}H_{12}FN_3OS_2$ Calcd. (%): C, 57.13; H, 3.38; N, 11.76; F, 5.32; S, 17.94. Found. (%): C, 57.01; H, 3.24; N, 11.68; F, 5.21; S, 17.98.

NMR (CDCl₃) δ: 2.87 (3H, s), 4.44 (2H, s), 7.07 (2H, m), 7.30–7.37 (2H, m), 7.33 (1H, d, J=8.4 Hz), 7.37 (1H, d, J=8.4 Hz), 12.10 (1H, brs).

IR (KBr): 1510, 1458 cm⁻¹.

Example 16

Compound I-62

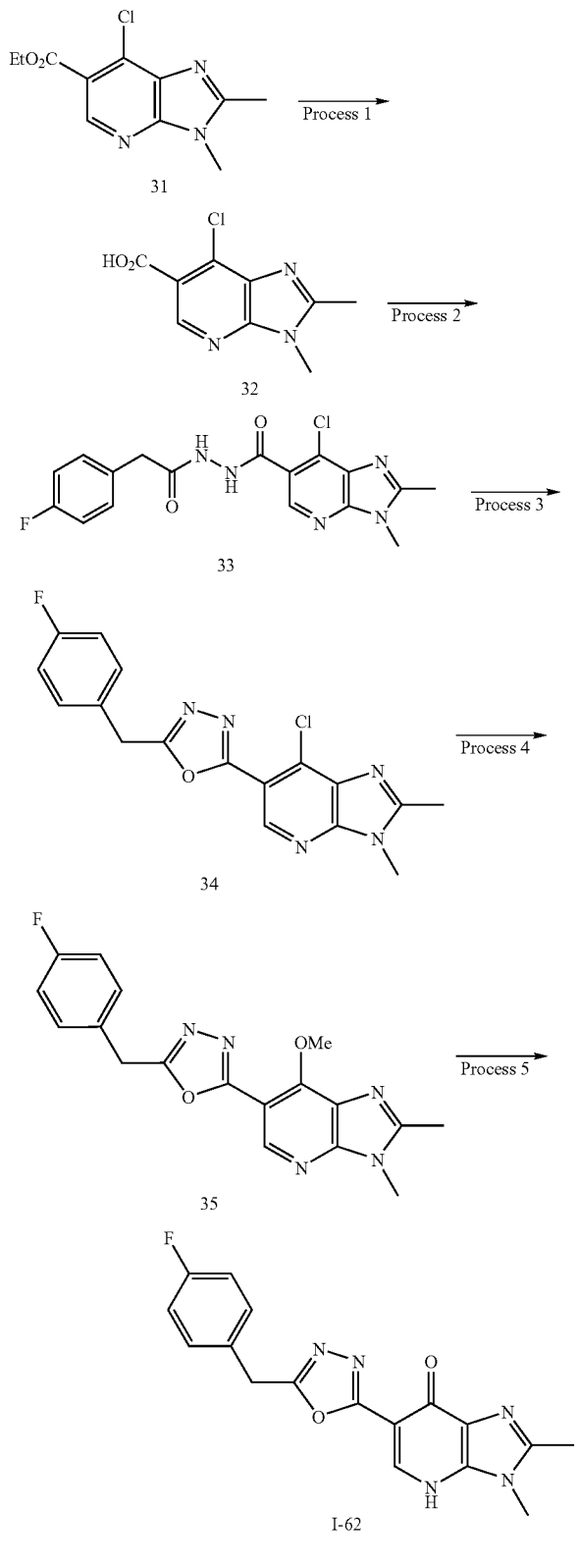

Process 1

1 N Sodium hydroxide solution (40 ml) was added to compound 31 (2.06 g, 8.12 mmol) described in the literature (J. Chem. Soc. Perkin Trans. 1, 2789–2811, (1992)) at room temperature, and the mixture was stirred for 1 hour. The reaction mixture was neutralized with 2 N hydrochloric acid under ice-cooling. Precipitated crystals were collected, washed with water and dried under vacuum to give compound 32 (1.49 g, 6.60 mmol, 81%) as colorless crystals.

NMR (DMSO-$d_6$) δ: 2.62 (3H, s), 3.78 (3H, s), 8.75 (1H, s), 13.43 (1H, brs).

Process 2

Compound 33 was synthesized in a same manner similar to the process 2 of Example 9.

NMR (DMSO-$d_6$) δ: 2.62 (3H, s), 3.55 (2H, s), 3.78 (3H, s), 7.16 (2H, m), 7.38 (2H, m), 8.33 (1H, s), 10.42 (1H, brs), 10.48 (1H, brs).

Process 3

Compound 34 was synthesized in a same manner similar to the process 3 of Example 9.

NMR (DMSO-$d_6$) δ: 2.65 (3H, s), 3.81 (3H, s), 4.42 (2H, s), 7.22 (2H, m), 7.47 (2H, m), 8.77 (1H, s).

Process 4

Sodium methoxide (28% methanol solution, 1.5 ml) was added to a suspension of compound 34 (599 mg, 1.67 mmol) in methanol (6 ml), and the mixture was refluxed for 1.5 hours. After the reaction was quenched with water (30 ml) under ice-cooling, the mixture was neutralized with 1 N hydrochloric acid. Precipitated crystals were collected, washed with water and dried under vacuum to give compound 35 (495 mg, 1.40 mmol, 84%) as colorless crystals.

NMR (DMSO-$d_6$) δ: 2.58 (3H, s), 3.75 (3H, s), 4.36 (2H, s), 4.55 (3H, s), 7.22 (2H, m), 7.44 (2H, m), 8.54 (1H, s).

Process 5

Compound I-62 was synthesized in a same manner similar to the process 1 of Example 4.

M.p.: 229–232° C. Recrystallization solvent: methanol

Elemental analysis for $C_{17}H_{14}FN_5O_2$ Calcd. (%): C, 60.17; H, 4.16; N, 20.64; F, 5.60. Found. (%): C, 59.94; H, 4.03; N, 20.41; F, 5.38.

NMR (DMSO-$d_6$) δ: 2.58 (3H, s), 3.74 (3H, s), 4.17 (1H, brs), 4.37 (2H, s), 7.20 (2H, m), 7.44 (2H, m), 8.53 (1H, s).

IR (KBr): 3433, 1604 cm$^{-1}$.

Example 17

Compound I-63

-continued

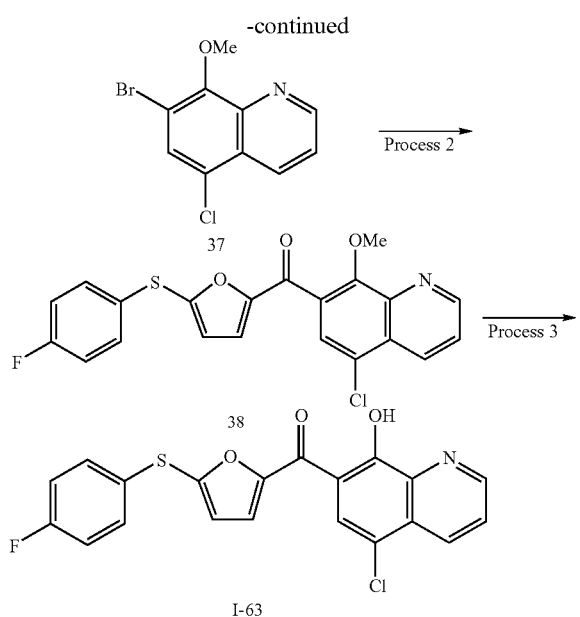

Process 1

Potassium carbonate (anhydrous, 8.3 g, 60.0 mmol) and methyl iodide (4.7 g, 33.0 mmol) were added to a solution of commercially available compound 36 (7.74 g, 30.0 mmol) in DMF (50 ml), and the mixture was stirred at room temperature for 3 hours. After the reaction mixture was filtered, water (100 ml) was added to the filtrate and the whole was extracted with ethyl acetate. The organic layer was washed with water (50 ml) and brine (50 ml), and dried over sodium sulfate. A crude product obtained by evaporation under reduced pressure was subjected to silica gel column chromatography. The fractions containing desired compound eluted with hexane-ethyl acetate (1:1 v/v) were concentrated under reduced pressure to give compound 37 (7.32 g, 26.9 mmol, 89.7%) as colorless crystals. p NMR (CDCl$_3$) δ: 4.17 (3H, s), 7.55 (1H, dd, J=4.2, 1.8 Hz), 7.80 (1H, s), 8.53 (1H, dd, J=1.8, 8.4 Hz), 9.01 (1H, dd, J=4.2, 1.8 Hz).

Process 2

Phenyl lithium (17.0% cyclohexane-diethyl ether solution, 1.0 ml) was added to diethyl ether (anhydrous, 10 ml), and the mixture was stirred at −75° C. for 5 minutes. A solution of compound 37 (272 mg, 1.0 mmol) in diethyl ether (5 ml) was carefully added dropwise to the solution, and the whole was stirred for 1.5 hours. A solution of 5-(4-fluorophenylsulfanyl)furan-2-carbonyl chloride in diethyl ether (6.0 ml) was added to the reaction mixture, and the whole was stirred for 1 hour. The reaction was quenched with hydrochloric acid-THF (2.5:7.5 v/v) dropwisely and allowed to warm to room temperature. Water (40 ml) was added to the reaction mixture, and the whole was extracted with ethyl acetate. The organic layer was washed with water (50 ml) and brine (50 ml), and dried over sodium sulfate. A crude product as a dark brown oil obtained by evaporation under reduced pressure was subjected to silica gel column chromatography. The fractions containing desired compound eluted with hexane-ethyl acetate (3:1 v/v) were concentrated under reduced pressure to give compound 38 (65.0 mg, 0.16 mmol, 16.0%) as a yellow oil.

NMR (CDCl$_3$) δ: 4.12 (3H, s), 6.50 (1H, d, J=3.3 Hz), 7.01–7.06 (2H, m), 7.13 (1H, d, J=3.3 Hz), 7.44–7.49 (2H, m), 7.60 (1H, s), 7.60–7.64 (1H, m), 8.60 (1H, dd, J=8.6, 1.8 Hz), 9.05 (1H, dd, J=4.2, 1.8 Hz).

Process 3

Pyridine hydrochloride (140 mg, 1.20 mmol) was added to compound 38 (50 mg, 0.12 mmol), and the mixture was stirred at 190° C. for 15 minutes. After cooling to room temperature, ice-water (15 ml) was added to the reaction mixture and the whole was extracted with ethyl acetate. The organic layer was washed with water (50 ml) and brine (50 ml), and dried over sodium sulfate. The yellow crystalline residue obtained by evaporation under reduced pressure was washed with diisopropyl ether to give compound I-63 (36 mg, 0.09 mmol, 75.0%).

M.p.: 120–122° C. Recrystallization solvent: diisopropyl ether

Elemental analysis for C$_{20}$H$_{11}$ClFNO$_3$S(HCl)$_{0.02}$(H$_2$O)$_{0.1}$ Calcd. (%): C, 59.70; H, 2.81; N, 3.48; Cl, 8.99; F, 4.72; S, 7.97. Found. (%): C, 59.61; H, 2.65; N, 3.44; Cl, 9.26; F, 4.60; S, 7.68.

NMR (CDCl$_3$) δ: 6.66 (1H, d, J=3.6 Hz), 7.06–7.11 (2H, m), 7.48 (1H, d, J=3.6 Hz), 7.53–7.61 (2H, m), 7.69 (1H, dd, J=8.6, 3.9 Hz), 8.23 (1H, s), 8.50–8.56 (1H, m), 900–9.20 (1H, m), 13.14 (1H, brs).

Compound I-64 was synthesized in a same manner similar to Example 17.

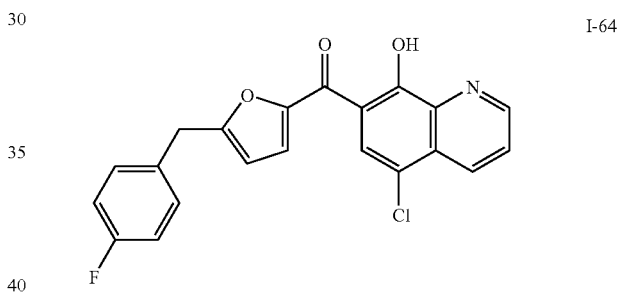

Compound I-64

M.p.: 126–128° C. Recrystallization solvent: diethyl ether

Elemental analysis for C$_{21}$H$_{13}$ClFNO$_3$(HCl)$_{0.1}$(C$_2$H$_5$O)$_{0.01}$(H$_2$O)$_{0.15}$ Calcd. (%): C, 64.98; H, 3.50; N, 3.60; Cl, 10.0; F, 4.89. Found. (%): C, 65.19; H, 3.21; N, 3.71; Cl, 9.91; F, 4.57.

NMR (CDCl$_3$) δ: 4.23 (2H, s), 6.30(1H, d, J=3.6 Hz), 7.04–7.12 (2H, m), 7.26–7.36 (2H, m), 7.43 (1H, d, J=3.6 Hz), 8.32 (1H, s), 8.54 (1H, dd, J=8.6, 1.8 Hz), 9.00–9.30 (1H, m), 13.18 (1H, brs).

Example 18

Compound I-65

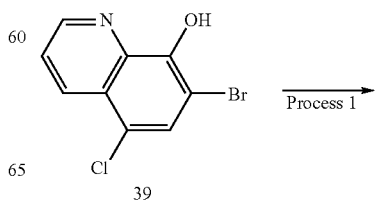

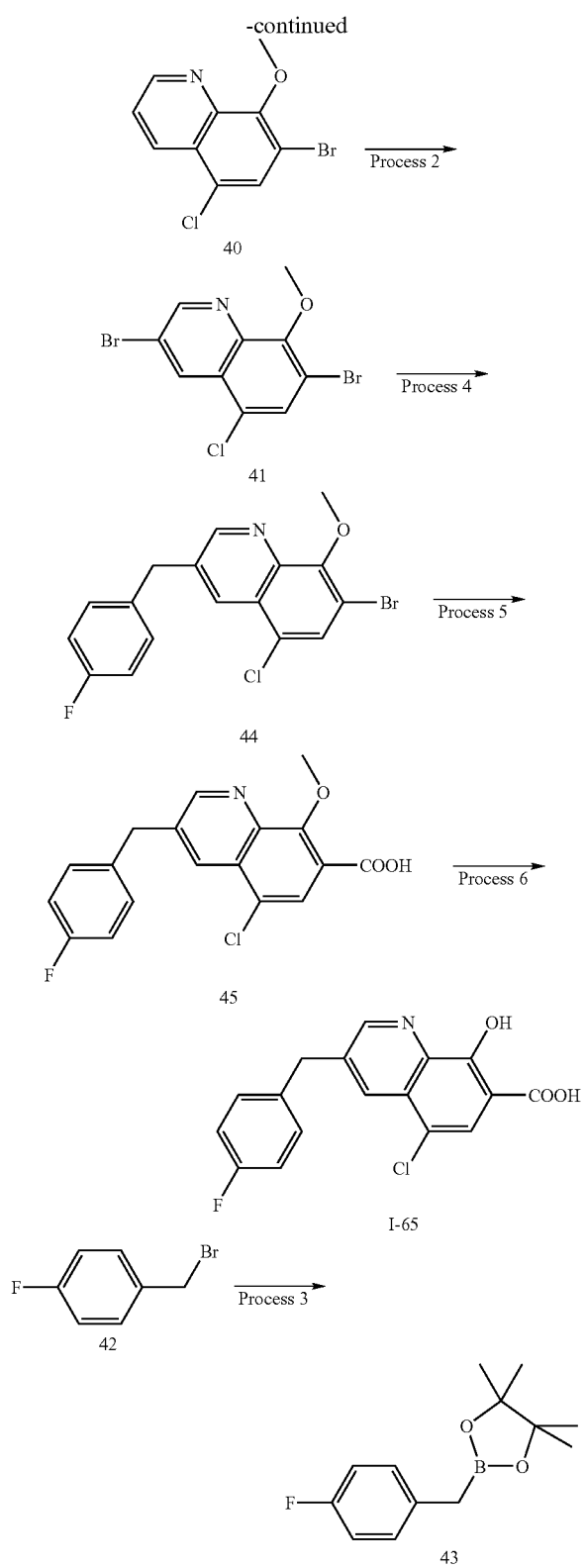

mmol) in DMF (70 ml), and the mixture was stirred for 3 hours at room temperature. After the reaction was quenched with water, precipitated crystals were collected and washed with water. The crystals were dissolved in ethyl acetate, dried over magnesium sulfate and treated with active carbon. Removal of solvent under reduced pressure gave crude compound 40 (9.0 g, 33.0 mmol, 87%) as colorless crystals.

Process 2

Bromine (6.4 g, 40 mmol) and pyridine (1.6 g, 40 mmol) were added dropwise to a solution of compound 40 (5.17 g, 20 mmol) obtained by the process 1 in carbon tetrachloride (40 ml) at room temperature, and the mixture was refluxed for 15 hours. After cooling, 2 N sodium hydroxide solution (22 ml, 44 mmol) was added dropwise to the reaction mixture. After stirring for 10 minutes, the whole was extracted with dichloromethane, washed with water and dried over magnesium sulfate. A crude product obtained by evaporation under reduced pressure was subjected to silica gel column chromatography. The fractions containing desired compound eluted with hexane-ethyl acetate (4:1 v/v) were concentrated under reduced pressure to give compound 41 (4.78 g, 13.6 mmol, 68%) as colorless crystals.

Process 3

Potassium acetate (8.84 g, 90 mmol), bis(pinacolato) diboron (16.8 g, 66 mmol) and tetrakis(triphenylphosphine) palladium (0) (1.7 g, 1.5 mmol) were added to a solution of compound 42 (8.68 g, 60 mmol) in toluene (40 ml), and the mixture was refluxed for 3 hours. After cooling, the reaction mixture was poured into ice-water and stirred for 5 minutes. The whole was extracted with ethyl acetate, washed with water and dried over magnesium sulfate. A crude product as a purple oil obtained by evaporation under reduced pressure was subjected to silica gel column chromatography. The fractions containing desired compound eluted with hexane-ethyl acetate (50:1 v/v) were concentrated under reduced pressure to give compound 43 (9.5 g, 40 mmol, 67%) as colorless crystals.

Process 4

Compound 43 (944 mg, 4 mmol) obtained by the process 3, 2 M potassium carbonate solution (4.5 ml, 9 mmol) and tetrakis(triphenylphosphine)palladium (0) (350 mg, 0.3 mmol) were added to a solution of compound 41 (1.05 g, 3 mmol) obtained by the process 2 in DMF (40 ml) at room temperature, and the mixture was stirred at 70° C. for 5 hours. The reaction mixture was filtered and water was added to the filtrate. The whole was extracted with ethyl acetate, washed with water and dried over magnesium sulfate. A crude product as a yellow oil obtained by evaporation under reduced pressure was subjected to silica gel column chromatography. The fractions containing desired compound eluted with hexane-ethyl acetate (3:1 v/v) were concentrated under reduced pressure to give compound 44 (340 mg, 0.89 mmol, 30%) as pale yellow crystals. The fractions obtained as a mixture were concentrated and subjected to silica gel column chromatography again. The fractions containing desired compound eluted with toluene-ethyl acetate (9:1 v/v) were concentrated under reduced pressure to give compound 44 (259 mg, 0.68 mmol) as pale yellow crystals. The total yield was 53%.

Process 5

Phenyl lithium (2 M cyclohexane solution, 0.5 ml, 1 mmol) was added to diethyl ether (10 ml), and the mixture was cooled to −78° C. A solution of compound 44 (200 mg, 0.53 mmol) in diethyl ether (5 ml) was added dropwise to the solution, and the whole was stirred at −78° C. for 30

Process 1

Potassium carbonate (10.5 g, 76.0 mmol) and methyl iodide (6.2 g, 43.7 mmol) were added to a solution of 7-bromo-5-chloro-8-hydroxyquinoline 39 (9.8 g, 38.0 minutes. CO₂ gas was bubbled through the reaction mixture for 60 minutes, which was allowed to warm 0° C., quenched with ammonium chloride aqueous solution. The whole was extracted with ethyl acetate, washed with water and dried over sodium sulfate. The crystalline residue obtained by evaporation under reduced pressure was washed with diethyl ether to give compound 45 (110 mg, 0.32 mmol, 64%) as colorless crystals.

Process 6

Hydrobromic acid-acetic acid (4 ml–1 ml) was added dropwise to compound 45 (70 mg, 0.2 mmol) at room temperature, and the mixture was stirred at 110° C. for 60 minutes. After cooling, water was added to the reaction mixture and the whole was extracted with ethyl acetate. The organic layer was washed with sodium hydrogencarbonate solution and water, and dried over sodium sulfate. The crystalline residue obtained by evaporation under reduced pressure was washed with ethyl acetate to give compound I-65 (59 mg, 0.18 mmol, 88%) as colorless crystals.

M.p.: 222–224° C. Recrystallization solvent: ethyl acetate

Elemental analysis for $C_{17}H_{11}ClFNO_3(H_2O)_{0.2}$ Calcd. (%): C, 60.89; H, 3.43; N, 4.18; Cl, 10.57; F, 5.67. Found. (%): C, 60.55; H, 3.30; N, 4.28; Cl, 10.96; F, 5.50.

NMR (DMSO-d₆) δ: 4.30 (2H, s), 7.12–7.22 (2H, m), 7.38–7.44 (2H, m), 7.98 (1H, s), 8.38 (1H, brs), 8.95 (1H, brs).

Example 19

Compounds I-66, I-67

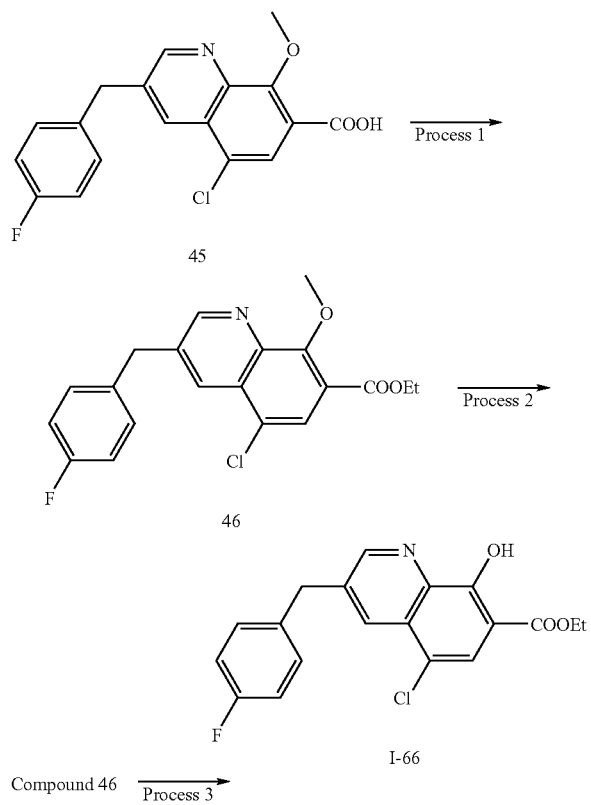

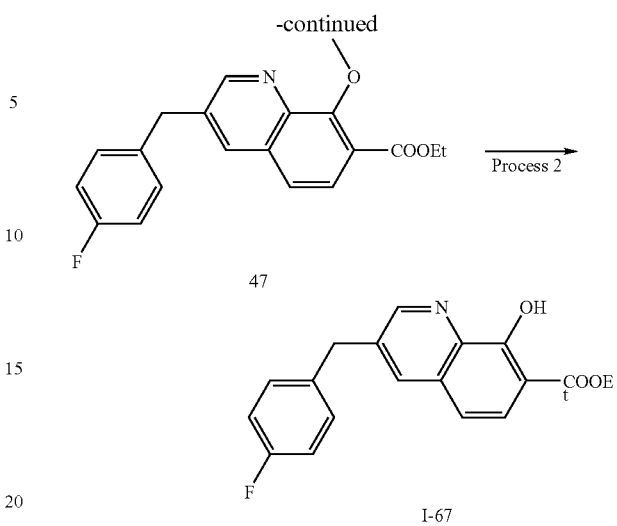

Process 1

1-Ethyl-3-(3-dimethylaminopropyl)carbodiimide hydrochloride (67 mg, 0.35 mmol) and 1-hydroxybenzotriazole (46 mg, 0.35 mmol) were added to a solution of compound 45 (100 mg, 0.29 mmol), which was synthesized in a same manner similar to Example 18, in DMF (10 ml), and the mixture was stirred at room temperature for 30 minutes. After ethanol (10 ml) and triethylamine (0.1 ml, 1 mmol) were added dropwise to the reaction mixture under ice-cooling, the mixture was refluxed for 30 minutes and concentrated under reduced pressure. The residue was extracted with ethyl acetate, washed with water and dried over magnesium sulfate. Removal of solvent under reduced pressure gave compound 46 (70 mg, 0.19 mmol, 65%) as pale yellow crystals.

Process 2

Aluminum chloride (48 mg, 0.36 mmol) was added to a solution of compound 46 (45 mg, 0.12 mmol) in dichloromethane (6 ml) under ice-cooling, and the mixture was stirred for 10 minutes. Ethanethiol (1 M in dichloromethane, 120 μl, 0.12 mmol) in dichloromethane was added dropwise to the reaction mixture, and the whole was stirred for 60 minutes. The reaction mixture was poured into ice-water and the whole was extracted with ethyl acetate. The organic layer was washed with sodium hydrogencarbonate solution, 1 N hydrochloric acid and water, and dried over sodium sulfate. Removal of solvent under reduced pressure gave a pale yellow crystalline residue, which was recrystallized from diethyl ether to give compound I-66 (22 mg, 0.061 mmol, 51%) as yellow crystals.

M.p.: 99–101° C. Recrystallization solvent: diethyl ether

Elemental analysis for $C_{19}H_{15}ClFNO_3(H_2O)_{0.5}$(diethyl ether)$_{0.02}$ Calcd. (%): C, 61.89; H, 4.41; N, 3.78; Cl, 9.57; F, 5.13. Found. (%): C, 61.84; H, 3.97; N, 3.80; Cl, 9.79; F, 4.73.

NMR (CDCl₃) δ: 1.45 (3H, t, J=7.2 Hz), 4.22 (2H, s), 4.45 (2H, dd, J=7.2, 7.2 Hz), 6.96–7.08 (2H, m), 7.16–7.24 (2H, m), 7.96 (1H, s), 8.28–8.32 (1H, m), 8.88–8.92 (1H, m).

Process 3

Triethylamine (122 mg, 1.2 mmol) and 10% palladium carbon (460 μg, 0.2%/w) were added to a solution of compound 46 (230 mg, 0.62 mmol) in methanol-DMF (10 ml-2 ml) under ice-cooling, and the mixture was stirred under 4 atm of hydrogen atmosphere for 96 hours. The reaction mixture was filtered, evaporated under reduced pressure, and extracted with ethyl acetate. The organic layer was washed with water and dried over magnesium sulfate. A crude product as a yellow oil obtained by evaporation under reduced pressure was subjected to silica gel column chromatography. The fractions containing desired compound eluted with hexane-ethyl acetate (2:1 v/v) were concentrated under reduced pressure to give compound 47 (56 mg, 0.172 mmol, 28%) as pale yellow crystals. Compound 47 (55 mg, 0.16 mmol) was reacted in a same manner similar to the process 2 to give compound I-67 (34 mg, 0.105 mmol, 65%).

M.p.: 103–105° C. Recrystallization solvent: diisopropyl ether

Elemental analysis for $C_{19}H_{16}FNO_3(H_2O)_{0.2}(HCl)_{0.08}$ Calcd. (%): C, 68.77; H, 5.01; N, 4.22; F, 5.72. Found. (%): C, 68;39; H, 4.79; N, 4.25; F, 5.43.

NMR (CDCl$_3$) δ: 1.46 (3H, t, J=7.2 Hz), 4.16 (2H, s), 4.48 (2H, dd, J=7.2, 7.2 Hz), 6.96–7.08 (2H, m), 7.16–7.24 (3H, m), 7.76–7.82 (1H, m), 7.86–7.90 (1H, m), 8.86–8.90 (1H, m).

Compounds I-68 and I-69 were synthesized in a same manner similar to Example 19.

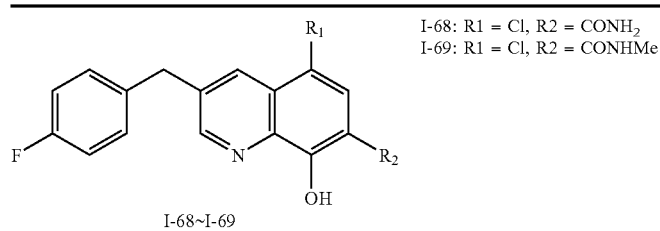

Compound I-68

M.p.: 226–228° C. Recrystallization solvent: diisopropyl ether

Elemental analysis for $C_{17}H_{12}ClFN_2O_2(H_2O)_{0.45}$ Calcd. (%): C, 60.08; H, 3.83; Cl, 10.74; N, 8.24; F, 5.59. Found. (%): C, 59.89; H, 3.42; Cl, 10.84; N, 8.10; F, 5.36.

NMR (CDCl$_3$) δ: 4.23 (2H, s), 5.60–6.0 (1H, brs), 7.00–7.20 (2H, m), 7.15–7.25 (2H, m), 7.50–7.80 (1H, brs), 8.20–8.35 (2H, m), 8.70–8.80 (1H, m).

Compound I-69

M.p.: 169–171° C. Recrystallization solvent: diisopropyl ether

NMR (CDCl$_3$) δ: 3.09 (3H, s), 4.22 (2H, s), 7.00–7.08 (2H, m), 7.12–7.25 (2H, m), 7.70–7.80 (1H, brs), 8.20–8.38 (2H, m), 8.68–8.80 (1H, m).

Example 20

Compound I-70

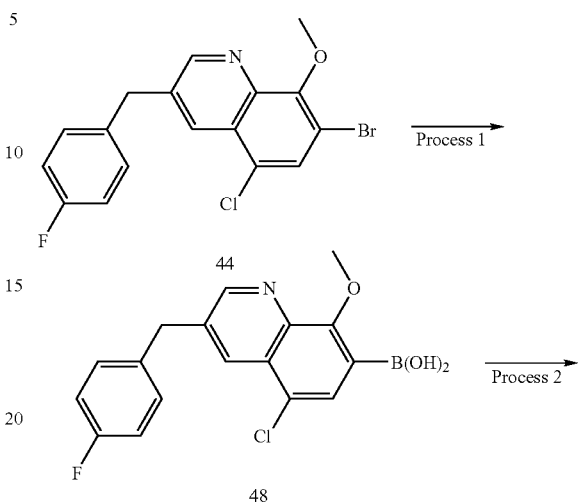

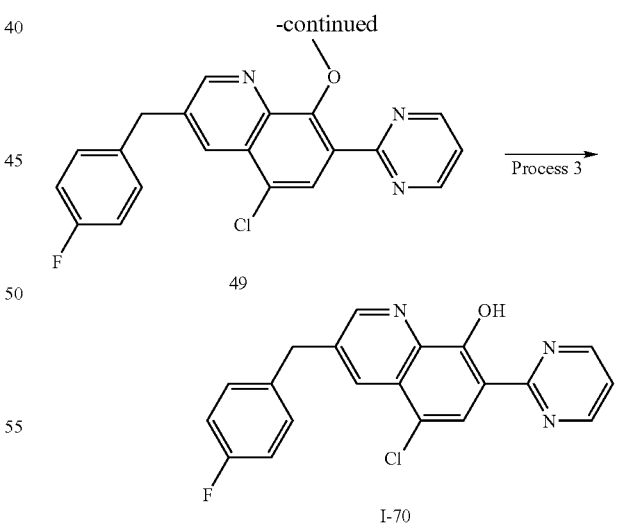

Process 1

Phenyl lithium (2 M cyclohexane solution, 1.8 ml, 3.6 mmol) was added to diethyl ether (25 ml), and the mixture was cooled to −78° C. A solution of compound 44 (700 mg, 1.84 mmol) in diethyl ether (10 ml) was added dropwise to the solution. After the mixture was stirred at −78° C. for 30 minutes, a solution of triisopropyl borate (383 mg, 3.7 mmol) in diethyl ether (2 ml) was added dropwise. After stirring for 30 minutes, the reaction mixture was allowed to warm to 0° C. and neutralized with 1 N hydrochloric acid. The whole was extracted with ethyl acetate, washed with water and dried over sodium sulfate. A crude product as a pale yellow oil obtained by evaporation under reduced pressure was subjected to silica gel column chromatography. The fractions containing desired compound eluted with hexane-ethyl acetate (1:2 v/v) were concentrated under reduced pressure to give compound 48 (70 mg, 0.2 mmol, 11%) as colorless crystals.

Process 2

Tetrakis(triphenylphosphine)palladium (0) (24 mg, 0.021 mmol), 2-bromopyrimidine (47.7 mg, 0.3 mmol) and 2 M sodium carbonate solution (110 μl, 0.22 mmol) were added to a solution of compound 48 (70 mg, 0.2 mmol) obtained by the process 1 in DME-ethanol (3 ml–2 ml) at room temperature, and the mixture was refluxed for 2 hours. After cooling, the reaction was quenched with ice-water, and the whole was extracted with ethyl acetate, washed with water and dried over magnesium sulfate. A crude product as a yellow oil obtained by evaporation under reduced pressure was subjected to silica gel column chromatography. The fractions containing desired compound eluted with hexane-ethyl acetate (2:1 v/v) were concentrated under reduced pressure to give compound 49 (40 mg, 0.11 mmol, 52%) as pale yellow crystals.

Process 3

Pyridine hydrochloride (100 mg, 0.87 mmol) was added to compound 49 (40 mg, 0.11 mmol) obtained by the process 2, and the mixture was stirred at 170° C. for 10 minutes. After cooling, ice water was added to the reaction mixture, and the whole was extracted with ethyl acetate, washed with water and dried over sodium sulfate. Removal of solvent under reduced pressure gave a pale yellow crystalline residue, which was recrystallized from diisopropyl ether to give compound I-70 (28 mg, 0.08 mmol, 70%) as pale yellow crystals.

M.p.: 204–207° C. Recrystallization solvent: diusopropyl ether

Elemental analysis for $C_{20}H_{13}ClFN_3O(H_2O)_{0.1}$ Calcd. (%): C, 65.35; H, 3.62; Cl, 9.64; N, 11.43; F, 5.17. Found. (%): C, 65.15; H, 3.48; Cl, 9.59; N, 11.19; F, 4.89.

NMR (CDCl$_3$) δ: 4.22 (2H, s), 6.98–7.06 (2H, m), 7.16–7.24 (2H, m), 7.31 (1H, t, J=4.8 Hz), 7.24–7.28 (1 H, m), 8.69(1H, s), 8.70–8.80 (1H, m), 8.88(2H, d, J=4.8 Hz).

Compound I-71 was synthesized in a same manner similar to Example 20.

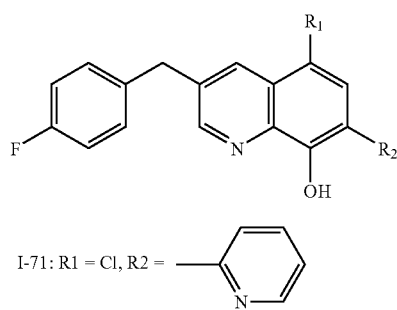

I-71: R1 = Cl, R2 = pyridyl

M.p.: 150–152° C. Recrystalihzation solvent: diisopropyl ether

Elemental analysis for $C_{21}H_{14}ClFN_2O(H_2O)_{0.25}$ Calcd. (%): C, 68.30; H, 3.96; Cl, 9.60; N, 7.59; F, 5.14. Found. (%): C, 68.27; H, 3.86; Cl, 9.41; N, 7.34; F, 4.85.

NMR (CDCl$_3$) δ: 4.22 (2H, s), 6.98–7.06 (2H, m), 7.16–7.26 (2H, m), 7.30–7.36 (1H, m), 7.88–8.00 (2H, m), 8.23 (1H, s), 8.60–8.64 (1H, m), 8.75–9.00 (1H, brs).

Example 22

Compound I-73

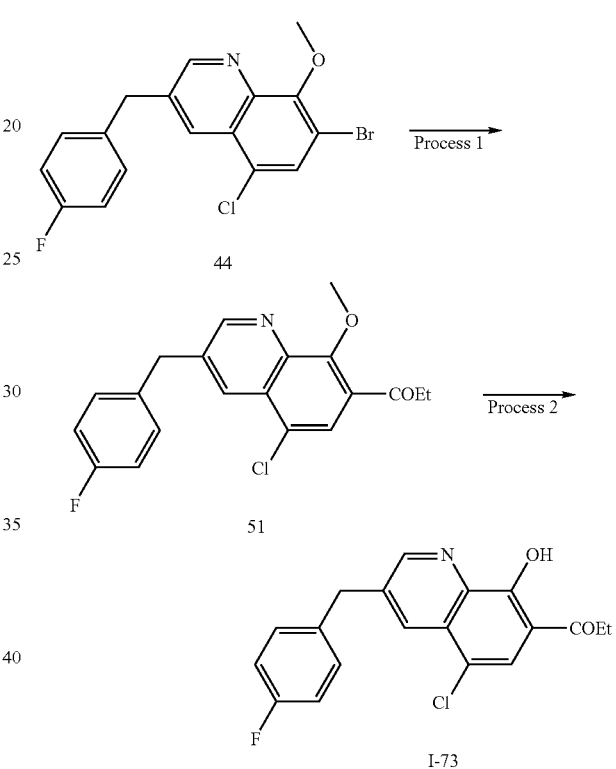

Process 1

Phenyl lithium (2 M cyclohexane solution, 0.5 ml, 1 mmol) was added to diethyl ether (15 ml), and the mixture was cooled to −78° C. A solution of compound 44 (190 mg, 0.5 mmol), synthesized in a same manner similar to Example 18, in diethyl ether (4 ml) was added dropwise to the solution. After the mixture was stirred at −78° C. for 30 minutes, a solution of propionyl chloride (92.5 mg, 1.0 mmol) in diethyl ether (2 ml) was added dropwise. After stirring for 30 minutes, the reaction was quenched with ammonium chloride solution. The whole was extracted with ethyl acetate, washed with water and dried over sodium sulfate. A crude product as a pale yellow oil obtained by evaporation under reduced pressure was subjected to silica gel column chromatography. The fractions containing desired compound eluted with hexane-ethyl acetate (3:1 v/v) were concentrated under reduced pressure to give compound 13 as a yellow oil. Compound 51 was reacted in a same manner similar to the process 3 of Example 20 to give compound I-73 (6 mg, 0.0174 mmol, 4%).

M.p: 125–127° C. Recrystallization solvent: ethyl acetate

Elemental analysis for $C_{16}H_{11}ClFNO_2(H_2O)_{0.25}$ Calcd. (%): C, 62.35; H, 3.76; N, 4.54; F, 6.16; Cl, 11.50. Found. (%): C, 62.26; H, 3.67; N, 4.58; F, 5.88; Cl, 11.52.

NMR (CDCl$_3$) δ: 1.30 (3H, t, J=7.2 Hz), 3.13 (2H, dd, J=7.2, 7.2 Hz), 4.22 (2H, s) 6.90–7.08 (2H, m), 7.16–7.24 (2H, m), 7.90 (1H, s), 8.20–8.24 (1H, m), 8.84–8.92 (1H, m).

Example 23

Compounds I-74, I-75

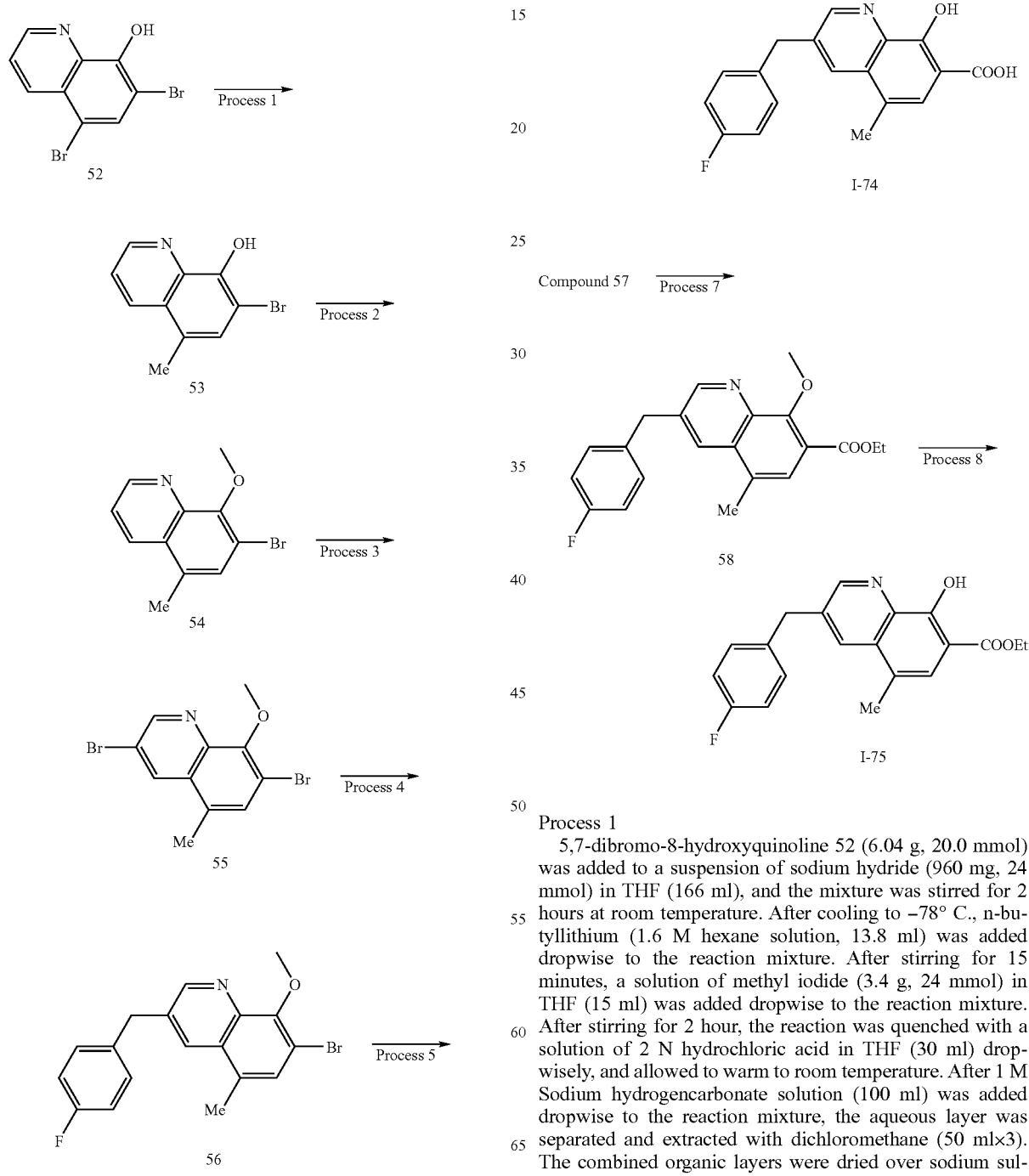

Process 1

5,7-dibromo-8-hydroxyquinoline 52 (6.04 g, 20.0 mmol) was added to a suspension of sodium hydride (960 mg, 24 mmol) in THF (166 ml), and the mixture was stirred for 2 hours at room temperature. After cooling to –78° C., n-butyllithium (1.6 M hexane solution, 13.8 ml) was added dropwise to the reaction mixture. After stirring for 15 minutes, a solution of methyl iodide (3.4 g, 24 mmol) in THF (15 ml) was added dropwise to the reaction mixture. After stirring for 2 hour, the reaction was quenched with a solution of 2 N hydrochloric acid in THF (30 ml) dropwisely, and allowed to warm to room temperature. After 1 M Sodium hydrogencarbonate solution (100 ml) was added dropwise to the reaction mixture, the aqueous layer was separated and extracted with dichloromethane (50 ml×3). The combined organic layers were dried over sodium sulfate. Removal of solvent under reduced pressure gave a crystalline residue, which was washed with chloroform-diisopropyl ether to give compound 53 (3.8 g, 16 mmol, 80%) as pale brown crystals.

Process 2

Potassium carbonate (4.2 g, 30.4 mmol) and methyl iodide (2.58 g, 18.2 mmol) were added to a solution of compound 53 (3.60 g, 15.2 mmol) obtained by the process 1 in DMF (30 ml), and the mixture was stirred for 3 hours at room temperature. After water was added to the reaction mixture, precipitated crystals were collected and washed with water. The crystals were dissolved in ethyl acetate, dried over magnesium sulfate and treated with active carbon. A crystalline residue was obtained by evaporation under reduced pressure. An aqueous filtrate were extracted with ethyl acetate, washed and dried. Removal of solvent under reduced pressure gave a purple oil. The crystalline residue and purple oil were combined and subjected to silica gel column chromatography. The fractions containing desired compound eluted with hexane-ethyl acetate (2:1 v/v) were concentrated under reduced pressure to give compound 54 (2.57 g, 10.2 mmol, 67%) as pale yellow crystals.

Process 3

Bromine (1.9 g, 11.2 mmol) was added to a solution of compound 54 (1.4 g, 5.6 mmol) obtained by the process 2 in carbon tetrachloride (8 ml) at room temperature, and the mixture was refluxed for 1 hour. After cooling to room temperature, pyridine (886 mg, 11.2 mmol) was added dropwise to the reaction mixture. The whole was refluxed for 4 hours, and an organic layer was separated by decantation after cooling. 2 N Sodium hydroxide solution (10 ml, 40 mmol) was added dropwise to the oily residue, and the whole was extracted with dichloromethane and washed, the combined organic layer were dried. A crude product as a oil obtained by evaporation under reduced pressure was subjected to silica gel column chromatography. The fractions containing desired compound eluted with hexane-ethyl acetate (3:1 v/v) were concentrated under reduced pressure to give compound 55 (470 mg, 1.4 mmol, 25%) as pale yellow crystals.

Process 4

Compound 43 (283 mg, 1.2 mmol) obtained by the process 3 of Example 8, 2 M potassium carbonate solution (1 ml, 2 mmol), palladium acetate (11 mg, 0.05 mmol) and triphenylphosphine (26.2 mg, 0.1 mmol) were added to a solution of compound 55 (331 mg, 1 mmol) obtained by the process 3 in DMF (4 ml) at room temperature, and the mixture was stirred for 30 minutes at 60° C. Compound 45 (28.3 mg, 0.12 mmol), palladium acetate (11 mg, 0.05 mmol) and triphenylphosphine (26.2 mg, 0.1 mmol) were added to the reaction mixture, and the whole was stirred under heating for 2 hours. After cooling, the reaction mixture was poured into ice water and the whole was extracted with ethyl acetate, washed and dried. A crude product as a yellow oil obtained by evaporation under reduced pressure was subjected to silica gel column chromatography. The fractions containing desired compound eluted with hexane-ethyl acetate (4:1 v/v) were concentrated under reduced pressure to give compound 56 (250 mg, 0.68 mmol, 68%) as pale yellow crystals.

Process 5

Compound 56 (290 mg, 0.81 mmol) was reacted in a same manner similar to the process 5 of Example 18 to give compound 57 (175 mg, 0.54 mmol, 66%) as pale yellow crystals.

Process 6

Compound 57 (50 mg, 0.15 mmol) was reacted in a same manner similar to the process 6 of Example 18 to give compound I-74 (36 mg, 0.12 mmol, 80%) as pale yellow crystals.

M.p.: 235–238° C. Recrystallization solvent: diisopropyl ether-ethyl acetate

Elemental analysis for $C_{18}H_{14}FNO_3(H_2O)_{0.2}$(ethyl acetate)$_{0.15}$ Calcd. (%): C, 68.08; H, 4.79; N, 4.23; F, 5.79. Found. (%): C, 68.23; H, 4.43; N, 4.23; F, 5.53.

NMR (DMSO-$d_6$) δ: 2.51 (3H, s), 4.24 (2H, s), 7.10–7.22 (2H, m), 7.30–7.50 (2H, m), 7.69 (1H, s), 8.34–8.44 (1H, m), 8.80–8.90 (1H, m).

Process 7

Compound 57 (115 mg, 0.35 mmol) was reacted in a same manner similar to the process 1 of Example 19 to give compound 58 (80 mg, 0.23 mmol, 65%) as pale yellow crystals.

Process 8

Compound 58 (80 mg, 0.23 mmol) was reacted in a same manner similar to the process 2 of Example 19 to give compound I-75 (19 mg, 0.06 mmol, 24%) as pale yellow crystals.

M.p.: 74–75° C. Recrystallization solvent: diisopropyl ether

NMR (CDCl$_3$) δ: 1.47 (3H, t, J=7.2 Hz), 2.51 (3H, s), 4.19 (2H, s), 4.48 (2H, dd, J=7.2, 7.2 Hz), 6.96–7.06 (2H, m), 7.14–7.22 (2H, m), 7.69 (1H, s), 7.76–8.00 (1H, m), 8.84–8.90 (1H, m).

Example 24

Compound I-76, I-77

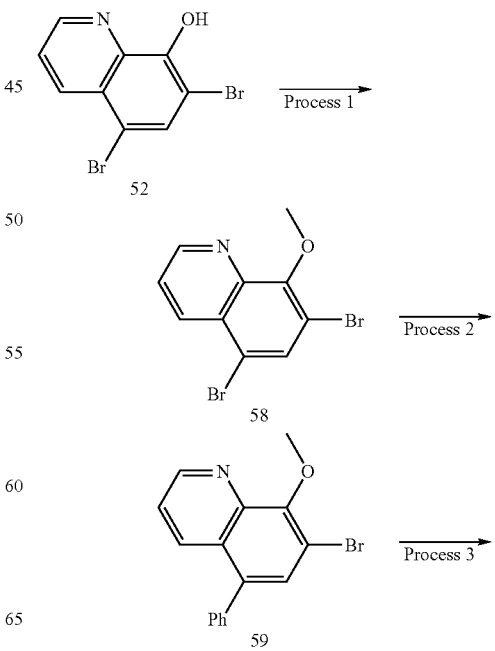

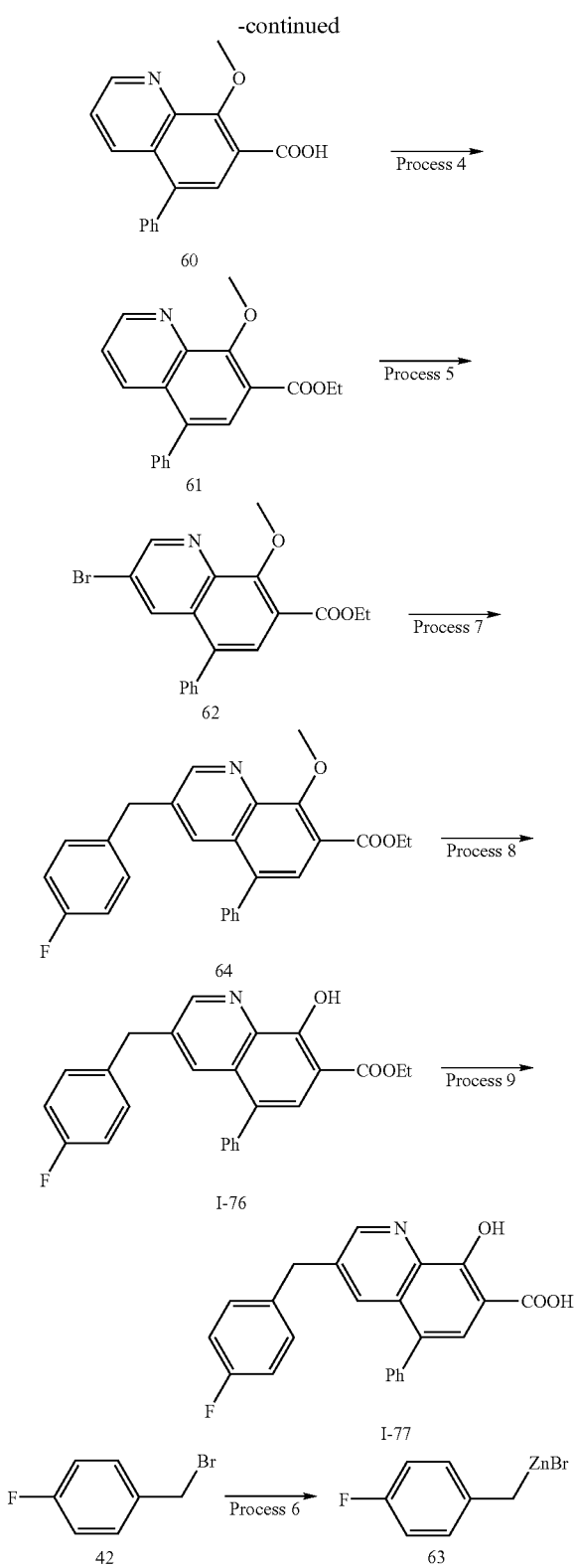

Process 1

Potassium carbonate (27.6 g, 200.0 mmol) and methyl iodide (15.6 g, 110 mmol) were added to a solution of 5,7-dibromo-8-hydroxyquinoline 52 (30.3 g, 100.0 mmol) in DMF (160 ml), and the mixture was stirred for 5 hours at room temperature. After water was added to the reaction mixture, precipitated crystals were collected and washed with water. The crystals were dissolved in ethyl acetate, dried over magnesium sulfate and treated with active carbon. The solvent was evaporated under reduced pressure to give crude compound 59 (28.3.0 g, 89.3 mmol, 89%) as colorless crystals.

Process 2

2 M potassium carbonate solution (10 ml, 20 mmol), tetrakis(triphenylphosphine)palladium (0) (350 mg, 0.3 mmol) and phenylboronic acid (1.46 g, 12 mmol) were added to a solution of compound 59 (3.17 g, 10 mmol) in toluene-methanol (100 ml–10 ml), and the mixture was stirred for 40 hours at 110° C. After the reaction mixture was poured into ice-water, the whole was stirred for 5 minutes, extracted with toluene, washed with water and dried over magnesium sulfate. A crude product as a yellow oil obtained by evaporation under reduced pressure was subjected to silica gel column chromatography. The fractions containing desired compound eluted with hexane-ethyl acetate (4:1 v/v) were concentrated under reduced pressure to give compound 60 (2.0 g, 6.4 mmol, 64%) as colorless crystals.

Process 3

Compound 60 (1.8 g, 5.7 mmol) was reacted in a same manner similar to the process 5 of Example 18 to give compound 61 (1.18 g, 4.2 mmol, 74%) as pale yellow. crystals.

Process 4

Compound 61 (860 mg, 3.1 mmol) was reacted in a same manner similar to the process 1 of Example 19 to give compound 62 (820 mg, 0.27 mmol, 86%) as pale yellow crystals.

Process 5

Compound 62 (830 mg, 2.7 mmol) was reacted in a same manner similar to the process 3 of Example 23 to give compound 64 (650 mg, 1.68 mmol, 62%) as pale yellow crystals.

Process 6

1,2-Dibromoethane (12 µl, 0.15 mmol), compound 42 (578 mg, 3 mmol) and chlorotrimethylsilane (12.5 µl, 0.1 mmol) were added to a suspension of zinc (210 mg, 3.23 mmol) in THF (3 ml), and the mixture was stirred for 20 minutes and left. The liquid above the precipitated zinc was used as compound 63 for the process 7.

Process 7

Palladium acetate (11 mg, 0.05 mmol), triphenylphosphine (26 mg, 0.1 mmol) and a solution of compound 63 in THF (2 ml) obtained by the process 6 were added to a solution of compound 64 (300 mg, 0.78 mmol) obtained by the process 5 in THF (10 ml), and the mixture was stirred for 90 minutes at 60° C. After cooling, the reaction mixture was quenched with sodium hydrogencarbonate solution, extracted with ethyl acetate, washed with water and dried over magnesium sulfate. A crude product as a yellow oil obtained by evaporation under reduced pressure was subjected to silica gel column chromatography. The fractions containing desired compound eluted with hexane-ethyl acetate (3:1 v/v) were concentrated under reduced pressure to give compound 65 (280 mg, 0.67 mmol, 86%) as a yellow oil.

Process 8

Compound 65 (280 mg, 0.67 mmol) was reacted in a same manner similar to the process 2 of Example 19 to give compound I-76 (91 mg, 0.23 mmol, 34%) as pale yellow crystals.

M.p.: 101–103° C. Recrystallization solvent: diisopropyl ether

Elemental analysis for $C_{25}H_{20}FNO_3(H_2O)_{0.2}$ Calcd. (%): C, 74.13; H, 4.85; N, 3.25; F, 4.35. Found. (%): C, 73.92; H, 4.85; N, 3.25; F, 4.35.

NMR (CDCl$_3$) δ: 1.44 (3H, t, J=7.2 Hz), 4.08 (2H, s), 4.48 (2H, dd, J=7.2, 7.2 Hz), 6.90–7.04 (2H, m), 7.05–7.14 (2H, m), 7.38–7.50 (5H, m), 7.85 (1H, s), 7.90–7.94 (1H, m), 8.80–8.84 (1H, m).

Process 9

4 N Lithium hydroxide solution (0.5 ml, 2 mmol) was added to a solution of compound I-76 (28 mg, 0.067 mmol) obtained by the process 8 in ethanol (2 ml), and the mixture was stirred for 3 hours at 70° C. A yellow residue obtained by evaporation under reduced pressure was extracted with ethyl acetate, washed with water and dried over sodium sulfate. The light green crystalline residue obtained by evaporation under reduced pressure was washed with ethyl acetate to give crude compound I-77 (20 mg, 0.054 mmol, 77%) as light green crystals.

M.p.: 221–224° C. Recrystallization solvent: ethyl acetate

NMR (DMSO-d$_6$) δ: 4.20 (2H, s), 7.06–7.20 (2H, m), 7.22–7.36 (2H, m), 7.38–7.56 (5H, m), 7.78 (1H, s), 8.10–8.18 (1H, m), 8.80–8.12 (1H, m).

Example 25

Compound I-78

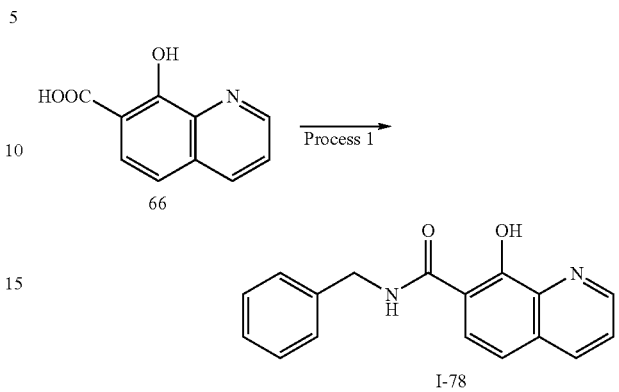

Process 1

1-Ethyl-3-(3-dimethylaminopropyl)carbodiimide hydrochloride (346 mg, 1.8 mmol) and 1-hydroxybenzotriazole (237 mg, 1.8 mmol) were added to a suspension of compound 66 (284 mg, 1.5 mmol) in DMF (10 ml), and the mixture was stirred for 30 minutes at room temperature. Benzylamine (171 mg, 1.6 mmol) was added dropwise to the reaction mixture under ice-cooling, and the whole was stirred for 60 minutes at room temperature. Ice-water was added to the reaction mixture and the whole was extracted with ethyl acetate, washed with water and dried over sodium sulfate. Removal of solvent under reduced pressure gave a crystalline residue, which was recrystallized from isopropanol to give compound I-78 (160 mg, 0.57 mmol, 38%) as pale yellow crystals.

M.p.: 125–127° C. Recrystallization solvent: isopropanol

Elemental analysis for $C_{18}H_{15}FN_2O_2$ Calcd. (%): C, 69.67; H, 4.87; N, 9.03; F, 6.12. Found. (%): C, 69.35; H, 4.77; N, 9.16; F, 5.99.

NMR (CDCl$_3$) δ: 4.75 (2H, s), 7.25–7.45 (6H, m), 7.50–7.58 (1H, m), 8.25–8.35 (3H, m), 8.80–8.88 (1H, m).

Compounds I-79–I-82 were synthesized in a same manner similar to Example 25.

Compound I-79

M.p.: 155–157° C. Recrystallization solvent: ethyl acetate

Elemental analysis for $C_{16}H_{12}N_2O_2$ Calcd. (%): C, 72.72; H, 4.58; N, 10.60. Found. (%): C, 72.57; H, 4.43; N, 10.67.

NMR (CDCl$_3$) δ: 7.12–7.20 (1H, m), 7.36–7.48 (3H, m), 7.56–7.60 (1H, m), 7.76–7.80 (2H, m), 8.20–8.38 (2H, m), 8.85–8.90 (1H, m), 9.86–9.96 (1H, brs).

Compound I-80

M.p.: 169–171° C. Recrystallization solvent: ethyl acetate

Elemental analysis for $C_{18}H_{16}N_2O_3(DMF)_{0.12}$ Calcd. (%): C, 69.34; H, 5.37; N, 9.34. Found. (%): C, 69.28; H, 5.18; N, 9.63.

NMR (DMSO-d$_6$) δ: 3.87 (3H, s), 4.56–4.6 (2H, m), 6.90–7.06 (2H, m), 7.24–7.31 (2H, m), 7.42–7.48 (1H, m), 7.64–7.70 (1H, m), 8.05–8.10 (1H, m), 8.36–8.40 (1H, m), 8.82–8.86 (1H, m), 9.20–9.30 (1H, m).

Compound I-81

M.p.: 218–220° C. Recrystallization solvent: chloroform

NMR (DMSO-d$_6$) δ: 4.50–4.6 (2H, m), 6.75–6.85 (2H, m), 7.26–7.30 (2H, m), 7.40–7.48 (1H, m), 7.62–7.70 (1H, m), 8.05–8.10 (1H, m), 8.36–8.40 (1H, m), (8.88–8.96 (1H, m), 9.48–9.28 (1H, m), 9.60–9.74 (1H, brs).

Compound I-82

M.p.: 156–158° C. Recrystallization solvent: ethyl acetate

Elemental analysis for $C_{18}H_{15}FN_2O_2$ Calcd. (%): C, 69.67; H, 4.87; N, 9.03; F, 6.12. Found. (%): C, 69.35; H, 4.77; N, 9.16; F, 5.99.

NMR (CDCl$_3$) δ: 2.94–3.00 (2H, m), 3.74–3.83 (2H, m), 6.98–7.06 (2H, m), 7.20–7.28 (2H, m), 7.38–7.40 (1H, m), 7.50–7.56 (1H, m), 7.84–7.94 (1H, brs), 8.12–8.20 (2H, m), 8.80–8.86 (1H, m).

Compounds I-83–I-104 were synthesized in a same manner similar to Example 10.

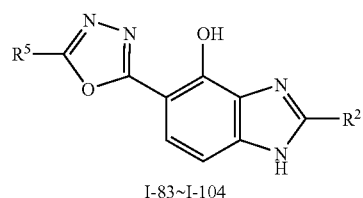

I-83~I-104

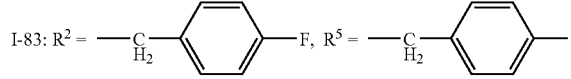 I-83: $R^2$ = —CH$_2$—C$_6$H$_4$—F, $R^5$ = —CH$_2$—C$_6$H$_4$—F

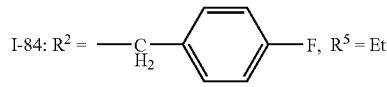 I-84: $R^2$ = —CH$_2$—C$_6$H$_4$—F, $R^5$ = Et

 I-85: $R^2$ = —CH$_2$—C$_6$H$_4$—F, $R^5$ = CH(CH$_3$)$_2$

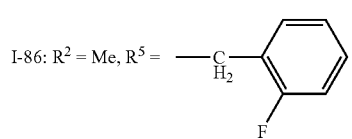 I-86: $R^2$ = Me, $R^5$ = —CH$_2$—C$_6$H$_4$—F

-continued

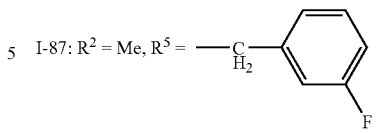 I-87: $R^2$ = Me, $R^5$ = —CH$_2$—C$_6$H$_4$—F

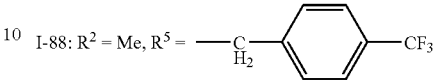 I-88: $R^2$ = Me, $R^5$ = —CH$_2$—C$_6$H$_4$—CF$_3$

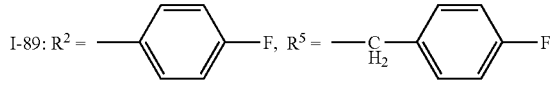 I-89: $R^2$ = —C$_6$H$_4$—F, $R^5$ = —CH$_2$—C$_6$H$_4$—F

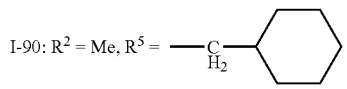 I-90: $R^2$ = Me, $R^5$ = —CH$_2$—C$_6$H$_{11}$

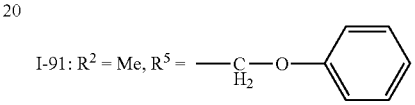 I-91: $R^2$ = Me, $R^5$ = —CH$_2$—O—C$_6$H$_5$

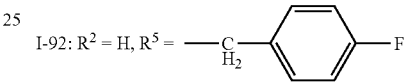 I-92: $R^2$ = H, $R^5$ = —CH$_2$—C$_6$H$_4$—F

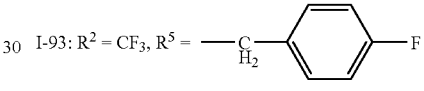 I-93: $R^2$ = CF$_3$, $R^5$ = —CH$_2$—C$_6$H$_4$—F

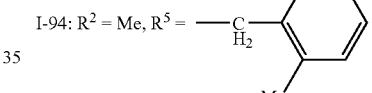 I-94: $R^2$ = Me, $R^5$ = —CH$_2$—C$_6$H$_4$—Me

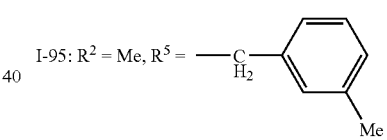 I-95: $R^2$ = Me, $R^5$ = —CH$_2$—C$_6$H$_4$—Me

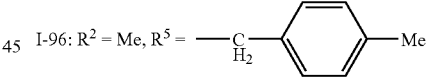 I-96: $R^2$ = Me, $R^5$ = —CH$_2$—C$_6$H$_4$—Me

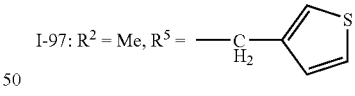 I-97: $R^2$ = Me, $R^5$ = —CH$_2$-thienyl

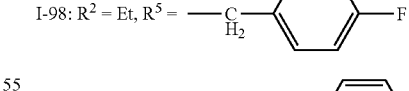 I-98: $R^2$ = Et, $R^5$ = —CH$_2$—C$_6$H$_4$—F

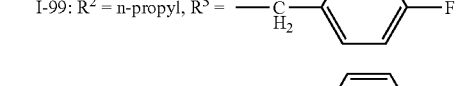 I-99: $R^2$ = n-propyl, $R^5$ = —CH$_2$—C$_6$H$_4$—F

 I-100: $R^2$ = isobutyl, $R^5$ = —CH$_2$—C$_6$H$_4$—F

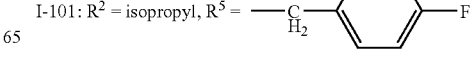 I-101: $R^2$ = isopropyl, $R^5$ = —CH$_2$—C$_6$H$_4$—F

-continued

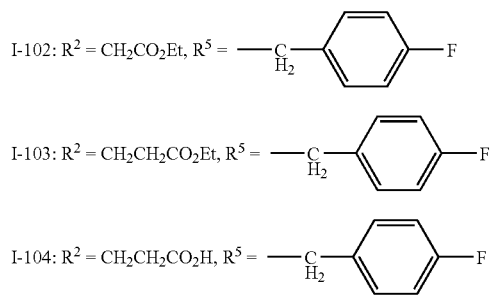

Compound I-83
M.p.: 220–224° C. Recrystallization solvent: ethanol
Elemental analysis for $C_{23}H_{16}F_2N_4O_2 \cdot 2H_2O$ Calcd. (%): C, 60.79; H, 4.44; N, 12.33; F, 8.36. Found. (%): C, 60.33; H, 3.66; N, 12.02; F, 8.04.
NMR (DMSO-$d_6$) δ: 4.35 (2H, s), 4.40 (2H, s), 7.17–7.24 (4H, m), 7.26 (1H, d, J=8.7 Hz), 7.42–7.48 (4H, m), 7.64 (1H, d, J=8.4 Hz).

Compound I-84
M.p.: 253–258° C. Recrystallization solvent: ethanol
Elemental analysis for $C_{18}H_{15}FN_4O_2$. Calcd. (%): C, 63.90; H, 4.47; F, 5.62; N, 16.56. Found. (%): C, 47.67; H, 4.18; F, 5.21; N, 12.31.
NMR (DMSO-$d_6$) δ: 1.08 (3H, t, J=7.5 Hz), 2.24 (2H, q, J=7.5 Hz), 4.43 (2H, s), 7.21 (1H, d, J=8.7 Hz), 7.24 (2H, d, J=8.7 Hz), 7.48 (2H, dd, J=8.7, 5.4 Hz), 7.93 (1H, d, J=8.7 Hz).

Compound I-85
M.p.: 242–246° C. Recrystallization solvent: isopropanol
Elemental analysis for $C_{19}H_{17}FN_4O_2 \cdot 0.5H_2O$ Calcd. (%): C, 63.15; H, 5.02; F, 5.26; N, 15.50. Found. (%): C, 63.27; H, 4.85; F, 5.14; N, 15.36.
NMR (DMSO-$d_6$) δ: 1.38 (6H, d, J=6.9 Hz), 3.30 (1H, quint, J=6.9 Hz), 4.27 (2H, s), 7.17 (1H, d, J=8.7 Hz), 7.20 (2H, dd, J=8.7, 1.2 Hz), 7.42 (2H, dd, J=9.0, 5.7 Hz), 7.61(1H, d, J=8.7 Hz).

Compound I-86
M.p.: 239–241° C. Recrystallization solvent: diisopropyl ether
Elemental analysis for $C_{17}H_{13}FN_4O_2 \cdot (H_2O)_{0.3}$ Calcd. (%): C, 61.93; H, 4.16; N, 16.99; F, 5.76. Found. (%): C, 61.94; H, 3.91; N, 16.85; F, 5.67.
NMR (DMSO-$d_6$) δ: 2.50 (3H, s), 4.40 (2H, s), 7.05 (1H, d, J=7.2 Hz), 7.18–7.29 (2H, m), 7.36–7.51 (3H, m), 12.51 (1H, br).

Compound I-87
M.p.: 283–284° C. Recrystallization solvent: methanol
Elemental analysis for $C_{17}H_{13}FN_4O_2(H_2O)_{0.2}$ Calcd. (%): C, 62.27; H, 4.12; N, 17.09; F, 5.79. Found. (%): C, 62.14; H, 3.85; N, 17.02; F, 5.67.
NMR (DMSO-$d_6$) δ: 2.51 (3H, s), 4.43 (2H, s), 7.09–7.19 (2H, m), 7.24–7.31 (2H, m), 7.40–7.49 (2H, m), 12.61 (1H, br).

Compound I-88
M.p.: 275–276° C. Recrystallization solvent: methanol
Elemental analysis for $C_{18}H_{13}F_3N_4O_2$ Calcd. (%): C, 57.76; H, 3.50; N, 14.97; F, 15.23. Found. (%): C, 57.71; H, 3.27; N, 15.00; F, 15.31.
NMR (DMSO-$d_6$) δ: 2.51 (3H, s), 4.52 (2H, s), 7.05 (1H, d, J=8.4 Hz), 7.48 (1H, d, J=8.4 Hz), 7.65 (2H, d, J=8.1 Hz), 7.76 (2H, d, J=8.1 Hz), 12.53 (1H, s).

Compound I-89
M.p.: 294–298° C. Recrystallization solvent: isopropanol
Elemental analysis for $C_{22}H_{14}F_2N_4O_2$. Calcd. (%): C, 65.35; H, 3.49; F, 9.40; N, 13.86. Found. (%): C, 54.37; H, 3.46; F, 8.40; N, 10.91.
NMR (DMSO-$d_6$) δ: 4.42 (2H, s), 7.19–7.25 (2H, m), 7.31 (1H, d, J=8.7 Hz), 7.45–7.52 (4H, m), 7.63 (1H, d, J=8.4 Hz), 8.29 (2H, dd, J=9.0, 5.4 Hz).

Compound I-90
M.p.: 252–254° C. Recrystallization solvent: ethanol
Elemental analysis for: $C_{17}H_{20}N_4O_2 \cdot (H_2O)_{0.3}$ Calcd. (%): C, 64.25; H, 6.53; N, 17.63. Found. (%): C, 64.02; H, 6.14; N, 17.53.
NMR (CD$_3$OD) δ: 1.06–1.36 (5H, m), 1.67–1.96 (6H, m), 2.86 (2H, d, J=6.9 Hz), 4.91 (3H, s), 7.14 (1H, d, J=8.4 Hz), 7.57 (1H, d, J=8.4 Hz).

Compound I-91
M.p.: 212–214° C. Recrystallization solvent: methanol
Elemental analysis for $C_{17}H_{14}N_4O_3 \cdot (H_2O)_{0.4}$ Calcd. (%): C, 61.93; H, 4.53; N, 17.00. Found. (%): C, 61.66; H, 4.10; N, 16.89.
NMR (CD$_3$OD) δ: 2.53 (3H, s), 5.41 (2H, s), 6.99–7.04 (1H, m), 7.08–7.15 (3H, m), 7.30–7.35 (2H, m), 7.58 (1H, d, J=8.7 Hz).

Compound I-92
M.p.: 249–252° C. Recrystallization solvent: methanol-acetonitrile-water
Elemental analysis for $C_{16}H_{11}FN_4O_2$ Calcd. (%): C, 61.93; H, 3.57; N, 18.06; F, 6.12. Found. (%): C, 61.58; H, 3.61; N, 18.04; F, 6.01.
NMR (DMSO-$d_6$) δ: 4.40 (2H, s), 7.22 (2H, m), 7.30 (1H, d, J=8.4 Hz), 7.47 (2H, m), 7.63 (1H, d, J=8.4 Hz), 8.68 (1H, s), 10.85 (1H, brs).
IR (KBr): 3427, 1639 cm$^{-1}$.

Compound I-93
M.p.: 279–281° C. Recrystallization solvent: ethyl acetate
Elemental analysis for $C_{17}H_{10}F_4N_4O_2$ Calcd. (%): C, 53.98; H, 2.66; N, 14.81; F, 20.09. Found. (%): C, 53.93; H, 2.57; N, 14.83; F, 19.80.
NMR (DMSO-$d_6$) δ: 4.40 (2H, s), 7.21 (2H, m), 7.29 (1H, d, J=8.4 Hz), 7.46 (2H, m), 7.73 (1H, d, J=8.4 Hz), 11.09 (1H, brs), 14.36 (1H, brs).
IR (KBr): 3400, 1644 cm$^{-1}$.

Compound I-94
M.p.: 119–121° C. Recrystallization solvent: ethanol
Elemental analysis for $C_{18}H_{16}N_4O_2$ Calcd. (%): C, 67.49; H, 5.03; N, 17.49. Found. (%): C, 63.81; H, 5.49; N, 15.71.
NMR (DMSO-$d_6$) δ: 2.36 (3H, s), 2.50 (3H, s), 4.35 (2H, s), 7.06 (2H, m), 7.21 (2H, m), 7.29 (1H, m), 7.43 (1H, m), 12.58 (1H, brs).

Compound I-95
M.p.: 222–224° C. Recrystallization solvent: ethanol
Elemental analysis for $C_{18}H_{16}N_4O_2$ Calcd. (%): C, 67.49; H, 5.03; N, 17.49. Found. (%): C, 66.77; H, 4.95; N, 17.28.
NMR (DMSO-$d_6$) δ: 2.30 (3H, s), 2.51 (3H, s), 4.32 (2H, s), 7.16 (5H, m), 7.45 (1H, d, J=7.8 Hz), 12.50 (1H, brs).

Compound I-96
M.p.: 257–259° C. Recrystallization solvent: ethanol
Elemental analysis for $C_{18}H_{16}N_4O_2$ Calcd. (%): C, 67.49; H, 5.03; N, 17.49. Found. (%): C, 66.27; H, 4.86; N, 17.17.

NMR (DMSO-d$_6$) δ: 2.29 (3H, s), 2.51 (3H, s), 4.32 (2H, s), 7.05 (1H, d, J=7.7 Hz), 7.18 (2H, d, J=7.8 Hz), 7.44 (1H, d, J=8.1 Hz), 7.18 (2H, d, J=7.8 Hz), 12.52 (1H, brs).

Compound I-97

M.p.: 250–252° C. Recrystallization solvent: methanol

Elemental analysis for C$_{15}$H$_{12}$N$_4$O$_2$S Calcd. (%): C, 57.68; H, 3.87; N, 17.94; S, 10.27. Found. (%): C, 57.54; H, 3.76; N, 17.79; S, 10.19.

NMR (CD$_3$OD) δ: 2.57 (3H, s), 4.37 (2H, s), 7.10 (1H, brs), 7.13–7.15 (1H, m), 7.37–7.38 (1H, m), 7.42–7.35 (1H, m), 7.53 (1H, d, J=8.4 Hz).

Compound I-98

M.p.: 202–205° C. Recrystallization solvent: ethanol

Elemental analysis for C$_{18}$H$_{15}$FN$_4$O$_2$ Calcd. (%): C, 63.90; H, 4.47; N, 16.56; F, 5.62. Found. (%): C, 64.08; H, 4.08; N, 16.55; F, 5.59.

NMR (CDCl$_3$) δ: 1.47 (3H, t, J=7.6 Hz), 3.00 (2H, q, J=7.6 Hz), 4.28 (2H, s), 7.06 (2H, m), 7.23 (1H, d, J=8.5 Hz), 7.35 (2H, m), 7.51 (1H, d, J=8.5 Hz).

Compound I-99

M.p.: 214–216° C. Recrystallization solvent: ethanol

Elemental analysis for C$_{18}$H$_{15}$FN$_4$O$_2$ Calcd. (%): C, 64.76; H, 4.86; N, 15.90; F, 5.39. Found. (%): C, 62.76; H, 4.55; N, 15.34; F, 5.17.

NMR (CDCl$_3$) δ: 1.04 (3H, t, J=7.4 Hz), 1.91 (2H, m, J=7.5 Hz), 2.93(2H, t, J=7.6 Hz), 4.27 (2H, s), 7.06 (2H, m), 7.22 (1H, d, J=8.4 Hz), 7.35 (2H, m), 7.50 (1H, d, J=8.6 Hz).

Compound I-100

M.p.: 224–226° C. Recrystallization solvent: ethanol

Elemental analysis for C$_{20}$H$_{19}$FN$_4$O$_2$ Calcd. (%): C, 65.56; H, 5.23; N, 15.29; F, 5.19. Found. (%): C, 65.49; H, 5.08; N, 15.20; F, 5.18.

NMR (CDCl$_3$) δ: 1.02 (6H, d, J=6.7 Hz), 2.26 (1H, m, J=6.7 Hz), 2.82 (2H, d, J=7.3 Hz), 4.28 (2H, s), 7.07 (2H, m), 7.23 (1H, d, J=8.5 Hz), 7.36 (2H, m), 7.51 (1H, d, J=8.5 Hz).

Compound I-101

M.p.: 221–223° C. Recrystallization solvent: ethanol

Elemental analysis for C$_{20}$H$_{19}$FN$_4$O$_2$ Calcd. (%): C, 64.76; H, 4.86; N, 15.90; F, 5.39. Found. (%): C, 64.68; H, 4.70; N, 15.87; F, 5.26.

NMR (CDCl$_3$) δ: 1.48 (6H, d, J=7.0 Hz), 3.28 (1H, m, J=7.0 Hz), 4.28 (2H, s), 7.07 (2H, m), 7.24 (1H, d, J=8.9 Hz), 7.36 (2H, m), 7.51 (1H, dd, J=8.5, 0.6 Hz).

Compound I-102

M.p.: 98–100° C. Recrystallization solvent: ethanol

Elemental analysis for C$_{20}$H$_{17}$FN$_4$O$_4$ Calcd. (%): C, 60.60; H, 4.32; N, 14.13; F, 4.79. Found. (%): C, 59.53; H, 4.19; N, 13.63; F, 4.68.

NMR (CDCl$_3$) δ: 1.34 (3H, t, J=7.1 Hz), 4.12(2H, s), 4.28 (2H, s), 4.29 (2H, q, J=7.2 Hz), 7.07 (2H, m), 7.20 (1H, d, J=9.5 Hz), 7.36 (2H, m), 7.54 (1H, d, J=9.5 Hz).

Compound I-103

M.p.: 179–181° C. Recrystallization solvent: ethanol

Elemental analysis for C$_{21}$H$_{19}$FN$_4$O$_4$ Calcd. (%): C, 61.46; H, 4.67; N, 13.65; F, 4.63. Found. (%): C, 60.98; H, 4.44; N, 13.49; F, 4.51.

NMR (CDCl$_3$) δ: 1.27 (3H, t, J=7.2 Hz), 2.91 (2H, m), 3.26 (2H, m), 4.20 (2H, q, J=7.2 Hz), 4.27(2H, s), 7.07 (2H, m), 7.18 (1H, d, J=8.5 Hz), 7.36 (2H, m), 7.51 (1H, d, J=8.5 Hz).

Compound I-104

Elemental analysis for C$_{19}$H$_{15}$FN$_4$O$_4$ Calcd. (%): C, 59.69; H, 3.95; N, 14.65; F, 4.97. Found. (%): C, 58.72; H, 3.73; N, 14.33; F, 4.78.

NMR (CDCl$_3$) δ: 2.92 (2H, t, J=7.4 Hz), 3.21 (2H, t, J=7.4 Hz), 4.31 (2H, s), 7.08 (2H, m), 7.17 (1H, d, J=8.8Hz), 7.40 (2H, m), 7.52 (1H, dd, J=8.4, 0.7 Hz).

Example 26

Compound I-105

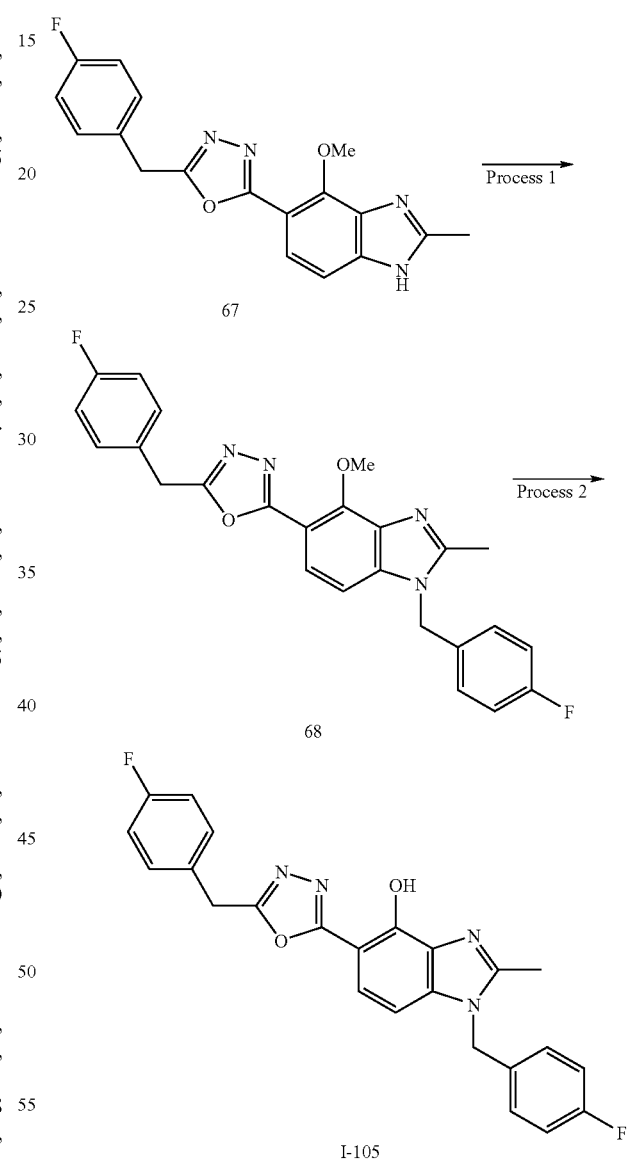

I-105

Process 1

Sodium hydride (60%, 68 mg, 1.70 mmol) and 4-fluorobenzylbromide (319 mg, 1.70 mmol) were added to a solution of compound 67 (440 mg, 1.30 mmol) in THF (4 ml)-DMF (1 ml) under ice-cooling, and the mixture was stirred for 1 hour under ice-cooling and for 3 hours at room temperature. The reaction mixture was quenched with water and extracted with ethyl acetate. The organic layer was separated, washed with water and dried over sodium sulfate. A crude product obtained by evaporation under reduced pressure was subjected to silica gel column chromatography. The fractions containing desired compound eluted with ethyl acetate were concentrated under reduced pressure. The crystalline residue was recrystallized from ethyl acetate. Compound 68 (191 mg, 0.430 mmol, 33%) as colorless crystals.

NMR (CDCl$_3$) δ: 2.57 (3H, s), 4.26(2H, s), 4.41 (3H, s), 5.28 (2H, s), 6.94 (1H, d, J=8.4 Hz), 7.01–7.06 (6H, m), 7.36 (2H, dd, J=9.0, 5.7 Hz), 7.71 (1H, d, J=8.4 Hz).

Process 2

Compound I-105 was synthesized in a same manner similar to the process 1 of Example 4.

M.p.: 244–246° C. Recrystallization solvent: methanol

Elemental analysis for C$_{24}$H$_{18}$F$_2$N$_4$O$_2$. Calcd. (%): C, 66.66; H, 4.20; F, 8.79; N, 12.96. Found. (%): C, 66.57; H, 4.13; F, 8.57; N, 12.92.

NMR (DMSO-d$_6$) δ: 2.53 (3H, s), 4.37 (2H, s), 5.48 (2H, s), 7.13–7.20 (6H, m), 7.21 (1H, d, J=9.0 Hz), 7.44 (2H, dd, J=8.7, 5.4 Hz), 7.52 (1H, d, J=8.7 Hz).

Compounds I-106–I-121 were synthesized in a same manner similar to Example 26.

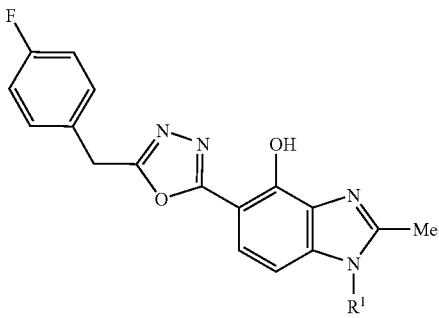

I-106~121
I-106: R$^1$ = n-propyl
I-107: R$^1$ = isopropyl
I-108: R$^1$ = Me
I-109: R$^1$ = CH$_2$OEt
I-110: R$^1$ = isobutyl
I-111: R$^1$ = CH$_2$CH$_2$CH$_2$CO$_2$Et
I-112: R$^1$ = CH$_2$CH$_2$CH$_2$CO$_2$H
I-113: R$^1$ = CH$_2$CO$_2$Et
I-114: R$^1$ = CH$_2$CO$_2$H
I-115: R$^1$ = CH$_2$CONH$_2$
I-116: R$^1$ = CH$_2$CONHEt
I-117: R$^1$ = CH$_2$CH$_2$CONH$_2$
I-118: R$^1$ = CH$_2$CH$_2$CH$_2$OCH$_2$CH=CH$_2$
I-119: R$^1$ = CH$_2$CH$_2$CH$_2$OH

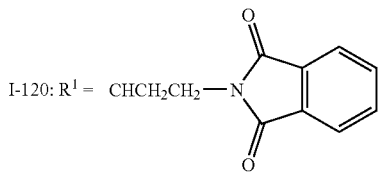

I-120: R$^1$ = CHCH$_2$CH$_2$—

I-121: R$^1$ = CONMe$_2$

Compound I-106

M.p.: 165–166° C. Recrystallization solvent: ethanol-diethyl ether

Elemental analysis for C$_{20}$H$_{19}$FN$_4$O$_2$ Calcd. (%): C, 65.56; H, 5.23; F, 5.19; N, 15.29. Found. (%): C, 65.70; H, 5.19; F, 5.05; N, 15.27.

NMR (DMSO-d$_6$) δ: 0.87 (3H, t, J=7.4 Hz), 1.73 (2H, sextet, J=7.2 Hz), 2.58 (3H, s), 4.14 (2H, t, J=7.2 Hz), 4.37 (2H, s), 7.16 (1H, d, J=8.4 Hz), 7.17–7.23 (2H, m), 7.45 (2H, dd, J=8.7, 5.4 Hz), 7.52 (1H, d, J=8.7 Hz).

Compound I-107

M.p.: 177–178° C. Recrystallization solvent: ethyl acetate-hexanhexane

Elemental analysis for C$_{20}$H$_{19}$FN$_4$O$_2$ Calcd. (%): C, 65.56; H, 5.23; F, 5.19; N, 15.29. Found. (%): C, 65.59; H, 5.19; F, 4.96; N, 15.22.

NMR (DMSO-d$_6$) δ: 1.55 (6H, d, J=6.9 Hz), 2.58 (3H, s), 4.37 (2H, s), 4.74 (1H, quint, J=6.9 Hz), 7.17–7.23 (2H, m), 7.29 (1H, d, J=8.7 Hz), 7.48 (2H, dd, J=8.4, 5.4 Hz), 7.48 (1H, d, J=8.4 Hz).

Compound I-108

M.p.: 240–243° C. Recrystallization solvent: ethanol

Elemental analysis for C$_{18}$H$_{15}$FN$_4$O$_2$ Calcd. (%): C, 63.90; H, 4.47; F, 5.62; N, 16.56. Found. (%): C, 63.63; H, 4.50; F, 5.46; N, 16.33.

NMR (DMSO-d$_6$) δ: 2.54 (3H, s), 3.73 (3H, s), 4.37 (2H, s), 7.14 (1H, d, J=8.4 Hz), 7.17–7.23 (2H, m), 7.45 (2H, dd, J=9.0, 5.4 Hz), 7.53 (1H, d, J=8.4 Hz).

Compound I-109

M.p.: 195–197° C. Recrystallization solvent: ethyl acetate

Elemental analysis for C$_{20}$H$_{19}$FN$_4$O$_3$ Calcd. (%): C, 62.82; H, 5.01; F, 4.97; N, 14.65. Found. (%): C, 62.64; H, 5.00; F, 4.83; N, 14.52.

NMR (CDCl$_3$) δ: 1.17 (3H, t, J=7.0 Hz), 2.68 (3H, s), 3.46 (2H, q, J=7.0 Hz), 4.37 (2H, s), 5.47 (2H, s), 7.01 (1H, d, J=8.7 Hz), 7.03–7.09 (2H, m), 7.35 (2H, dd, J=8.7, 5.4 Hz), 7.53 (1H, d, J=8.7 Hz).

Compound I-110

M.p.: 203–205° C. Recrystallization solvent: ethyl acetate

Elemental analysis for C$_{21}$H$_{21}$FN$_4$O$_2$.0.5H$_2$O Calcd. (%): C, 65.07; H, 5.67; F, 4.90; N, 14.45. Found. (%): C, 65.06; H, 5.52; F, 4.69; N; 14.42.

NMR (CDCl$_3$) δ: 0.96 (6H, d, J=6.6 Hz), 2.20 (1H, m), 2.62 (3H, s), 3.88 (2H, d J=7.5 Hz), 4.37 (2H, s), 6.87 (1H, d, J=8.4 Hz), 7.03–7.09 (2H, m), 7.35 (2H, dd, J=8.7, 5.4 Hz), 7.49 (1H, d, J=8.4 Hz).

Compound I-111

M.p.: 154–156° C. Recrystallization solvent: ethanol

Elemental analysis for C$_{23}$H$_{23}$FN$_4$O$_4$.1.1H$_2$O Calcd. (%): C, 60.28; H, 5.54; F, 4.15; N, 12.23. Found. (%): C, 59.97; H, 5.08; F, 4.37; N, 12.10.

NMR (CDCl$_3$) δ: 1.26 (3H, t, J=7.0 Hz), 2.10 (2H, quint, J=7.1 Hz), 2.36 (2H, t, J=6.7 Hz), 2.62 (3H, s), 4.15 (2H, q, J=7.2 Hz), 4.17 (2H, t, J=7.4 Hz), 4.27 (2H, s), 6.94 (1H, d, J=8.7 Hz), 7.03–7.09 (2H, m), 7.34 (2H, dd, J=8.7, 5.4 Hz), 7.51 (1H, d, J=8.7 Hz).

Compound I-112

M.p.: 219–221° C. Recrystallization solvent: methanol

Elemental analysis for C$_{21}$H$_{19}$FN$_4$O$_4$. Calcd. (%): C, 61.46; H, 4.67; F, 4.63; N, 13.65. Found. (%): C, 61.38; H, 4.57; F, 4.43; N, 13.59.

NMR (DMSO-d$_6$) δ: 1.92 (2H, quint, J=7.3 Hz), 2.30 (2H, t, J=7.2 Hz), 2.55 (3H, s), 4.19 (2H, t, J=7.3 Hz), 4.37 (2H, s), 7.17 (1H, d, J=8.4 Hz), 7.17–7.23 (2H, m), 7.45 (2H, dd, J=8.7, 5.4 Hz), 7.53 (1H, d, J=8.7 Hz).

Compound I-113

M.p.: 246–248° C. Recrystallization solvent: methanol

Elemental analysis for $C_{21}H_{19}FN_4O_4$. Calcd. (%): C, 61.46; H, 4.67; F, 4.63; N, 13.65. Found. (%): C, 61.26; H, 4.58; F, 4.45; N, 13.52.

NMR (DMSO-$d_6$) δ: 1.22 (3H, t, J=7.2 Hz), 2.51 (3H, s), 4.18 (2H, q, J=7.1 Hz), 4.37 (2H, s), 5.21 (2H, s), 7.14 (1H, d, J=8.7 Hz), 7.17–7.23 (2H, m), 7.45 (2H, dd, J=8.7, 5.4 Hz), 7.53 (1H, d, J=8.4 Hz).

Compound I-114

M.p.: 291–292° C. Recrystallization solvent: methanol

Elemental analysis for $C_{19}H_{15}FN_4O_4 \cdot 1.4H_2O$ Calcd. (%): C, 55.99; H, 4.40; F, 4.66; N, 13.75. Found. (%): C, 55.69; H, 4.10; F, 4.45; N, 13.49.

NMR (DMSO-$d_6$) δ: 2.48 (3H, s), 4.37 (2H, s), 5.09 (2H, s), 7.14 (1H, d, J=8.7 Hz), 7.17–7.23 (2H, m), 7.45 (2H, dd, J=8.7, 5.4 Hz), 7.52 (1H, d, J=8.7 Hz).

Compound I-115

M.p.: 292–297° C. Recrystallization solvent: ethanol

Elemental analysis for $C_{19}H_{16}FN_5O_3 \cdot 1.0H_2O$ Calcd. (%): C, 57.14; H, 4.54; F, 4.76; N, 17.54. Found. (%): C, 56.99; H, 4.22; F, 5.04; N, 17.49.

NMR (DMSO-$d_6$) δ: 2.48 (3H, s), 4.37 (2H, s), 4.84 (2H, s), 7.06 (1H, d, J=8.7 Hz), 7.17–7.23 (2H, m), 7.40 (1H, brs), 7.45 (2H, dd, J=8.7, 5.4 Hz), 7.52 (1H, d, J=8.7 Hz), 7.78 (1H, brs).

Compound I-116

M.p.: 292–295° C. Recrystallization solvent: ethanol

Elemental analysis for $C_{21}H_{20}FN_5O_3 \cdot 0.8H_2O$ Calcd. (%): C, 59.51; H, 5.14; F, 4.48; N, 16.52. Found. (%): C, 59.56; H, 4.73; F, 4.31; N, 16.69.

NMR (DMSO-$d_6$) δ: 1.04 (3H, t, J=7.2 Hz), 2.48 (3H, s), 3.07–3.16 (2H, m), 4.37 (2H, s), 4.83 (2H, s), 7.05 (1H, d, J=8.4 Hz), 7.17–7.23 (2H, m), 7.45 (2H, dd, J=8.7, 5.4 Hz), 7.52 (1H, d, J=8.7 Hz), 8.35 (1H, t, J=5.3 Hz).

Compound I-117

M.p.: 270–272° C. Recrystallization solvent: methanol

Elemental analysis for $C_{21}H_{20}FN_5O_3 \cdot 0.2H_2O$ Calcd. (%): C, 61.07; H, 4.98; F, 4.60; N, 16.96. Found. (%): C, 61.15; H, 4.87; F, 4.44; N, 16.74.

NMR (DMSO-$d_6$) δ: 1.91 (2H, quint, J=6.9 Hz), 2.11 (2H, t, J=7.2 Hz), 2.56 (3H, s), 4.17 (2H, t, J=7.2 Hz), 4.37 (2H, s), 6.81 (1H, brs), 7.17 (1H, d, J=8.4 Hz), 7.17–7.23 (2H, m), 7.45 (2H, dd, J=8.7, 5.7 Hz), 7.52 (1H, d, J=8.4 Hz).

Compound I-118

M.p.: 128–130° C. Recrystallization solvent: ethanol-diethyl ether

Elemental analysis for $C_{23}H_{23}FN_4O_3$. Calcd. (%): C, 65.39; H, 5.49; F, 4.50; N, 13.26. Found. (%): C, 65.36; H, 5.34; F, 4.38; N, 13.19.

NMR (CDCl$_3$) δ: 2.06 (2H, quint, J=6.1 Hz), 2.64 (3H, s), 3.33 (2H, t, J=5.6 Hz), 3.92–3.95 (2H, m), 4.25 (2H, t, J=6.6 Hz), 4.27 (2H, s), 5.19–5.32 (2H, m), 5.87–5.97 (1H, m), 6.93 (1H, d, J=8.4 Hz), 7.03–7.08 (2H, m), 7.35 (2H, dd, J=8.7, 5.7 Hz), 7.50 (1H, d, J=8.7 Hz).

Compound I-119

M.p.: 146–148° C. Recrystallization solvent: ethanol

Elemental analysis for $C_{20}H_{19}FN_4O_3 \cdot 1.2H_2O$ Calcd. (%): C, 59.46; H, 5.34; F, 4.70; N, 13.87. Found. (%): C, 59.69; H, 5.45; F, 4.66; N, 12.92.

NMR (CDCl$_3$) δ: 2.04 (2H, quint, J=6.2 Hz), 2.66 (3H, s), 3.64 (2H, t, J=5.7 Hz), 4.27 (2H, s), 4.28 (2H, t, J=6.6 Hz), 6.97 (1H, d, J=8.4 Hz), 7.03–7.08 (2H, m), 7.35 (2H, dd, J=8.7, 5.4 Hz), 7.51 (1H, d, J=8.7 Hz).

Compound I-120

M.p.: 246–247° C. Recrystallization solvent: methanol

Elemental analysis for $C_{28}H_{22}FN_5O_4$ Calcd. (%): C, 65.75; H, 4.34; F, 3.71; N, 13.69. Found. (%): C, 65.66; H, 4.34; F, 3.69; N, 13.69.

NMR (DMSO-$d_6$) δ: 2.08 (2H, quint, J=6.9 Hz), 2.55 (3H, s), 3.66 (2H, t, J=7.1 Hz), 4.29 (2H, t, J=7.2 Hz), 4.37 (2H, s), 7.17–7.23 (2H, m), 7.19 (1H, d, J=8.7 Hz), 7.45 (2H, dd, J=8.7, 5.4 Hz), 7.50 (1H, d, J=8.7 Hz), 7.78–7.85 (4H, m).

Compound I-121

M.p.: 245–249° C. Recrystallization solvent: ethanol-ethyl acetate

NMR (CDCl$_3$—CD$_3$OD) δ: 2.67 (3H, s), 2.82–3.35 (6H, brs), 4.29 (2H, s), 6.88 (1H, d, J=8.7 Hz), 7.03–7.09 (2H, m), 7.45 (2H, dd, J=8.7, 5.4 Hz), 7.59 (1H, d, J=8.7 Hz).

Example 27

Compound I-122

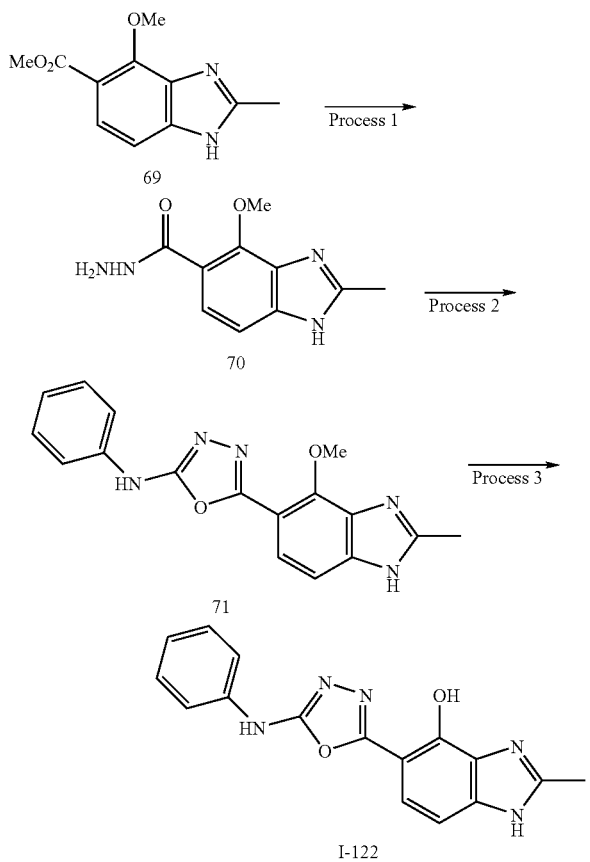

Process 1

Hydrazine monohydrate (16.3 ml) was added to a solution of compound 69 (5.97 g, 27.1 mmol) in ethanol (81 ml), and the mixture was refluxed for 2 hours. Hydrazine monohydrate (16.3 ml) was added to the reaction mixture and refluxed for 3 hours. Removal of solvent under reduced pressure gave a dark brown crystalline residue, which was washed with isopropanol to give compound 70 (5.28 g, 24.0 mmol, 88%) as pale brown crystals.

NMR (DMSO-d$_6$) δ: 2.49 (3H, s), 4.36 (3H, s), 4.49 (2H, brs), 7.11 (1H, d, J=8.4 Hz), 7.59 (1H, d, J=8.4 Hz), 9.14 (1H, brs), 12.45 (1H, brs).

Process 2

Phenyl isothiocyanate (92 mg, 0.681 mmol) was added to a solution of compound 70 (150 mg, 0.681 mmol) in toluene (3 ml)-THF (3 ml)-DMF (3 ml), and the mixture was stirred for 30 minutes at 80° C. Dicyclohexylcarbodiimide (155 mg, 0.749 mmol) was added to the reaction mixture and the whole was stirred for 16 hours at 80° C. The reaction mixture was quenched with water and extracted with ethyl acetate. The organic layer was separated, washed with water and brine, and dried over sodium sulfate. A crude product obtained by evaporation under reduced pressure was subjected to silica gel column chromatography. The fractions containing desired compound eluted with chloroform-methanol (9:1 v/v) were concentrated under reduced pressure. The crystalline residue was recrystallized from isopropanol to give compound 71 (143 mg, 0.445 mmol, 65%) as colorless crystals.

M.p.: 231.5–233° C. Recrystallization solvent: isopropanol

Elemental analysis for C$_{17}$H$_{15}$N$_5$O$_2$ Calcd. (%): C, 63.54; H, 4.71; N, 21.79. Found. (%): C, 63.18; H, 4.67; N, 21.35.

NMR (DMSO-d$_6$) δ: 2.53 (3H, s), 4.32 (3H, brs), 6.98–7.03 (1H, m), 7.24 (1H, brs), 7.34–7.39 (2H, m), 7.51 (1H, d, J=8.7 Hz), 7.63 (2H, d, J=8.7 Hz), 10.57 (1H, brs), 12.65 (1H, brs).

Process 3

Compound I-122 (75 mg, 0.244 mmol) was synthesized as colorless crystals from compound 71 (358 mg, 1.11 mmol, 22%) in a same manner similar to the process 1 of Example 4.

M.p.: >300° C. Recrystallization solvent: methanol

Elemental analysis for C$_{16}$H$_{13}$N$_5$O$_2$.(H$_2$O)$_{0.5}$ Calcd. (%): C, 60.75; H, 4.46; N, 22.14. Found. (%): C, 60.55; H, 4.49; N, 21.77.

NMR (CD$_3$OD) δ: 2.61 (3H, s), 7.05–7.16 (2H, m), 7.36–7.41 (2H, m), 7.50–7.58 (3H, m).

Compound I-123 was synthesized in a same manner similar to Example 27.

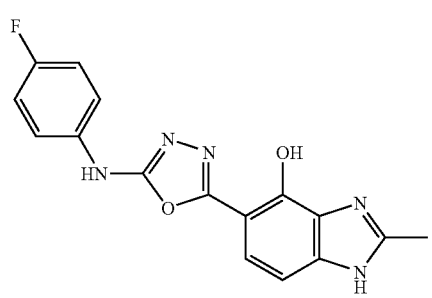

I-123

Compound I-123

M.p.: >300° C. Recrystallization solvent: methanol

Elemental analysis for C$_{16}$H$_{12}$NF$_5$O$_2$.(H$_2$O)$_{1.0}$ Calcd. (%): C, 55.98; H, 4.11; N, 20.40; F, 5.53. Found. (%): C, 56.01; H, 4.23; N, 20.16; F, 5.31.

NMR (DMSO-d$_6$) δ: 2.57 (3H, s), 7.18–7.26 (3H, m), 7.47 (1H, d, J=8.4 Hz), 7.62–7.67 (2H, m), 10.81 (1H, brs).

Example 28

Compound I-124

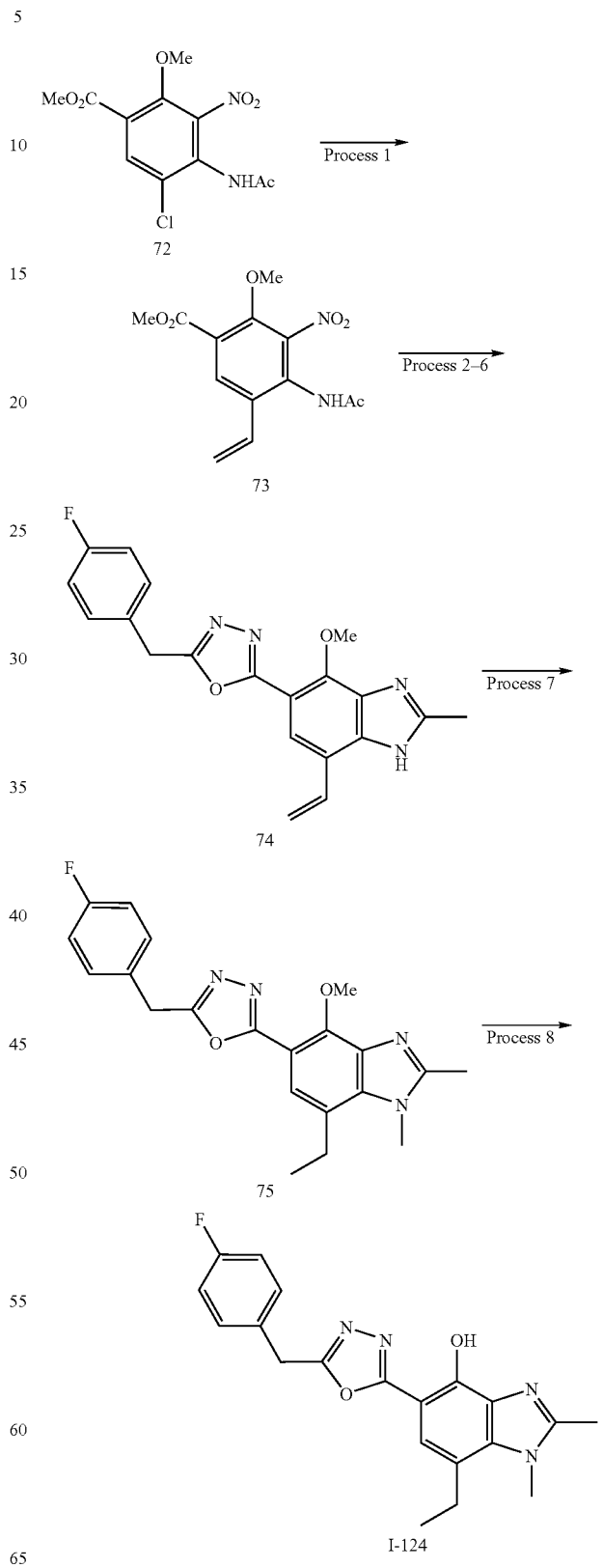

Process 1

A solution of tri-tert-butylphosphine (133 mg, 0.605 mmol) in dioxane (6 ml) and tributylvinylstannane (3.15 ml, 10.5 mmol) were added to a suspension of compound 72 (3.03 g, 10.0 mmol), cesium fluoride (3.45 g, 22.7 mmol) and tris(dibenzylidene acetone)dipalladium (0) (137 mg, 0.150 mmol) in dioxane (6 ml) at room temperature, and the mixture was stirred for 24 hours at 100° C. The reaction mixture was filtered through silica gel and a remained residue was washed with ethyl acetate. A crude product obtained by evaporation under reduced pressure was subjected to silica gel column chromatography. The fractions containing desired compound eluted with hexane-ethyl acetate (2:1 v/v) were concentrated under reduced pressure to give compound 73 (419 mg, 14%) as yellow crystals.

NMR (CDCl$_3$) δ: 3.13 (3H, s), 3.98 (3H, s), 4.01 (3H, s), 5.57 (1H, d, J=10.8 Hz), 5.92 (1H, d, J=17.4 Hz), 6.57 (1H, d, J=10.8, 17.4 Hz), 8.25 (1H, s).

Process 2–6

Compound 74 was synthesized in a same manner similar to Example 3 and 9.

Process 7

A suspension of compound 74 (153 mg, 0.420 mmol) and 10% palladium carbon (16.4 mg) in methanol (5 ml) was stirred under 1 atm of hydrogen atmosphere for 3 hours at room temperature. The reaction mixture was filtered, evaporated under reduced pressure, and subjected to silica gel column chromatography. The fractions containing desired compound eluted with ethyl acetate-methanol (30:1 v/v) were concentrated under reduced pressure to give compound 75 (111 mg, 72%) as colorless crystals.

NMR (CDCl$_3$) δ: 1.34 (3H, t, J=7.4 Hz), 2.66 (3H, s), 3.03 (2H, q, J=7.4 Hz), 3.96 (3H, s), 4.19 (3H, s), 4.28 (2H, s), 7.04 (2H, m), 7.38 (2H, m), 7.54 (1H, s).

Process 8

Compound I-124 (71 mg, 64%) was synthesized as colorless crystals from compound 75 (111 mg, 0.303 mmol) in a same manner similar to the process 1 of Example 4.

M.p.: 181–182° C. Recrystallization solvent: acetonitrile

Elemental analysis for C$_{19}$H$_{17}$FN$_4$O$_2$ Calcd. (%): C, 64.76; H, 4.86; N, 15.90; F, 5.39. Found. (%): C, 65.15; H, 5.01; N, 15.32; F, 5.13.

NMR (DMSO-d$_6$) δ: 1.26 (3H, t, J=7.4 Hz), 2.54 (3H, s), 3.02 (2H, q, J=7.4 Hz), 3.91 (3H, s), 4.37 (2H, s), 7.21 (2H, m), 7.27 (1H, s), 7.44 (2H, m), 10.39 (1H, brs).

IR (KBr): 3421, 1621 cm$^{-1}$.

Example 29

Compound I-125

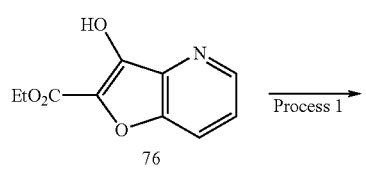

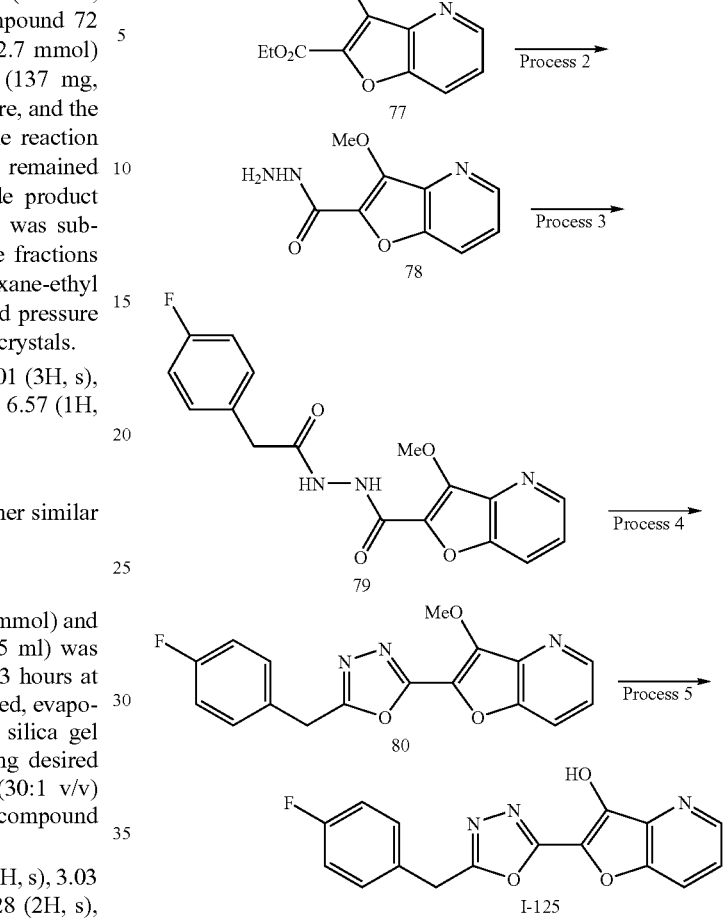

Process 1

Methyl iodide was added (3.50 ml, 56.2 mmol) to a suspension of compound 76 (3.85 g, 18.6 mmol) described in the literature (J. Heterocycl. Chem., 23, 665–668, (1986)) and potassium carbonate (5.14 g, 37.2 mmol) in acetone-DMF (4:1 v/v, 75 ml) at room temperature, and the mixture was refluxed for 2 hours. After the reaction reaction mixture was neutralized with 2 N hydrochloric acid under ice-cooling, and the whole was extracted with ethyl acetate. The organic layer was dried over sodium sulfate. A crude product obtained by evaporation under reduced pressure was subjected to silica gel column chromatography. The fractions containing desired compound eluted with hexane-ethyl acetate (2:1 v/v) were concentrated under reduced pressure. The crystalline residue was recrystallized from diisopropyl ether-hexane to give compound 77 (2.45 g, 60%) as colorless crystals.

NMR (CDCl$_3$) δ: 1.44 (3H, t, J=7.2 Hz), 4.47 (2H, q, J=7.2 Hz), 4.57 (3H, s), 7.38 (1H, dd, J=4.5, 8.7 Hz), 7.80 (1H, dd, J=1.2, 8.7 Hz), 8.61 (1H, dd, J=1.2, 4.5 Hz).

Process 2

Hydrazine monohydrate (5 ml) was added to a solution of compound 77 (2.37 g, 10.7 mmol) in ethanol (25 ml) at room temperature, and the mixture was refluxed for 1 hour. After the reaction mixture was cooled to 0° C., precipitated crystals were collected and washed with ethanol to give compound 78 (1.59 g, 72%) as colorless crystals.

Process 3

1-Ethyl-3-(3-dimethylaminopropyl)carbodiimide hydrochloride (1.66 g, 8.66 mmol) was added to a suspension of compound 78 (1.59 g, 7.67 mmol), p-fluorophenylacetic acid (1.33 g, 8.46 mmol) and 1-hydroxybenzotriazole (203 mg, 1.50 mmol) in THF-DMF (4:1 v/v, 37.5 ml) at room temperature, and the mixture was stirred for 2 hours. Water (75 ml) was added dropwise to the reaction mixture at room temperature. After water (75 ml) was added under ice-cooling, precipitated crystals were collected and washed with water to give compound 79 (2.36 g, 90%) as colorless crystals.

NMR (DMSO-$d_6$) δ: 3.55 (2H, s), 4.42 (3H, s), 7.16 (2H, m), 7.37 (2H, m), 7.55 (1H, dd, J=4.7, 8.6 Hz), 8.11 (1H, dd, J=1.2, 8.7 Hz), 8.65 (1H, dd, J=1.2, 4.7 Hz), 9.96 (1H, brs), 10.30 (1H, brs).

Process 4

A mixture of compound 79 (314 mg, 0.915 mmol) and phosphorus oxychloride (3 ml) was refluxed for 3 hours. Removal of an excess of phosphorus oxychloride under reduced pressure gave the residue, which was added ice-water and neutralized with 1 N sodium hydroxide solution. Precipitated crystals were collected, washed with water and recrystallized from ethyl acetate to give compound 80 (205 mg, 69%) as pale brown crystals.

NMR (CDCl$_3$) δ: 4.30 (2H, s), 4.57 (3H, s), 7.06 (2H, m), 7.36 (3H, m), 7.80 (1H, m), 8.62 (1H, m).

Process 5

Compound I-125 (82%) was synthesized as a colorless crystal in a same manner similar to the process 1 of Example 4.

M.p.: 220–223° C. Recrystallization solvent: acetonitrile

Elemental analysis for $C_{16}H_{10}FN_3O_3$ Calcd. (%): C, 61.74; H, 3.24; N, 13.50; F, 6.10. Found. (%): C, 61.73; H, 2.92; N, 13.51; F, 5.92.

NMR (DMSO-$d_6$) δ: 4.40 (2H, s), 7.22 (2H, m), 7.44 (2H, m), 7.54 (1H, dd, J=4.5, 8.4 Hz), 7.80 (1H, dd, J=1.2, 8.4 Hz), 8.65 (1H, dd, J=1.2, 4.5 Hz), 11.71 (1H, brs).

IR (KBr): 3431, 1651 cm$^{-1}$.

Example 30

Compound I-126

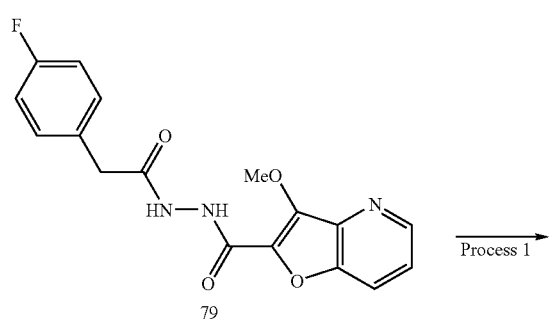

79

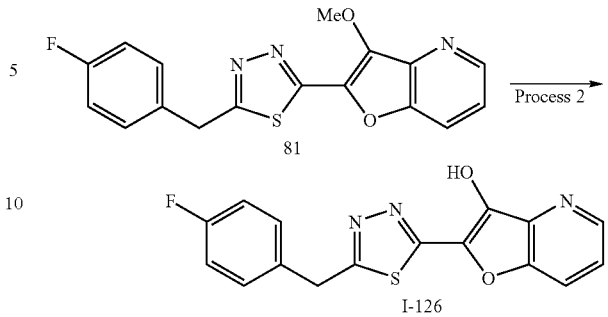

81

I-126

Process 1

Lawesson's reagent (1.20 g, 2.82 mmol) was added to a suspension of compound 79 (482 mg, 1.40 mmol) in toluene (10 ml) at room temperature, and the mixture was refluxed for 1 hour. A crude product obtained by evaporation under reduced pressure was subjected to silica gel column chromatography. The fractions containing desired compound eluted with chloroform-methanol (50:1 v/v) were concentrated under reduced pressure. The crystalline residue was recrystallized from ethyl acetate-hexane to give compound 81 (383 mg, 88%) as colorless crystals.

NMR (CDCl$_3$) δ: 4.49 (2H, s), 4.55 (3H, s), 7.06 (2H, m), 7.33 (2H, m), 7.34 (1H, dd, J=4.7, 8.4 Hz), 7.83 (1H, dd, J=1.2, 8.4 Hz), 8.58 (1H, dd, J=1.2, 4.7 Hz).

Process 2

Compound I-126 (86%) was synthesized as pale brown crystals in a same manner similar to the process 1 of Example 4.

M.p.: 261–265° C. Recrystallization solvent: DMF-ethyl acetate

Elemental analysis for $C_{16}H_{10}FN_3O_2S$ Calcd. (%): C, 58.71; H, 3.08; N, 12.84; F, 5.80; S, 9.80. Found. (%): C, 58.47; H, 2.88; N, 12.75; F, 5.59; S, 9.54.

NMR (DMSO-$d_6$) δ: 4.54 (2H, s), 7.21 (2H, m), 7.46 (2H, m), 7.52 (1H, dd, J=4.7, 8.4 Hz), 8.12 (1H, dd, J=1.2, 8.4 Hz), 8.62 (1H, dd, J=1.2, 4.7 Hz), 12.05 (1H, brs).

IR (KBr): 3448, 1637 cm$^{-1}$.

Example 31

Compound I-127

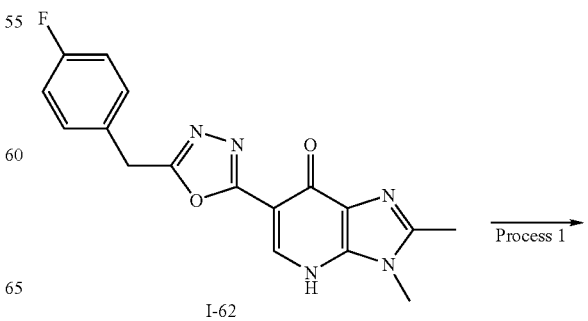

I-62

-continued

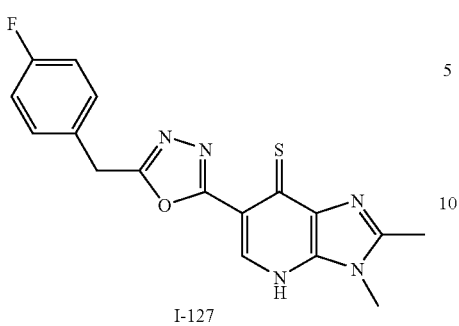

I-127

Process 1

Phosphorus pentasulfide (282 mg, 1.27 mmol) was added to a suspension of compound I-62 (393 mg, 1.16 mmol) in pyridine (4 ml) at room temperature, and the mixture was refluxed for 6 hours. Water (12 ml) and 2 N hydrochloric acid (4 ml) were added to the reaction mixture under ice-cooling. Precipitated crystals were collected, washed with water and recrystallized from DMF to give compound I-127 (111 mg, 27%) as colorless crystals.

M.p.: >300° C. Recrystallization solvent: DMF

NMR (DMSO-d$_6$) δ: 2.72 (3H, s), 3.80 (3H, s), 4.44 (2H, s), 7.19 (2H, m), 7.42 (2H, m), 9.21 (1H, s), 14.37 (1H, brs).

Example 32

Compound I-128

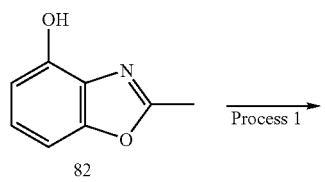

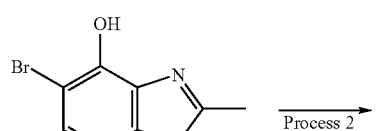

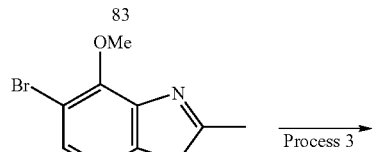

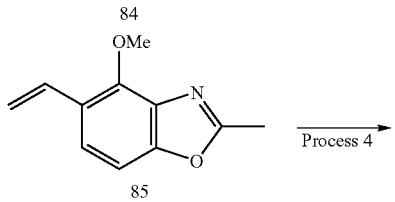

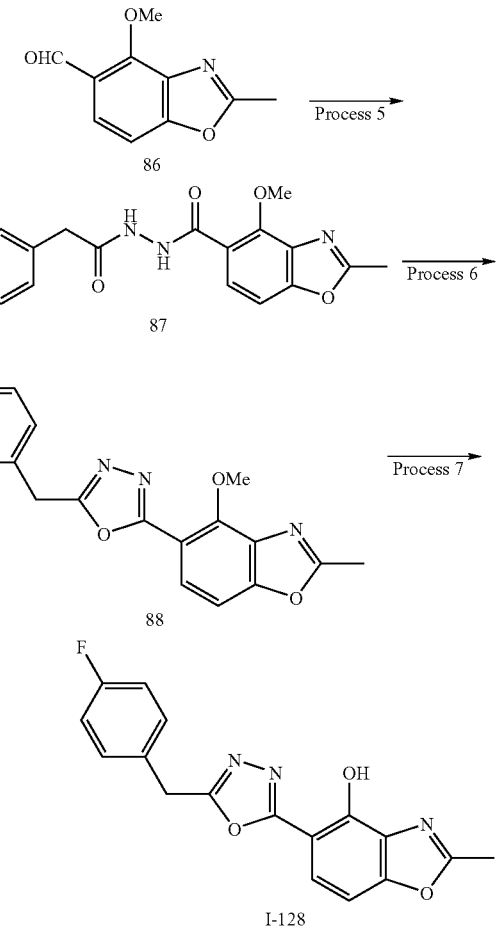

Process 1

A solution of diisopropylamine (0.36 ml, 2.57 mmol) and N-bromosuccinimide (4.57 g, 25.7 mmol) in dichloromethane (150 ml) was added to a solution of 4-hydroxy-2-methylbenzoxazole 82 (3.83 g, 25.7 mmol) in dichloromethane (85 ml) at room temperature, and the mixture was stirred for 1 hour at room temperature. Water and 10% hydrochloric acid were added to the reaction mixture and the whole was extracted with chloroform. The organic layer was washed with 10% hydrochloric acid, 5% sodium sulfite solution and brine, and dried over magnesium sulfate. The crystalline residue obtained by evaporation under reduced pressure was washed with hexane-diisopropyl ether (1:1) to give crude compound 83 (4.83 g) as colorless crystals.

NMR (CDCl$_3$) δ: 2.71 (3H, s), 6.97 (1H, d, J=8.4 Hz), 7.44 (1H, d, J=8.4 Hz), 9.39 (1H, brs).

Process 2

Potassium carbonate (3.68 g, 26.7 mmol) and methyl iodide (1.91 ml, 30.8 mmol) were added to a solution of compound 83 (4.67 g, 20.5 mmol) in DMF (40 ml) at room temperature, and the mixture was stirred for 1 hour at room temperature. Water and 10% hydrochloric acid were added to the reaction mixture and the whole was extracted with ethyl acetate. The organic layer was washed with 10% hydrochloric acid, 5% sodium sulfite solution and brine, and dried over sodium sulfate. A crude product obtained by evaporation under reduced pressure was subjected to silica gel column chromatography. The fractions containing desired compound eluted with hexane-yethyl acetate (5:1 v/v) were concentrated under reduced to give compound 84 (3.46 g, 70%) as a colorless oil.

NMR (CDCl₃) δ: 2.62 (3H, s), 4.38 (3H, s), 7.01 (1H, d, J=8.7 Hz), 7.43 (1H, d, J=8.7 Hz).

Process 3

A solution of compound 84 (740 mg, 3.06 mmol) in dioxane (8 ml), a solution of tri-tert-butylphosphine (37 mg, 0.183 mmol) in dioxane (4 ml) and tributylvinylstannane (0.98 ml, 3.36 mmol) were added to a mixture of cesium fluoride (1.02 g, 6.73 mmol) and tris(dibenzylideneacetone) dipalladium (0) (42 mg, 0.0459 mmol), and the mixture was stirred for 15 hours at 80° C. under argon atmosphere. After diisopropyl ether was added to the reaction mixture and insoluble materials were filtered off, the filtrate was concentrated. A crude product obtained by evaporation under reduced pressure was subjected to silica gel column chromatography. The fractions containing desired compound eluted with hexane-ethyl acetate (8:1 v/v) were concentrated under reduced to give compound 85 (260 mg, 45%) as a colorless oil.

NMR (CDCl₃) δ: 2.60 (3H, s), 4.31 (3H, s), 5.24 (1H, dd, J=11.4, 1.5 Hz), 5.68 (1H, dd, J=17.7, 1.5 Hz), 7.08 (1H, d, J=8.4 Hz), 7.11 (1H, dd, J=17.7, 11.4 Hz), 7.42 (1H, d, J=8.4 Hz).

Process 4

Trimethylamine N-oxide dihydrate (191 mg, 1.72 mmol), water (0.4 ml) and 5% osmium tetroxide solution (0.40 ml, 0.0782 mmol) were added to a solution of compound 85 (296 mg, 1.56 mmol) in THF (8 ml) under ice-cooling, and the mixture was stirred for 2 hours at room temperature. 5% Sodium thiosulfate was added to the reaction mixture and the whole was stirred for 15 minutes at room temperature and extracted with ethyl acetate. The organic layer was washed with 10% hydrochloric acid, saturated sodium hydrogencarbonate solution and brine, and dried over sodium sulfate. Removal of solvent under reduced pressure gave diol intermediate (320 mg) as a brown oil. A solution of sodium periodate (362 mg, 1.69 mmol) in water (3 ml) was added to a solution of diol intermediate (315 mg, 1.41 mmol) in THF (12 ml) under ice-cooling, and the mixture was stirred for 2 hours. Water was added to the reaction mixture and the whole was extracted with ethyl acetate. The organic layer was washed with water, saturated sodium hydrogencarbonate solution and brine, and dried over sodium sulfate. Removal of solvent under reduced pressure gave compound 86 (245 mg, 82%) as colorless crystals.

NMR (CDCl₃) δ: 2.64 (3H, s), 4.49 (3H, s), 7.12 (1H, dd, J=8.4, 0.9 Hz), 7.82 (1H, d, J=8.4 Hz), 10.47 (1H, d, J=0.9 Hz).

Process 5

2-Methyl-2-butene (4 ml), a solution of sodium chlorite (590 mg, 6.53 mmol) in water (6 ml) and sodium dihydrogen phosphate dihydrate (783 mg, 5.02 mmol) were added to a solution of compound 86 (240 mg, 1.26 mmol) in methanol (5 ml)-dioxane (5 ml) at room temperature, and the mixture was stirred for 6 hours. The reaction mixture was quenched with 5% sodium thiosulfate solution, stirred for 10 minutes at room temperature, acidified with 5% citric acid solution and extracted with ethyl acetate. The organic layer was washed with water and brine, and dried over sodium sulfate. Removal of solvent under reduced pressure gave carboxylic acid intermediate (264 mg). Compound 87 (330 mg, 74%) was synthesized as colorless crystals from the carboxylic acid intermediate (264 mg, 1.26 mmol) in a same manner similar to the process 2 of Example 9.

Process 6

Compound 88 (128 mg, 77%) was synthesized as colorless crystals from compound 87 (176 mg, 0.493 mmol) in a same manner similar to the process 3 of Example.

NMR (CDCl₃) δ: 2.64 (3H, s), 4.26 (2H, s), 4.41 (3H, s), 7.04 (2H, m), 7.18 (1H, d, J=8.4 Hz), 7.35 (2H, m), 7.79 (1H, d, J=8.4 Hz).

Process 7

Compound I-128 (79 mg, 67%) was synthesized as colorless crystals from compound 88 (123 mg, 0.362 mmol) in a same manner similar to the process 1 of Example 4.

M.p.: 178–179° C. Recrystallization solvent: chloroform-ethanol

Elemental analysis for C₁₇H₁₂FN₃O₃ Calcd. (%): C, 62.77; H, 3.72; N, 12.92; F, 5.84. Found. (%): C, 62.71; H, 3.62; N, 12.88; F, 5.72.

NMR (CDCl₃) δ: 2.66 (3H, s), 4.28 (2H, s), 7.07 (2H, m), 7.11 (1H, d, J=8.7 Hz), 7.35 (2H, m), 7.62 (1H, d, J=8.7 Hz), 10.73 (1H, brs).

IR (KBr): 3431, 1649, 1612, 1549, 1518, 1489, 1381, 1232 cm⁻¹.

Example 33

Compound I-129

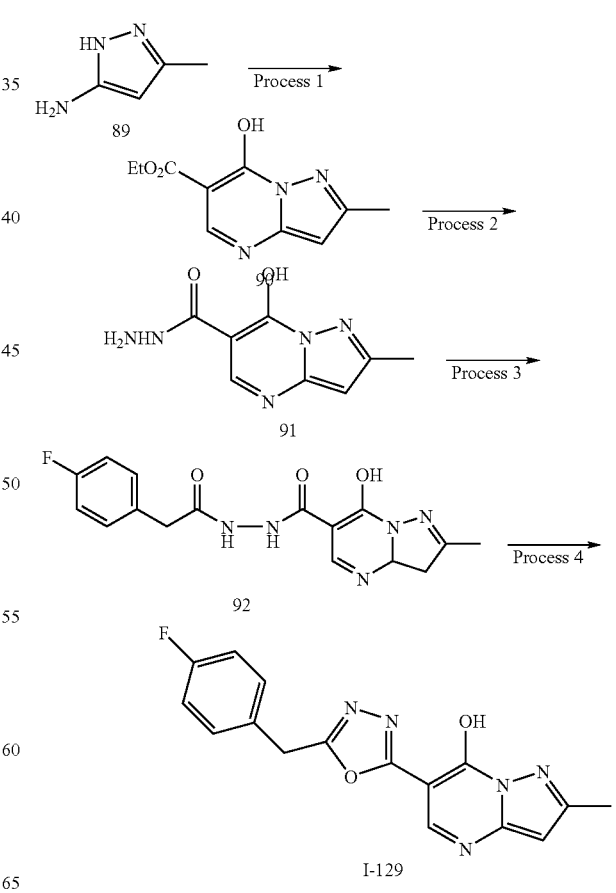

Process 1

Diethyl ethoxymethylenemalonate (47.0 ml, 230 mmol) was added to a solution of compound 89 (22.4 g, 231 mmol) in acetic acid (200 ml) at room temperature, and the mixture was refluxed for 2 hours. After cooling to 0° C., precipitated crystals were collected and washed with ethanol and diethyl ether to give compound 90 (34.4 g, 67%) as colorless crystals.

NMR (DMSO-$d_6$) δ: 1.27 (3H, t, J=7.2 Hz), 2.29 (3H, s), 4.22 (2H, q, J=7.2 Hz), 6.12 (1H, s), 8.51 (1H, s), 12.94 (1H, brs).

Process 2

A mixture of compound 90 (2.00 g, 10.7 mmol) and hydrazine monohydrate (2 ml) was refluxed for 15 hours. After water (8 ml) was added to the reaction mixture under ice-cooling, precipitated crystals were collected and washed with water and diethyl ether to give compound 91 (1.27 g, 68%) as colorless crystals.

NMR (DMSO-$d_6$) δ: 2.30 (3H, s), 6.09 (1H, s), 8.53 (1H, s), 9.83 (1H, brs).

Process 3

Crude compound 92 was synthesized as colorless crystals in a same manner similar to the process 3 of Example 29.

Process 4

Compound I-129 (9% overall yield) was synthesized as pale brown crystals from compound 91 in a same manner similar to the process 1 of Example 4. M.p.: >300° C. Recrystallization solvent: acetonitrile-methanol NMR (DMSO-$d_6$) δ: 2.32 (3H, s), 4.34 (2H, s), 6.18 (1H, s), 7.21 (2H, m), 7.42 (2H, m), 8.57 (1H, s), 13.14 (1H, brs).
IR (KBr): 3427, 1674 cm$^{-1}$.

Example 34

Compound I-130

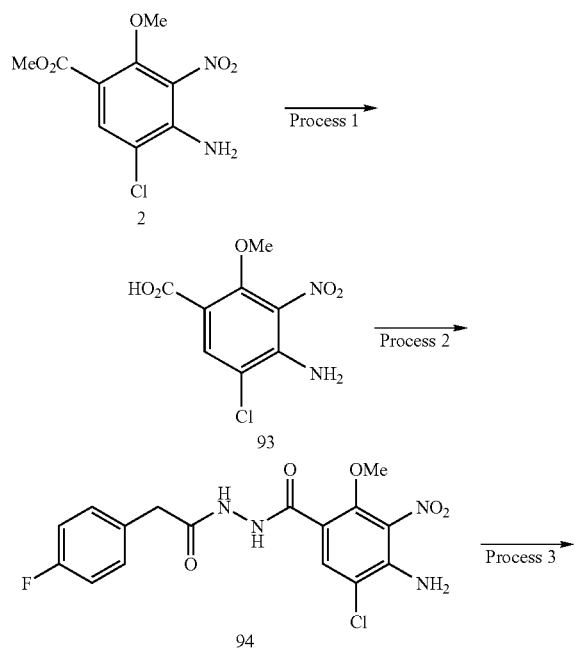

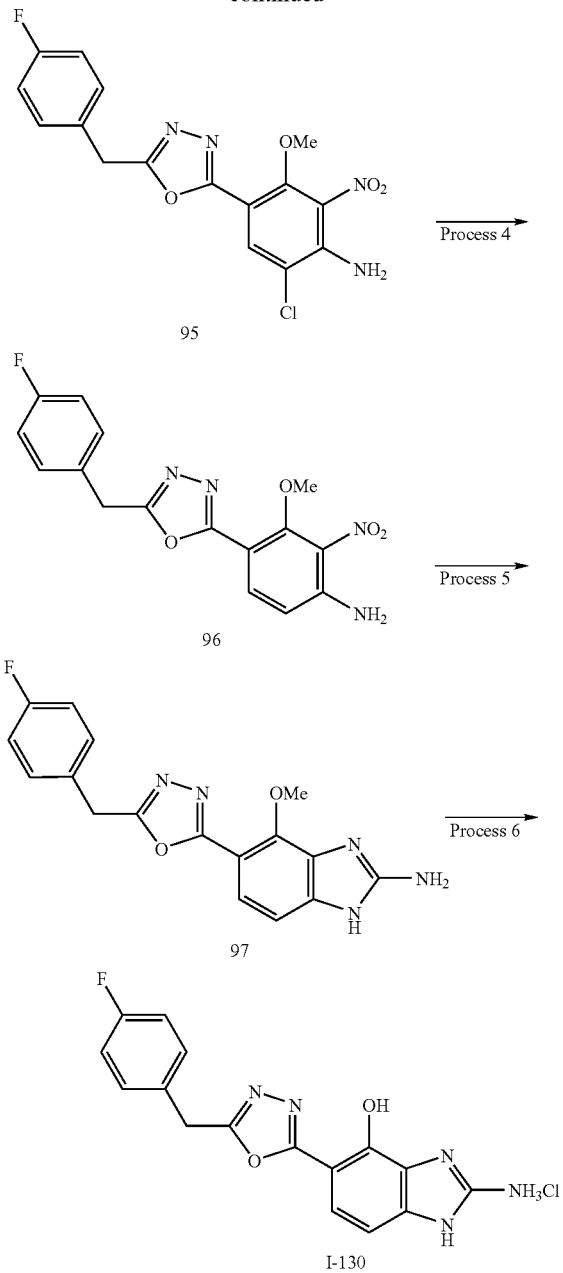

Process 1

1 N Sodium hydroxide solution (10 ml) was added to a solution of compound 2 (2.00 g, 7.67 mmol) in ethanol (10 ml) at room temperature, and the mixture was stirred for 50 minutes at 50° C. The reaction mixture was neutralized with 2 N hydrochloric acid under ice-cooling and extracted with ethyl acetate. The organic layer was washed with brine (40 ml) and dried over sodium sulfate. Removal of solvent under reduced pressure gave crude compound 93 (1.95 g).

NMR (CDCl$_3$) δ: 4.03 (3H, s), 5.87 (2H, brs), 8.17 (1H, s).

Process 2

1-Ethyl-3-(3-dimethylaminopropyl)carbodiimide hydrochloride (1.68 g, 8.76 mmol) was added to a solution of compound 93 (1.95 g), p-fluorophenylacetic hydrazide (1.48 g, 8.80 mmol) and 1-hydroxybenzotriazole (213 mg, 1.58 mmol) in DMF (20 ml) at room temperature, and the mixture was stirred for 1 hour. Water (180 ml) was added dropwise to the reaction mixture at room temperature. After ice-cooling, precipitated crystals were collected and washed with water and diethyl ether to give compound 94 (3.04 g, 100% from compound 2) as yellow crystals.

NMR (DMSO-d$_6$) δ: 3.52 (2H, s), 3.84 (3H, s), 6.59 (2H, brs), 7.15 (2H, m), 7.35 (2H, m), 7.56 (1H, s), 10.09 (1H, brs), 10.27 (1H, brs).

Process 3

Compound 95 (72%) was synthesized as yellow crystals in a same manner similar to the process 3 of Example 9.

Process 4

A suspension of compound 95 (2.12 g, 5.60 mmol), 10% palladium carbon (402 mg) and triethylamine (8 ml) in methanol (80 ml) was stirred under 4 atm of hydrogen atmosphere for 15 hours. The reaction mixture was filtered, evaporated under reduced pressure. The residue was diluted with ethyl acetate, washed with water (20 ml) and brine (20 ml), and dried over sodium sulfate. The crystalline residue obtained by evaporation under reduced pressure was recrystallized from ethyl acetate-hexane to give compound 96 (1.54 g, 88%) as colorless crystals.

NMR (CDCl$_3$) δ: 3.55 (4H, br), 3.75 (3H, s), 4.24 (2H, s), 6.55 (1H, d, J=8.7 Hz), 7.04 (2H, m), 7.27 (1H, d, J=8.7 Hz), 7.34 (2H, m).

Process 5

A solution of compound 96 (493 mg, 1.57 mmol) in methanol (5 ml) was added dropwise to a solution of cyanogen bromide (181 mg, 1.62 mmol) in water (2.5 ml) at room temperature, and the mixture was stirred for 20 hours. The reaction mixture was neutralized with saturated sodium carbonate solution and water under ice-cooling. Precipitated crystals were collected and washed with water to give compound 97 (504 mg, 95%) as colorless crystals.

NMR (DMSO-d$_6$) δ: 4.04 (3H, s), 4.33 (2H, s), 6.42 (2H, brs), 6.96 (1H, d, J=8.1 Hz), 7.21 (2H, m), 7.28 (1H, d, J=8.1 Hz), 7.44 (2H, m), 11.18 (1H, brs).

Process 6

Compound I-130 (63%) was synthesized as colorless crystals in a same manner similar to the process 1 of Example 4.

M.p.: 261–266° C. Recrystallization solvent: acetonitrile
Elemental analysis for $C_{16}H_{13}ClFN_5O_2(H_2O)_{0.4}$ Calcd. (%): C, 51.83; H, 3.81; N, 18.89; Cl, 9.56; F, 5.12. Found. (%): C, 51.91; H, 3.35; N, 18.75; Cl, 9.60; F, 5.02.

NMR (DMSO-d$_6$) δ: 4.39 (2H, s), 7.05 (1H, d, J=8.4 Hz), 7.21 (2H, m), 7.45 (2H, m), 7.58 (1H, d, J=8.4 Hz), 8.56 (2H, brs), 10.70 (1H, brs), 12.93 (1H, brs).
IR (KBr): 1697 cm$^{-1}$.

Example 35

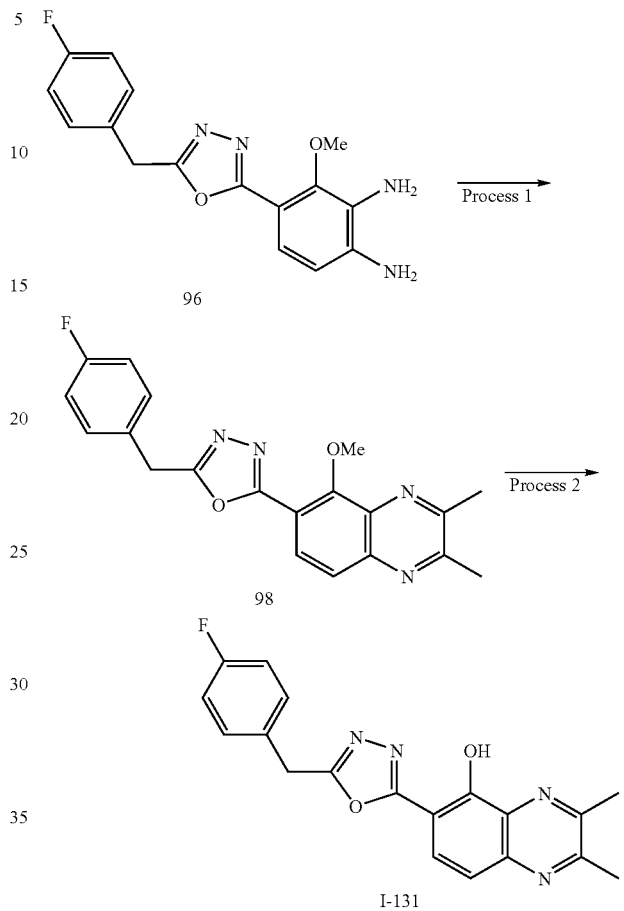

Process 1

Diacetyl (89.9 mg, 1.04 mmol) was added to a solution of compound 96 (222 mg, 0.706 mmol) in ethanol (2 ml) at 60° C., and the mixture was refluxed for 7 hours. After cooling to 0° C., precipitated crystals were collected and washed with ethanol to give compound 98 (97.2 mg, 38%) as yellow crystals.

NMR (CDCl) (DMSO-d$_6$) δ: 2.76 (3H, s), 2.79 (3H, s), 4.19 (3H, s), 4.32 (2H, s), 7.06 (2H, m), 7.39 (2H, m), 7.80 (1H, d, J=8.9 Hz), 8.18 (1H, d, J=8.9 Hz).

Process 2

Compound I-131 (75%) was synthesized as pale brown crystals in a same manner similar to the process 1 of Example 4.

M.p.: 226–228° C. Recrystallization solvent: acetonitrile
Elemental analysis for $C_{19}H_{15}FN_4O_2$ Calcd. (%): C, 65.14; H, 4.32; N, 15.99; F, 5.42. Found. (%): C, 65.10; H, 4.08; N, 16.02; F, 5.37.

NMR (DMSO-d$_6$) δ: 2.70 (3H, s), 2.74 (3H, s), 4.41 (2H, s), 7.21 (2H, m), 7.46 (2H, m), 7.52 (1H, d, J=8.7 Hz), 8.01 (1H, d, J=8.7 Hz), 10.92 (1H, brs).
IR (KBr): 3423, 1631 cm$^{-1}$.

Compound I-132 was synthesized in a same manner similar to Example 35.

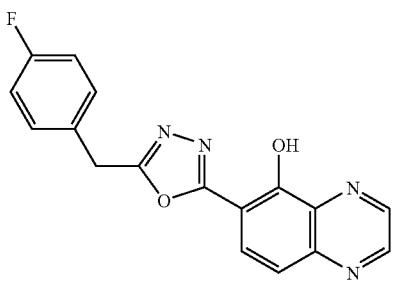

Compound I-132

M.p.: 163–164° C. Recrystallization solvent: methanol

NMR (DMSO-d$_6$) δ: 4.43 (2H, s), 7.21 (2H, m), 7.47 (2H, m), 7.68 (1H, d, J=9.0 Hz), 8.19 (1H, d, J=9.0 Hz), 8.99 (1H, d, J=1.5 Hz), 9.07 (1H, d, J=1.5 Hz), 11.52 (1H, brs).

Example 36

Compound I-133

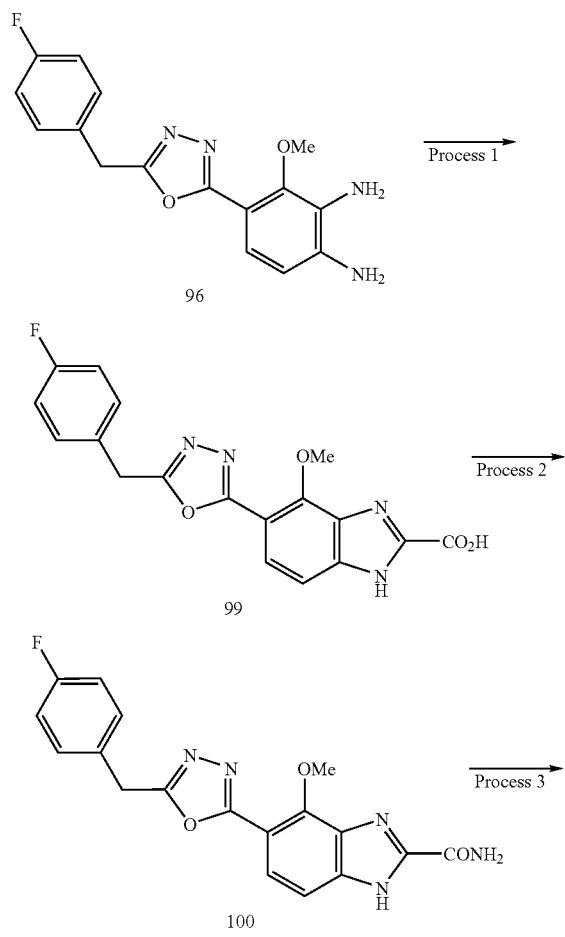

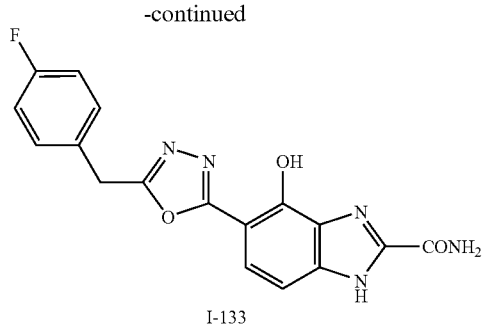

Process 1

Methyl 2,2,2-trichloroacetimidate (408 ml, 3.30 mmol), diisopropylethylamine (473 ml, 2.72 mmol) and ammonium chloride (73 mg, 1.36 mmol) were added to a solution of compound 96 (943 mg, 3.00 mmol) in acetic acid (6.0 ml) under ice-cooling, and the mixture was stirred for 45 minutes at room temperature. After water (15 ml) was added to the reaction mixture, precipitated crystals were collected and dissolved in THF (27 ml). 5 N sodium hydroxide solution (3 ml) was added to the solution and the mixture was stirred for 1.5 hours at room temperature. The reaction mixture was concentrated and acidified to pH 3–4 with 2 N hydrochloric acid. Precipitated crystals were collected and washed with water to give compound 99 (770 mg, 70%) as reddish-brown crystals.

NMR (CDCl$_3$) δ: 4.28 (3H, s), 4.45 (2H, s), 7.06 (2H, m), 7.33 (1H, d, J=8.5 Hz), 7.39 (2H, m), 7.80 (1H, d, J=8.6 Hz).

Process 2

1-Hydroxybenzotriazole (138 mg, 1.02 mmol), diisopropylethylamine (473 ml, 2.72 mmol), ammonium chloride (73 mg, 1.36 mmol) and benzotriazol-1-yloxytripyrrolidinophosphonium hexafluorophosphate (531 mg, 1.02 mmol) were added to a solution of compound 99 (250 mg, 0.68 mmol) in DMF (3.4 ml) at room temperature, and the mixture was stirred for 1 hour. The reaction mixture was poured into a mixture of 1 N hydrochloric acid (4 ml)-ice-water-ethyl acetate, and the mixture was extracted with ethyl acetate. The organic layer was washed with diluted hydrochloric acid (×2), water (×2), saturated sodium hydrogencarbonate solution and brine, and dried over sodium sulfate. A crude product obtained by evaporation under reduced pressure was subjected to silica gel column chromatography. The fractions containing desired compound eluted with chloroform-methanol (10:1 v/v) were concentrated under reduced pressure to give compound crude compound 100 (409 mg) of as yellow crystals.

NMR (DMSO-d$_6$) δ: 4.36 (3H, s), 4.40 (2H, s), 7.22 (2H, m), 7.28 (1H, d, J=8.6 Hz), 7.46 (2H, m), 7.69 (1H, d, J=8.6 Hz), 7.95 (1H, s), 8.26 (1H, s), 13.60 (1H, s).

Process 3

Compound I-133 (54%) was synthesized as pale brown crystals in a same manner similar to the process 1 of Example 4.

Elemental analysis for $C_{17}H_{12}FN_5O_3$ Calcd. (%): C, 57.79; H, 3.42; N, 19.82; F, 5.38. Found. (%): C, 54.64; H, 3.33; N, 18.17; F, 4.97.

NMR (CDCl$_3$) δ: 4.39 (2H, s), 7.15 (1H, d, J=8.6 Hz), 7.21 (2H, m), 7.46 (2H, m), 7.61 (1H, d, J=8.6 Hz), 7.90 (1H, s), 8.27 (1H, s).

Example 37

Compound I-134

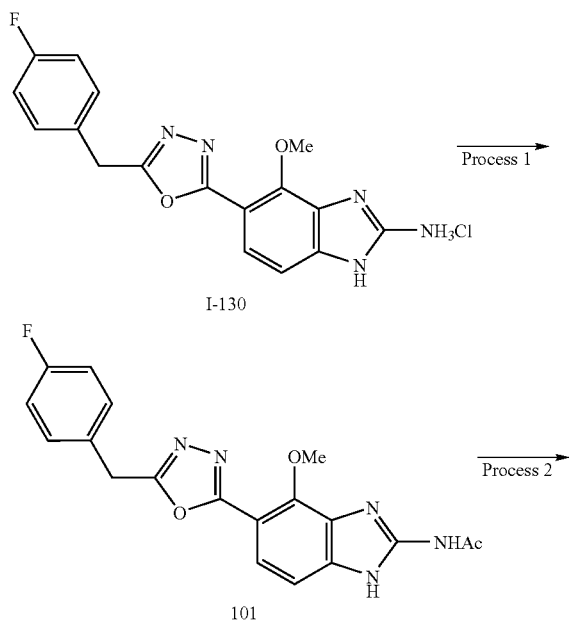

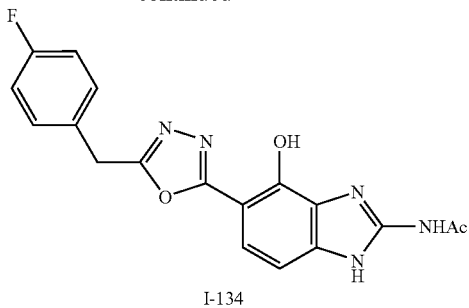

Process 1

A solution of triethylamine (253 ml, 1.82 mmol) and acetyl chloride (129 ml, 1.82 mmol) in THF (5 ml) was added to a solution of compound I-130 (556 mg, 1.65 mmol) in THF (15 ml) under ice-cooling, and the mixture was stirred for 1 hour at 0° C. and for 15 minutes at room temperature. The reaction mixture was diluted with water (30 ml) and acidified to pH 3–4 with 10% hydrochloric acid. Precipitated crystals were collected and washed with water to give N-acetyl intermediate (327 mg). The crystals were dissolved in xylene (15 ml) and the mixture was refluxed at 170° C. for 22 hours. After cooling, crystals were collected and washed with a small amount of diethyl ether to give compound 101 (264 mg, 41%) as red crystals.

NMR (CDCl$_3$) δ: 2.17 (3H, s), 4.20 (3H, s), 4.34 (2H, s), 7.21 (2H, m), 7.30 (1H, d, J=8.3 Hz), 7.44 (2H, m), 7.47 (1H, d, J=8.2 Hz).

Process 2

Compound I-134 (22%) was synthesized as colorless crystals in a same manner similar to the process 1 of Example 4.

M.p.: >300° C. Recrystallization solvent: THF-chloroform

Elemental analysis for C$_{18}$H$_{14}$FN$_5$O$_3$ Calcd. (%): C, 58.85; H, 3.84; N, 19.07; F, 5.17. Found. (%): C, 54.64; H, 3.33; N, 18.17; F, 5.02.

NMR (DMSO-d$_6$) δ: 2.18 (3H, s), 4.37 (2H, s), 7.21 (3H, m), 7.46 (3H, m), 11.64 (1H, brs).

Compounds I-135 and I-136 were synthesized in a same manner similar to the process 1 of Example 17.

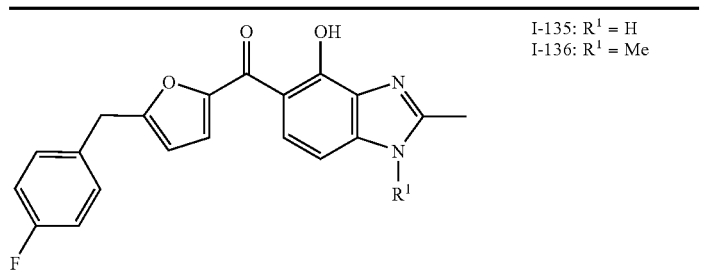

I-135: R$^1$ = H
I-136: R$^1$ = Me

Compound I-135

M.p.: 238–241° C. Recrystallization solvent: acetonitrile

Elemental analysis for C$_{20}$H$_{15}$FN$_2$O$_3$(H$_2$O)$_{0.1}$ Calcd. (%): C, 68.21; H, 4.35; N, 7.96; F, 5.40. Found. (%): C, 68.08; H, 4.19; N, 7.91; F, 5.34.

NMR (DMSO-d$_6$) δ: 2.50 (3H, s), 4.18 (2H, s), 6.48 (1H, d, J=3.6 Hz), 7.02 (1H, d, J=8.9 Hz), 7.20 (2H, m), 7.38 (2H, m), 7.41 (1H, d, J=3.6 Hz), 7.84 (1H, d, J=8.9 Hz), 12.88 (1H, brs).

IR (KBr): 3431, 1635 cm$^{-1}$.

Compound I-136

M.p.: 205–207° C. Recrystallization solvent: methanol-ethyl acetate

Elemental analysis for C$_{21}$H$_{18}$ClFN$_2$O$_3$(H$_2$O)$_{0.6}$ Calcd. (%): C, 61.27; H, 4.70; N, 6.81; Cl, 8.61; F, 4.62. Found. (%): C, 61.24; H, 4.65; N, 6.79; Cl, 8.14; F, 4.48.

NMR (DMSO-d$_6$) δ: 2.76 (3H, s), 3.89 (3H, s), 4.17 (2H, s), 6.52 (1H, d, J=3.6 Hz), 7.20 (2H, m), 7.34–7.42 (4H, m), 7.93 (1H, d, J=8.7 Hz), 12.19 (1H, brs).

IR (KBr): 3280, 1651 cm$^{-1}$.

Example 38

Compound I-137

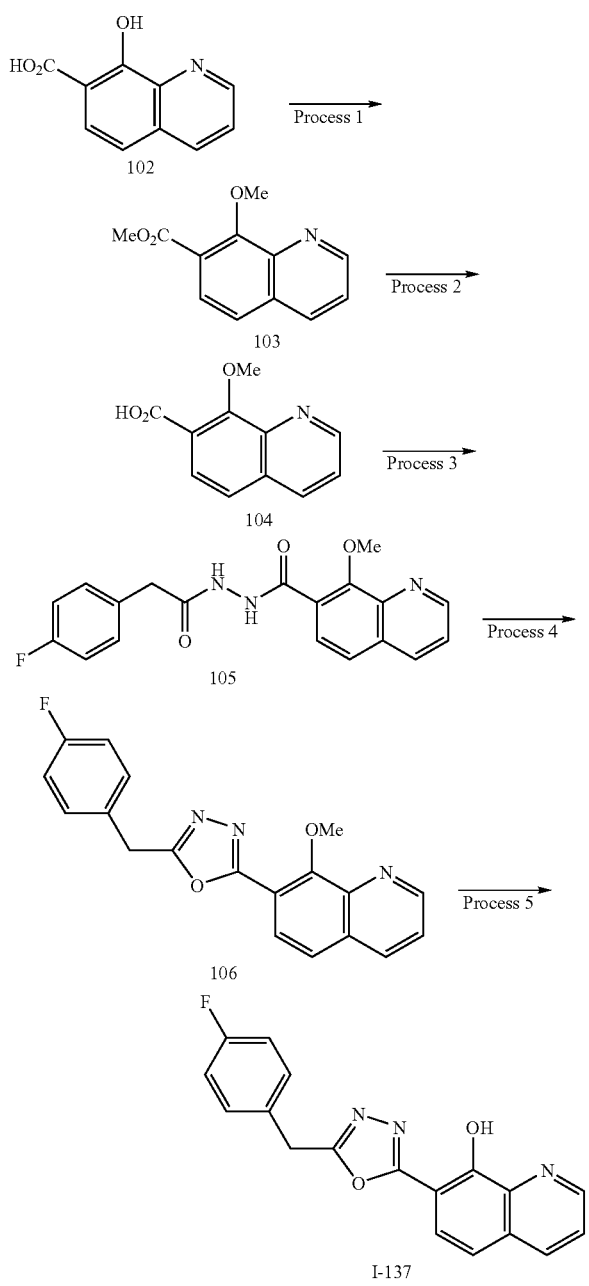

Process 1

A solution of diazomethane in diethyl ether was added to a suspension of compound 102 (3.50 g, 18.5 mmol) and silica gel (1 g) in methanol (8 ml) under ice-cooling, and the mixture was stirred for 1.5 hours at room temperature. Insoluble materials were filtered off and the filtrate was concentrated. The residue was diluted with water and extracted with ethyl acetate. The organic layer was washed with water and dried over sodium sulfate. A crude product obtained by evaporation under reduced pressure was subjected to silica gel column chromatography. The fractions containing desired compound eluted with ethyl acetate were concentrated under reduced to give compound 103 (1.01 g, 25%) as a colorless oil.

NMR (DMSO-$d_6$) δ: 3.91 (3H, s), 4.13 (3H, s), 7.67 (1H, dd, J=8.4, 3.9 Hz), 7.78 (1H, d, J=8.7 Hz), 7.80 (1H, d, J=8.7 Hz), 8.45 (1H, dd, J=8.4, 1.8 Hz), 9.01 (1H, dd, J=4.2, 1.8 Hz).

Process 2

1N lithium hydroxide solution (8 ml) was added to a solution of compound 103 (1.40 g, 6.45 mmol) in ethanol (30 ml) at room temperature, and the mixture was stirred for 2 hours at 75° C. The reaction mixture was acidified with 1 N hydrochloric acid under ice-cooling and the whole was concentrated under reduced pressure. The residue was diluted with water and extracted with ethyl acetate. The organic layer was washed with brine and dried over sodium sulfate. The crystalline residue obtained by evaporation under reduced pressure was triturated with diethyl ether to give crude compound 104 (0.900 g, 69%).

M.p.: 184–185° C.

NMR (DMSO-$d_6$) δ: 4.11 (3H, s), 7.64 (1H, dd, J=8.4, 3.9 Hz), 7.76 (2H, m), 8.43 (1H, dd, J=8.4, 1.8 Hz), 8.99 (1H, dd, J=4.2, 1.8 Hz), 13.15 (1H, brs).

Process 3

Compound 105 (1.8 g, 5.7 mmol, 49%) was synthesized as colorless crystals in a same manner similar to the process 2 of Example 9.

M.p.: 167–168° C.

NMR (DMSO-$d_6$) δ: 3.57 (2H, s), 4.18 (3H, s), 7.16 (2H, m), 7.38 (2H, m), 7.56 (1H, d, J=8.4 Hz), 7.64 (1H, dd, J=8.4, 4.2 Hz), 7.80 (1H, d, J=8.4 Hz), 8.43 (1H, dd, J=8.4, 1.5 Hz), 8.99 (1H, dd, J=4.2, 1.5 Hz), 10.33 (1H, s), 10.55 (1H, s).

Process 4

Triphenylphosphine (256 mg, 0.976 mmol) was added to a solution of bromine in dichloromethane (0.1 M, 9.76 ml, 0.976 mmol) under ice-cooling, and the mixture was stirred for 30 minutes under ice-cooling and for 30 minutes at room temperature. Triethylamine (257 mg, 2.55 mmol) was added to the reaction mixture under ice-cooling and the whole was stirred for 10 minutes. After compound 105 (300 mg, 0.850 mmol) was added to the mixture, the whole was stirred for 2 hours at room temperature and quenched with water and extracted with chloroform. The organic layer was washed with water and dried over sodium sulfate. A crude product obtained by evaporation under reduced pressure was subjected to silica gel column chromatography. The fractions containing desired compound eluted with ethyl acetate were concentrated under reduced to give compound 106 (94 mg, 33%) as colorless crystals.

M.p.: 119–120° C.

NMR (DMSO-$d_6$) δ: 4.12 (3H, s), 4.43 (2H, s), 7.23 (2H, m), 7.49 (2H, m), 7.50 (1H, d, J=8.7 Hz), 7.68 (1H, dd, J=8.4, 4.2 Hz), 7.88 (1H, d, J=8.7 Hz), 8.48 (1H, dd, J=8.7, 1.8 Hz), 9.02 (1H, dd, J=4.2, 1.8 Hz).

Process 5

Compound I-137 (66%) was synthesized as colorless crystals in a same manner similar to the process 1 of Example 4.

M.p.: 172–173° C.

NMR (DMSO-$d_6$) δ: 4.41 (2H, s), 7.21 (2H, m), 7.45 (2H, m), 7.54 (1H, d, J=8.7 Hz), 7.70 (1H, dd, J=8.4, 4.2 Hz), 7.94 (1H, d, J=8.7 Hz), 8.43 (1H, dd, J=8.4, 1.5 Hz), 8.96 (1H, dd, J=4.2, 1.5 Hz), 10.97 (1H, brs).

Example 39

Compound I-138

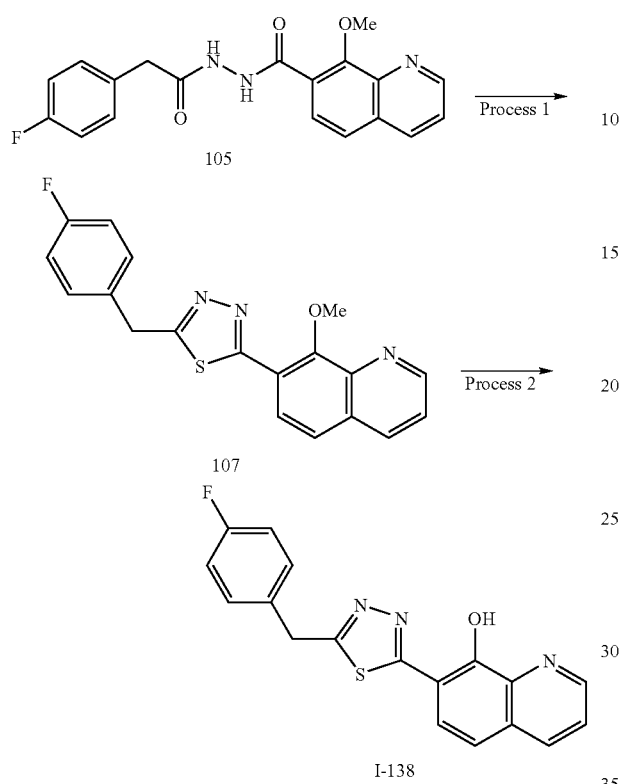

Process 1

Compound 107 (24%) was synthesized as colorless crystals in a same manner similar to the process 1 of Example 30.

M.p.: 119–120° C.

NMR (CDCl$_3$) δ: 4.28 (3H, s), 4.50 (2H, s), 7.05 (2H, m), 7.36 (2H, m), 7.49 (1H, dd, J=8.1, 4.2 Hz), 7.67 (1H, d, J=9.0 Hz), 8.20 (1H, dd, J=8.4, 1.8 Hz), 8.61 (1H, d, J=9.0 Hz), 8.97 (1H, dd, J=4.2, 1.8 Hz).

Process 5

Compound I-138 (87%) was synthesized as colorless crystals in a same manner similar to the process 1 of Example 4.

M.p.: 164–165° C.

NMR (DMSO-d$_6$) δ: 4.53 (2H, s), 7.21 (2H, m), 7.46 (2H, m), 7.54 (1H, d, J=8.7 Hz), 7.67 (1H, dd, J=8.4, 4.2 Hz), 8.40 (1H, d, J=8.7 Hz), 8.42 (1H, dd, J=8.4, 1.5 Hz), 8.94 (1H, dd, J=4.2, 1.5 Hz).

Example 40

Compound I-139

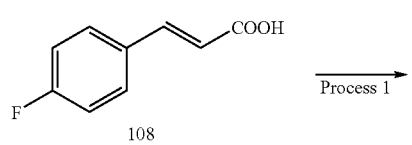

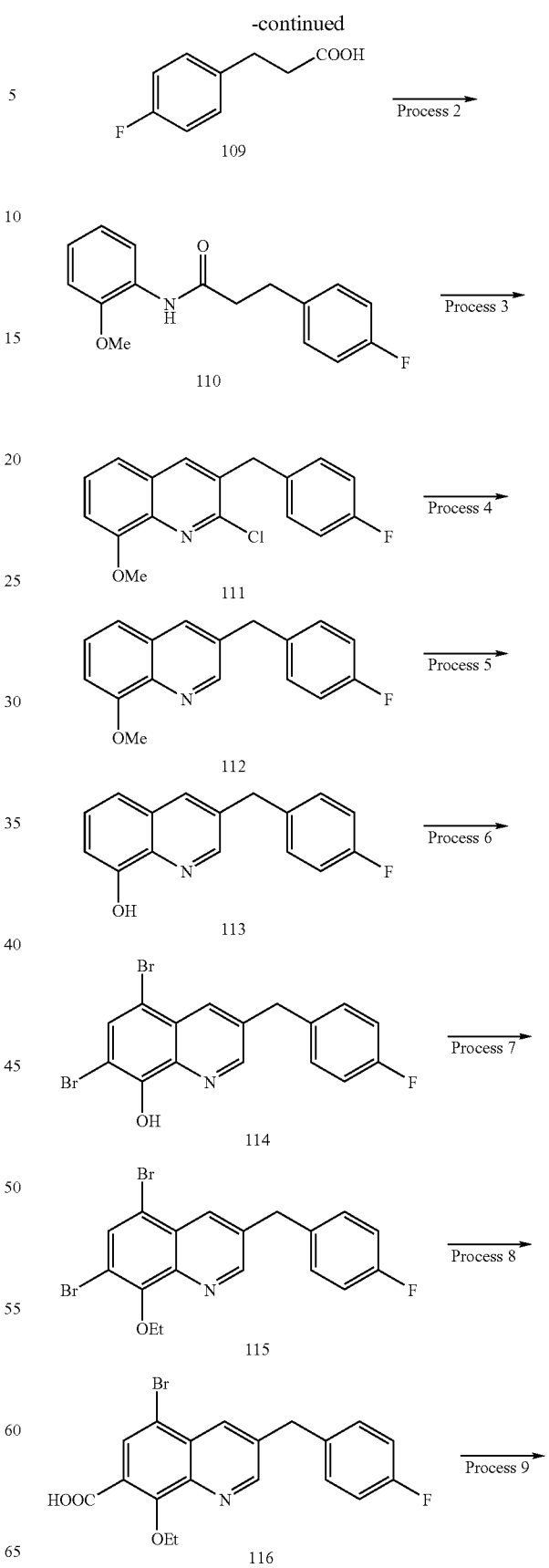

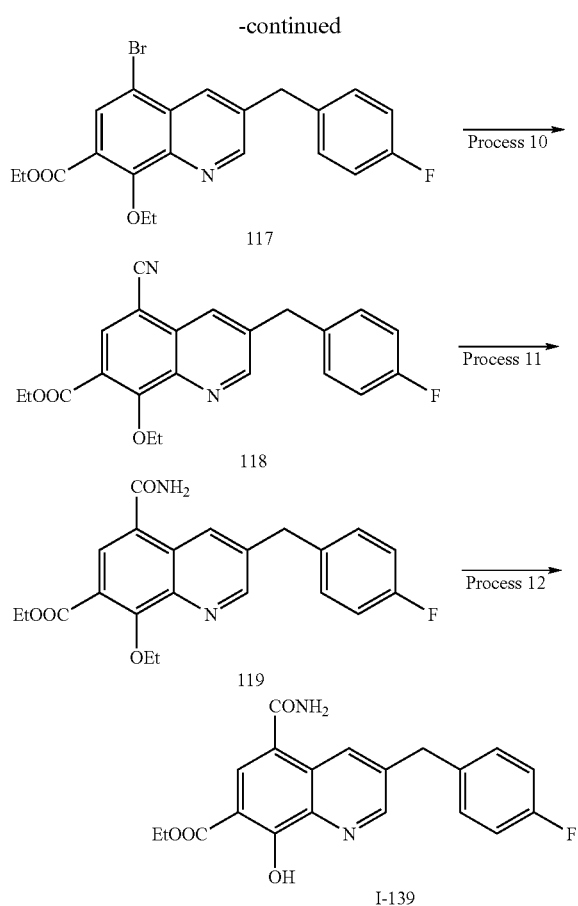

Process 1

A suspension of 4-fluorocinnamic acid (50 g, 300 mmol), 10% palladium carbon (10 wt %) in DMF (500 ml) was stirred under 1 atm of hydrogen atmosphere for 6.5 hours at room temperature. The reaction mixture was filtered through Celite, and DMF was evaporated from the filtrate under reduced pressure. Ethyl acetate (300 ml) was added to the residue and the solution was filtered again through Celite. The filtrate was evaporated under reduced pressure to give crude compound 109 (61.8 g) as colorless crystals.

Process 2

1-Ethyl-3-(3-dimethylaminopropyl)carbodiimide hydrochloride (69.2 g, 360 mmol) and 1-hydroxybenzotriazole (4.07 g, 31 mmol) were added to a solution of the crude compound 109 (61.8 g) in dichloromethane (350 ml) at room temperature, and the mixture was stirred for 60 minutes. A solution of 2-methoxyaniline (40.6 g, 330 mmol) in dichloromethane (30 ml) was added dropwise to the reaction mixture and the whole was stirred for 2 hours at room temperature. After the reaction was quenched with ice-water, the organic layer was separated and the water layer was extracted with dichloromethane. The combined organic layers were washed with 1 N hydrogen chloride solution, saturated sodium hydrogencarbonate solution and brine, and dried over magnesium sulfate. Removal of solvent under reduced pressure gave a colorless crystalline residue, which was washed with diisopropyl ether to give compound 110 (69.4 g, 254 mmol, 84.6%).

Process 3

DMF (27.4 g, 375 mmol) was added dropwise to phosphorus oxychloride (310 g, 2.0 mol) under ice-cooling, and the mixture was stirred for 30 minutes. Compound 110 (684 g, 250 mmol) was added to the reaction mixture and the whole was allowed to warm to room temperature and stirred for 30 minutes. After the reaction mixture was stirred for 18 hours at 75° C. Removal of an excess of phosphorus oxychloride under reduced pressure gave the residue, which was added ice-water (500 ml) and extracted with ethyl acetate, washed with brine and saturated sodium hydrogencarbonate solution and dried over magnesium sulfate. Removal of solvent under reduced pressure gave a crystalline residue, which was washed with ice-cooled ethyl acetate to give compound 111 (45.1 g, 149 mmol) as colorless crystals. The second crystal (4.4 g, 14.6 mmol) was obtained after the filtrate was concentrated under reduced pressure. These crystals were combined to give compound 111 (65.6%).

Process 4

5% palladium carbon (10 wt %) and triethylamine (24.6 g, 244 mmol) was added to a solution of compound 111 (49.0 g, 162.4 mmol) in ethyl acetate (400 ml)-ethanol (800 ml) under ice-cooling. The reaction was stirred under 1 atm of hydrogen atmosphere for 2 hours at room temperature. The reaction mixture was filtered through Celite, and the filtrate was concentrated under reduced pressure. After ethyl acetate (500 ml) and water (300 ml) were added to the residue, the organic layer was separated. The aqueous layer was extracted with ethyl acetate, and the combined organic layers were washed with brine and dried over magnesium sulfate. Removal of solvent under reduced pressure gave crude compound 112 (43.7 g) as pale orange crystals.

Process 5

Pyridine hydrochloride (100 g, 865 mmol) was added to the crude compound 112 (43.7 g), and the mixture was stirred at 180° C. for 1.5 hours. After cooling to room temperature, the reaction mixture was poured into ice-cooled dichloromethane (300 ml)-water (300 ml). After the whole was stirred for 30 minutes, the organic layer was separated and the aqueous layer was extracted with dichloromethane. The combined organic layers were dried over sodium sulfate. The pale yellow crystalline residue obtained by evaporation under reduced pressure was recrystallized from ethanol-diisopropyl ether. The 1st–4th crystals were combined to give compound 113 (36.9 g, 145.7 mmol, 90.5%) as pale yellow crystals.

Process 6

Diisopropylamine (1.52 g, 15 mmol) was added to a solution of compound 113 (19.0 g, 75 mmol) in dichloromethane (500 ml) at room temperature. A solution of N-bromosuccinimide (32.0 g, 180 mmol) in dichloromethane (1000 ml) was added dropwise, subsequently. After stirring for 2 hours, the reaction mixture was poured dropwise into ice-cooled 2 N hydrogen chloride (500 ml), and the organic layer was separated. The aqueous layer was extracted with dichloromethane and the combined organic layers were washed with brine and dried over magnesium sulfate. The residue obtained by evaporation under reduced pressure was recrystallized from ethanol-dichloromethane to give compound 114 (14.0 g, 34.1 mmol, 42.5%) as pale orange crystals.

Process 7

Potassium carbonate (1.97 g, 14.3 mmol) was added to a solution of compound 114 (4.9 g, 11.9 mmol) in DMF (30 ml), and the mixture was stirred for 30 minutes at room temperature. Ethyl bromide (2.6 g, 23.8 mmol) was added to the reaction mixture and the whole was stirred for 60 minutes at 60° C. After cooling, the reaction mixture was poured into ice-water and extracted with ethyl acetate. The organic layer was washed with brine and dried over magnesium sulfate. Removal of solvent under reduced pressure gave crude compound 115 (4.07 g) as a dark brown oil.

Process 8

Phenyl lithium (2 M cyclohexane solution, 8 ml, 16 mmol) was added dropwise to diethyl ether (120 ml), and the mixture was cooled to −78° C. A solution of compound 115 (3.45 g, 7.9 mmol) in diethyl ether (60 ml) was added dropwise to the solution, and the whole was stirred for 30 minutes at −78° C. $CO_2$ gas was bubbled through the reaction mixture for 60 minutes, which was allowed to warm 0° C., neutralized with 2 N hydrogen chloride solution. After the mixture was alkalified with 2 N sodium hydroxide solution, the aqueous layer was washed with diethyl ether and acidified with 2 N hydrogen chloride solution. Precipitated colorless crystals were collected and washed with water and diisopropyl ether to give compound 116 (880 mg, 2.2 mmol, 28%) as colorless crystals.

Process 9

1-Ethyl-3-(3-dimethylaminopropyl)carbodiimide hydrochloride (600 mg, 3.12 mmol) and 1-hydroxybenzotriazole (410 mg, 3.12 mmol) were added to a solution of compound 116 (1.06 g, 2.6 mmol) in dichloromethane at room temperature, and the mixture was stirred for 30 minutes. Ethanol (10 ml) and triethylamine (316 mg, 3.12 mmol) were added to the reaction mixture and the whole was refluxed for 60 minutes. After cooling, the reaction mixture was concentrated and extracted with ethyl acetate. The organic layer was washed with brine and dried over sodium sulfate. Removal of solvent under reduced pressure gave compound 117 (960 mg, 2.22 mmol, 85.4%) as pale yellow crystals.

Process 10

A solution of compound 117 (432 mg, 1 mmol), copper cyanide (358 mg, 4 mmol), tetraethylammonium cyanide (156 mg, 1 mmol), tris(dibenzylideneacetone)dipalladium (37 mg, 0.04 mmol) and 1,1′-bis(diphenylphosphino)ferrocene (89 mg, 0.16 mg) in dioxane (5 ml) was refluxed for 4 hours. Tris(dibenzylideneacetone)dipalladium (37 mg, 0.04 mmol) and 1,1′-bis(diphenylphosphino)ferrocene (89 mg, 0.16 mg) were added to the reaction mixture and the whole was refluxed for 60 minutes. After cooling to room temperature, the mixture was diluted with ethyl acetate (30 ml) and stirred for 10 minutes. The reaction mixture was filtered through Celite and the filtrate was washed with saturated sodium hydrogencarbonate solution and brine, and dried over magnesium sulfate. A crude product as a pale yellow oil obtained by evaporation under reduced pressure was subjected to silica gel column chromatography. The fractions containing desired compound eluted with hexane-ethyl acetate (3:1 v/v) were concentrated under reduced pressure to give compound 118 (347 mg, 0.917 mmol, 91.7%) as pale yellow crystals.

Process 11 hydrogen chloride gas was bubbled through a solution of compound 118 (200 mg, 0.57 mmol) in chloroform (10 ml)-methanol (3 ml) under ice-cooling for 60 minutes. The reaction mixture was sealed up and allowed to stand for 5 days at 4° C. Methanol (5 ml) and water (5 ml) were added to the reaction mixture and the whole was stirred for 30 minutes at 50° C. After cooling, the reaction was quenched with ice-water and extracted with chloroform. The organic layer was washed with brine and dried over sodium sulfate. A crude product as a colorless crystalline residue obtained by evaporation under reduced pressure was subjected to silica gel column chromatography. The fractions containing desired compound eluted with hexane-ethyl acetate (2:1 v/v) were concentrated under reduced pressure to give compound 119 (121 mg, 0.31 mmol, 53.6%) as pale yellow crystals.

Process 12

Boron tribromide (1 M dichloromethane solution, 0.69 ml, 0.69 mmol) was added dropwise to a solution of compound 119 (99.1 mg, 0.23 mmmol) in dichloromethane (5 ml) at −20° C. After stirring for 30 minutes, boron tribromide (1 M dichloromethane solution, 0.69 ml, 0.69 mmol) was added dropwise to the reaction mixture. After stirring for 30 minutes, 1 N hydrogen chloride solution and ice-water were added to the mixture and the whole was extracted with dichloromethane, washed with brine and dried over sodium sulfate. Removal of solvent under reduced pressure gave a crystalline residue, which was recrystallized from ethyl acetate to give compound I-139 (35 mg, 0.095 mmol, 41.3%) as pale yellow crystals.

M.p.: 212–214° C. Recrystallization solvent: ethyl acetate

Elemental analysis for $C_{20}H_{17}FN_2O_4(H_2O)_{1.2}$ Calcd. (%): C, 61.60; H, 5.01; N, 7.18; F, 4.87. Found. (%): C, 61.59; H, 4.25; N, 7.07; F, 4.66.

NMR (DMSO-$d_6$) δ: 1.37 (3H, t, J=6.9 Hz), 4.23 (2H, s), 4.41 (2H, q, J=6.9 Hz), 7.10–7.20 (2H, m), 7.30–7.40 (2H, m), 7.49 (1H, brs), 8.04–8.12 (2H, m), 8.68–8.72 (1H, m), 8.88–8.90(1H, m), 11.3–11.5(1H, brs).

Example 41

Compound I-140

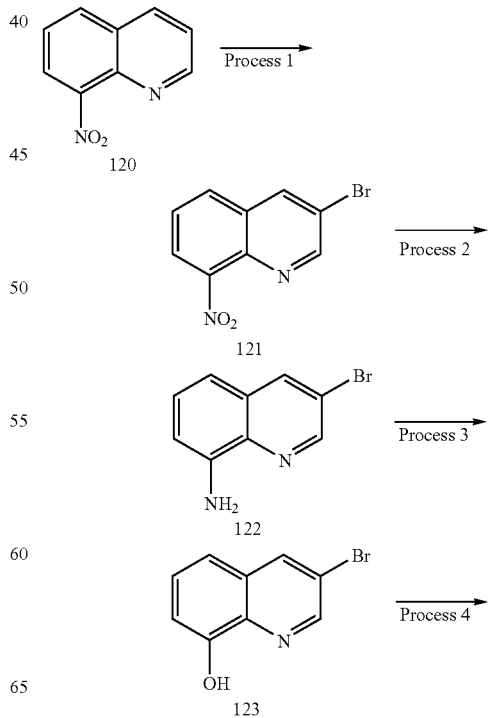

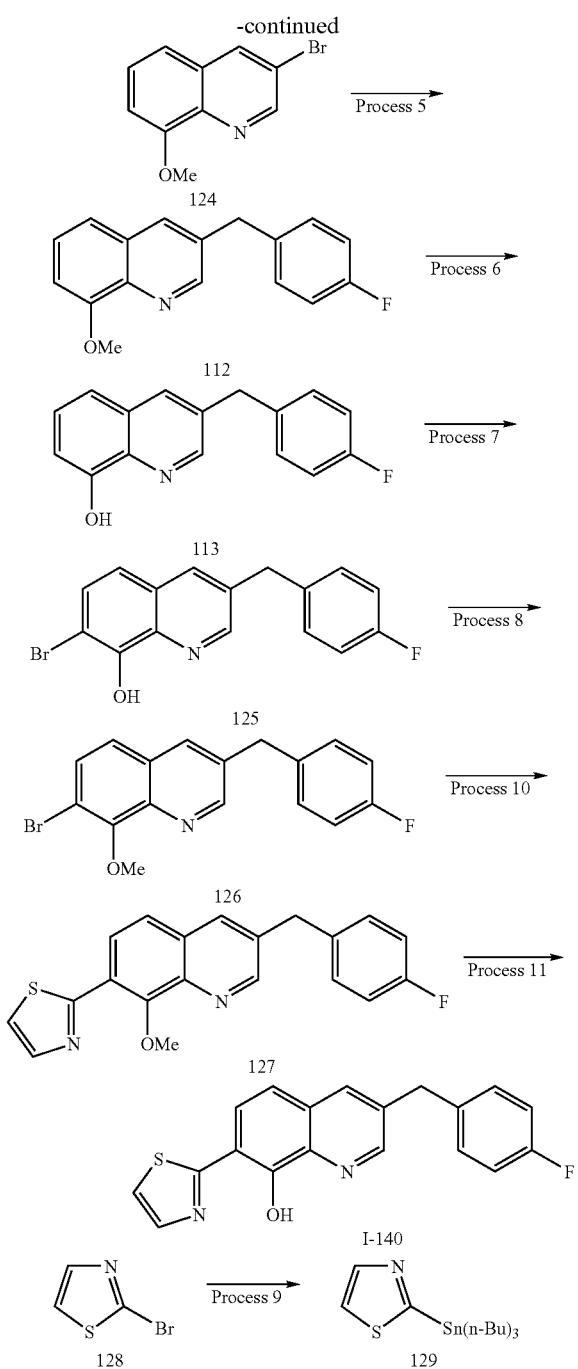

Process 1

A solution of 8-nitro quinoline (compound 120)(14.72 g, 84.52 mmol) in acetic acid (120 ml) was heated at 110° C. and N-bromosuccinimide (16.55 g, 92.98 mmol) was added to the solution over 30 minutes, and the mixture was stirred for 2.5 hours. This reaction mixture was added to water (700 ml), and the precipitated crystals were filtered and washed with water (350 ml). The crystals were dissolved in methylene chloride (300 ml), and the solution was washed with water and dried over sodium sulfate. A crude product obtained by evaporation under reduced pressure was subjected to silica gel column chromatography. The fractions containing desired compound eluted with n-hexane-ethyl acetate-methylene chloride (20:2:5 v/v) were concentrated under reduced pressure to give compound 121 (17.40 g, 68.76 mmol, 81.4%) as pale yellow crystals.

Process 2

To a solution of compound 121 (22.00 g, 86.94 mmol) obtained by process 1 in ethanol (1100 ml) were added water (66 ml), concentrated hydrochloric acid (66 ml) and iron powder (24.28 g, 434.8 mmol) at room temperature. The reaction mixture was refluxed for 1 hour and cooled to room temperature, and the insoluble materials were filtered off by passing through Celite pad. To the residue obtained by evaporation under reduced pressure were added 10% sodium hydrogen carbonate solution (700 ml) and ethyl acetate (500 ml), and the mixture was stirred for 30 minutes. The insoluble materials were filtered off by passing through Celite pad, and the organic layer obtained by filtration was washed with brine, dried over magnesium sulfate and decolorized with activated carbon. The solvent was concentrated under reduced pressure to give compound 122 (18.11 g, 81.19 mmol, 93.4%) as pale yellow crystals.

Process 3

To compound 122 (2.67 g, 10.6 mmol) obtained by process 2 was added a solution of 54 wt % sulfuric acid (16 ml), and the mixture was sealed up. The reaction mixture was heated at 220° C. for 16 hours and then cooled. This reaction mixture was added to ice water (270 ml) and neutralized (pH=7.9) with 28 wt % aqueous ammonia (20 ml). Water (110 ml) was added to the mixture, and the precipitated crystals were stirred at room temperature for 30 minutes. The crystals were collected by filtration, washed with water (30 ml) and dried at 70° C. under reduced pressure for 1 hour to give compound 123 as crude crystals (2.51 g).

Process 4

To a solution of compound 123 (2.51 g) obtained by process 3 in DMF (15 ml) was added potassium carbonate (1.61 g, 11.6 mmol), and the mixture was stirred at room temperature for 15 minutes. Methyl iodide (2.4 ml, 15.8 mmol) was added dropwise to the reaction mixture and the mixture was stirred at room temperature for 15 hours. To the reaction mixture were added water (60 ml) and 5 N hydrochloric acid (5 ml), and the mixture was extracted with methylene chloride (200 ml×2). The organic layer was washed with brine and dried over magnesium sulfate. Black oil obtained by evaporation under reduced pressure was subjected to silica gel column chromatography. The fractions containing desired compound eluted with n-hexane-ethyl acetate (3:1 v/v) were concentrated under reduced pressure to give compound 124 (1.43 g, 5.99 mmol, 56.8% from compound 122) as colorless crystals.

Process 5

To zinc powder (420 mg, 6.4 mmol) were added THF (6 ml), 1,2-dibromoethane (0.026 ml, 0.30 mmol), benzyl bromide (0.76 ml, 6.1 mmol) and chlorotrimethylsilane (0.026 ml, 0.20 mmol), and the mixture was refluxed for 30 minutes. This solution was added to a solution of compound 124 (580 mg, 2.44 mmol) in THF (19 ml). Then, triphenyl phosphine (64 mg, 0.24 mmol) and palladium acetate (27 mg, 0.12 mmol) were added to the reaction mixture, and the mixture was stirred at 60° C. for 15 minutes. The reaction mixture was cooled to room temperature, and 1% sodium hydrogen carbonate solution (80 ml) was added to the solution, and the mixture was extracted with ethyl acetate (50 ml). The organic layer was washed with brine and dried over magnesium sulfate. The residue obtained by evaporation under reduced pressure was subjected to silica gel column chromatography. The fractions containing desired compound eluted with n-hexane-ethyl acetate (1:2 v/v) were concentrated under reduced pressure to give compound 112 (529 mg, 1.98 mmol, 81.0%) as yellow oil.

Process 6

To compound 112 (3.995 g, 14.95 mmol) obtained by process 5 was added pyridine hydrochloride (17.28 g, 149.5 mmol), and the mixture was warmed up gradually to 180° C. and stirred for 30 minutes. The reaction mixture was gradually cooled to room temperature and allowed to stand for 14 hours. Water (120 ml) was added to the solution, and the mixture was extracted with methylene chloride (120 ml×2). The organic layer was washed with brine, dried over sodium sulfate and evaporated under reduced pressure to give compound 113 (3.778 g, 14.92 mmol, 99.8%) as yellow oil.

Process 7

To a solution of compound 113 (22.96 g, 90.65 mmol) obtained by process 6 in methylene chloride (500 ml) was added dropwise diisopropylamine (12.7 ml, 90.62 mmol) and a solution of N-bromosuccinimide (16.13 g, 90.62 mmol) in methylene chloride (1000 ml) at room temperature. The reaction mixture was stirred at room temperature for 1 hour. This reaction mixture was added to 2 N hydrochloric acid (1000 ml), and the precipitated crystals were filtered. The crystals were dissolved in ethyl acetate (1500 ml), washed with water (500 ml×2) and dried over magnesium sulfate. The crude product by evaporation under reduced pressure was recrystallized with diisopropyl ether (180 ml) to give compound 125 (12.80 g, 38.53 mmol, 42.5%) as pale yellow crystals.

Process 8

To a solution of the crude crystal (579 mg, about 1.8 mmol) of compound 125 obtained by process 7 in DMF (3.5 ml) was added potassium carbonate (276 mg, 2.0 mmol), and the reaction mixture was stirred at room temperature for 15 minutes. Methyl iodide (0.82 ml, 5.4 mmol) was added dropwise to the solution, and the mixture was stirred at room temperature for 1.5 hours. Furthermore, methyl iodide (0.41 ml, 2.7 mmol) was added dropwise to the reaction mixture, and the mixture was stirred at room temperature for 1 hour. To the reaction mixture were added water (15 ml) and 2 N hydrochloric acid (3 ml), and the mixture was extracted with ethyl acetate (40+20 ml). The organic layer was washed with brine and dried over magnesium sulfate. The residual oil obtained by evaporation under reduced pressure was subjected to silica gel column chromatography. The fractions containing desired compound eluted with n-hexane-ethyl acetate (5:2 v/v) were concentrated under reduced pressure to give compound 126 (108 mg, 0.31 mmol, 17%) as colorless crystals.

Process 9

1.59 M n-butyllithium (13.0 ml, 20.7 mmol) in n-hexane was added dropwise to ether (24 ml). This solution was cooled to −78° C., and a solution of 2-bromothiazole (compound 128)(1.70 ml, 18.9 mmol) in ether (6 ml) was added dropwise to the solution. The reaction mixture was stirred at −78° C. for 20 minutes, and a solution of tri n-butyl tin chloride (5.20 ml, 19.2 mmol) in ether (6 ml) was added dropwise to the mixture. The reaction mixture was stirred for 1 hour and warmed up to 0° C. 10% Sodium hydrogen carbonate solution (24 ml) was added to the reaction mixture. The organic layer was separated and the aqueous layer was extracted with ether (24 ml). The combined organic layer was dried over sodium sulfate. The solvent was evaporated under reduced pressure (50° C., 4 mmHg) to give yellow oil (7.15 g). This crude yellow oil (1.65 g) was purified by distillation (170° C., 0.4 mmHg) to give compound 129 as a colorless oil (1.28 g).

Process 10

To a mixture of compound 126 (100 mg, 0.29 mmol) obtained by process 8 and compound 129 (162 mg, 0.43 mmol) obtained by process 9 in THF (5 ml) was added tetrakis(triphenylphosphine)palladium (0) (17 mg, 0.015 mmol) at room temperature, and the reaction mixture was sealed up and heated at 110° C. for 39 hours. The reaction mixture was cooled, and 10% sodium hydrogen carbonate solution was added to the reaction mixture, and the mixture was extracted with ethyl acetate. The organic layer was washed with brine and dried over magnesium sulfate. The residue obtained by evaporation under reduced pressure was subjected to silica gel column chromatography. The fractions containing desired compound eluted with n-hexane-ethyl acetate (3:1 v/v) were concentrated evaporated under reduced pressure to give compound 127 (84 mg, 0.24 mmol, 83.0%) as pale yellow oil.

Process 11

To compound 127 (84 mg, 0.24 mmol) obtained by process 10 was added pyridine hydrochloride (1.14 g, 9.87 mmol), and the mixture was warmed up gradually to 180° C. and stirred for 10 minutes. The reaction mixture was gradually cooled to room temperature, and water was added to it. The mixture was extracted with methylene chloride. The organic layer was washed with 10% sodium hydrogen carbonate solution and brine and dried over sodium sulfate. The solvent was evaporated under reduced pressure to give yellow crystals (73 mg). The crude yellow crystals (63-mg) were recrystallized from ethyl acetate to give compound I-140 as pale yellow crystals (39 mg).

M.p.: 247–248° C. Recrystallization solvent: ethyl acetate

Elemental analysis for $C_{19}H_{13}FN_2OS$ Calcd. (%): C, 67.84; H, 3.90; F, 5.65; N, 8.33; S, 9.53. Found. (%): C, 67.77; H, 3.88; F, 5.78; N, 8.15; S, 9.45.

NMR (DMSO-$d_6$) δ: 4.21 (2H, s), 7.13–7.19 (2H, m), 7.36–7.41 (2H, m), 7.43 (1H, d, J=9.0 Hz), 7.83 (1H, d, J=3.0 Hz), 7.99 (1H, d, J=9.0 Hz), 8.16 (1H, d, J=1.8 Hz), 8.36 (1H, d, J=9.0 Hz), 8.85 (1H, d, J=1.8 Hz).

Example 42

Compound I-141

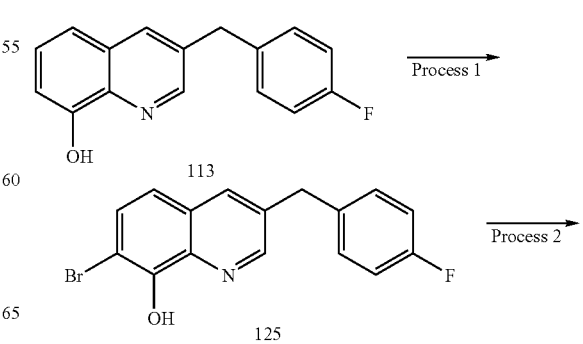

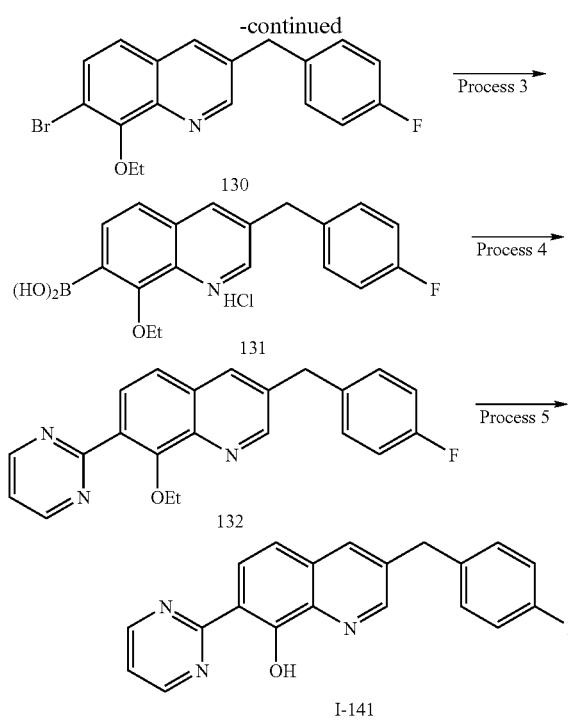

Process 1

This process was carried out by process 5 of Example 40.

Process 2

To a solution of compound 125 (4.81 g, 14.5 mmol) obtained by process 1 in DMF (30 ml) was added potassium carbonate (2.20 g, 15.9 mmol), and the mixture was stirred at room temperature for 30 minutes. Ethyl bromide (2.2 ml, 29.5 mmol) was added to the reaction mixture and the mixture was warmed up gradually to 60° C. and stirred for 20 minutes. The reaction mixture was gradually cooled to room temperature, and water (150 ml) was added to it. The mixture was extracted with ethyl acetate (200 ml) and washed with water (150 ml×4) and dried over magnesium sulfate. The solvent was evaporated under reduced pressure, and the residual purple oil was subjected to silica gel column chromatography The fractions containing desired compound eluted with n-hexane-ethyl acetate-methylene chloride (5:1:3 v/v) were concentrated under reduced pressure to give yellow oil (5.06 g). This oil was subjected to silica gel column chromatography again. The fractions containing desired compound eluted with n-hexane-ethyl acetate (3:1 v/v) were concentrated under reduced pressure to give compound 130 (4.97 g, 13.8 mmol, 95.3%) as colorless crystals.

Process 3

1.8 M phenyl lithium (12.4 ml, 22.3 mmol) in ether-cyclohexane (7:3 v/v) was added dropwise to ether (160 ml), and the mixture was cooled to −78° C. and then a solution of compound 130 (4.00 g, 11.1 mmol) in ether (60 ml) was added dropwise to the mixture over 3 hours. The reaction mixture was stirred at −78° C. for 30 minutes, and boric acid triisopropyl (6.4 ml, 27.7 mmol) was added dropwise to it, and the mixture was warmed up gradually to 0° C. This reaction mixture was added to 2 N hydrochloric acid (100 ml), and the precipitated crystals were stirred at room temperature for 1 hour. The crystals were collected by filtration and washed with ethyl acetate (30 ml) and water (15 ml), and dried at room temperature under reduced pressure to give compound 131 (1.97 g, 5.45 mmol, 49.1%) as yellow crystals.

Process 4

To a solution (15 ml) of compound 131 (200 mg, 0.55 mmol) obtained by process 3 and 2-bromopyrimidine (147 mg, 0.92 mmol) in dimethoxyethane-ethanol (3:2 v/v) were added 2 M sodium carbonate solution (0.34 ml, 0.68 mmol) and tetrakis(triphenyl phosphine)palladium (0)(71 mg, 0.06 mmol) at room temperature, and the mixture was refluxed for 18 hours. The reaction mixture was cooled to room temperature and 2-bromopyrimidine (147 mg, 0.92 mmol) was added to it, and the mixture was refluxed for 10 hours. The reaction mixture was cooled, and water was added to it, and the mixture was extracted with ethyl acetate. The organic layer was washed with brine and dried over magnesium sulfate. The residue obtained by evaporation under reduced pressure was subjected to silica gel column chromatography. The fractions containing desired compound eluted with n-hexane-ethyl acetate (1:3 v/v) were concentrated under reduced pressure to give compound 132 (106 mg, 0.29 mmol, 53.0%) as colorless oil.

Process 5

To compound 132 (106 mg, 0.29 mmol) obtained by process 4 was added pyridine hydrochloride (680 mg, 5.9 mmol), and the mixture was warmed up gradually to 180° C. and stirred for 5 minutes. The reaction mixture was gradually cooled to room temperature, and water was added to it, and the mixture was extracted with ethyl acetate. The organic layer was washed with water, brine, dried over sodium sulfate and evaporated under reduced pressure to give compound I-002 (90 mg, 0.27 mmol, 92.0%) as yellow crystals. The crystals were recrystallized from ethyl acetate to give compound I-141 as yellow crystals (49 mg).

M.p.: 192–193° C. Recrystallization solvent: ethyl acetate

Elemental analysis for $C_{20}H_{14}FN_3O$ Calcd. (%): C, 72.50; H, 4.26; F, 5.73; N, 12.68. Found. (%): C, 72.08; H, 4.21; F, 5.40; N, 12.40.

NMR (DMSO-$d_6$) δ: 4.19 (2H, s), 7.13–7.19 (2H, m), 7.36–7.40 (2H, m), 7.41 (1H, d, J=9.0 Hz), 7.56(1H, t, J=5.1 Hz), 8.10 (1H, d, J=2.1 Hz), 8.50 (1H, d, J=9.0 Hz), 8.84 (1H, d, J=2.1 Hz), 9.05 (2H, d, J=5.1 Hz), 14.41 (1H, s).

Example 43

Compound I-142

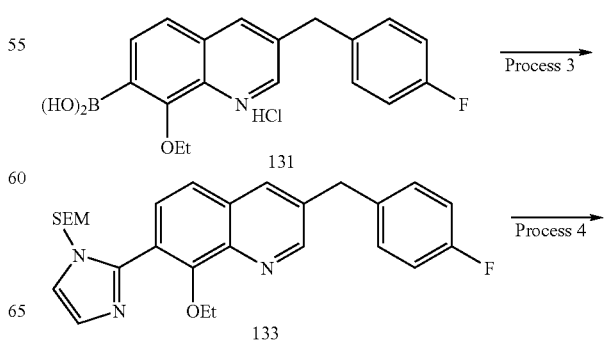

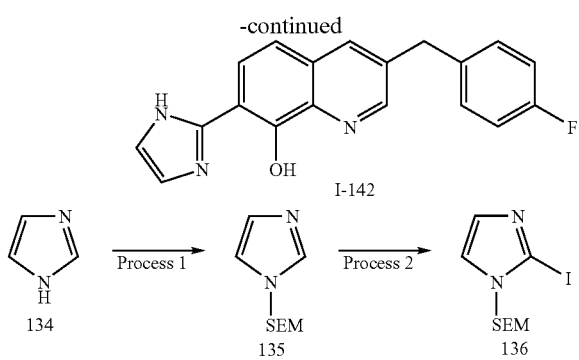

Process 1

To a solution of imidazole (compound 134)(6.80 g, 99.9 mmol) in THF (100 ml) was added N,N-diisopropylethylamine (15.5 g, 120 mmol), and 2-(trimethylsilyl)-ethoxymethyl chloride (18.3 g, 110 mmol) was added dropwise to the reaction mixture at room temperature. The mixture was stirred for 1.5 hours and allowed to stand for 18 hours. Water (200 ml) was added to the reaction mixture and the mixture was extracted with ether (100 ml×3). The organic layer was washed with brine and dried over sodium sulfate. A crude product obtained by evaporation under reduced pressure was distilled (124–126° C., 5 mmHg) under reduced pressure to give compound 135 (12.4 g, 62.5 mmol, 62.6%) as colorless oil.

Process 2

1.59 M n-butyllithium (7.0 ml, 11.1 mmol) in n-hexane was added dropwise to a solution of compound 135 (2.00 g, 10.1 mmol) obtained by process 1 in TMF (50 ml) at 0° C., and the mixture was stirred at room temperature for 1.5 hours. The reaction mixture was cooled to 0° C. again and a solution of iodine (3.07 g, 12.1 mmol) in THF (25 ml) was added dropwise to it, and then the mixture was stirred for 30 minutes. This reaction mixture was added to ice-cooled 0.1 N sodium thiosulfate solution (150 ml) and the mixture was extracted with ethyl acetate (100 ml×2). The organic layer was washed with N sodium thiosulfate solution, water and brine successively and dried over magnesium sulfate. The residue obtained by evaporation under reduced pressure was subjected to silica gel column chromatography. The fractions containing desired compound eluted with hexane-ethyl acetate (3:1 v/v) were concentrated under reduced pressure to give compound 136 (1.21 g, 3.73 mmol, 37.0%) as light brown oil.

Process 3

To a solution (20 ml) of compound 131 (250 mg, 0.69 mmol) obtained by process 3 of Example 42 and compound 136 (247 mg, 0.76 mmol) obtained by process 2 in dimethoxyethane-ethanol (3:2 v/v) were added 2 M sodium carbonate solution (1.04 ml, 2.08 mmol) and tetrakis(triphenyl phosphine)palladium (0)(80 mg, 0.07 mmol) at room temperature, and then the mixture was refluxed for 12 hours. The reaction mixture was cooled to room temperature and allowed to stand for 12 hours. To the reaction mixture were added compound 136 (247 mg, 0.76 mmol), 2 M sodium carbonate solution (1.04 ml, 2.08 mmol) and tetrakis(triphenyl phosphine)palladium (0)(80 mg, 0.07 mmol), and the mixture was refluxed for 12 hours. The reaction mixture was cooled to room temperature and allowed to stand for 12 hours. Water was added to the reaction mixture and the mixture was extracted with ethyl acetate. The organic layer was washed with brine and dried over magnesium sulfate. The residue obtained by evaporation under reduced pressure was subjected to silica gel column chromatography. The fractions containing desired compound eluted with hexane-ethyl acetate (1:1 v/v) were concentrated under reduced pressure to give compound 133 (104 mg, 0.22 mmol, 31.0%) as colorless oil.

Process 4

A solution of compound 133 (103 mg, 0.21 mmol) obtained by process 3 in methylene chloride (5 ml) was cooled to −20° C. A solution (0.64 ml, 0.64 mmol) of 1.0 M boron tribromide in methylene chloride was added dropwise to the solution and the mixture was warmed up to 0° C. and stirred for 15 minutes. Furthermore, a solution (0.64 ml, 0.64 mmol) of 1.0 M boron tribromide in methylene chloride was added to the reaction mixture again and the mixture was warmed up to room temperature and stirred for 30 minutes. This reaction mixture was added to ice-cooled 0.2 N hydrochloric acid (20 ml), and then neutralized (pH=7) with sodium hydrogen carbonate and was extracted with ethyl acetate. The organic layer was washed with water, brine and dried over sodium sulfate. A crude product obtained by evaporation under reduced pressure was recrystallized from ethyl acetate to give compound I-142 (34 mg, 0.076 mmol, 35.0%) as orange crystals.

M.p.: 213–215° C. Recrystallization solvent: ethyl acetate

Elemental analysis for $C_{19}H_{14}FN_3O$ Calcd. (%): C, 71.46; H, 4.42; F, 5.95; N, 13.16. Found. (%): C, 69.85; H, 4.27; F, 5.49; N, 12.63.

NMR (CDCl$_3$) δ: 4.16 (2H, s), 6.99–7.05 (2H, m), 7.17–7.22 (2H, m), 7.25 (2H, s), 7.35(1H, d, J=8.7 Hz), 7.87 (1H, d, J=2.4 Hz), 8.33 (1H, d, J=J=8.7 Hz), 8.69 (1H, d, J=2.4 Hz).

Example 44

Compound I-143

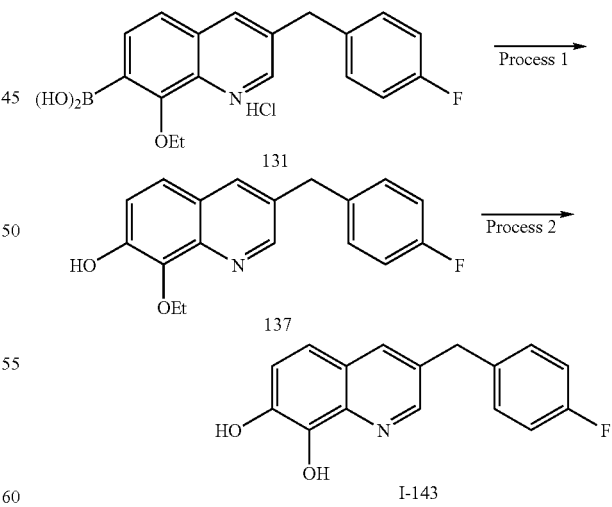

Process 1

To a solution of compound 131 (150 mg, 0.41 mmol) obtained by process 3 of Example 42 in ethanol (4 ml) was added 30% hydrogen peroxide solution (0.24 ml, 2.1 mmol) at room temperature, and the mixture was stirred for 30 minutes and allowed to stand for 12 hours. To the reaction mixture was added 1 N sodium thiosulfate solution (5 ml), and the mixture was extracted with ethyl acetate. The organic layer was washed with 5% sodium hydrogen carbonate solution, brine and dried over sodium sulfate anhydride. A crude product obtained by evaporation under reduced pressure was recrystallized from diisopropyl ether to give compound 137 (75 mg, 0.25 mmol, 61.0%) as colorless crystals.

Process 2

A solution of compound 137 (63 mg, 0.21 mmol) obtained by process 1 in methylene chloride (6 ml) was cooled to 0° C., and a solution (0.32 ml, 0.32 mmol) of aluminum chloride (283 mg, 2.1 mmol) and 1.0 M ethanethiol in methylene chloride were added dropwise to the solution, and the mixture was warmed up to room temperature and stirred for 1 hour. Ice-cooled 0.2 N hydrochloric acid (10 ml) was added to the reaction mixture, and the mixture was extracted with ethyl acetate. The organic layer was washed with brine, dried over sodium sulfate and evaporated under reduced pressure to give compound I-143 (36 mg, 0.13 mmol, 63.0%) as colorless crystals. The crystals were recrystallized from ethyl acetate to give compound I-143 as colorless crystals (7 mg).

M.p.: 184–185° C. Recrystallization solvent: ethyl acetate
NMR (CDCl$_3$) δ: 4.12 (2H, s), 6.98–7.04 (2H, m), 7.15–7.20 (2H, m), 7.26(1H, d, J=8.7 Hz), 7.31 (1H, d, J=J=8.7 Hz), 7.88 (1H, d, J=1.8 Hz), 8.61 (1H, d, J=1.8 Hz).

Example 45

Compound I-144

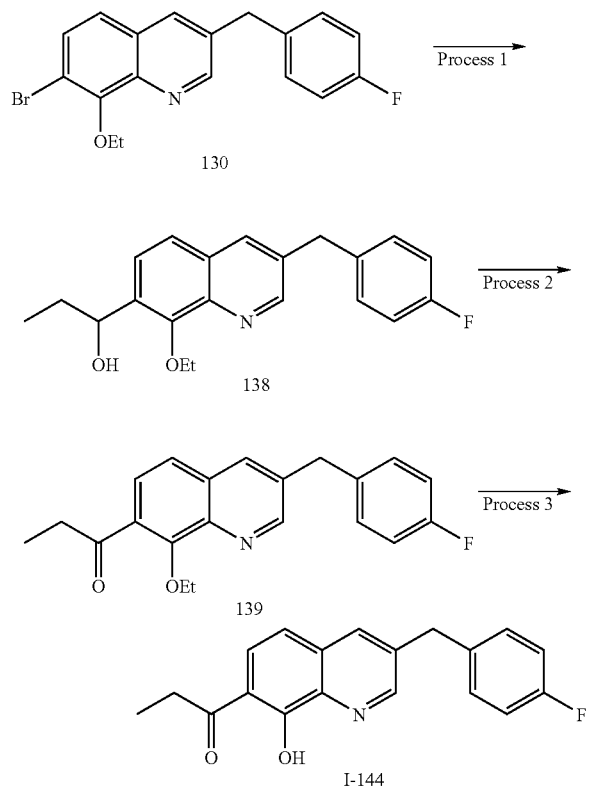

Process 1

1.8 M phenyl lithium (0.93 ml, 1.7 mmol) in ether cyclohexane (7:3 v/v) was added dropwise to ether (20 ml), and the mixture was cooled to −78° C., and a solution of compound 130 (300 mg, 0.83 mmol) obtained by process 2 of Example 42 in ether (10 ml) was added dropwise to the reaction mixture over 30 minutes. The mixture was stirred at −78° C. for 1 hour, and acetic aldehyde (0.3 ml, 4.2 mmol) was added to the reaction solution. The reaction mixture was warmed up gradually to room temperature. This reaction mixture was added to ice-cooled 1% ammonium chloride solution (100 ml), and the mixture was extracted with ethyl acetate. The organic layer was washed with brine and dried over magnesium sulfate. The yellow oil obtained by evaporation under reduced pressure was subjected to silica gel column chromatography. The fractions containing desired compound eluted with n-hexane-ethyl acetate (3:1 v/v) were concentrated under reduced pressure to give compound 138 (114 mg, 0.33 mmol, 40.0%) as pale yellow oil.

Process 2

Oxalyl chloride (0.10 ml, 1.1 mmol) was added to methylene chloride (4 mL), and the mixture was cooled to −78° C. A solution of dimethylsulfoxide (0.16 ml, 2.3 mmol) in methylene chloride (2 ml) was added dropwise to the reaction mixture over 5 minutes, and the mixture was stirred for 15 minutes. A solution of compound 138 (114 mg, 0.33 mmol) obtained by process 1 in methylene chloride (4 ml) was added to the reaction mixture at −78° C. over 10 minutes, and the mixture was stirred for 30 minutes. To the reaction mixture was added dropwise triethylamine (0.63 ml, 4.5 mmol) at −78° C. over 2 minutes, and the mixture was stirred for 15 minutes. The reaction mixture was warmed up gradually to 0° C., and brine was added to it, and the mixture was extracted with ethyl acetate. The organic layer was washed with brine and dried over sodium sulfate. The residue obtained by evaporation under reduced pressure was subjected to silica gel column chromatography. The fractions containing desired compound eluted with n-hexane-ethyl acetate (4:1 v/v) were concentrated under reduced pressure to give compound 139 (65 mg, 0.19 mmol, 57.0%) as colorless oil.

Process 3

To compound 139 (65 mg, 0.19 mmol) obtained by process 2 was added pyridine hydrochloride (550 mg, 4.8 mmol), and the mixture was warmed up gradually to 180° C. and stirred for 10 minutes. The reaction mixture was cooled gradually to room temperature, and water was added to it, and the mixture was extracted with ethyl acetate. The organic layer was washed with water and dried over sodium sulfate, and evaporated under reduced pressure to give compound I-144 (54 mg, 0.18 mmol, 91.0%) as yellowish-brown crystals. The crystals were recrystallized from ethyl acetate to give compound I-144 as dark yellow crystals (17 mg).

M.p.: 87–88° C. Recrystallization solvent: ethyl acetate
NMR (CDCl$_6$) δ: 1.23 (3H, d, J=7.5 Hz), 3.15 (2H, d, J=7.5 Hz), 4.16 (2H, s), 7.00–7.05 (2H, m), 7.16–7.21 (2H, m), 7.18 (1H, d, J=9.0 Hz), 7.77 (1H, d, J=2.1 Hz), 7.79 (1H, d, J=9.0 Hz), 8.85 (1H, d, J=2.1 Hz), 13.65 (1H, s).

Example 46

Compound I-145

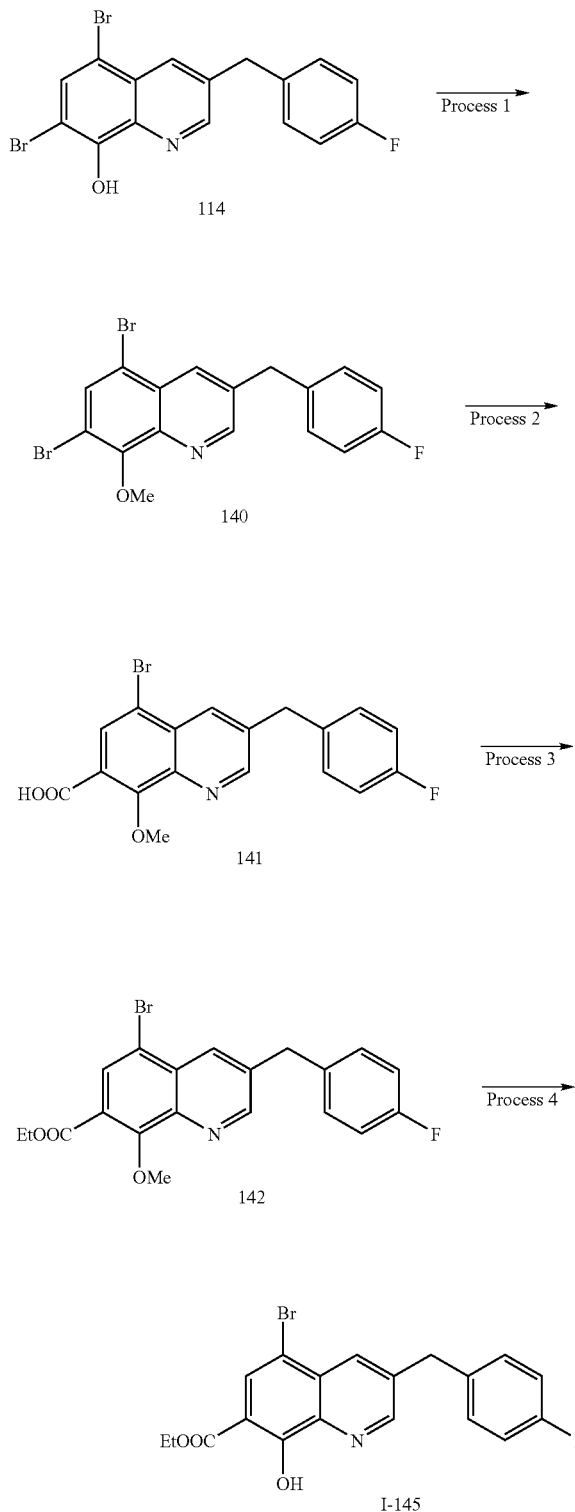

Process 1

To a solution of compound 114 (4.1 g, 10.0 mmol) prepared in a same manner similar to procedure of Example 40 in DMF (30 ml) were added potassium carbonate (1.66 g, 12.0 mmol) and methyl iodide (2.2 g, 15.0 mmol), and the mixture was stirred at 50° C. for 45 minutes. Water was added to the reaction mixture, and the precipitated crystals were filtered and washed with water. The crystals were dissolved in ethyl acetate, dried over magnesium sulfate and decolorized with activated carbon. The solvent was evaporated under reduced pressure to give a crude product (2.1 g, 4.94 mmol, 49.4%) of compound 140 as light purple crystals.

Process 2

1.8 M phenyl lithium (4.7 ml, 8.4 mmol) in ether-cyclohexane (7:3 v/v) was added to ether (80 ml) and cooled to −78° C., and a solution of compound 140 (1.8 g, 4.2 mmol) obtained by process 1 in ether (100 ml) was added dropwise to the reaction mixture over 30 minutes. The reaction mixture was stirred at −78° C. for 30 minutes and $CO_2$ gas was injected to the reaction mixture for 60 minutes. The reaction mixture was warmed up to 0° C., neutralized with hydrochloric acid aqueous solution and alkalized with sodium hydroxide solution. The aqueous layer was washed with ether and neutralized with hydrochloric acid. The precipitated pale yellow crystals were filtered, washed with water and dried under reduced pressure. The crystals were washed with isopropyl ether to give compound 141 (760 mg, 1.95 mmol, 46.4%) as colorless crystals.

Process 3

Compound 142 (720 mg, 1.72 mmol, 90.6%) was prepared as pale yellow crystals in a same manner similar to procedure of process 9 of Example 40.

Process 4

To a solution of compound 142 (100 mg, 0.24 mmol) in acetonitrile (5 ml) were added sodium iodide (217 mg, 2.0 mmol) and trimethylsilyl chloride (300 mg, 2.0 mmol) at room temperature, and the mixture was stirred for 5 minutes and then refluxed for 90 minutes. The reaction mixture was cooled to room temperature, and ice water was added to it, and the mixture was extracted with ethyl acetate. The organic layer was washed with sodium hydrogen sulfite solution and brine. The light purple crystals obtained by evaporation under reduced pressure were recrystallized with ethanol to give a title compound I-145 (70 mg, 0.173 mmol 72.2%) as pale yellow crystals.

M.p.: 108–110° C. Recrystallization solvent: ethanol

Elemental analysis for: $C_{19}H_{15}BrFNO_3$ Calcd. (%): C, 56.45; H, 3.74; Br, 19.77; F, 4.70; N, 3.47. Found. (%): C, 56.31; H, 3.61; Br, 19.36; F, 4.50; N, 3.44.

NMR (CDCl$_3$) δ: 1.48 (3H, t, J=7.2 Hz), 4.22 (2H, s), 4.50 (2H, q, J=7.2 Hz), 7.00–7.08 (2H, m), 7.15–7.24 (2H, m), 8.17 (1H, s), 8.22 (1H, brs), 8.86 (1H, brs), 11.96(1H, brs).

Example 47

Compound I-146, I-147

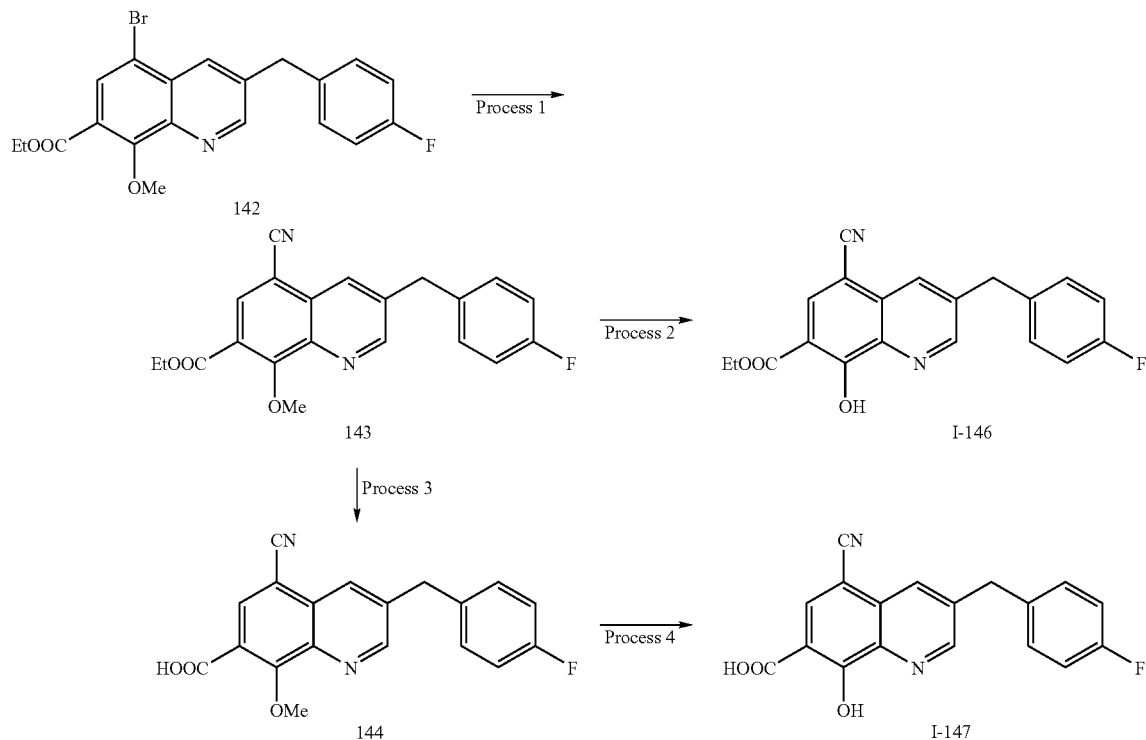

Elemental analysis for $C_{20}H_{15}FN_2O_3(H_2O)_{0.2}$ Calcd. (%): C, 68.57; H, 4.32; F, 5.42; N, 8.00. Found. (%): C, 67.83; H, 4.18; F, 5.27; N, 7.85.

Process 1

To a solution of compound 142 (500 mg, 1.2 mm) obtained by Example 46 in dioxane (6 ml) were added copper cyanide (430 mg, 4.8 mmol), 1,1'-bisdiphenyl phosphinoferrocene (107 mg, 0.19 mmol), trisdibenzylidene acetone dipalladium (0)(44.4 mg, 0.048 mmol) and tetraethylammonium cyanide (187 mg, 1.2 mmol), and the mixture was refluxed for 2 hours. To the reaction mixture were added 1,1'-bisdiphenyl phosphinoferrocene (107 mg, 0.19 mmol) and trisdibenzylidene acetone dipalladium (0) (44.4 mg, 0.048 mmol), and the mixture was refluxed for 45 minutes. The reaction mixture was cooled to room temperature, and ethyl acetate (50 ml) was added to it. Insoluble materials were filtered off by passing through Celite pad. The organic layer was separated and washed with saturated sodium hydrogen carbonate solution and brine. The organic layer was dried over magnesium sulfate and the residue obtained by evaporation under reduced pressure was subjected to silica gel column chromatography. The fractions containing desired compound eluted with n-hexane-acetic acid (3:1 v/v) were concentrated under reduced pressure to give compound 143 (410 mg, 1.1 mmol, 90.3%) as pale yellow crystals.

Process 2

A solution of compound 143 (124 mg, 0.33 mmol) obtained by process 1 in acetonitrile (10 ml) was reacted by process 4 of Example 46 to give a title compound I-146 (45 mg, 0.13 mmol, 39.4%) as pale yellow crystals.

M.p.: 145–147° C. Recrystallization solvent: isopropylether

NMR (CDCl$_3$) δ: 1.50 (3H, t, J=7.2 Hz), 4.23 (2H, s), 4.53 (2H, q, J=7.2 Hz), 7.00–7.10 (2H, m), 7.15–7.24 (2H, m), 8.21 (1H, s), 8.38 (1H, s), 8.94 (1H, brs), 12.50(1H, m).

Process 3

To a suspension of compound 143 (125 mg, 0.33 mmol) obtained by process 1 in ethanol (10 ml) was added 1.0 M sodium ethoxide (400 ul, 0.4 mmol) with stirring under ice cooling. The reaction mixture was warmed up to 50° C. and then stirred for 30 minutes. To the residue obtained by evaporation under reduced pressure were added ethyl acetate and hydrochloric acid. The aqueous layer was separated and extracted with ethyl acetate. The combined organic layer was washed with brine, dried over sodium sulfate, and the solvent was evaporated to give crude crystals of compound 144 (75 mg, 0.22 mmol, 67.6%).

Process 4

A solution of compound 144 (65 mg, 0.19 mmol) obtained by process in acetonitrile (8 ml) was reacted with the same procedure as process 4 of Example 46 to give a title compound I-147 (38 mg, 0.12 mmol, 62.0%) as pale yellow crystals.

M.p.: 231–234° C. Recrystallization solvent: ethanol

Elemental analysis for $C_{18}H_{11}FN_2O_3(H_2O)_{0.6}$ Calcd. (%): C, 65.26; H, 3.65; F, 5.73; N, 8.46. Found. (%): C, 65.37; H, 3.36; F, 5.65; N, 8.38.

NMR (DMSO-d$_6$) δ: 4.22 (2H, s), 7.10–7.20 (2H, m), 7.32–7.40 (2H, m), 7.98–8.02 (1H, bm), 8.19 (1H, s), 8.68–8.72(1H, m).

Example 48

Compound I-148, I-149, I-150

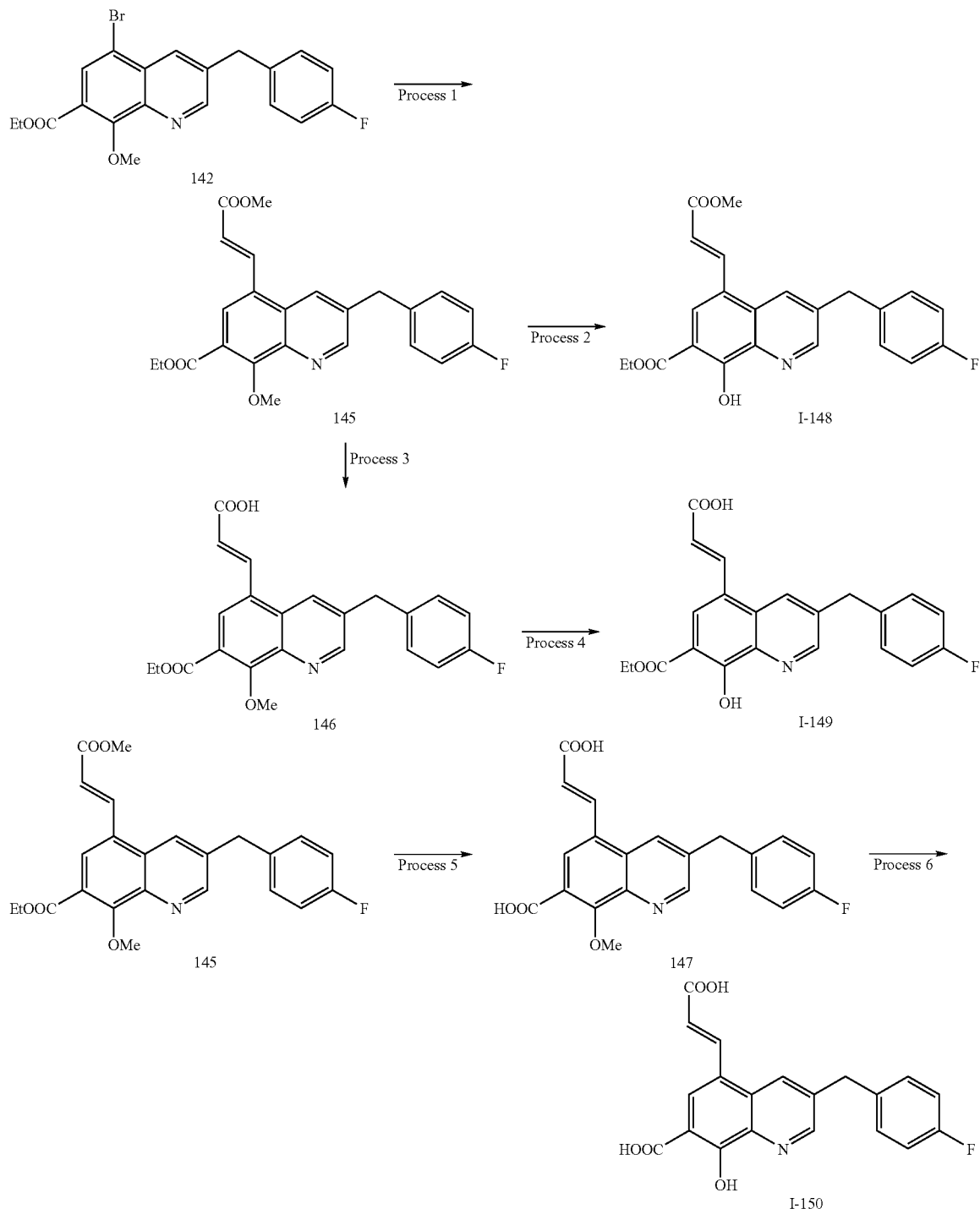

Process 1

Compound 142 (837.0 mg, 2.0 mmol) which was prepared by Example 46, palladium acetate (22.5 mg, 0.1 mmol), tritolylphosphine (61.0 mg, 0.2 mmol), triethylamine (808.0 mg, 8.0 mmol) and methyl acrylate (448.0 mg, 5.2 mmol) were sealed up, and the reaction mixture were heated at 110° C. for 16 hours. The reaction mixture was cooled to room temperature and diluted with ethyl acetate (30 ml), and the mixture was stirred for 30 minutes. Insoluble materials were filtered off by passing through Celite pad, and the filtrate was washed with brine. The organic layer was dried over sodium sulfate, and the residue obtained by evaporation under reduced pressure was subjected to silica gel column chromatography. The fractions containing desired compound eluted with hexane-acetic acid (3:1 v/v) were concentrated under reduced pressure to give compound 145 (582 mg, 1.38 mmol, 68.8%) as pale yellow crystals.

Process 2

To a solution of compound 145 (100 mg, 0.24 mmol) obtained by process 1 in methylene chloride (5 ml) was added dropwise a solution of 1.0 M boron tribromide in methylene chloride (0.28 ml, 0.28 mmol) under ice-cooling, and the mixture was warmed up to 0° C. and stirred for 15 minutes. To the reaction mixture was added a solution of 1.0 M boron tribromide in methylene chloride (0.10 ml, 0.10 mmol), and the mixture was warmed up to room temperature and stirred for 30 minutes. This reaction mixture was added to ice-cooled 0.2 N hydrochloric acid (20 ml), and the mixture was neutralized (pH=7) with sodium hydrogen carbonate and extracted with ethyl acetate. The organic layer was washed with water and brine, dried over sodium sulfate. A crude product obtained by evaporation under reduced pressure was recrystallized from isopropyl ether to give a title compound I-148 (30 mg, 0.073 mmol, 30.6%) as pale yellow crystals.

M.p.: 102–105° C. Recrystallization solvent: isopropyl ether

Elemental analysis for $C_{23}H_{20}FNO_5(H_2O)_{0.6}$ Calcd. (%): C, 65.74; H, 5.09; F, 4.52; N, 3.33. Found. (%): C, 65.46; H, 4.73; F, 4.32; N, 3.33.

NMR (CDCl$_3$) δ: 1.50 (3H, t, J=7.5 Hz), 3.86 (3H, s), 4.21 (2H, s), 4.52 (2H, q, J=7.5 Hz), 6.51(1H, d, J=15.6 Hz), 6.98–7.16 (2H, m), 7.14–7.22 (2H, m), 8.20–8.30 (3H, m), 8.89 (1H, brs), 12.26(1H, m).

Process 3

To a solution of compound 145 (111 mg, 0.26 mmol) obtained by process 1 in dioxane (5 ml) was added 1 N hydrochloric acid, and the mixture was refluxed for 2 hours. The solvent was evaporated, and the residue was extracted with ethyl acetate. The organic layer was washed with brine, dried over sodium sulfate. The crude crystals obtained by evaporation under reduced pressure were subjected to silica gel columnchromatography. The fractions containing desired compound eluted with methanol-ethyl acetate (1:10 v/v) were concentrated under reduced pressure to give compound 146 (40 mg, 0.1 mmol, 38.5%) as pale yellow crystals.

Process 4

A solution of compound 146 (35 mg, 0.085 mmol) obtained by process 3 in methylene chloride (5 ml) was reacted with a same manner similar to process 2 of Example 48. A crude product was recrystallized from methanol-methylene chloride to give a title compound I-149 (15 mg, 0.038 mmol, 44.6%) as pale yellow crystals.

M.p.: 248–250° C. Recrystallization solvent: methanol-methylene chloride

Elemental analysis for $C_{22}H_{18}FN_2O_5$ $(H_2O)_{0.5}$ Calcd. (%): C, 65.34; H, 4.74; F, 4.70; N, 3.46. Found. (%): C, 65.38; H, 4.48; F, 4.69; N, 3.53.

NMR (DMSO-d$_6$) δ: 1.38 (3H, t, J=7.2 Hz), 4.27 (2H, s), 4.41 (2H, q, J=7.2 Hz), 6.52(1H, d, J=15.6 Hz), 7.08–7.20 (2H, m), 7.34–7.48 (2H, m), 8.18–8.28 (2H, m), 8.58–8.64 (1H, m), 8.90(1H, brs), 12.51 (1H, m).

Process 5

To a solution of compound 145 (108 mg, 0.26 mmol) obtained by process 1 in ethanol (5 ml) was added 1 N sodium hydroxide (1.12 ml, 1.12 mmol) under ice-cooling, and the mixture was allowed to stand for 15 hours. The reaction mixture was concentrated under reduced pressure, and water (30 ml) and ether (30 ml) were added to the solution. After being stirred for few minutes, the aqueous layer was separated. The aqueous layer was acidified with 2 N hydrochloric acid (3 ml, 3 mmol), and the solution was extracted with ethyl acetate, washed with brine, dried over sodium sulfate and evaporated to give compound 147 (94.5 mg, 0.25 mmol, 99.1%) as pale yellow crystals.

Process 6

A solution of compound 147 (94.5 mg, 0.25 mmol) obtained by process 5 in methylene chloride (5 ml) was reacted with a same manner similar to process 2 of Example 47. A crude product obtained was recrystallized from methanol-methylene chloride to give a title compound I-150 (15 mg, 0.04 mmol, 16.3%) as pale yellow crystals.

M.p.: 226–228° C. Recrystallization solvent: ethanol

NMR (DMSO-d$_6$) δ: 4.33 (2H, s), 6.45(1H, d, J=15.3 Hz), 7.04–7.22 (2H, m), 7.30–7.50 (2H, m), 8.10–8.44 (2H, m), 8.50–9.10 (2H, m), 12.40(1H, brs).

Example 49

Compound I-151, I-152

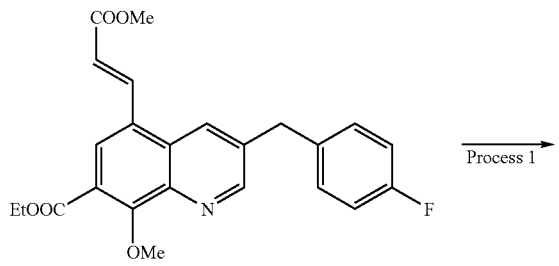

145

-continued

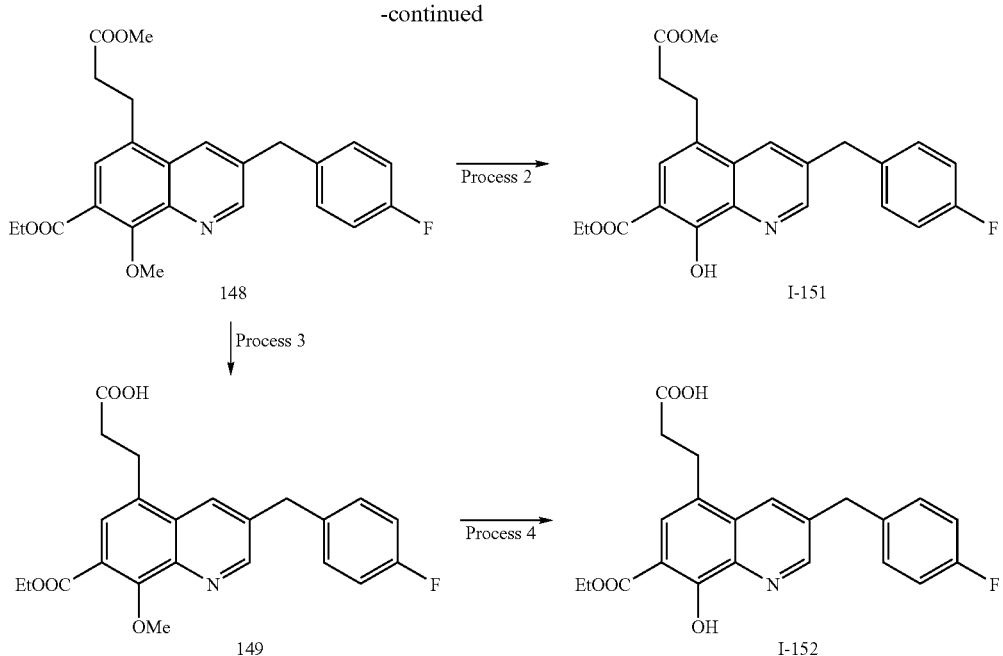

To a solution of compound 145 (100 mg, 0.24 mmol) synthesized with the same procedure as process 1 of Example 48 in ethyl acetate (3.0 ml) was added 5% palladium carbon (10 mg, 10% w) under ice-cooling and the mixture was stirred at room temperature for 5 hr. under hydrogen atmosphere. 5% palladium carbon (10 mg, 10% w) was added and then the mixture was stirred for 5 hours. After reaction was completed, the reaction mixture was filtered and the residue by evaporation under reduced pressure was subjected to silica gel column chromatography. The fractions containing desired compound eluted with hexane-ethyl acetate (2:1 v/v) were concentrated under reduced pressure to give compound 148 (62 mg, 0.15 mmol, 62.5%) as pale yellow crystals.

Process 2

A solution of compound 148 (85 mg, 0.2 mmol) obtained by process 1 in methylene chloride (5 ml) was reacted with a same manner similar to process 2 of Example 48. A crude product obtained was recrystallized from isopropyl ether to give a title compound I-151 (42 mg, 0.10 mmol, 51.0%) as pale yellow crystals.

M.p.: 72–75° C. Recrystallization solvent: isopropyl ether

Elemental analysis for $C_{23}H_{22}FN_2O_5(H_2O)_{0.7}$ Calcd. (%): C, 65.15; H, 5.56; F, 4.48; N, 3.30. Found. (%): C, 65.11; H, 5.06; F, 4.23; N, 3.31.

NMR (CDCl$_3$) δ: 1.47 (3H, t, J=7.2 Hz), 2.66(2H, t, J=7.8 Hz), 3.24(2H, t, J=7.8 Hz), 3.68 (3H, s), 4.21 (2H, s), 4.49 (2H, q, J=7.2 Hz), 6.98–7.10 (2H, m), 7.14–7.22 (2H, m), 7.75 (1H, s), 8.08 (1H, s), 8.93 (1H, brs), 11.86(1H, brs).

Process 3

A solution of compound 148 (68 mg, 0.16 mmol) obtained by process 1 in dioxan (5.0 ml) was reacted with a same manner similar to process 3 of Example 48. A crude product obtained was recrystallized from isopropyl ether to give compound 149 (35 mg, 0.085 mmol, 53.2%) as pale yellow crystals.

Process 4

A solution of compound 149 (35 mg, 0.085 mmol) obtained by process 3 in methylene chloride (5 ml) was reacted with a same manner similar to process 2 of Example 48. A crude product obtained was recrystallized from ethanol-isopropylether to give compound I-152 (24 mg, 0.06 mmol, 71.1%) as pale yellow crystals.

M.p.: 214–216° C. Recrystallization solvent: ethanol isopropyl ether

Elemental analysis for $C_{22}H_{20}FNO_5$ $(H_2O)_{0.2}$ Calcd. (%): C, 65.89; H, 5.13; F, 4.74; N, 3.49. Found. (%): C, 65.72; H, 4.90; F, 4.63; N, 3.46.

NMR (DMSO-d$_6$) δ: 1.37 (3H, t, J=6.9 Hz), 2.58(2H, t, J=7.5 Hz), 3.17(2H, t, J=7.5 Hz), 4.24 (2H, s), 4.39 (2H, q, J=7.2 Hz), 7.10–7.20 (2H, m), 7.36–7.44 (2H, m), 7.68 (1H, s), 8.35–8.41 (1H, m), 8.82–8.88 (1H, s), 11.14(1H, s), 12.21(1H, s).

Example 50

Compound I-153, I-154

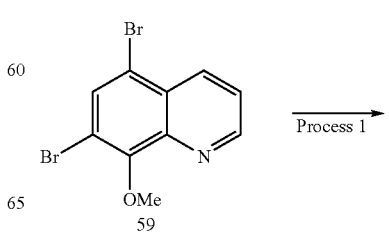

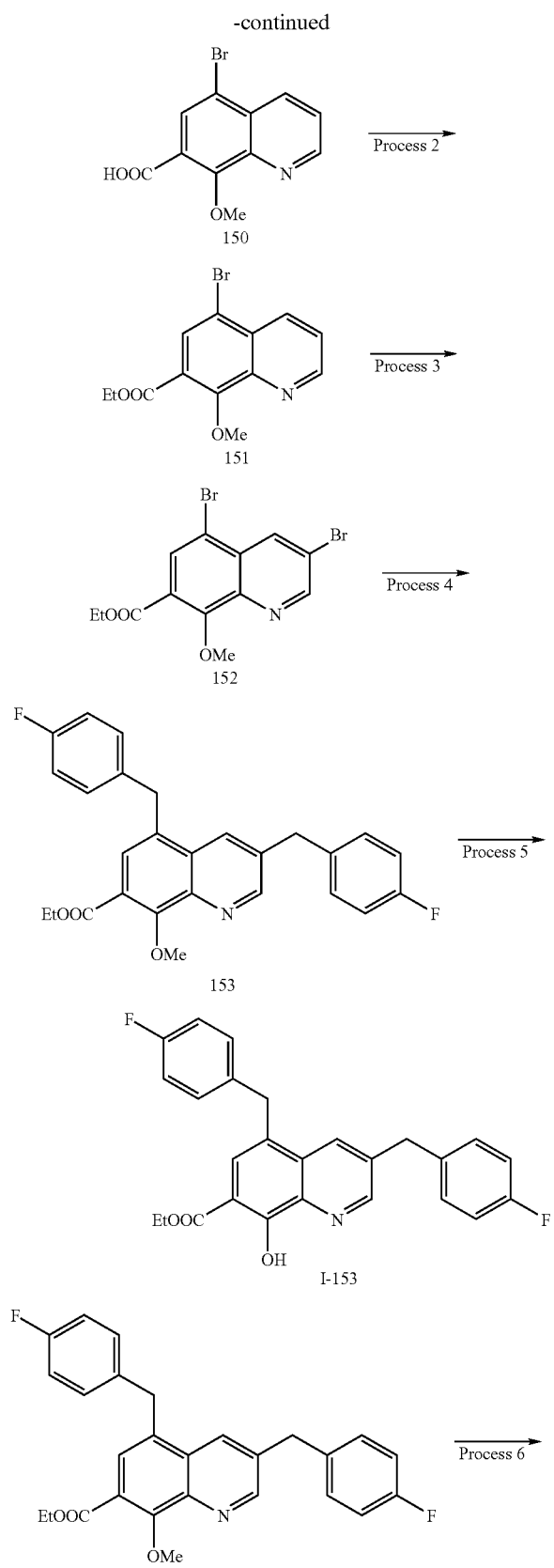

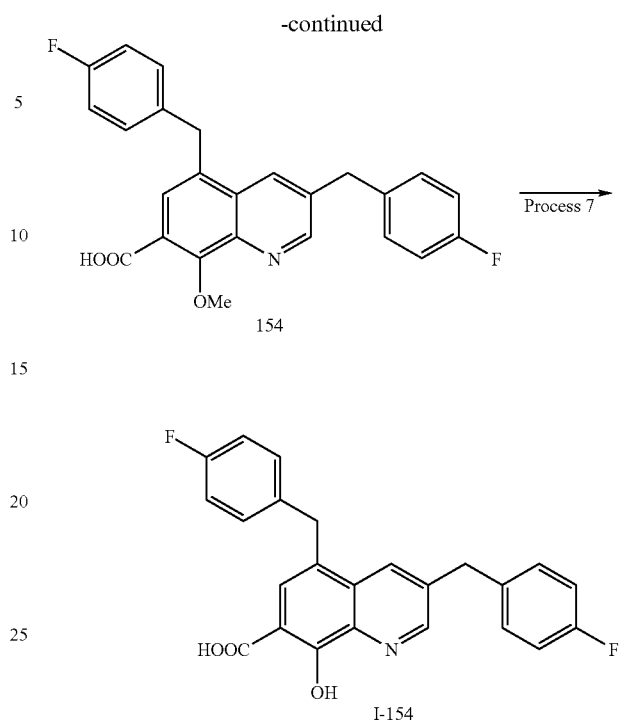

Process 1

Compound 59 was reacted with a same manner similar to process 5 of Example 18 to give compound 150 (2.5 g, 8.9 mmol, 44.5%) as colorless crystals.

Process 2

Compound 150 (2.5 g, 8.9 mmol) obtained by process 1 was reacted with a same manner similar to process 9 of Example 40 to give compound 151 (667 mg, 2.1 mmol, 24.1%) as pale yellow crystals.

Process 3

Compound 151 obtained by process 2 was reacted with a same manner similar to process 2 of Example 18 to give compound 152 (345 mg, 0.89 mmol, 42.2%) as pale yellow crystals.

Process 4

To zinc powder (210 mg, 3.2 mmol) were added THF (3.0 ml), 1,2-dibromoethane (0.012 ml, 0.15 mmol), benzyl bromide (210 mg, 3.23 mmol) and chlorotrimethylsilane (0.0125 ml, 0.10 mmol), and the mixture was refluxed for 30 minutes. This reaction mixture was added to a solution of compound 152 (345 mg, 0.89 mmol) obtained by process 3 in THF (10.0 ml). Triphenylphosphine (26.0 mg, 0.1 mmol) and palladium acetate (11.0 mg, 0.05 mmol) were added to the reaction mixture and the mixture was stirred at 60° C. for 10 minutes. The reaction mixture was cooled to room temperature, and 1% sodium hydrogen carbonate solution (40 ml) was added to it, and the mixture was extracted with ethyl acetate (50 ml). The organic layer was washed with brine and dried over magnesium sulfate. The residue obtained by evaporation under reduced pressure was subjected to silica gel column chromatography. The fractions containing desired compound eluted with n-hexane-ethyl acetate (3:1 v/v) were concentrated under reduced pressure to give compound 153 (179 mg, 0.4 mmol, 45.0%) as yellow oil.

Process 5

Compound 153 obtained by process 4 was reacted with a same manner similar to process 2 of Example 19 to give a title compound I-153 (40.0 mg, 0.092 mmol, 23.1%) as pale yellow crystals.

M.p.: 137–139° C. Recrystallization solvent: isopropyl ether

Elemental analysis for $C_{26}H_{21}F2NO_3(EtOAc)_{0.4}$ Calcd. (%): C, 70.73; H, 5.20; F, 8.11; N, 2.99. Found. (%): C, 70.71; H, 4.75; F, 7.87; N, 3.10.

NMR (CDCl$_3$) δ: 1.46 (3H, t, J=7.2 Hz), 4.06 (2H, s), 4.19 (2H, s), 4.48 (2H, q, J=7.2 Hz), 6.80–7.08 (8H, m), 7.68–7.74 (2H, m), 8.81–8.84 (1H, m), 11.90(1H, s).

Process 6

To a solution of compound 153 (400.0 mg, 0.92 mmol) obtained by process 4 in ethanol (15.0 ml) was added 4 N lithium hydroxide (1 ml, 4 mmol), and the mixture was refluxed for 40 minutes. To the crude crystals obtained by evaporation under reduced pressure were added water (10.0 ml) and 2 N hydrochloric acid (3 ml, 6 mmol) with stirring. The slurry of whitish crystals were filtered to give compound 154(380 mg, 0.91 mmol, 98.5%) as colorless crystals.

Process 7

Compound 154 (139 mg, 0.33 mmol) obtained by process 6 was reacted with a same manner similar to process 6 of Example 18. The colorless crystals were recrystallized with ethyl acetate to give a title compound I-154 (85.0 mg, 0.21 mmol, 63.5%).

M.p.: 207–209° C. Recrystallization solvent: isopropyl ether

Elemental analysis for $C_{24}H_{17}F2NO_3(H_2O)_{0.2}(EtOAc)_{0.15}$ Calcd. (%): C, 69.98; H, 4.44; F, 9.00; N, 3.32. Found. (%): C, 69.87; H, 4.08; F, 8.78; N, 3.43.

NMR (DMSO-d$_6$) δ: 4.16 (2H, s), 4.26 (2H, s), 7.00–7.22 (6H, m), 7.22–7.32 (2H, m), 7.74 (1H, s), 8.26–8.32 (1H, m), 8.80–8.84 (1H, m).

Example 51

Compound I-155

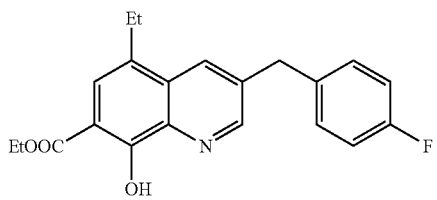

I-155

Compound I-155 was prepared in a same manner similar to Example 23.

Compound I-155

M.p.: 78–80° C. Recrystallization solvent: isopropyl ether

Elemental analysis for $C_{21}H_{20}FNO_3$ Calcd. (%): C, 71.37; H, 5.70; F, 5.38; N, 3.96. Found. (%): C, 71.03; H, 5.71; F, 5.63; N, 3.84.

NMR (CDCl$_3$) δ: 1.29 (3H, t, J=7.5 Hz), 1.47 (3H, t, J=6.9 Hz), 2.91 (2H, q, J=6.9 Hz), 4.19 (2H, s), 4.48 (2H, q, J=7.5 Hz), 6.98–7.06 (2H, m), 7.14–7.20 (2H, m), 7.70 (1H, s), 7.98–8.02 (1H, m), 8.84–8.88 (1H, m), 11.80(1H, s).

Example 52

Compound I-156

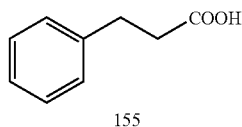

155

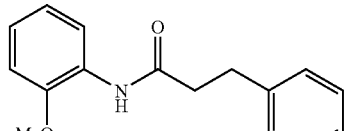

156

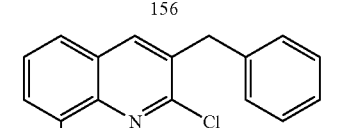

157

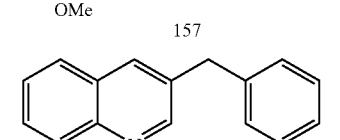

158

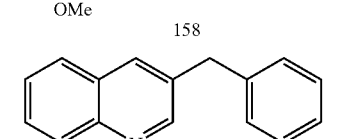

159

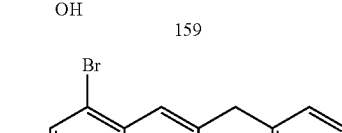

160

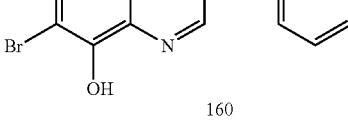

161

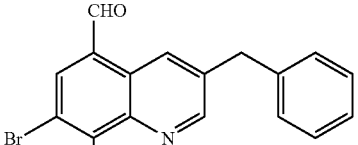

162

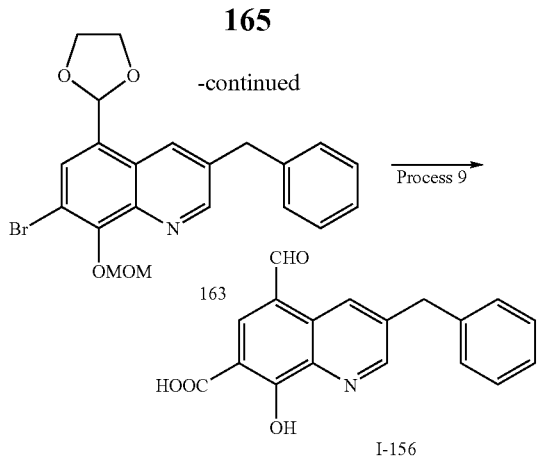

Process 7

To a solution of compound 161 (680 mg, 2.0 mmol) obtained by process 6 in benzene (20 ml) were added ethylene glycol (620 mg, 10.0 mmol) and p-toluenesulfonic acid (1.9 mg, 0.1 mmol), and the mixture was refluxed for 5.5 hours. Water was added to the reaction mixture and the mixture was extracted with methylene chloride. The organic layer was washed with saturated sodium hydrogen carbonate solution and brine and dried over sodium sulfate. The solvent was evaporated to give compound 162 (430 mg, 1.1 mmol, 55.7%) as dark brown oil.

Process 8

To a solution of sodium hydride (51 mg, 1.3 mmol) in THF (10 ml) was added dropwise a solution of compound 162 (410 mg, 1.1 mmol) obtained by process 7 in THF (10 ml) at room temperature. The reaction mixture was stirred for 30 minutes, and methoxy methyl chloride (111.0 mg, 1.3 mmol) was added dropwise to the reaction mixture and stirred at 40° C. for 60 minutes. The reaction mixture was cooled to room temperature and ice water was added to it, and the mixture was extracted with methylene chloride. The organic layer was washed with brine and dried over sodium sulfate. Dark brown oil obtained by evaporation was subjected to silica gel column chromatography. The fractions containing desired compound eluted with n-hexane-ethyl acetate (3:1 v/v) were concentrated under reduced pressure to give compound 163 (260 mg, 0.6 mmol, 55.0%) as yellow oil.

Process 9

1.8 M phenyl lithium (0.67 ml, 0.6 mmol) in ether-cyclohexane (7:3 v/v) was added dropwise to ether (15 ml) and cooled to −78° C. A solution of compound 163 (250 mg, 0.6 mmol) in ether (5 ml) was added dropwise to the solution over 30 minutes. The reaction mixture was stirred at −78° C. for 30 minutes, and then $CO_2$ gas was injected to it for 30 minutes, and the reaction mixture was gradually warm up to 0° C. Saturated ammonium chloride solution (10.0 ml) was added to this reaction mixture and extracted with ethyl acetate, washed with brine and dried over sodium sulfate. The yellow crystals obtained by evaporation was washed with ethyl acetate-isopropyl ether, and recrystallized with ethanol to give a title compound I-156 (35 mg, 0.11 mmol, 19.0%) as yellow crystals.

M.p.: 247–249° C. Recrystallization solvent: ethanol

NMR (DMSO-$d_6$) δ: 4.36 (2H, s), 7.20–7.40 (5H, m), 8.59 (1H, s), 8.95 (1H, brs), 9.78–10.10 (2H, m).

Example 53

Compound I-157

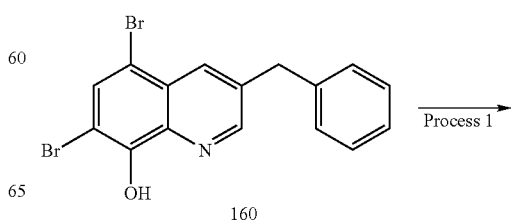

Process 1

Phenyl propionate (7.4 g, 60 mmol) was reacted with a same manner similar to process 2 of Example 40 to give compound 156 (13.6 g, 53.3 mmol, 88.8%) as light pink crystals.

Process 2

Compound 156 (13.0 g, 51 mmol) obtained by process 1 was reacted with a same manner similar to process 3 of Example 40 to give compound 157 (9.0 g, 37.8 mmol, 74.1%) as pale yellow crystals.

Process 3

Compound 157 (8.8 g, 31 mmol) obtained by process 2 was reacted with a same manner similar to process 4 of Example 40 to give compound 158 (6.2 g, 24.9 mmol, 80.2%) as pale yellow crystals.

Process 4

Compound 158 (1.8 g, 7.2 mmol) obtained by process 3 was reacted with a same manner similar to process 5 of Example 40 to give compound 159 (1.5 g, 6.4 mmol, 89.0%) as pale yellow crystals.

Process 5

Compound 159 (1.55 g, 6.6 mmol) obtained by process 4 was reacted with a same manner similar to process 6 of Example 40 to give compound 160 (1.95 g, 5.0 mmol, 75.2%) as pale yellow crystals.

Process 6

To a solution of sodium hydride (180 mg, 4.5 mmol) in THF (90 ml) was added compound 160 (1.2 g, 3.0 mmol) obtained by process 5 at room temperature, and the mixture was stirred for 2 hours. The reaction mixture was cooled to −78° C. and a solution of 1.59 M n-butyl lithium in n-hexane solution (2.9 ml, 4.5 mmol) was added dropwise to the reaction mixture and stirred for 60 minutes. To the reaction mixture was added dropwise a solution of N-formyl piperidine (509 mg, 4.5 mmol) in THF (5.0 ml) and stirred for 30 minutes. And a solution (10.0 ml, 20 mmol) of 2 N hydrochloric acid in THF was added dropwise to the reaction mixture and warmed up to room temperature. The saturated sodium hydrogen carbonate solution was added to the mixture with stirring. The organic layer was separated and the aqueous layer was extracted with methylene chloride. The combined organic layer was dried over sodium sulfate. The orange crystals obtained by evaporation was washed with isopropyl ether to give compound 161 (720 mg, 2.1 mmol, 70.2%).

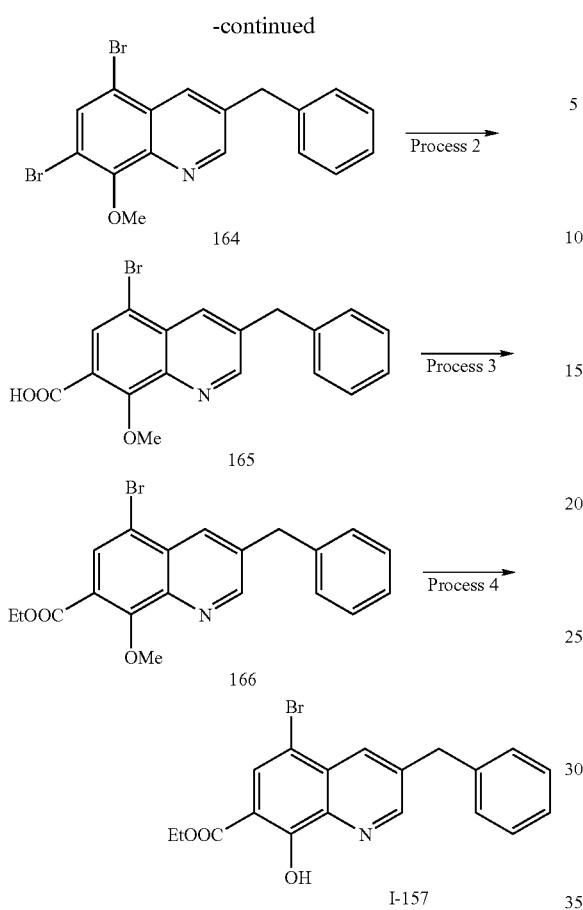

Example 54

Compound I-158, I-159

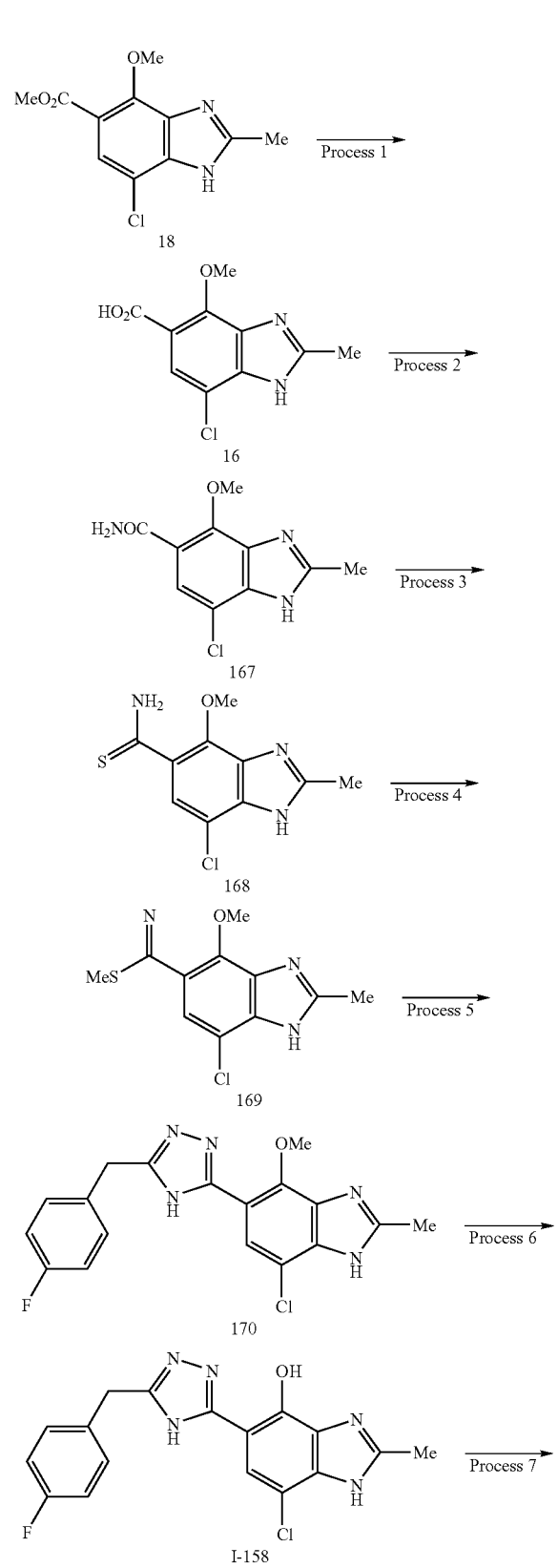

Process 1

Compound 160 (2.1 g, 5.3 mmol) obtained by process 5 of Example 52 was reacted with a same manner similar to process 1 of Example 46 to give compound 164 (550 mg, 1.35 mmol, 25.5%) as oil.

Process 2

Compound 164 (1.1 g, 2.7 mmol) obtained by process 1 was reacted with a same manner similar to process 8 of Example 40 to give compound 165 (440 mg, 1.2 mmol, 43.8%) as colorless crystals.

Process 3

Compound 165 (410 mg, 1.1 mmol) obtained by process 2 was reacted with a same manner similar to process 9 of Example 40 to give compound 166 (240 mg, 0.6 mmol, 55.0%) as pale yellow crystals.

Process 4

Compound 166 (100 mg, 0.25 mmol) obtained by process 3 was reacted with a same manner similar to process 4 of Example 46 to give a title compound I-157 (48.0 mg, 0.124 mmol, 49.6%) as pale yellow crystals.

M.p.: 104–106° C. Recrystallization solvent: ethyl acetate

Elemental analysis for $C_{19}H_{16}BrNO_3(EtOAc)_{0.2}$ Calcd. (%): C, 58.88; H, 4.39; Br, 19.78; N, 3.47. Found. (%): C, 58.60; H, 3.95; Br, 19.93; N, 3.57.

NMR (CDCl$_3$) δ: 1.48 (3H, t, J=7.2 Hz), 4.25 (2H, s), 4.50 (2H, q, J=7.2 Hz), 7.20–7.40 (5H, m), 8.15 (1H, s), 8.20–8.28 (1H, m), 8.84–8.92 (1H, m), 11.95(1H, brs).

-continued

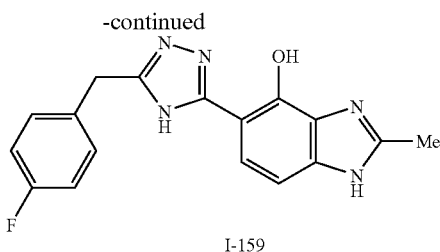

I-159

Process 1

Compound 18 (16.8 g, 66 mmol) was dissolved in a mixture of ethanol (100 ml) and water (100 ml). Lithium hydroxide (3.2 g, 134 mmol) was added to the reaction mixture and the mixture was refluxed for 4 hours. The solvent was evaporated under reduced pressure, and concentrated hydrochloric acid and sodium chloride were added, and the mixture was extracted with 2-butanone. The organic layer was washed with brine and dried over magnesium sulfate. The solvent was evaporated under reduced pressure to give a crude product of compound 16 (15.8 g, 99.0%).

NMR (DMSO-$d_6$) δ: 2.53 (3H, s), 3.94 and 4.22 (3H, bs), 7.51 (1H, s).

Process 2

To a solution of compound 16 (4.0 g, 16.6 mmol) in THF (50 ml) was added triethylamine (2.0 g, 19.8 mmol) at room temperature. And a solution of chloroethyl formate (1.9 g, 17.5 mmol) in THF (5 ml) was added dropwise to the reaction mixture under ice-cooling. The mixture was stirred at 0° C. for 30 minutes, and the precipitated salts was removed by filtration, and the filtrate was added dropwise to 2 N ammonia (ethanol solution, 50 ml) under ice-cooling. The mixture was stirred at room temperature for 30 minutes, and the solvent was evaporated under reduced pressure, and the obtained residue was subjected to silica gel column chromatography and eluted with ethyl acetate-THF (1:1 v/v). The fractions containing desired compound were concentrated under reduced pressure to give compound 167 (3.32 g, 83.0%).

NMR (DMSO-$d_6$) δ: 2.53 (3H, s), 4.00 and 4.36 (3H, bs), 7.50–7.80 (3H, m).

Process 3

Compound 167 (3.3 g, 13.9 mmol) was dissolved in THF (50 ml), and Lawson reagent (6.7 g, 16.6 mmol) was added to the solution and refluxed for 1 hour. The reaction mixture was cooled and the solvent was evaporated under reduced pressure. Ice crush was added to the residue, and the mixture was acidified with concentrated hydrochloric acid and washed with ethyl acetate. The aqueous layer was alkalized with sodium hydrogen carbonate and extracted with ethyl acetate. The organic layer was washed with water and brine and dried over magnesium sulfate. The solvent was evaporated under reduced pressure and crystallized with ether to give a crude product of compound 168 (2.4 g, 67.0%). NMR (DMSO-$d_6$) δ: major; 2.53 (3H, s), 4.31 (3H, s), 7.67 (1H, s), 9.36 (1H, s), 9.99 (1H, s), 12.86 (1H, s), minor; 2.53 (3H, s), 3.91 (3H, s), 7.46 (1H, s), 9.42 (1H, s), 10.07 (1H, s), 12.90 (1H, s).

Process 4

To a solution of compound 168 (2.4 g, 9.3 mmol) in THF (70 ml) was added diisopropyl ethylamine (1.2 g, 9.3 mmol) and methyl iodide (2.8 g, 20 mmol), and the mixture was stirred at 60° C. for 1 hour. The reaction mixture was added to ice water, and extracted with ethyl acetate. The organic layer was washed with saturated sodium hydrogen carbonate solution and brine and dried over magnesium sulfate. The solvent was evaporated under reduced pressure and crystallized from ether to give a crude product (2.1 g, 83.0%) of compound 169.

NMR DMSO-$d_6$) δ: major; 2.39 (3H, s), 2.53 (3H, s), 4.18 (3H, brs), 7.09 (1H, s), 10.07 (1H, s), 12.86 (1H, s), minor; 2.36 (3H, s), 2.53 (3H, s), 4.00 (3H, brs), 7.20 (1H, s), 10.30 (1H, brs), 12.86 (1H, s).

Process 5

A mixture of compound 169 (300 mg, 1.1 mmol) and p-fluoro phenyl hydrazide acetate (280 mg, 1.66 mmol) in acetic acid (5 ml) was refluxed for 1 hour. The solvent was evaporated under reduced pressure, and ethyl acetate was added to the residue, and the mixture was washed with saturated sodium hydrogen carbonate solution and brine. The mixture was dried over magnesium sulfate and, the residue obtained by evaporation under reduced pressure was subjected to silica gel column chromatography and eluted with ethyl acetate-methanol (50:1 v/v). The fractions containing desired compound were concentrated under reduced pressure and crystallized from ether to give compound 170 (330 mg, 81.0%).

NMR (DMSO-$d_6$) δ: 2.53 (3H, s), 4.03 (2H, s), 4.36 (3H, brs), 7.08–7.18 (2H, m), 7.32–7.40 (2H, m), 7.78 (1H, s), 12.90 (1H, brs), 13.45 (1H, brs).

Process 6

Compound 170 (300 mg, 0.81 mmol) was dissolved in acetic acid (6 ml), and 47% hydrobromic acid (2 ml) was added to it. The mixture was refluxed for 4 hours. The solvent was evaporated under reduced pressure, and sodium hydrogen carbonate solution was added, and the mixture was extracted with ethyl acetate. The organic layer was washed with saturated sodium hydrogen carbonate aqueous solution and brine and dried over sodium sulfate. The residue obtained by evaporation was recrystallized from acetone to give compound I-158 (200 mg, 70.0%) as colorless crystals.

M.p.: 295° C. Recrystallization solvent: acetone

Elemental analysis for $C_{17}H_{13}ClFN_5O$ Calcd. (%): C, 57.07; H, 3.66; N, 19.57; Cl, 9.91; F, 5.31. Found. (%): C, 56.99; H, 3.59; N, 19.23; Cl, 9.59; F, 5.15.

NMR (DMSO-$d_6$) δ: 2.51 (3H, s), 4.11 and 4.23 (2H, brs), 7.10–7.25 (2H, m), 7.32–7.40 (2H, m), 7.67 and 7.74 (1H, brs), 11.73 (1H, brs), 12.89 and 13.00 (1H, brs), 14.28 (1H, brs).

Process 7

Compound I-159 (100 mg, 69.0%) was obtained as colorless crystals from compound I-158 (160 mg, 0.45 mmol) by process 1 of Example 6.

M.p.: 170° C. Recrystallization solvent: acetonitrile

Elemental analysis for $C_{17}H_{14}FN_5O \cdot 0.4H_2O$ Calcd. (%): C, 61.77; H, 4.51; N, 21.19; F, 5.75. Found. (%): C, 61.77; H, 4.32; N, 21.41; F, 5.79.

NMR (DMSO-$d_6$) δ: 2.50 (3H, s), 4.14 (2H, s), 7.04 (1H, m), 7.10–7.20 (2H, m), 7.34–7.42 (2H, m), 7.50 (1H, d, J=8.7 Hz), 12.30 (1H, brs), 12.56 (1H, brs).

Example 55

Compound I-160, I-161

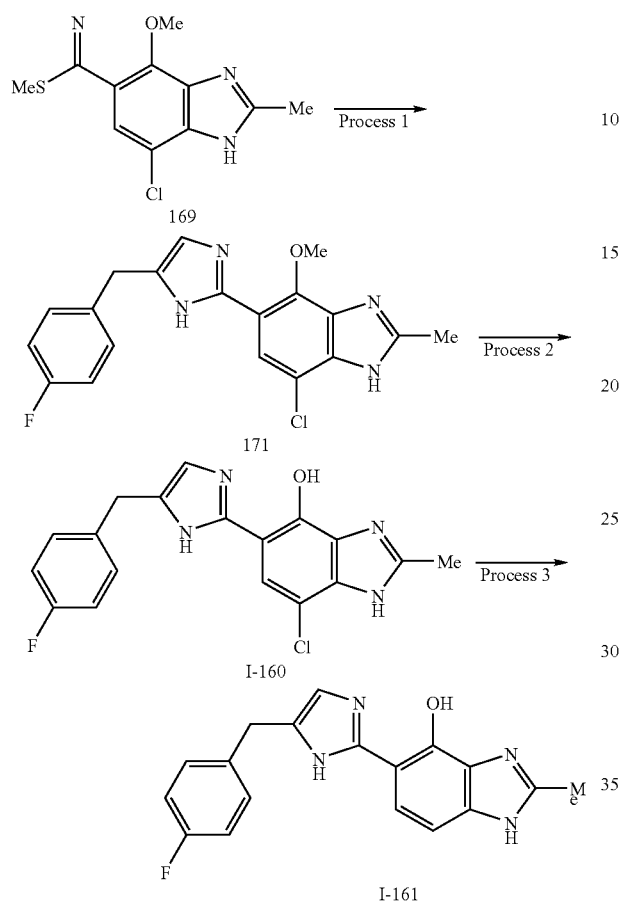

Process 1

Compound 171 (220 mg, 32.0%) was obtained from compound I-169 (500 mg, 1.85 mmol) and 1-amino-3-(4-fluoro phenyl)propane 2-on hydrochloride (560 mg, 2.75 mmol) by process 5 of Example 54. NMR (CDCl$_3$) δ: 2.58 (3H, s), 3.99 (2H, s), 4.17 (3H, s), 6.72 (1H, s), 6.96–7.03 (2H, m), 7.23–7.33 (2H, m), 7.94 (1H, s).

Process 2

Compound I-160 (410 mg, 94%) was obtained as colorless crystals from compound 171 (450 mg, 1.22 mmol) by process 6 of Example 54.

M.p.: 193–195° C. (dissolve) Recrystallization solvent: acetone

Elemental analysis for C$_{18}$H$_{14}$FN$_4$O.0.5H$_2$O Calcd. (%): C, 59.10; H, 4.13; N, 15.32; Cl, 9.69; F, 5.19. Found. (%): C, 59.36; H, 3.84; N, 15.22; Cl, 9.79; F, 4.91.

NMR (CDCl$_3$) δ: 2.58 (3H, brs), 3.96 (2H, s), 6.68 (1H, s), 7.00–7.03 (2H, m), 7.21–7.30 (2H, m), 7.36 (1H, s).

Process 3

Compound I-161 (300 mg, 83.0%) was obtained as colorless crystals from compound I-160 (400 mg, 1.12 mmol) by process 1 of Example 6.

M.p.: 167° C. Recrystallization solvent: ethanol

Elemental analysis for C$_{18}$H$_{15}$FN$_4$O.0.7H$_2$O Calcd. (%): C, 64.55; H, 4.94; N, 16.73; F, 5.67. Found. (%): C, 64.68; H, 4.87; N, 16.91; F, 5.42.

NMR (DMSO-d$_6$) δ: 2.51 (3H, s), 3.94 (2H, brs), 6.95 (1H, brs), 7.02 (1H, d, J=8.1 Hz), 7.10–7.20 (2H, m), 7.30–7.40 (2H, m), 7.53 (1H, d, J=8.1 Hz), 12.19 (1H, brs), 12.37 (1H, brs).

Example 56

Compound I-162, I-163

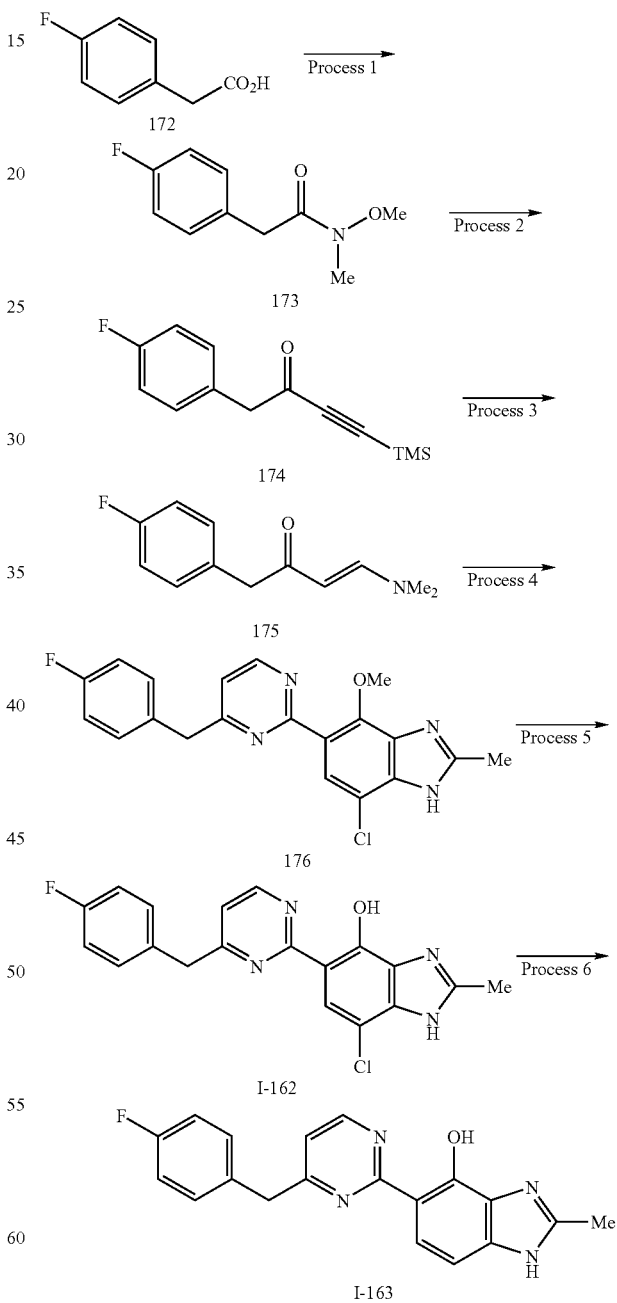

Process 1

Compound 172 (5 g, 32.4 mmol) was dissoved in chloroform (30 ml) and acetonitrile (15 ml). N,O-dimethylhydroxyamine (3.48 g, 35.6 mmol), HOBt (4.8 g, 35.6 mmol), triethylamine (3.6 g, 35.6 mmol) and WSCD (5.5 g, 35.6 mmol) were added to the solution. The reaction mixture was stirred at room temperature for 1 hour. The solvent was evaporated under reduced pressure. The obtained residue was subjected to silica gel chromatography and eluted with chloroform methanol (49:1 v/v). The fractions containing desired compound were concentrated under reduced pressure to give compound 173 (5.27 g, 82.0%). NMR (CDCl$_3$) δ: 3.19 (3H, s), 3.63 (3H, s), 3.74 (2H, s), 6.97–7.03 (2H, m), 7.23–7.28 (2H, m).

Process 2

To a solution of trimethylsilylacetylene (982 mg, 10 mmol) in THF (10 ml) was added dropwise n-butyllithium at −78° C. The mixture was stirred for 30 minutes, and a solution of compound 173 (1.97 g, 10 mmol) in THF (5 ml) was added to the reaction mixture and the mixture was warmed up to 0° C. The reaction mixture was stirred for 30 minutes, and ammonium chloride aqueous solution was added and extracted with ethyl acetate. The organic layer was washed with water, brine and dried over magnesium sulfate. The solvent was evaporated under reduced pressure to give a crude product (2.1 g) of compound 174.

Process 3

To a solution of the crude product (2.1 g) of compound 174 in ethanol (10 ml) was added 40 wt % methylamine aqueous solution (20 mmol), and the mixture was stirred at room temperature for 1 hour. The solvent was evaporated under reduced pressure and the residue was subjected to silica gel chromatography. The fractions containing desired compound eluted with ethyl acetate were concentrated under reduced pressure to give compound 175 (547 mg). The yield of process 2 and 3 was 26%.

NMR (CDCl$_3$) δ: 2.77 (3H, bs), 3.07 (3H, bs), 3.60 (2H, s), 4.98 (1H, d, J=12.3 Hz), 6.95–7.01 (2H, m), 7.20–7.26 (2H, m), 7.60 (1H, d, J=12.3 Hz).

Process 4

Compound 169 (1.36 g, 5.04 mmol) of Example 54 was dissolved in ethanol (30 ml) and ammonium chloride (280 mg, 5.24 mmol) was added to it, and the mixture was refluxed for 30 minutes. The solvent was evaporated and crystallized from ether to give quantitatively hydrochloride of amidine. This hydrochloride (280 mg, 1 mmol) was dissolved in methanol (5 ml), and compound 175 (250 mg, 1.2 mmol) and 28% sodium methoxide solution (methanol, 1 ml, 5 mmol) were added to the solution and the mixture was refluxed for 6 hours. The mixture was cooled to room temperature and added to saturated ammonium chloride solution, and the mixture was extracted with chloroform at 3 times. The organic layer was washed with brine and dried over magnesium sulfate. The solvent was evaporated under reduced pressure. The obtained residue was subjected to silica gel column chromatography and eluted with chloroform-methanol (20:1 v/v). The fractions containing desired compound were concentrated under reduced pressure to give compound 176 (260 mg 68.0%).

NMR (CDCl$_3$) δ: 2.59 (3H, s), 4.00 (3H, s), 4.16 (2H, s), 6.97–7.10 (3H, m), 7.25–7.31 (2H, m), 7.37 (1H, s), 8.72 (1H, d, J=5.1 Hz).

Process 5

Compound I-162 (220 mg, 88%) was obtained as colorless crystals from compound 176 (260 mg, 0.68 mmol) by process 6 of Example 54.

M.p.: 280° C. Recrystallization solvent: acetone

Elemental analysis for C$_{19}$H$_{14}$ClFN$_4$O Calcd. (%): C, 61.88; H, 3.83; N, 15.19; Cl, 9.61; F, 5.15. Found. (%): C, 61.60; H, 3.75; N, 15.03; Cl, 9.69; F, 4.93.

NMR (DMSO-d$_6$) δ: 2.51 (3H, s), 4.25 (2H, s), 7.15–7.25 (2H, m), 7.35–7.46 (3H, m), 8.15 (1H, s), 8.83 (1H, d, J=5.1 Hz), 13.79 (1H, s).

Process 6

Compound I-163 (60 mg, 55.0%) was obtained as colorless crystals from compound I-162 (120 mg, 0.33 mmol) by process 1 of Example 6.

M.p.: 203° C. Recrystallization solvent: ethyl acetate

Elemental analysis for C$_{19}$H$_{15}$FN$_4$O Calcd. (%): C, 68.25; H, 4.52; N, 16.76; F, 5.68. Found. (%): C, 68.05; H, 4.42; N, 16.57; F, 5.43.

NMR (CDCl$_3$) δ: 2.59 (3H, s), 4.13 (2H, s), 6.93 (1H, d, J=5.1 Hz), 7.00–7.08 (2H, m), 7.13 (1H, d, J=5.1 Hz), 7.24–7.30 (2H, m), 8.30 (1H, d, J=8.7 Hz), 8.59 (1H, d, J=5.1 Hz).

Compound I-164 was prepared in same manner similar to Example 56.

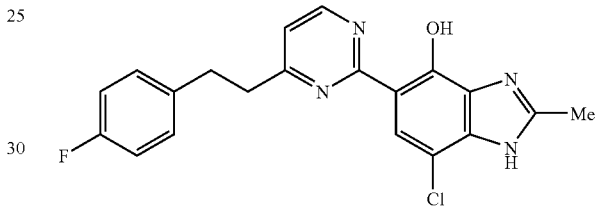

I-164

Compound I-164

A colorless crystal, the yield was 87%.

M.p.: 273° C. Recrystallization solvent: acetone

Elemental analysis for C$_{20}$H$_{16}$ClFN$_4$O Calcd. (%): C, 62.75; H, 4.21; N, 14.64; Cl, 9.26; F, 4.96. Found. (%): C, 62.52; H, 4.18; N, 14.34; Cl, 9.17; F, 4.70.

NMR (DMSO-d$_6$) δ: 2.51 (3H, s), 3.06–3.20 (4H, m), 7.06–7.15 (2H, m), 7.26–7.36 (3H, m), 8.15 (1H, s), 8.78 (1H, d, J=5.4 Hz), 13.02 (1H, s), 14.11 (1H, s).

Example 57

Compound I-165

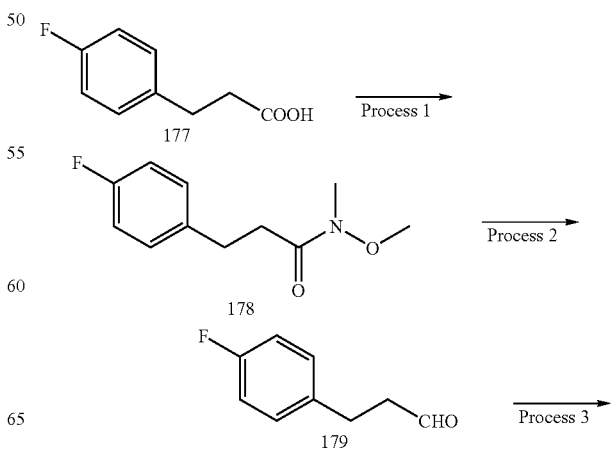

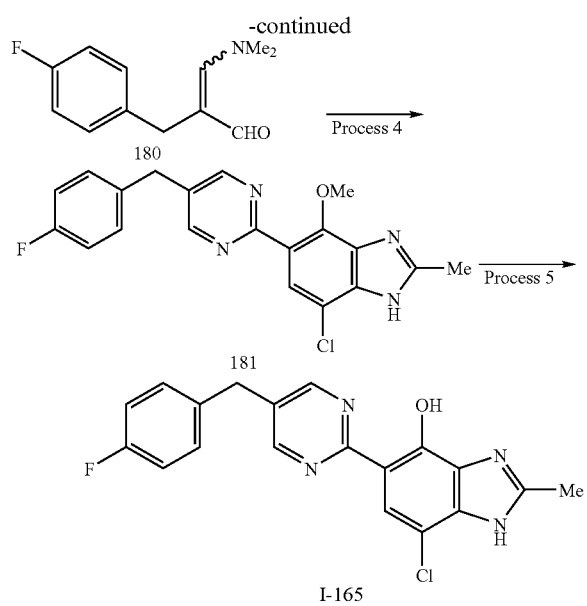

Process 1

Compound 178 (10.97 g, 87.0%) was obtained from compound 177 (10.1 g, 60 mmol) by process 1 of Example 56.

NMR (CDCl$_3$) δ: 2.72 (2H, t, J=7.5 Hz), 2.94 (2H, t, J=7.6 Hz), 3.18 (3H, s), 3.61(3H, s), 6.94–7.00 (2H, m), 7.16–7.26 (2H, m).

Process 2

To a solution of lithium aluminum hydride (1.31 g, 34.63 mmol) in THF (50 ml) was added dropwise a solution of compound 178 (6.65 g, 31.48 mmol) in THF (10 ml) at −78° C. The mixture was warmed up to 0° C. and stirred for 1 hour. Potassium hydrogen sulfate solution was added, and the precipitate was filtered off, and the organic layer was separated, and dried over magnesium sulfate. The solvent was evaporated under reduced pressure to give a crude product (5.49 g) of compound 179.

Process 3

A solution of a crude product (5.49 g) of compound 179 and dimethyl formamide dimethylacetal (3.4 g, 31 mmol) in DMF (20 ml) was stirred at 130° C. for 8 hours. Water was added to the reaction mixture, and the mixture was extracted with diethyl ether and dried over magnesium sulfate. The solvent was evaporated under reduced pressure, and the obtained residue was subjected to silica gel column chromatography. The fractions containing desired compound eluted with ethyl acetate were concentrated to give compound 180 (588 mg, 9.0%).

NMR (CDCl$_3$) δ: 3.04 (6H, s), 3.80 (2H, s), 6.73 (1H, s), 6.91–6.96 (2H, m), 7.06–7.12 (2H, m), 9.03 (1H, s).

Process 4

Compound 181 (240 mg, 63.0%) was obtained from compound 180 (250 mg, 1.2 mmol) by process 4 of Example 56.

NMR (CDCl$_3$) δ: 2.62 (3H, s), 3.99 (2H, s), 4.06 (3H, s); 7.00–7.08 (2H, m), 7.16–7.24 (2H, m), 7.74 (1H, s), 8.68 (2H, s).

Process 5

Compound I-165 (180 mg 78.0%) was obtained as colorless crystals from compound 181 (240 mg, 0.68 mmol) by process 6 of Example 54.

M.p.: >300° C. Recrystallization solvent: acetone

M.p.: 280° C. Recrystallization solvent: acetone

Elemental analysis for $C_{19}H_{14}ClFN_4O$ Calcd. (%): C, 61.88; H, 3.83; N, 15.19; Cl, 9.61; F, 5.15. Found. (%): C, 61.50; H, 3.69; N, 15.02; Cl, 10.02; F, 4.94.

NMR (DMSO-d$_6$) δ: 2.51 (3H, s), 4.05 (2H, s), 7.12–7.20 (2H, m), 7.35–7.41 (2H, m), 8.11 (1H, s), 8.85 (2H, s), 13.00 (1H, s), 13.78 (1H, s).

Compound I-166 was prepared in a same manner similar to Example 57.

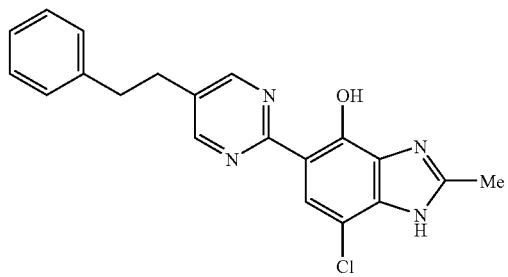

Compound I-166

A colorless crystal, the yield was 65%.

M.p.: 293° C. Recrystallization solvent: acetone

Elemental analysis for $C_{20}H_{17}ClN_4O$ Calcd. (%): C, 65.84; H, 4.70; N, 15.36; Cl, 9.72. Found. (%): C, 65.84; H, 4.57; N, 15.38; Cl, 9.84.

NMR (DMSO-d$_6$) δ: 2.51 (3H, s), 2.98 (4H, m), 7.15–7.32 (5H, m), 8.10 (1H, s), 8.78 (1H, s), 13.00 (1H, s), 13.85 (1H, s).

Example 58

Compound I-167

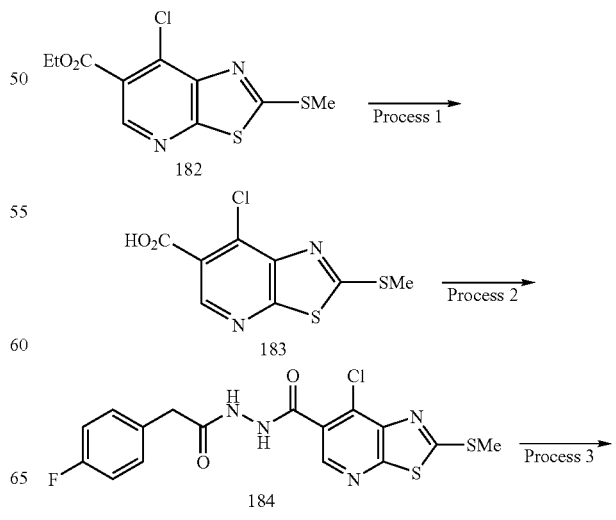

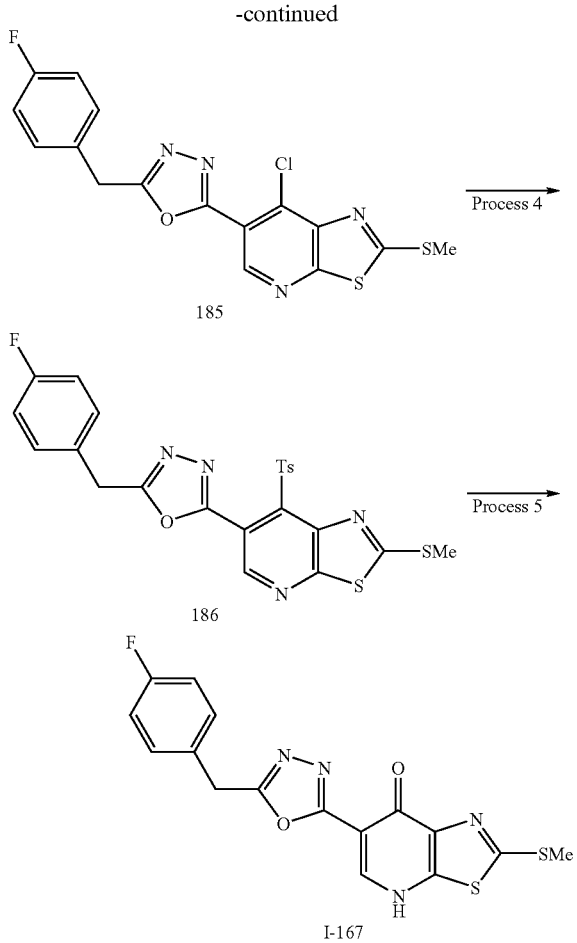

NMR (DMSO-$d_6$) δ: 2.39 (3H, s), 2.87 (3H, s), 4.48 (2H, s), 7.23 (2H, m), 7.46 (4H, m), 7.88 (2H, d, J=8.4 Hz), 8.83 (1H, s).

Process 5

To a solution of dioxane-water (5:1 v/v, 8.4 ml) of compound 186 (356 mg, 0.694 mmol) was added lithium hydroxide (33.7 mg, 1.38 mmol) at room temperature, and the mixture was stirred for 24 hours. To the reaction mixture was added water (14 ml) under ice-cooling and the mixture was neutralized with 2 N hydrochloric acid. The precipitated crystals were filtered and washed with water. The obtained crude crystals were recrystallized from ethanol to give compound I-167 (126 mg, 43.0%) as dark yellow crystals.

M.p.: 280–290° C. Recrystallization solvent: ethanol

Elemental analysis for $C_{17}H_{12}FN_3O_3(H_2O)_{0.2}$ Calcd. (%): C, 50.84; H, 3.04; N, 14.82; F, 5.03; S, 16.97. Found. (%): C, 50.55; H, 2.66; N, 14.63; F, 4.86; S, 17.08.

NMR (DMSO-$d_6$) δ: 2.73 (3H, s), 4.33 (2H, s), 7.20 (2H, m), 7.44 (2H, m), 8.39 (1H, s).

IR (KBr): 3442, 1603 cm$^{-1}$.

Example 59

Compound I-168

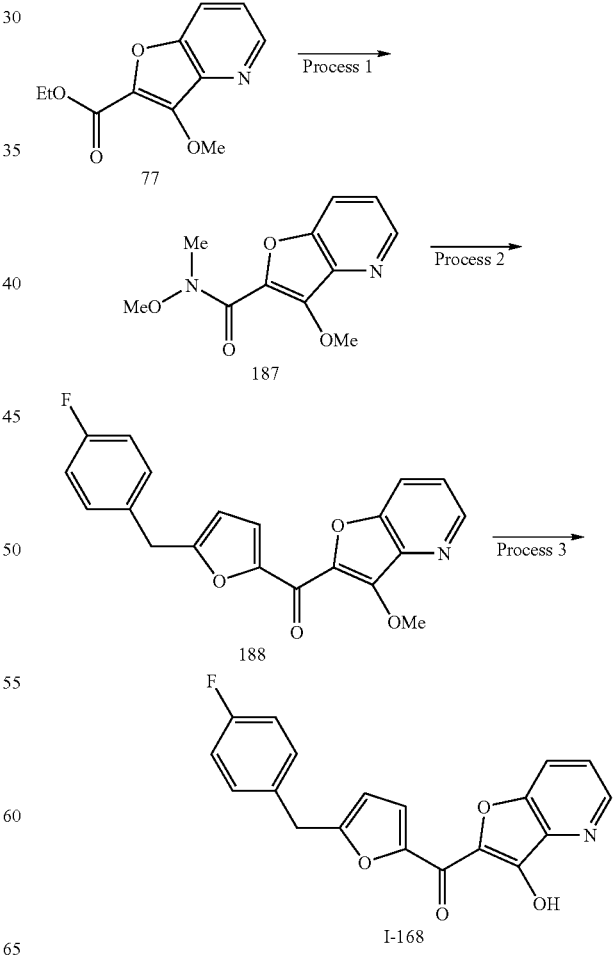

Process 1

To a solution of dioxane-water (2:1 v/v, 60 ml) of compound 182 (3.93 g, 13.6 mmol) described in the document (J. Heterocycl. Chem., 21, 401–406, (1984)) was added lithium hydroxide (688 mg, 28.2 mmol) at room temperature, and the mixture was stirred for 2 hours. To the reaction mixture was added water (40 ml) at room temperature, and the mixture was acidified with 2 N hydrochloric acid. The precipitated crystals were filtered and washed with water to give compound 183 (3.42 g, 96.0%) as colorless crystals.

Process 2

Compound 184 (5.28 g, 84.0%) was obtained as light yellow crystals from compound 183 (3.42 g, 13.1 mmol) by process 2 of Example 9.

Process 3

Compound 185 (806 mg, 84.0%) was obtained as light blackish brown crystals from compound 184 (1.01 g, 2.46 mmol) by process 3 of Example 9.

Process 4

A solution of compound 185 (514 mg, 1.31 mmol) and sodium p-toluenesulfinic acid (706 mg, 3.96 mmol) in ethanol (20 ml) was refluxed for 25 hours. Water (40 ml) was added to the reaction mixture under ice-cooling. The precipitated crystals were filtered and washed with water. The obtained crude crystals were recrystallized from ethanol to give compound 186 (583 mg, 80.0%) as colorless crystals.

Process 1

A suspension of N,O-dimethyl hydroxyl amine hydrochloride (467 mg, 4.78 mmol) in tetrahydrofuran (100 ml) was cooled at −78° C., and 1.55 M n-butyllithium/n-hexane (6.2 ml, 9.61 mmol) was added dropwise to the suspension over 5 minutes, and the mixture was stirred for 3 minutes at the same temperature and for 12 minutes at 0° C. The reaction mixture was cooled at −78° C., and a solution of compound 77 (Refer to Example 29)(529 mg, 2.39 mmol) in tetrahydrofuran (5 ml) was added to the reaction mixture and stirred for 15 minutes at the same temperature. Saturated ammonium chloride aqueous solution was added to the reaction mixture and extracted with ethyl acetate. The organic layer was washed with brine and dried over sodium sulfate. The residue obtained by evaporation under reduced pressure was subjected to silica gel column chromatography and eluted with chloroform-methanol (100:1 v/v). The fractions containing desired compound were concentrated under reduced pressure to give compound 187 (495 mg).

NMR (CDCl$_3$) δ: 3.39 (3H, s), 3.84 (3H, s), 4.42 (3H, s), 7.34 (1H, dd, J=8.4, 4.7 Hz), 7.75 (1H, d, J=8.4 Hz), 8.60 (1H, d, J=4.7 Hz).

Process 2

A solution of 2-bromo5-(p-fluorobenzil)furan (578 mg, 2.27 mmol) in tetrahydrofuran (5 ml) was cooled to −78° C., and 1.55 M n-butyllithium/n-hexane (1.4 ml, 2.17 mmol) was added dropwise to the solution over 2 minutes and stirred for 13 minutes at the same temperature. A solution of compound 187 (480 mg, 2.03 mmol) in tetrahydrofuran (5 ml) was added to the reaction mixture and stirred at the same temperature for 6 hours. Saturated ammonium chloride aqueous solution was added to the reaction mixture, and the mixture was extracted with ethyl acetate. The organic layer was washed with water, brine and dried over magnesium sulfate. The residue obtained by evaporation was subjected to silica gel column chromatography and eluted with hexane-ethyl acetate (3:2 v/v). The fractions containing desired compound were concentrated under reduced pressure to give compound 188 (400 mg).

NMR (CDCl$_3$) δ: 4.10(2H, s), 4.57 (3H, s), 6.17 (1H, d, J=3.8 Hz), 6.99–7.06 (2H, m), 7.24–7.29 (2H, m), 7.42 (1H, dd, J=8.7, 4.5 Hz), 7.62 (1H, d, J=3.8 Hz), 7.81 (1H, dd, J=8.7, 1.2 Hz), 8.64 (1H, dd, J=4.5, 1.2 Hz).

Process 3

A solution of compound 188 (136 mg, 0.387 mmol) in methylene chloride (3 ml) was cooled to 0° C., and 1.0 M boron tribromide in methylene chloride (0.58 ml, 0.580 mmol) was added to the solution, and the mixture was stirred at the same temperature for 30 minutes. Saturated sodium hydrogen carbonate solution was added to the reaction mixture, and the mixture was extracted with chloroform. The organic layer was washed with brine and dried over sodium sulfate. The residue obtained by evaporation under reduced pressure was washed with a mixture of acetone-methanol (1:10) to give yellow solids (87 mg). And the solids were recrystallized from a mixture of acetone-methanol to give I-168 (34 mg) as yellow crystals.

M.p.: 186–188° C. Recrystallization solvent: acetone-methanol

NMR (CDCl$_3$) δ: 4.13 (2H, s), 6.26 (1H, d, J=3.8 Hz), 7.00–7.10 (2H, m), 7.24–7.30 (2H, m), 7.48 (1H, dd, J=8.6, 4.7 Hz), 7.818 (1H, d, J=3.8 Hz), 7.823 (1H, dd, J=8.6, 1.1 Hz), 8.71 (1H, dd, J=4.7, 1.1 Hz).

Example 60

Compound I-169

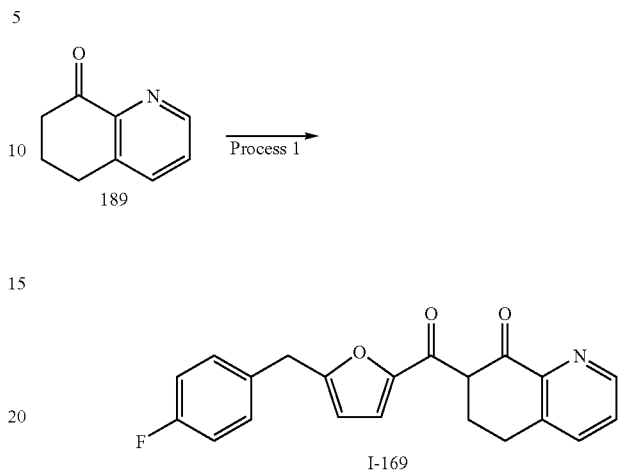

Process 1

To a solution of 6,7-dihydroxy-5H-quinoline-8-on (compound 189) (147 mg, 1.0 mmol) described in the document (J. Chem. Soc., Perkin Trans. 1,1985, p213) in tetrahydrofuran (3 ml) was added 1 M lithium bis(trimethylsilyl) acetamide (1.2 ml, 1.2 mmol) in tetrahydrofuran under ice-cooling with dry ice. The mixture was stirred for 45 minutes, and acid chloride (239 mg, 1.0 mmol) was added to the solution. The mixture was warmed up naturally and stirred for 1 hour at room temperature. To the reaction mixture was added saturated ammonium chloride solution, and the mixture was extracted with ethyl acetate. The organic layer was washed with saturated ammonium chloride solution, brine and dried over magnesium sulfate. The residue obtained by evaporation under reduced pressure was subjected to silica gel column chromatography and eluted with ethyl acetate. The fractions containing desired compound were concentrated under reduced pressure concentrate to give compound I-169 (88 mg, 25.0%) as oil.

Negative ESIMS m/z 348 (M−H)
Positive ESIMS m/z 350 (M+H)
NMR (CDCl$_3$) (enol-form:keto-form=3:1) δ: 2.88–3.05 (4H, m), 4.00 (0.25H, s), 4.05 (0.75H, s), 4.41 (0.25H, dd, J=5.0, 9.2 Hz), 6.14 (0.25H, d, J=3.3 Hz), 6.19 (0.75H, d, J=3.3 Hz), 6.9–7.5 (6H, m), 7.58 (0.75H, d, J=7.5 Hz), 7.68 (0.25H, d, J=8.1 Hz), 8.68 (0.75H, d, J=5.1 Hz), 8.73 (0.25H, d, J=4.8 Hz).

IR (neat): 3051, 1601, 1506, 1223, 1157, 1018, 810, 735 cm$^{-1}$.

Example 61

Compound I-170

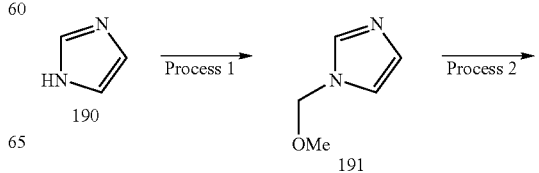

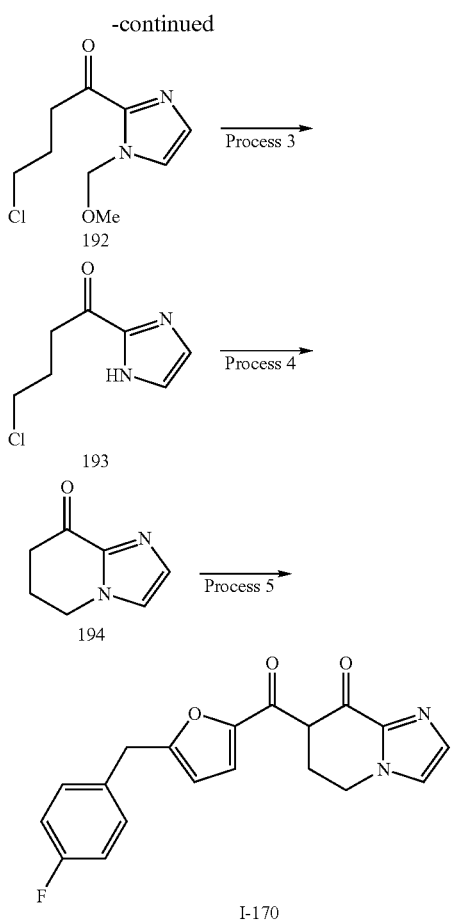

Process 1

To a solution of compound 190 (5.45 g, 80.0 mmol) in methylene chloride (160 ml), were added diisopropyl ethylamine (20.9 ml, 120 mmol) and chloro methylmethyl ether (7.90 ml, 104 mmol) under ice-cooling, and the reaction mixture was stirred at room temperature for 18 hours. The reaction mixture was concentrated, and water was added to it, and the mixture was extracted with ethyl acetate. The organic layer was washed with water, saturated sodium hydrogen carbonate solution, brine and dried over sodium sulfate. The residue obtained by evaporation under reduced pressure was distilled (84–87° C./6 mmHg) under reduced pressure to give compound 191 (3.06 g, 34.0%) as colorless oil. NMR (CDCl$_3$) δ: 3.28 (3H, s), 5.25 (2H, s), 7.06 (1H, t, J=1.2 Hz), 7.12 (1H, s), 7.61 (1H, s).

Process 2

To a solution of compound 191 (1.12 g, 10.0 mmol) in tetrahydrofuran (40 ml) was added 1.55 M n-butyllithium/n-hexane (6.77 ml, 10.5 mmol) at −40° C., and the mixture was stirred at the same temperature for 30 minutes. A solution of Weinreb amide (2.00 g, 12.0 mmol) in tetrahydrofuran (8 ml) was added to the reaction mixture at −60° C., and the mixture was stirred for 30 minutes at the same temperature. Water was added to the reaction mixture, and the mixture was extracted with ethyl acetate. The organic layer was washed with brine and dried over sodium sulfate. The residue obtained by evaporation under reduced pressure was subjected to silica gel column chromatography and eluted with n-hexane-ethyl acetate (1:1 v/v). The fractions containing desired compound were concentrated under reduced pressure to give compound 192 (2.19 g) as colorless oil.

Process 3

To a solution of compound 192 (2.14 g) obtained by process 2 in dioxane (30 ml) was added 6 N hydrochloric acid (10 ml), and the mixture was stirred at 80° C. for 3 hours. The solvent was evaporated and neutralized with sodium hydroxide aqueous solution. The precipitated crystals were filtered, washed with water and dried to give compound 193 (840 mg. 49.0%) as colorless crystals.

NMR (CDCl$_3$) δ: 2.23 (2H, quintet, J=6.9 Hz), 3.31 (2H, t, J=7.2 Hz), 3.65 (2H, t, J=6.6 Hz), 7.27 (2H, brs), 10.58 (1H, brs).

Process 4

To a solution of compound 193 (556 mg, 3.22 mmol) in acetonitrile (16 ml) were added potassium carbonate (890 mg, 6.44 mmol) and sodium iodide (480 mg, 3.20 mmol) under ice-cooling, and the mixture was stirred at room temperature for 3 hours and then it was stirred at 70° C. for 20 hours. The residue obtained by evaporation was subjected to silica gel column chromatography and eluted with chloroform-methanol (9:1 v/v). The fractions containing desired compound were concentrated under reduced pressure to give compound 194 (358 mg, 82.0%) as colorless crystals.

NMR (CDCl$_3$) δ: 2.39 (2H, m), 2.77 (2H, m), 4.26 (2H, m), 7.08 (1H, s), 7.34 (1H, d, J=0.9 Hz).

Process 5

Compound I-170 (69 mg, 20.0%) was obtained as yellow oil from compound 194 (136 mg, 1.00 mmol) by process 1 of Example 60.

FABMS m/z 339 (M+H)+

High resolution mass analysis for C$_{19}$H$_{16}$FN$_2$O$_3$ Calcd. (m/z): 339.1145. Found. (m/z): 339.1153.

NMR (CDCl$_3$) (enol-form:keto-form=1:1) δ: 2.50–2.62 and 2.72–2.86 (total 1H, both m), 3.28 (1H, t, J=7.2 Hz), 4.01 and 4.05 (total 2H, both s), 4.08–4.70 (total 3H, m), 6.17 and 6.6.22 (total 1H, both d, J=3.6 Hz), 6.96–7.42 (7H, m).

IR (neat): 3014, 1660, 1508, 1227, 1213, 1205 cm$^{-1}$.

Example 62

Compound I-171

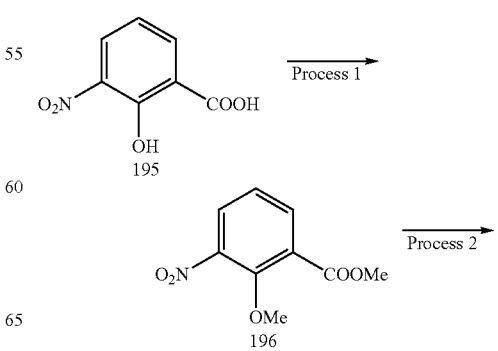

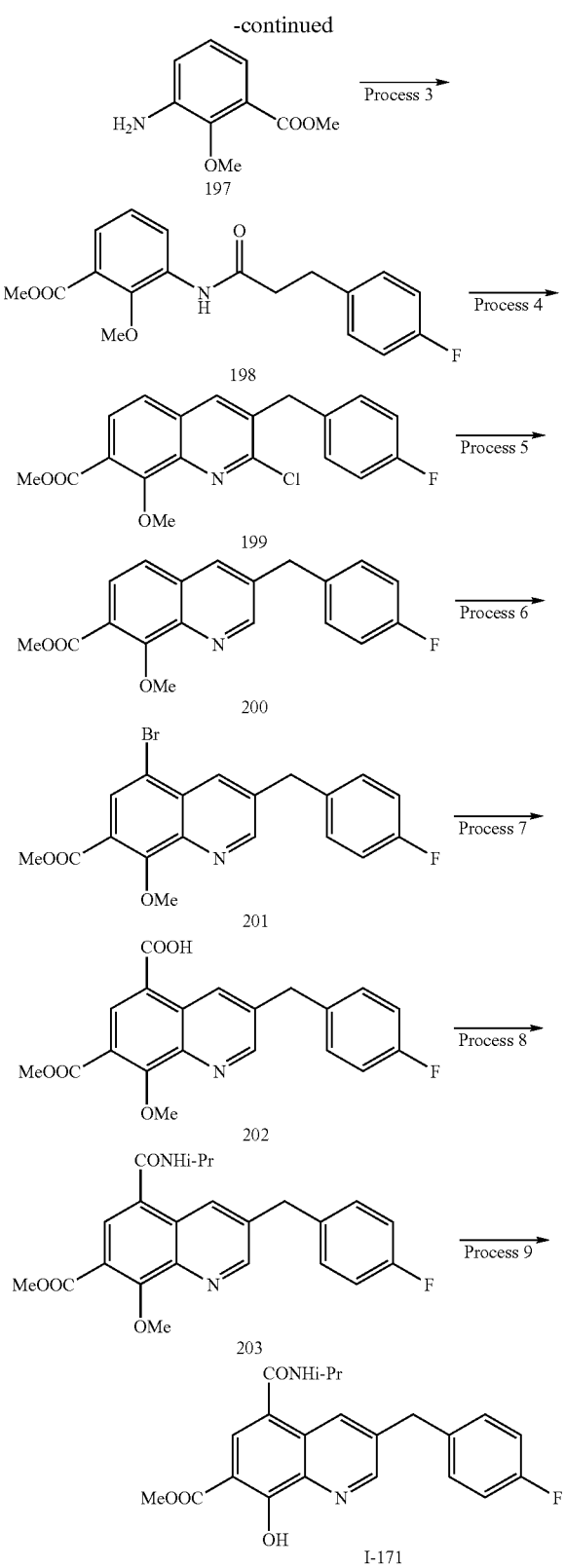

Process 1

To a solution of 3-nitro salicylic acid (51 g, 279 mmol) of compound 195 in DMF (250 ml) was added potassium carbonate (77 g) and added dropwise dimethyl sulfate (58 ml) keeping under 25° C. The reaction mixture was stirred over night at room temperature, and ammonium chloride solution was added to it, and the mixture was extracted with ethyl acetate. The extract was washed with water, brine and dried over magnesium sulfate. The solvent was evaporated under reduced pressure to give a crude product (56.3 g) of compound 196 as colorless crystals.

Process 2

The crude product (56.3 g) of compound 196 was dissolved in a mixture of ethanol (200 ml)-dioxane (200 ml)-water (40 ml). A suspension of 10% palladium carbon (2.82 g) in water (20 ml) was added to the reaction mixture, and the mixture was stirred for 5.5 hours under hydrogen atmosphere. The reaction mixture was filtered through celite pad, and the filtrate was evaporated under reduced pressure. Water (300 ml) was added to the residue, and the reaction mixture was extracted twice with ether. The extract was washed with water, brine and dried over magnesium sulfate. The solvent was evaporated under reduced pressure to give a crude product (48.4 g, 266 mmol) of compound 197 as oil.

Process 3

Compound 198 (78.5 g, 237.0 mmol, 89.1%) was obtained as crystals from compound 109 (47.0 g, 279 mmol) of Example 40 and the crude product (48.4 g, 266 mmol) of compound 197 of Example 40.

M.p.: 90–92° C.

Process 4

Compound 199 (24.2 g, 28.5%) was obtained as crystals from compound 198 (78.0 g, 235 mmol) by process 3 of Example 40.

M.p.: 126–127° C.

Process 5

Compound 200 (19.3 g, 89.2%) was obtained as crystals from compound 199 (23.9 g, 66.4 mmol) by process 4 of Example 40.

M.p.: 60–60.5° C.

Process 6

To a solution of Compound 200 (32.3 g, 99.2 mmol) in acetic acid (400 ml) were added sodium acetate (10.4 g, 127 mmol) and a solution of bromine (5.62 ml, 109 mmol) in acetic acid (10 ml) was added dropwise over 15 minutes. The mixture was stirred at room temperature for 1 hour 40 minutes, and sodium acetate (10.4 g, 127 mmol) and a solution of bromine (5.62 ml, 109 mmol) in acetic acid (10 ml) were added to the reaction mixture in the same way. The mixture was stirred for 1.5 hours, and sodium acetate (20.4 g, 249 mmol) was added to the reaction mixture, and the mixture was stirred under ice-cooling. To the reaction mixture were added 10% sodium hydrogen sulfite aqueous solution (260 ml) and water (250 ml), and the mixture was stirred for 30 minutes. The precipitated crystals were filtered and washed with water. The obtained crystals were dissolved in ethyl acetate (600 ml) and washed successively with 10% sodium hydrogen sulfite aqueous solution, sodium hydrogen carbonate aqueous solution water, and dried over magnesium sulfate. The crystallized residue obtained by evaporation under reduced pressure was recrystallized from acetone-hexane to give compound 201 (37.4 g, 92.5 mmol, 93.2%) as crystals.

M.p.: 110–111° C.

Process 7

To a suspension of compound 201 (3.05 g, 7.55 mmol), palladium acetate (II) (339 mg, 1.51 mmol) and 1,3-bis (diphenyl phosphino)propane (781 mg, 1.89 mmol) in dimethylsulfoxide (60 ml) were added triethylamine (10.5 ml, 75.3 mmol) and water (15 ml) at room temperature. The mixture was stirred at room temperature for 30 minutes, and then it was stirred at room temperature for 1 hour under carbon monoxide atmosphere of 1 atm and 2 hours at 70° C. The reaction mixture was diluted with ethyl acetate (120 ml) and water (120 ml), and it was filtrated through celite pad. The filtrate was washed with ethyl acetate (60 ml) and water (60 ml). Ethyl acetate was evaporated under reduced pressure, and 10% citric acid solution (60 ml) was added to the residue. The precipitated crystals were filtered, washed with water and recrystallized from ethyl acetate-methanol (1:1 v/v) to give compound 202 (2.16 g, 58.5 mmol, 78.0%) as dark brown crystals.

Process 8

To a suspension of compound 202 (199 mg, 0.539 mmol) and 1-hydroxy benzotriazole (7.5 mg, 0.056 mmol) in DMF (2 ml) were added isopropyl amine (0.056 ml, 0.66 mmol) and 1-ethyl-3-(3-dimethylaminopropyl)carbodiimide hydrochloride (125 mg, 0.652 mmol) at room temperature, and the mixture was stirred for 90 minutes. Water (4 ml) was added dropwise to the reaction mixture at room temperature. The precipitated crystals were filtered and washed with water to give compound 203 (194 mg, 88.0%) as colorless crystals.

Process 9

To a solution of compound 203 (90.0 mg, 0.219 mmol) in methylene chloride (4.5 ml) was added dropwise 1 M boron tribromide (0.880 ml, 0.880 mmol) in methylene chloride under ice-cooling, and the mixture was stirred for 30 minutes. Water (9 ml) was added to the reaction mixture under ice-cooling. The precipitated crystals were filtered, washed with water and recrystallized with ethyl acetate to give a title compound I-171 (31.6 mg, 0.08 mmol, 36.0%) as dark brown crystals.

M.p.: 210–212° C. Recrystallization solvent: ethyl acetate
NMR (DMSO-d$_6$) δ: 1.16 (6H, d, J=6.9 Hz), 3.93 (3H, s), 4.10 (1H, m), 4.23 (2H, s), 7.16 (2H, m), 7.35 (2H, m), 7.96 (1H, s), 8.42 (1H, brd), 8.51 (1H, m), 8.90 (1H, m).

Compound I-172 to I-179 were prepared in a same manner similar to Example 18 and Example 62.

Compound I-174

M.p.: 198–200° C. Recrystallization solvent: ethyl acetate
NMR (CDCl$_3$) δ: 1.30 (3H, t, J=7.2 Hz), 3.49–3.59 (2H, m), 4.03 (3H, s), 4.14 (2H, s), 6.99 (2H, t, J=8.7 Hz), 7.14–7.27 (2H, m), 8.02 (1H, s) 8.64 (1H, d, J=2.1 Hz), 8.80 (1H, d, J=2.1 Hz).

Compound I-175

M.p.: 190–193° C. Recrystallization solvent: acetone-ether
NMR (CDCl$_3$) δ: 1.02(3H, t, J=7.5 Hz), 1.68(2H, m), 3.46(2H, m), 4.04(3H, s), 4.15(2H, s), 6.06(2H, m), 6.99 (2H, m), 7.17(1H, m), 8.04(1H, s), 8.64(1H, s), 8.83(1H, s).

Compound I-176

NMR (CDCl$_3$) δ: 1.00–1.60 (2H, m), 1.60–1.80 (4H, m), 3.10–3.20 (2H, m), 3.40–4.00 (2H, m), 4.09 (3H, s), 4.34 (2H, s), 7.04–7.21 (2H, m), 7.22–7.28 (2H, m), 8.06 (1H, s), 8.49 (1H, s), 9.45 (1H, d, J=1.5 Hz).

Compound I-177

M.p.: 228–230° C. Recrystallization solvent: methanol
NMR (DMSO-d$_6$) δ: 3.92 (3H, s), 4.21 (2H, s), 4.49 (2H, d, J=5.7 Hz), 7.15 (2H, m), 7.28 (2H, m), 8.09 (1H, s), 8.62 (1H, s), 8.91 (1H, s), 9.14 (1H, brt).

Compound I-178

M.p.: 158–161° C. Recrystallization solvent: ethyl acetate
NMR (CDCl$_3$) δ: 2.82 (3H, s), 3.17 (3H, s), 4.02 (3H, s), 4.15 (2H, s), 6.14 (1H, br.s), 7.01 (2H, t, J=8.7 Hz), 7.13–7.19 (2H, m), 7.87 (1H, d, J=2.1 Hz), 7.89 (1H, s), 8.85 (1H, d, J=2.1 Hz), 11.94 (1H, br.s).

Compound I-179

M.p.: 159–163° C. Recrystallization solvent: acetone-isopropanol
NMR (CDCl$_3$) δ: 3.96(3H, s), 4.07(3H, s), 4.20(2H, s), 7.01(2H, m), 7.20(2H, m), 8.76(1H, s), 8.88(1H, s), 9.30 (1H, s).

Example 63

Compound I-180

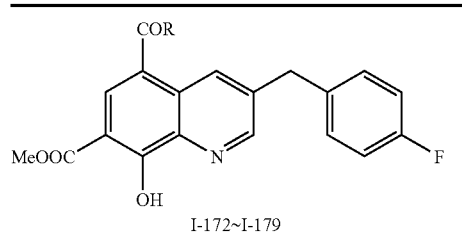

I-172: R = NH$_2$
I-173: R = NHMe
I-174: R = NHEt
I-175: R = NHn-Pr
I-176: R = piperidine
I-177: R = NHBn
I-178: R = NMe$^2$
I-179: R = OMe Compound I-172

M.p.: 247–249° C. Recrystallization solvent: methanol-isopropanol
NMR (DMSO-d$_6$) δ: 3.93 (3H, s), 4.23 (2H, s), 7.15 (2H, m), 7.35 (2H, m), 7.48 (1H, brs), 8.06 (1H, brs), 8.11 (1H, s), 8.73 (1H, d, J=4.2 Hz), 8.90 (1H, d, J=4.2 Hz).

Compound I-173

M.p.: 219–221° C. Recrystallization solvent: methanol
NMR (DMSO-d$_6$) δ: 2.81 (3H, d, J=4.2 Hz), 3.93 (3H, s), 4.22 (2H, s), 7.15 (2H, m), 7.35 (2H, m), 8.04 (1H, s), 8.52 (1H, brt), 8.67 (1H, m), 8.90 (1H, m).

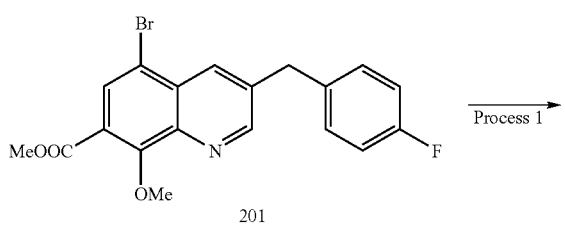

-continued

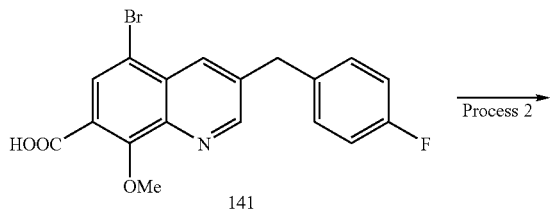
141

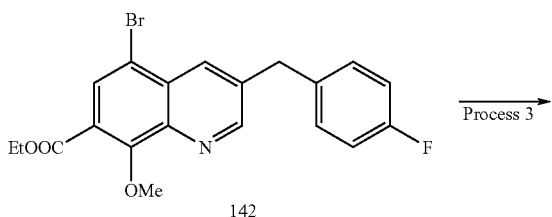
142

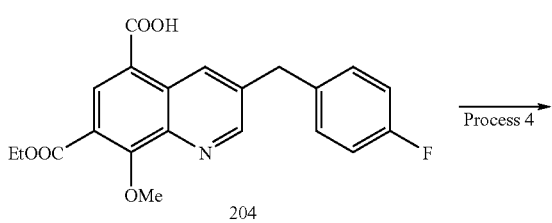
204

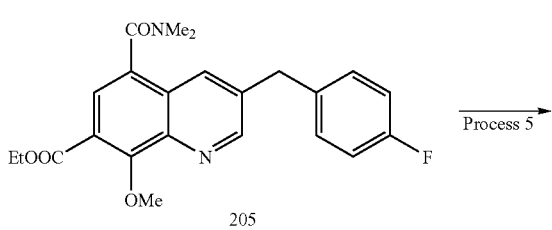
205

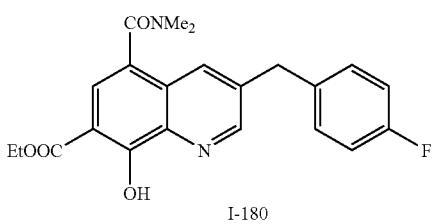
I-180

Process 1

To a solution of compound 201 (1.5 g, 3.71 mmol) in tetrahydrofuran (12.5 ml)-methanol (12.5 ml) was added 2 N sodium hydroxide aqueous solution (2.20 ml, 4.45 mmol) under ice-cooling, and the mixture was refluxed for 30 minutes. 2 N hydrochloric acid (2.2 ml) and water (75 ml) were added to the reaction mixture at room temperature, and the mixture was stirred for 30 minutes under ice-cooling. The precipitated crystals were filtered and washed with water to give compound 141 (1.4 g, 97.0%).

NMR (CDCl$_3$) δ: 4.23 (2H, s), 4.49 (3H, s), 7.01–7.09 (2H, m), 7.17–7.29 (2H, m), 8.31 (1H, d, J=1.8 Hz), 8.49 (1H, s), 8.66 (1H, d, J=1.8 Hz), 11.40 (1H, brs).

Process 2

To a solution of compound 141 (1.4 g, 3.59 mmol) in methylene chloride (30 ml) were added 1-ethyl-3-(3-dimethylaminopropyl)carbodiimide hydrochloride (827 mg, 4.31 mmol) and 1-hydroxy benzotriazole (566 mg, 4.31 mmol) at room temperature, and the mixture was stirred for 40 minutes. Ethanol (20 ml) and triethylamine (0.60 ml, 4.31 mmol) were added to the reaction mixture, and the mixture was refluxed for 1 hour. The reaction mixture was cooled and evaporated under reduced pressure. Ice water was added to the residue, and the mixture was extracted with ethyl acetate. The organic layer was washed successively with water, saturated sodium hydrogen carbonate solution, brine and dried over magnesium sulfate. The residue obtained by evaporation under reduced pressure was purified with column chromatography (ethyl acetate: n-hexane=1:2–1:1) to give compound 142 (1.30 g, 87.0%).

NMR (CDCl$_3$) δ: 1.45 (3H, t, J=7.2 Hz), 4.21 (2H, s), 4.21 (3H, s), 4.45 (2H, q, J=7.2 Hz), 6.99–7.08 (2H, m), 7.16–7.29 (2H, m), 8.41 (1H, s), 8.24 (1H, d, J=2.1 Hz), 8.85 (1H, d, J=2.1 Hz).

Process 3

Compound 204 (2.38 g, 87.0%) was obtained as pale yellow crystals from compound 142 (3.0 g, 7.18 mmol) by process 7 of Example 62.

NMR (CDCl$_3$) δ: 1.37 (3H, t, J=7.1 Hz), 4.18 (3H, s), 4.25 (2H, s), 4.38 (2H, q, J=7.1 Hz), 7.13–7.20 (2H, m), 7.34–7.40 (2H, m), 8.45 (1H, s), 8.98 (1H, d, J=2.0 Hz), 9.18 (1H, d, J=2.0 Hz), 13.40 (1H, brs).

Process 4

Compound 205 (173 mg, 81.0%) was obtained as colorless crystals from compound 204 (200 mg, 0.52 mmol) by process 8 of Example 62.

NMR (CDCl$_3$) δ: 1.44 (3H, t, J=7.2 Hz), 2.83 (3H, s), 3.20 (3H, s), 4.15 (2H, s), 4.23 (3H, s), 4.44 (2H, q, J=7.2 Hz), 6.98–7.05 (2H, m), 7.14–7.20 (2H, m), 7.83 (1H, s), 7.89 (1H, d, J=2.1 Hz), 8.85 (1H, d, J=2.1 Hz).

Process 5

A title compound I-180 (90 mg, 55.0%) was obtained pale yellow crystals from compound 205 (170 mg, 0.41 mmol) by process 9 of Example 62.

M.p.: 127–128° C. Recrystallization solvent: methanol-diisopropylether

NMR (CDCl$_3$) δ: 1.46 (3H, t, J=7.2 Hz), 2.80 (3H, s), 3.17 (3H, s), 4.15 (2H, s), 4.48 (2H, q, J=7.2 Hz), 6.96–7.07 (2H, m), 7.12–7.22 (2H, m), 7.84 (1H, d, J=2.1 Hz), 7.90 (1H, s), 8.86 (1H, d, J=2.1 Hz), 12.07 (1H, brs).

Compound I-181 to I-190 were prepared in a same manner similar to Example 63.

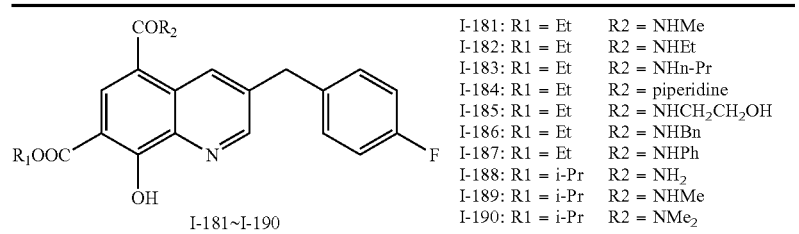

| | | |
|---|---|---|
| I-181: R1 = Et | R2 = NHMe | |
| I-182: R1 = Et | R2 = NHEt | |
| I-183: R1 = Et | R2 = NHn-Pr | |
| I-184: R1 = Et | R2 = piperidine | |
| I-185: R1 = Et | R2 = NHCH$_2$CH$_2$OH | |
| I-186: R1 = Et | R2 = NHBn | |
| I-187: R1 = Et | R2 = NHPh | |
| I-188: R1 = i-Pr | R2 = NH$_2$ | |
| I-189: R1 = i-Pr | R2 = NHMe | |
| I-190: R1 = i-Pr | R2 = NMe$_2$ | |

I-181~I-190

Compound I-181

M.p.: 208–210° C. Recrystallization solvent: methanol

NMR (CDCl$_3$) δ: 1.48 (3H, t, J=7.2 Hz), 3.75 (3H, d, J=3.9 Hz), 4.16 (2H, s), 4.50 (2H, q, J=7.2 Hz), 6.07 (1H, brs), 6.95–7.05 (2H, m), 7.12–7.23 (2H, m), 8.06 (1H, s), 8.67 (1H, s), 8.30 (1H, s), 12.15 (1H, brs).

Compound I-182

M.p.: 153–155° C. Recrystallization solvent: ethyl acetate

NMR (CDCl$_3$) δ: 1.35 (3H, t, J=7.1 Hz), 1.51 (3H, t, J=7.1 Hz), 3.57 (2H, q, J=7.1 Hz), 4.28 (2H, s), 4.55 (2H, q, J=7.1 Hz), 6.91 (1H, brs), 7.03–7.12 (2H, m), 7.18–7.28 (2H, m), 8.36 (1H, s), 9.22 (1H, s), 9.40 (1H, s), 12.26 (1H, brs).

Compound I-183

M.p.: 134–137° C. Recrystallization solvent: ethyl acetate

NMR (CDCl$_3$) δ: 1.04 (3H, t, J=7.2 Hz), 1.50 (3H, t, J=7.0 Hz), 1.66–1.79 (2H, m), 3.49 (2H, q, J=6.5 Hz), 4.23 (2H, s), 4.52 (2H, q, J=7.0 Hz), 6.93 (1H, brs), 7.01–7.09 (2H, m), 7.18–7.28 (2H, m), 8.28 (1H, s), 9.07 (1H, s), 9.16 (1H, s).

Compound I-184

M.p.: 140–143° C. Recrystallization solvent: ethyl acetate

NMR (CDCl$_3$) δ: 1.10–1.50 (2H, m), 1.48 (3H, t, J=7.1 Hz), 1.60–1.74 (4H, m), 3.06–3.22 (2H, m), 3.54–3.96 (2H, m), 4.37 (2H, s), 4.54 (2H, q, J=7.1 Hz), 7.03–7.12 (2H, m), 7.21–7.29 (2H, m), 8.06 (1H, s), 8.47 (1H, s), 9.50 (1H, s), 12.39 (1H, brs).

Compound I-185

M.p.: 194–195° C. Recrystallization solvent: ethyl acetate-methanol

NMR (CDCl$_3$) δ: 1.48 (3H, t, J=7.2 Hz), 3.65–3.74 (2H, m), 3.86–3.95 (2H, m), 4.14 (2H, s), 4.51 (2H, q, J=7.2 Hz), 6.57 (1H, brs), 6.94–7.05 (2H, m), 7.12–7.23 (2H, m), 8.07 (1H, s), 8.62 (1H, s), 8.81 (1H, d, J=2.1 Hz), 12.13 (1H, brs).

Compound I-186

M.p.: 214–217° C. Recrystallization solvent: ethyl acetate

NMR (CDCl$_3$) δ: 1.46 (3H, t, J=7.1 Hz), 4.15 (2H, s), 4.49 (2H, q, J=7.1 Hz), 4.70 (2H, d, J=5.7 Hz), 6.35 (1H, brs), 6.95–7.04 (2H, m), 7.13–7.21 (2H, m), 7.31–7.42 (5H, m), 8.08 (1H, s), 8.67 (1H, s), 8.83 (1H, d, J=1.5 Hz), 12.14(1H, brs).

Compound I-187

M.p.: 168° C. Recrystallization solvent: ethyl acetate-diisopropylether

NMR (CDCl$_3$) δ: 1.49 (3H, t, J=6.9 Hz), 4.15 (2H, s), 4.53 (2H, q, J=6.9 Hz), 6.94–7.70 (9H, m), 7.77 (1H, brs), 8.23 (1H, s), 8.72 (1H, s), 8.87 (1H, d, J=1.8 Hz), 12.17 (1H, brs).

Compound I-188

M.p.: 218–219° C. Recrystallization solvent: acetone-ethyl acetate

NMR (CDCl$_3$) δ: 1.45 (6H, d, J=6.3 Hz), 4.17 (2H, s), 5.39 (1H, sep, J=6.3 Hz), 5.92 (2H, brs), 6.96–7.04 (2H, m), 7.14–7.21 (2H, m), 8.17 (1H, s), 8.76 (1H, s), 8.84 (1H, s), 12.29 (1H, brs).

Compound I-189

M.p.: 208–209° C. Recrystallization solvent: acetone-methanol

NMR (CDCl$_3$) δ: 1.46 (6H, d, J=6.2 Hz), 3.08 (3H, d, J=3.9 Hz), 4.16 (2H, s), 5.39 (1H, sep, J=6.2 Hz), 6.07 (1H, brs), 6.96–7.03 (2H, m), 7.15–7.21 (2H, m), 8.03 (1H, s), 8.67 (1H, s), 8.84 (1H, s), 12.23 (1H, brs).

Compound I-190

NMR (CDCl$_3$) δ: 1.43 (6H, d, J=6.3 Hz), 2.78 (3H, s), 3.17 (3H, s), 4.16 (2H, s), 5.36 (1H, sep, J=6.3 Hz), 6.97–7.06 (2H, m), 7.12–7.20 (2H, m), 7.82 (1H, s), 7.89 (1H, s), 8.87 (1H, d, J=2.1 Hz), 12.23 (1H, brs).

Example 64

Compound I-191

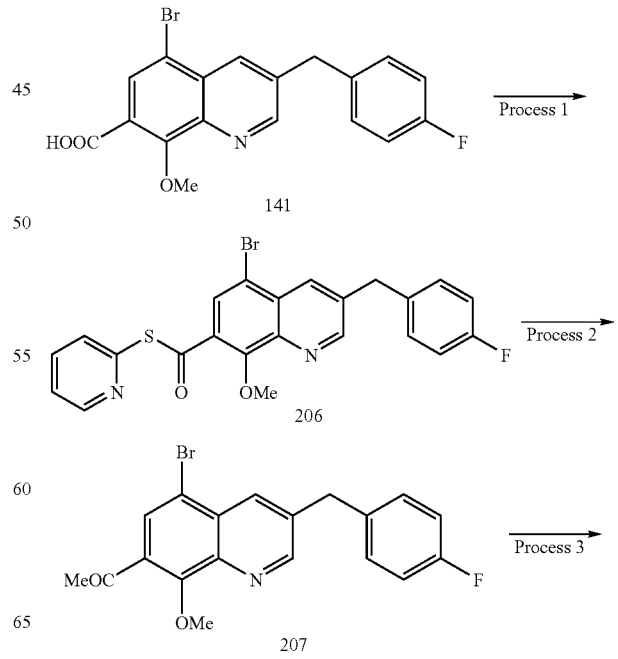

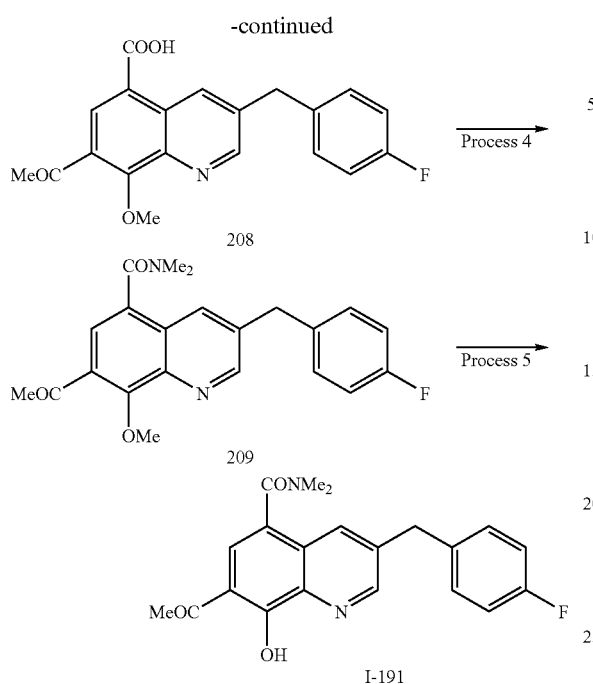

Process 1

To a solution of compound 141 (390 mg, 1.0 mmol) in tetrahydrofuran (20 ml) were added 2,2'-dipyridyldisulfide (242 mg, 1.1 mmol) and triphenyl phosphine (288 mg, 1.1 mmol). After being stirred for 2 hours, 2,2'-dipyridyldisulfide (242 mg, 1.1 mmol) and triphenyl phosphine (288 mg, 1.1 mmol) were added to the reaction mixture. The reaction mixture was allowed to stand over night and evaporated under reduced pressure. The residue was subjected to column chromatography and crystallized from diisopropyl ether to give compound 206 (436 mg, 90%).

Process 2

To a solution of compound 206 (2.20 g, 4.55 mmol) obtained by process 1 in tetrahydrofuran (50 ml) was added 1M methyl magnesium bromide (5.0 ml, 5.0 mmol) under ice-cooling with dry ice. After 40 minutes, 1M methyl magnesium bromide (0.9 ml, 0.9 mmol) was added to the reaction mixture. After 15 minutes, saturated ammonium chloride solution was added to reaction mixture, and the mixture was extracted twice with ethyl acetate. The organic layer was washed with water, brine and dried over magnesium sulfate. The solvent was evaporated, and the residue was subjected to column chromatography and crystallized with n-hexane-diisopropyl ether to give compound 207 (1.64 g, 93.0%).

Process 3

Compound 207 (1.6 g, 4.2 mmol) obtained by process 2 was reacted with a same manner similar to process 7 of Example 62 to give compound 208 (1.18 g, 3.34 mmol, 80.5%) as colorless crystals.

Process 4

Compound 208 (194.3 mg, 0.55 mmo) obtained by process 3 was reacted with a same manner similar to process 8 of Example 62 to give compound 209 (148 mg, 0.39 mmoll, 70.7%) as colorless crystals.

Process 5

Compound 209 (100.0 mg, 0.26 mmol) obtained by process 4 was reacted with a same manner similar to process 3 of Example 45 to give a title compound I-191 (51.8 mg, 0.39 mmol, 54.4%) as light green crystals.

M.p.: 141–142° C. Recrystallization solvent: ethanol-isopropyl ether

NMR (CDCl$_3$) δ: 2.74 (3H, s), 2.80 (3H, s), 3.18(3H, s), 4.16 (2H, s), 6.96–7.06(2H, m), 7.10–7.20 (2H, m), 7.80 (1H, s), 7.80–7.86 (1H, m), 8.82–8.90(1H, m).

Compound I-192 to I-243 were prepared in a same manner similar to process 3 of Example 45, process 7 and 8 of Example 62 and Example 64.

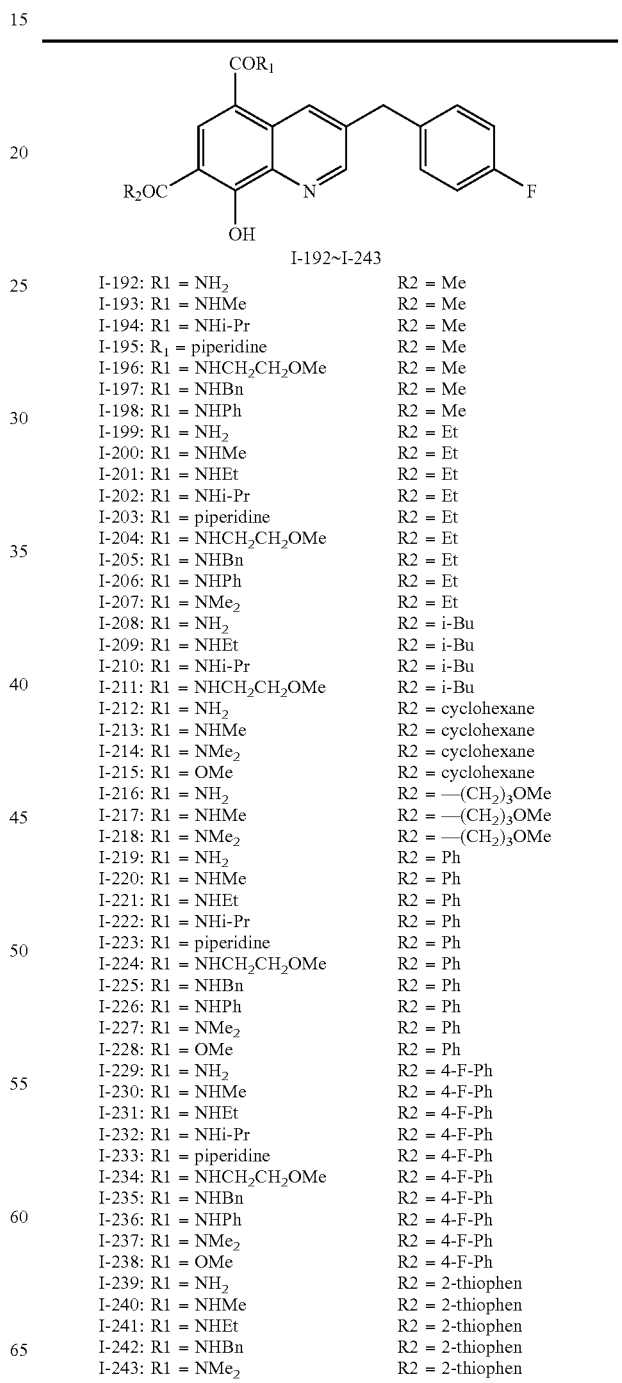

I-192~I-243

| | | |
|---|---|---|
| I-192: R1 = NH$_2$ | | R2 = Me |
| I-193: R1 = NHMe | | R2 = Me |
| I-194: R1 = NHi-Pr | | R2 = Me |
| I-195: R$_1$ = piperidine | | R2 = Me |
| I-196: R1 = NHCH$_2$CH$_2$OMe | | R2 = Me |
| I-197: R1 = NHBn | | R2 = Me |
| I-198: R1 = NHPh | | R2 = Me |
| I-199: R1 = NH$_2$ | | R2 = Et |
| I-200: R1 = NHMe | | R2 = Et |
| I-201: R1 = NHEt | | R2 = Et |
| I-202: R1 = NHi-Pr | | R2 = Et |
| I-203: R1 = piperidine | | R2 = Et |
| I-204: R1 = NHCH$_2$CH$_2$OMe | | R2 = Et |
| I-205: R1 = NHBn | | R2 = Et |
| I-206: R1 = NHPh | | R2 = Et |
| I-207: R1 = NMe$_2$ | | R2 = Et |
| I-208: R1 = NH$_2$ | | R2 = i-Bu |
| I-209: R1 = NHEt | | R2 = i-Bu |
| I-210: R1 = NHi-Pr | | R2 = i-Bu |
| I-211: R1 = NHCH$_2$CH$_2$OMe | | R2 = i-Bu |
| I-212: R1 = NH$_2$ | | R2 = cyclohexane |
| I-213: R1 = NHMe | | R2 = cyclohexane |
| I-214: R1 = NMe$_2$ | | R2 = cyclohexane |
| I-215: R1 = OMe | | R2 = cyclohexane |
| I-216: R1 = NH$_2$ | | R2 = —(CH$_2$)$_3$OMe |
| I-217: R1 = NHMe | | R2 = —(CH$_2$)$_3$OMe |
| I-218: R1 = NMe$_2$ | | R2 = —(CH$_2$)$_3$OMe |
| I-219: R1 = NH$_2$ | | R2 = Ph |
| I-220: R1 = NHMe | | R2 = Ph |
| I-221: R1 = NHEt | | R2 = Ph |
| I-222: R1 = NHi-Pr | | R2 = Ph |
| I-223: R1 = piperidine | | R2 = Ph |
| I-224: R1 = NHCH$_2$CH$_2$OMe | | R2 = Ph |
| I-225: R1 = NHBn | | R2 = Ph |
| I-226: R1 = NHPh | | R2 = Ph |
| I-227: R1 = NMe$_2$ | | R2 = Ph |
| I-228: R1 = OMe | | R2 = Ph |
| I-229: R1 = NH$_2$ | | R2 = 4-F-Ph |
| I-230: R1 = NHMe | | R2 = 4-F-Ph |
| I-231: R1 = NHEt | | R2 = 4-F-Ph |
| I-232: R1 = NHi-Pr | | R2 = 4-F-Ph |
| I-233: R1 = piperidine | | R2 = 4-F-Ph |
| I-234: R1 = NHCH$_2$CH$_2$OMe | | R2 = 4-F-Ph |
| I-235: R1 = NHBn | | R2 = 4-F-Ph |
| I-236: R1 = NHPh | | R2 = 4-F-Ph |
| I-237: R1 = NMe$_2$ | | R2 = 4-F-Ph |
| I-238: R1 = OMe | | R2 = 4-F-Ph |
| I-239: R1 = NH$_2$ | | R2 = 2-thiophen |
| I-240: R1 = NHMe | | R2 = 2-thiophen |
| I-241: R1 = NHEt | | R2 = 2-thiophen |
| I-242: R1 = NHBn | | R2 = 2-thiophen |
| I-243: R1 = NMe$_2$ | | R2 = 2-thiophen |

Compound I-192
M.p.: 230–232° C. Recrystallization solvent: diethylether
NMR (DMSO) δ: 2.75 (3H, s), 4.23 (2H, s), 7.12–7.18 (2H, m), 7.32–7.37 (2H, m), 7.46 (1H, brs), 8.05 (1H, brs), 8.13 (1H, s), 8.75 (1H, s), 8.89 (1H, s).

Compound I-193
M.p.: 207–209° C. Recrystallization solvent: ethanol-diethylether
NMR (DMSO) δ: 2.75 (3H, s), 2.81 (3H, d, J=4.4 Hz), 4.22 (2H, s), 7.12–7.18(2H, m), 7.32–7.36 (2H, m), 8.07 (1H, s), 8.52 (1H, d, J=4.7 Hz), 8.70 (1H, s), 8.90 (1H, s).

Compound I-194
M.p.: 211–213° C. Recrystallization solvent: ethanol-diethylether
NMR (DMSO) δ: 1.17 (6H, d, J=6.6 Hz), 2.75 (3H, s), 4.10 (1H, sept, J=6.7 Hz), 4.23 (2H, s), 7.12–7.18(2H, m), 7.32–7.37 (2H, m), 7.98 (1H, s), 8.39 (1H, d, J=7.7 Hz), 8.53 (1H, s), 8.90 (1H, s).

Compound I-195
M.p.: 191–193° C. Recrystallization solvent: ethanol-isopropyl ether
NMR (CDCl$_3$) δ: 1.00–1.80 (6H, m), 2.73 (3H, s), 3.00–3.12 (2H, m), 3.48–4.02 (2H, m), 4.16(2H, s), 6.98–7.08 (2H, m), 7.14–7.22 (2H, m), 7.74 (1H, s), 7.78–7.82 (1H, m), 8.86–7.92(1H, m).

Compound I-196
M.p.: 180–183° C. Recrystallization solvent: ethyl acetate-isopropyl ether
NMR (CDCl$_3$) δ: 2.78 (3H, s), 3.40 (3H, s), 3.58–3.64 (2H, m), 3.66–3.74(2H, m), 4.16 (2H, s), 6.37–6.49(1H, m), 6.96–7.04(2H, m), 7.14–7.21 (2H, m), 8.04(1H, s), 8.64–8.67(1H, m), 8.77–8.84(1H, m).

Compound I-197
M.p.: 208–210° C. Recrystallization solvent: ethanol-diethylether
NMR (DMSO) δ: 2.75 (3H, s), 4.22 (2H, s), 4.51 (2H, d, J=6.1 Hz), 7.12–7.18(2H, m), 7.27–7.34 (5H, m), 7.33–7.37 (2H, m), 8.13 (1H, s), 8.65 (1H, s), 8.91 (1H, s), 9.12 (1H, t, J=5.5 Hz).

Compound I-198
M.p.: 212–215° C. Recrystallization solvent: isopropyl ether
NMR (CDCl$_3$) δ: 2.76 (3H, s), 4.11 (2H, s), 6.92–7.02 (2H, m), 7.10–7.28(3H, m), 7.38–7.46 (2H, m), 7.60–7.70 (2H, m), 7.80–8.08(1H, brs), 8.12 (1H, s), 8.60–8.66 (1H, m), 8.72–8.80 (1H, m).

Compound I-199
M.p.: 217–219° C. Recrystallization solvent: ethanol
NMR (CDCl$_3$) δ: 1.30 (3H, t, J=7.2 Hz), 3.19 (2H, q, J=7.2 Hz), 4.18 (2H, s), 5.85 (2H, bs), 6.97–7.03 (2H, m), 7.16–7.20 (2H, m), 8.19 (1H, s), 8.77 (1H, s), 8.80 (1H, d, J=2.0 Hz).

Compound I-200
M.p.: 214–216° C. Recrystallization solvent: ethanol
NMR (CDCl$_3$) δ: 1.29 (3H, t, J=7.2 Hz), 3.07 (3H, d, J=4.0 Hz), 3.18 (2H, q, J=7.2 Hz), 4.16 (2H, s), 6.09 (1H, bs), 6.97–7.04 (2H, m), 7.16–7.20 (2H, m), 8.05 (1H, s), 8.68 (1H, s), 8.79 (1H, d, J=2.1 Hz).

Compound I-201
M.p.: 194–195° C. Recrystallization solvent: ethanol
NMR (CDCl$_3$) δ: 1.29 (3H, t, J=7.2 Hz), 1.29 (3H, t, J=7.2 Hz), 3.17 (2H, q, J=7.2 Hz), 3.50–3.59 (2H, m), 4.16 (2H, s), 6.07 (1H, bs), 6.97–7.03 (2H, m), 7.16–7.21 (2H, m), 8.03 (1H, s), 8.63 (1H, d, J=1.8 Hz), 8.79(1H, d, J=1.8 Hz).

Compound I-202
M.p.: 196–197° C. Recrystallization solvent: ethanol
NMR (CDCl$_3$) δ: 1.29 (3H, t, J=7.2 Hz), 1.29 (6H, d, J=6.5 Hz), 3.19 (2H, q, J=7.2 Hz), 4.17 (2H, s), 4.25–4.40 (1H, m), 5.82 (1H, bs), 6.98–7.04 (2H, m), 7.16–7.21 (2H, m), 8.01 (1H, s), 8.58 (1H, s), 8.80 (1H, d, J=2.1 Hz).

Compound I-203
M.p.: 136–138° C. Recrystallization solvent: ethanol
NMR (CDCl$_3$) δ: 1.29 (3H, t, J=7.2 Hz), 1.00–1.75 (6H, m), 3.00–3.17 (4H, m), 3.60 (1H, bs), 3.92 (1H, bs), 4.16 (2H, s), 6.99–7.05 (2H, m), 7.16–7.19 (2H, m), 7.77 (1H, s), 7.80 (1H, d, J=1.8 Hz), 8.88 (1H, d, J=2.1 Hz).

Compound I-204
NMR (CDCl$_3$) δ: 1.29 (3H, t, J=7.2 Hz), 3.18 (2H, q, J=7.2 Hz), 3.41 (3H, s), 3.61 (2H, d, J=5.0 Hz), 3.71 (2H, d, J=5.0 Hz), 4.16 (2H, s), 6.41 (1H, bs), 6.97–7.03 (2H, m), 7.16–7.20 (2H, m), 8.07 (1H, s), 8.65 (1H, s), 8.80 (1H, d, J=2.1 Hz).

Compound I-205
M.p.: 201–203° C. Recrystallization solvent: ethanol
NMR (CDCl$_3$) δ: 1.26 (3H, t, J=7.2 Hz), 3.14 (2H, q, J=7.2 Hz), 4.14 (2H, s), 4.68 (2H, d, J=5.5 Hz), 6.41 (1H, bs), 6.97–7.03 (2H, m), 7.14–7.19 (2H, m), 7.26–7.40 (5H, m), 8.06 (1H, s), 8.66 (1H, d, J=2.1 Hz), 8.77 (1H, d, J=2.1 Hz).

Compound I-206
M.p.: 196–197° C. Recrystallization solvent: ethanol
NMR (CDCl$_3$) δ: 1.28 (3H, t, J=7.2 Hz), 3.16 (2H, q, J=7.2 Hz), 4.12 (2H, s), 6.94–7.01 (2H, m), 7.13–7.26 (3H, m), 7.40–7.45 (2H, m), 7.67 (2H, d, J=7.6 Hz), 8.01 (1H, s), 8.16 (1H, s), 8.64 (1H, s), 8.78 (1H, d, J=2.1 Hz).

Compound I-207
M.p.: 150–152° C. Recrystallization solvent: ethanol
NMR (CDCl$_3$) δ: 1.29 (3H, t, J=7.2 Hz), 2.81 (3H, s), 3.14 (2H, q, J=7.2 Hz), 3.18 (3H, s), 4.16 (2H, s), 6.99–7.05 (2H, m), 7.14–7.19 (2H, m), 7.83 (1H, s), 7.84 (1H, s), 8.85 (1H, d, J=2.1 Hz).

Compound I-208
M.p.: 178–180° C. Recrystallization solvent: ethyl acetate-isopropyl ether
NMR (CDCl$_3$) δ: 1.05(6H, d, J=6.7 Hz), 2.30(1H, m), 3.00(2H, d, J=6.7 Hz), 4.18(2H, s), 5.68–6.12(2H, brs), 6.95–7.05(2H, m), 7.14–7.24(2H, m), 8.16(1H, s), 8.74–8.78(1H, m), 8.80–8.84(1H, m).

Compound I-209
M.p.: 170–171° C. Recrystallization solvent: ethyl acetate
NMR (CDCl$_3$) δ: 1.05(6H, d, J=6.7 Hz), 1.30(3H, t, J=7.4 Hz), 2.36(1H, m), 3.04(2H, d, J=6.7 Hz), 3.50–3.62(2H, m), 4.17(2H, s), 5.95–6.03(1H, m), 6.96–7.05(2H, m), 7.14–7.24(2H, m), 8.02 (1H, s), 8.60–8.64(1H, m), 8.79–8.82(1H, m).

Compound I-210
M.p.: 171–173° C. Recrystallization solvent: ethanol-isopropyl ether
NMR (DMSO) δ: 0.97(6H, d, J=6.4 Hz), 1.17(6H, d, J=6.4 Hz), 2.23(1H, sept, J=6.7 Hz), 3.07(2H, d, J=6.7 Hz), 4.04–4.16(1H, m), 4.23(2H, s), 7.12–7.18(2H, m), 7.32–7.36(2H, m), 7.96(1H, s), 8.38(1H, d, J=7.6 Hz), 8.52(1H, d, J=1.8 Hz), 8.89(1H, d, J=1.5 Hz).

Compound I-211
M.p.: 140–142° C. Recrystallization solvent: ethanol-isopropyl ether
NMR (DMSO) δ: 0.97(6H, d, J=6.7 Hz), 2.24(1H, sept, J=6.7 Hz), 3.07(2H, d, J=6.7 Hz), 3.29(3H, s), 3.30–3.49 (4H, m), 4.22(2H, s), 7.12–7.18(2H, m), 7.32–7.36(2H, m), 8.03(1H, s), 8.62(1H, d, J=1.8 Hz), 8.65(1H, brs), 8.89(1H, d, J=2.1 Hz).

Compound I-212
M.p.: 260–262° C. Recrystallization solvent: ethyl acetate
NMR (CDCl$_3$) δ: 1.30–2.00(10H, m), 3.38–3.49(1H, m), 4.18(2H, s), 5.70–6.00(1H, brs), 6.96–7.04(2H, m), 7.16–7.22(2H, m), 8.15(1H, s), 8.72–8.76(2H, m), 8.80–8.82(1H, m).

Compound I-213
M.p.: 163–164° C. Recrystallization solvent: isopropyl ether
NMR (CDCl$_3$) δ: 1.20–2.00(10H, m), 3.08(3H, d, J=2.3 Hz), 3.36–3.48(1H, m), 4.16(2H, s), 6.00–6.11(1H, m), 6.96–7.04(2H, m), 7.14–7.20(2H, m), 8.01(1H, s), 8.62–8.68(1H, m), 8.78–8.82(1H, m).

Compound I-214
NMR (CDCl$_3$) δ: 1.06–2.00(10H, m), 2.80(3H, s), 3.19 (3H, s), 3.28–3.44(1H, m), 4.16(2H, s), 6.96–7.08(2H, m), 7.10–7.20(2H, m), 7.78–7.86(2H, m), 8.80–8.92(1H, m), 13.6–14.2(1H, brs).

Compound I-215
M.p.: 163–164° C. Recrystallization solvent: isopropyl ether-isopropanol
NMR (CDCl$_3$) δ: 1.20–2.00(10H, m), 3.08(3H, d, J=2.3 Hz), 3.36–3.48(1H, m), 4.16(2H, s), 6.00–6.11(1H, m), 6.96–7.04(2H, m), 7.14–7.20(2H, m), 8.01(1H, s), 8.62–8.68(1H, m), 8.78–8.82(1H, m).

Compound I-216
M.p.: 165° C. Recrystallization solvent: ethyl acetate
NMR (CDCl$_3$) δ: 2.04–2.14 (2H, m), 3.25 (2H, t, J=7.5 Hz), 3.37 (3H, s), 3.52 (2H, t, J=5.7 Hz), 4.17 (2H, s), 5.94 (2H, brs), 6.96–7.05 (2H, m), 7.14–7.22 (2H, m), 8.23 (1H, s), 8.81 (2H, s).

Compound I-217
M.p.: 148° C. Recrystallization solvent: ethyl acetate-diisopropyl ether
NMR (CDCl$_3$) δ: 2.03–2.14 (2H, m), 3.07 (3H, d, J=5.1 Hz), 3.23 (2H, t, J=7.5 Hz), 3.37 (3H, s), 3.51 (2H, t, J=6.0 Hz), 4.16 (2H, s), 6.16 (1H, brs), 6.95–7.05 (2H, m), 7.14–7.22 (2H, m), 8.08 (1H, s), 8.71 (1H, m), 8.79 (1H, d, J=1.2 Hz), 12.63 (1H, brs).

Compound I-218
M.p.: 123–126° C. Recrystallization solvent: ethyl acetate-diisopropyl ether
NMR (CDCl$_3$) δ: 2.03–2.13 (2H, m), 2.81 (3H, s), 3.18 (3H, s), 3.21 (2H, t, J=7.2 Hz), 3.35 (3H, s), 3.50 (2H, t, J=6.0 Hz), 4.16 (2H, s), 6.97–7.06 (2H, m), 7.12–7.20 (2H, m), 7.83 (1H, s), 7.85 (1H, s), 8.85 (1H, d, J=1.2 Hz), 13.44 (1H, brs).

Compound I-219
M.p.: 259–261° C. Recrystallization solvent: methanol
Elemental analysis for C$_{24}$H$_{17}$FN$_2$O$_3$ Calcd. (%): C, 71.99; H, 4.28; F, 4.74; N, 7.00. Found. (%): C, 71.87; H, 4.15; F, 4.63; N, 6.90.
NMR (CDCl$_3$) δ: 4.20 (2H, s), 5.76 (2H, m), 7.01 (2H, m), 7.20 (2H, m), 7.54 (2H, m), 7.65 (1H, m), 7.80 (2H, m), 8.00 (1H, s), 8.82 (1H, m), 8.85 (1H, m).

Compound I-220
M.p.: 88–89° C. Recrystallization solvent: methanol
Elemental analysis for C$_{25}$H$_{19}$FN$_2$O$_3$(H$_2$O)$_{0.6}$ Calcd. (%): C, 70.61; H, 4.79; F, 4.47; N, 6.59. Found. (%): C, 70.52; H, 4.58; F, 4.33; N, 6.43.
NMR (CDCl$_3$) δ: 3.02 (3H, d, J=4.5 Hz), 4.18 (2H, s), 6.00 (1H, brq), 7.01 (2H, m), 7.19 (2H, m), 7.54 (2H, m), 7.64 (1H, m), 7.78 (2H, m), 7.86 (1H, s), 8.75 (1H, m), 8.81 (1H, m).

Compound I-221
M.p.: 70–72° C. Recrystallization solvent: methanol
Elemental analysis for C$_{26}$H$_{21}$FN$_2$O$_3$(H$_2$O)$_{0.5}$ Calcd. (%): C, 71.38; H, 5.07; F, 4.34; N, 6.40. Found. (%): C, 71.25; H, 5.08; F, 4.32; N, 6.46.
NMR (CDCl$_3$) δ: 1.24 (3H, t, J=7.4 Hz), 3.50 (2H, m), 4.19 (2H, s), 5.95 (1H, brt), 7.01 (2H, m), 7.20 (2H, m), 7.53 (2H, m), 7.64 (1H, m), 7.80 (2H, m), 7.86 (1H, s), 8.72 (1H, m), 8.80 (1H, m).

Compound I-222
M.p.: 77–78° C. Recrystallization solvent: methanol
Elemental analysis for C$_{27}$H$_{23}$FN$_2$O$_3$(H$_2$O)$_{1.0}$ Calcd. (%): C, 70.42; H, 5.47; F, 4.13; N, 6.08. Found. (%): C, 70.47; H, 5.32; F, 4.01; N, 5.93.
NMR (CDCl$_3$) δ: 1.25 (6H, d, J=6.3 Hz), 4.19 (2H, s), 4.29 (1H, m), 5.79 (1H, brd), 7.01 (2H, m), 7.20 (2H, m), 7.53 (2H, m), 7.64 (1H, m), 7.80 (2H, m), 7.84 (1H, s), 8.67 (1H, m), 8.80 (1H, m).

Compound I-223
M.p.: 150–151° C. Recrystallization solvent: methanol-isopropyl ether
Elemental analysis for C$_{29}$H$_{25}$FN$_2$O$_3$ Calcd. (%): C, 74.34; H, 5.38; F, 4.05; N, 5.98. Found. (%): C, 74.07; H, 5.25; F, 4.01; N, 5.87.
NMR (CDCl$_3$) δ: 1.12 (1H, m), 1.29 (1H, m), 1.58 (4H, m), 3.08 (2H, m), 3.50 (1H, m), 3.92 (1H, m), 4.18 (2H, s), 7.03 (2H, m), 7.19 (2H, m), 7.53 (2H, m), 7.60 (1H, s), 7.63 (1H, m), 7.75 (2H, m), 7.87 (1H, m), 8.90 (1H, m).

Compound I-224
M.p.: 178–180° C. Recrystallization solvent: methanol
Elemental analysis for C$_{27}$H$_{23}$FN$_2$O$_4$ Calcd. (%): C, 70.73; H, 5.06; F, 4.14; N, 6.11. Found. (%): C, 70.46; H, 4.89; F, 4.04; N, 6.03.
NMR (CDCl$_3$) δ: 3.34 (3H, s), 3.55 (2H, m), 3.65 (2H, m), 4.19 (2H, s), 6.33 (1H, brt), 7.01 (2H, m), 7.19 (2H, m), 7.54 (2H, m), 7.64 (1H, m), 7.79 (2H, m), 7.90 (1H, s), 8.73 (1H, m), 8.81 (1H, m).

Compound I-225
M.p.: 164–165° C. Recrystallization solvent: methanol
Elemental analysis for C$_{31}$H$_{23}$FN$_2$O$_3$ Calcd. (%): C, 75.90; H, 4.73; F, 3.87; N, 5.71. Found. (%): C, 75.54; H, 4.56; F, 3.82; N, 5.63.
NMR (CDCl$_3$) δ: 4.19 (2H, s), 4.65 (2H, d, J=5.7 Hz), 6.26 (1H, brt), 7.01 (2H, m), 7.19 (2H, m), 7.33 (5H, m), 7.52 (2H, m), 7.64 (1H, m), 7.78 (2H, m), 7.91 (1H, s), 8.76 (1H, m), 8.81 (1H, m).

Compound I-226
M.p.: 103–104° C. Recrystallization solvent: methanol
Elemental analysis for C$_{30}$H$_{21}$FN$_2$O$_3$ Calcd. (%): C, 75.62; H, 4.44; F, 3.99; N, 5.88. Found. (%): C, 75.23; H, 4.24; F, 4.02; N, 5.78.
NMR (CDCl$_3$) δ: 4.16 (2H, s), 6.99 (2H, m), 7.18 (3H, m), 7.40 (2H, m), 7.53 (2H, m), 7.63 (3H, m), 7.79 (2H, m), 7.86 (1H, brs), 8.00 (1H, s), 8.77 (1H, m), 8.79 (1H, m).

Compound I-227
  M.p.: 79–81° C. Recrystallization solvent: isopropanol
  NMR (CDCl$_3$) δ: 2.81 (3H, s), 3.14 (3H, s), 4.18 (2H, s), 7.02 (2H, m), 7.16 (2H, m), 7.53 (2H, m), 7.62 (1H, m), 7.65 (1H, s), 7.76 (2H, m), 7.93 (1H, m), 8.86 (1H, m), 12.73 (1H, brs).

Compound I-228
  M.p.: 174–175° C. Recrystallization solvent: methanol-chloroform
  NMR (CDCl$_3$) δ: 3.90 (3H, s), 4.22 (2H, s), 7.03 (2H, m), 7.22 (2H, m), 7.55 (2H, m), 7.66 (1H, m), 7.80 (2H, m), 8.58 (1H, s), 8.84 (1H, m), 9.30 (1H, m).

Compound I-229
  M.p.: 243–245° C. Recrystallization solvent: ethyl acetate
  NMR (d$_6$-DMSO) δ: 4.25 (2H, s), 7.13–7.19 (2H, m), 7.32–7.38 (4H, m), 7.43 (1H, brs), 7.83 (1H, s), 7.85–7.90 (2H, m), 8.01 (1H, brs), 8.84 (1H, d, J=2.1 Hz), 8.89 (1H, d, J=2.1 Hz).

Compound I-230
  M.p.: 156–158° C. Recrystallization solvent: ethyl acetate-isopropyl ether
  NMR (d$_6$-DMSO) δ: 2.79 (3H, d, J=4.5 Hz), 4.24 (2H, s), 7.13–7.19 (2H, m), 7.32–7.38 (4H, m), 7.75 (1H, s), 7.84–7.89 (2H, m), 8.48 (1H, d, J=4.5 Hz), 8.76 (1H, d, J=1.8 Hz), 8.89 (1H, d, J=1.8 Hz), 11.11(1H, brs).
  Elemental analysis for C$_{25}$H$_{18}$F$_2$N$_2$O$_3$ Calcd. (%): C, 69.44; H, 4.20; F, 8.79; N, 6.48. Found. (%): C, 69.14; H, 4.09; F, 8.53; N, 6.43.

Compound I-231
  M.p.: 152–153° C. Recrystallization solvent: ethyl acetate-isopropylether
  NMR (d$_6$-DMSO) δ: 1.12 (3H, t, J=2.1 Hz), 3.29 (2H, m), 4.25 (2H, s), 7.13–7.19 (2H, m), 7.33–7.38 (4H, m), 7.74 (1H, s), 7.85–7.90 (2H, m), 8.52 (1H, t, J=5.7 Hz), 8.73 (1H, d, J=2.1 Hz), 8.90 (1H, d, J=2.1 Hz), 10.80(1H, brs).
  Elemental analysis for C$_{26}$H$_{20}$F$_2$N$_2$O$_3$ Calcd. (%): C, 69.95; H, 4.52; F, 8.51; N, 6.27. Found. (%): C, 69.65; H, 4.48; F, 8.25; N, 6.15.

Compound I-232
  M.p.: 167–169° C. Recrystallization solvent: ethanol
  NMR (CDCl$_3$) δ: 1.26(6H, d, J=6.7 Hz), 4.19(2H, s), 4.27–4.34(1H, m), 5.87(1H, d, J=7.3 Hz), 6.98–7.04(2H, m), 7.16–7.22(4H, m), 7.82(1H, s), 7.83–7.88(2H, m), 8.71 (1H, s), 8.77(1H, s).

Compound I-233
  M.p.: 114–116° C. Recrystallization solvent: methanol-isopropyl ether
  NMR (CDCl$_3$) δ: 1.12 (1H, m), 1.31 (1H, m), 1.59 (4H, m), 3.09 (2H, m), 3.53 (1H, m), 3.91 (1H, m), 4.18 (2H, s), 7.00–7.06 (2H, m), 7.17–7.23 (4H, m), 7.58 (1H, s), 7.79–7.84 (2H, m), 7.89 (1H, d, J=1.8 Hz), 8.88 (1H, d, J=1.8 Hz), 12.07(1H, brs).

Compound I-234
  M.p.: 152–154° C. NMR (CDCl$_3$) δ: 3.36(3H, s), 3.54–3.60(2H, m), 3.62–3.70(2H, m), 4.19(2H, s), 6.38–6.44(1H, m), 6.98–7.06(2H, m), 7.16–7.24(4H, m), 7.80–7.90(3H, m), 8.74–8.80(2H, m).

Compound I-235
  M.p.: 172–173° C. Recrystallization solvent: isopropanol
  NMR (CDCl$_3$) δ: 4.19(2H, s), 4.66(2H, d, J=3.1 Hz), 6.28–6.36(1H, m), 6.98–7.06(2H, m), 7.14–7.23(4H, m), 7.30–7.38(4H, m), 7.80–7.86(2H, m), 8.78–8.82(2H, m).

Compound I-236
  M.p.: 95–98° C. Recrystallization solvent: isopropyl ether
  NMR (CDCl$_3$) δ: 4.16(2H, s), 6.94–7.04(2H, m), 7.12–7.24(5H, m), 7.34–7.44(2H, m), 7.60–7.72(2H, m), 7.80–792(2H, m), 8.04(1H, s), 8.22(1H, brs), 8.54–8.90(2H, m).

Compound I-237
  M.p.: 115–116° C. Recrystallization solvent: ethyl acetate-isopropyl ether
  NMR (d$_6$-DMSO) δ: 2.79 (3H, s), 3.06 (3H, s), 4.25 (2H, s), 7.14–7.20 (2H, m), 7.32–7.39 (4H, m), 7.46 (1H, s), 7.85–7.89 (2H, m), 8.01 (1H, d, J=2.1 Hz), 8.90 (1H, d, J=2.1 Hz), 10.84(1H, brs).
  Elemental analysis for C$_{26}$H$_{20}$F$_2$N$_2$O$_3$ Calcd. (%): C, 69.95; H, 4.52; F, 8.51; N, 6.27. Found. (%): C, 69.71; H, 4.65; F, 7.97; N, 5.99.

Compound I-238
  M.p.: 181–183° C. Recrystallization solvent: methanol
  NMR (d$_6$-DMSO) δ: 3.86 (3H, s), 4.28 (2H, s), 7.15–7.21 (2H, m), 7.31–7.40 (4H, m), 7.84–7.89 (2H, m), 8.30 (1H, s), 8.92 (1H, d, J=2.1 Hz), 9.23 (1H, d, J=2.1 Hz).

Compound I-239
  M.p.: 209–210° C. Recrystallization solvent: methanol-acetone
  NMR (d$_6$-DMSO) δ: 4.25 (2H, s), 7.13–7.19 (2H, m), 7.24 (1H, dd, J=4.0, 4.9 Hz), 7.33–7.38 (2H, m), 7.42 (1H, brs), 7.66 (1H, d, J=4.0 Hz), 7.84 (1H, s), 7.99 (1H, brs), 8.10 (1H, d, J=4.6 Hz), 8.86 (1H, d, J=1.5 Hz), 8.90 (1H, d, J=2.1 Hz).

Compound I-240
  M.p.: 200–201° C. Recrystallization solvent: methanol-acetone
  NMR (CDCl$_3$) δ: 3.06 (3H, d, J=4.9 Hz), 4.15 (2H, s), 6.37 (1H, brd, J=4.3 Hz), 6.97–7.03 (2H, m), 7.16–7.20 (3H, m), 7.71 (1H, dd, J=0.9, 3.6 Hz), 7.77 (1H, dd, J=0.9, 4.9 Hz), 7.99 (1H, s), 8.72–8.73 (2H, m).

Compound I-241
  M.p.: 174–175° C. Recrystallization solvent: methanol-isopropyl ether
  NMR (CDCl$_3$) δ: 1.28 (3H, t, J=7.3 Hz), 3.49–3.58 (2H, m), 4.17 (2H, s), 6.18 (1H, brt), 6.97–7.03 (2H, m), 7.17–7.21 (3H, m), 7.73 (1H, dd, J=1.1, 3.8 Hz), 7.77 (1H, dd, J=0.6, 4.9 Hz), 8.00 (1H, s), 8.72–8.75(2H, m).

Compound I-242
  M.p.: 202–204° C. Recrystallization solvent: methanol-acetone
  NMR (CDCl$_3$) δ: 4.17 (2H, s), 4.68 (2H, d, J=5.8 Hz), 6.45 (1H, brt), 6.98–7.04 (2H, m), 7.16–7.21 (2H, m), 7.31–7.37 (5H, m), 7.73 (1H, dd, J=0.9, 3.6 Hz), 7.77 (1H, dd, J=1.2, 4.9 Hz), 8.06 (1H, s), 8.76–8.77 (2H, m).

Compound I-243
  M.p.: 158–160° C. Recrystallization solvent: methanol-isopropyl ether
  NMR (CDCl$_3$) δ: 2.85 (3H, s), 3.18 (3H, s), 4.18 (2H, s), 6.99–7.05 (2H, m), 7.15–7.22 (3H, m), 7.75–7.79 (2H, m), 7.90 (1H, s), 7.94–7.95 (1H, m), 8.83 (1H, d, J=1.8 Hz).

Example 65

Compound I-244

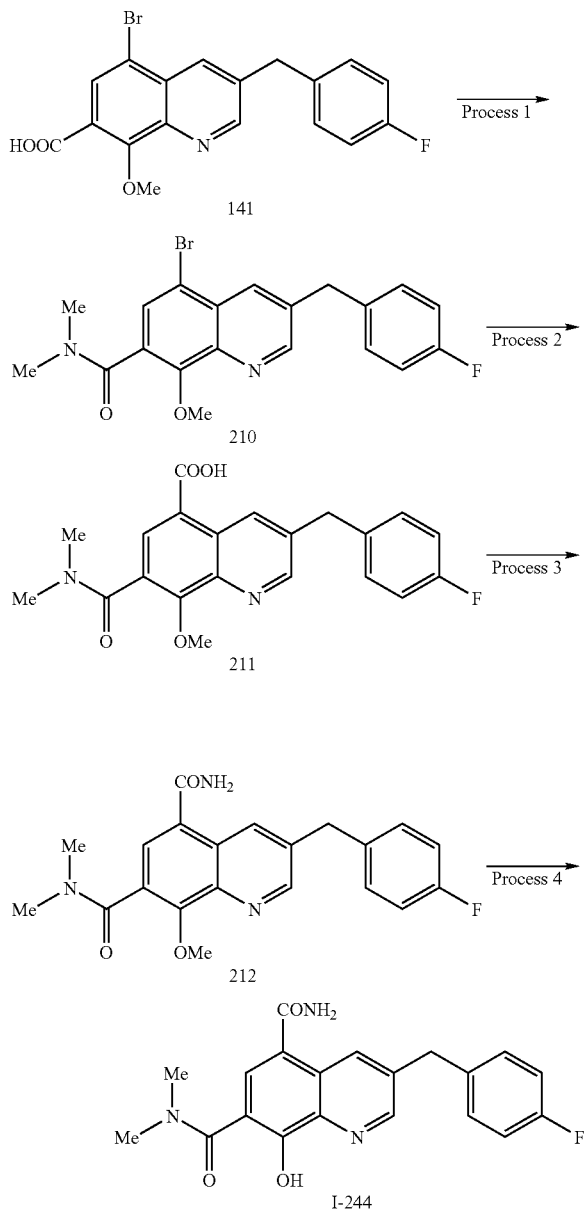

Process 1

To a suspension of compound 141 (1.52 g, 3.90 mmol) obtained by process 1 of Example 63 and 1-hydroxy benzotriazole (52.6 mg, 0.39 mmol) in DMF (15 ml) were added 2.0 M dimethylamine in THF (2.92 ml, 5.84 mmol), 1-ethyl-3-(3-dimethylaminopropyl)carbodiimide hydrochloride (896.0 mg, 3.90 mmol) at room temperature, and the mixture was stirred for 60 minutes. Water (20 ml) was added dropwise to the reaction mixture. The precipitated crystals were filtered, washed with water and dried to give compound 210 (1.47 g, 3.52 mmol, 90.3%) as colorless crystals.

Process 2

Compound 210 (1.47 g, 3.52 mmol) obtained by process 1 was reacted with a same manner similar to 7 of Example 62 to give quantitatively compound 211 (1.38 g) as colorless crystals.

Process 3

Compound 211 (191.0 mg, 0.5 mmol) obtained by process 2 was reacted a same manner similar to process 8 of Example 62 to give compound 212 (165.0 mg, 0.43 mmol, 86.0%).

Process 4

Compound 212 (165.0 mg, 0.43 mmol) obtained by process 3 was reacted a same manner similar to process 3 of Example 45 to give a title compound I-244 (82.5 mg, 0.25 mmol, 52.5%) as light green crystals.

M.p.: 177–178° C. Recrystallization solvent: ether

NMR (CDCl$_3$) δ: 3.11(6H, s), 4.17(2H, s), 5.72(1H, brs), 6.29(1H, brs), 6.95–7.05(2H, m), 7.14–7.24(2H, m), 7.86 (1H, s), 8.64–8.66(1H, m), 8.90–8.94(1H, m), 14.6(1H, brs).

Compound I-245 to I-248 were prepared in a same manner similar to Example 62 and Example 65.

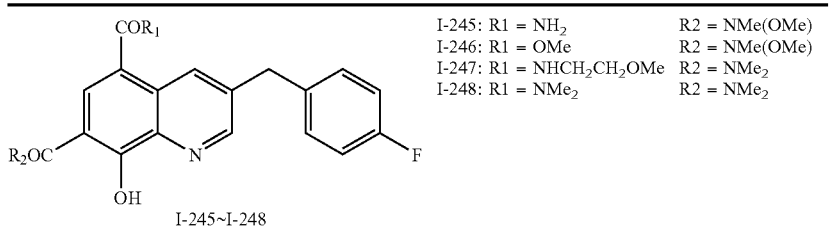

| | | |
|---|---|---|
| I-245: R1 = NH$_2$ | R2 = NMe(OMe) |
| I-246: R1 = OMe | R2 = NMe(OMe) |
| I-247: R1 = NHCH$_2$CH$_2$OMe | R2 = NMe$_2$ |
| I-248: R1 = NMe$_2$ | R2 = NMe$_2$ |

I-245~I-248

Compound I-245

M.p.: 199–202° C. Recrystallization solvent: ethyl acetate-isopropyl ether

NMR (CDCl₃) δ: 3.41(3H, s), 3.67(3H, s), 4.17(2H, s), 5.56–6.40(2H, m), 6.95–7.05(2H, m), 7.15–7.23(2H, m), 7.98(1H, s), 8.67–8.72(1H, m), 8.88–8.93(1H, m).

Compound I-246

M.p.: 99–102° C. Recrystallization solvent: isopropyl ether

NMR (CDCl₃) δ: 3.43(3H, s), 3.67(3H, s), 3.94(3H, s), 4.20(2H, s), 7.00–7.08(2H, m), 7.15–7.25(2H, m), 8.58(1H, s), 8.70–8.78(1H, m), 9.30–9.35(1H, m).

Compound I-247

M.p.: 90–91° C. Recrystallization solvent: methanol-isopropyl ether

NMR (CDCl₃) δ: 3.10(6H, s), 3.39(3H, s), 3.58(2H, t, J=4.8 Hz), 3.68(2H, q, J=5.4 Hz), 4.16(2H, s), 6.56(1H, brs), 7.00(2H, t-like, J=8.4 Hz), 7.18(2H, dd, J=8.4H&5.4 Hz), 7.77(1H, s), 8.64(1H, d, J=2.1 Hz), 8.83(1H, d, J=2.1 Hz).

Compound I-248

M.p.: 160–161° C. Recrystallization solvent: ether

NMR (CDCl₃) δ: 2.90(3H, s), 3.10(6H, s), 3.20(3H, s), 4.15(2H, s), 7.01(2H, t-like, J=8.7 Hz), 7.16(2H, dd, J=8.7&5.4 Hz), 7.49(1H, s), 8.03(1H, d, J=1.8 Hz), 8.67(1H, d, J=1.8 Hz).

Example 66

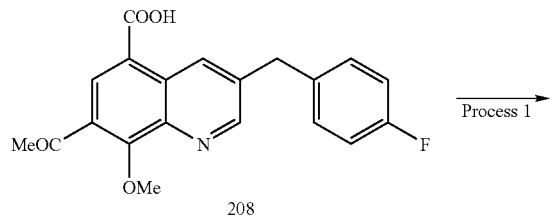

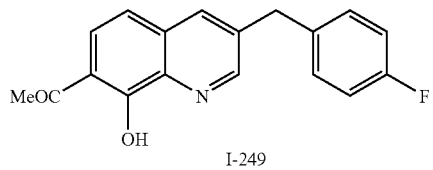

Process 1

Compound 208 (87.0 mg, 0.25 mmol) obtained by process 3 of Example 64 was reacted with a same manner similar to process 3 of Example 45 to give a title compound I-249 (43.2 mg, 0.15 mmol, 59.4%) as gray crystals.

M.p.: 134–136° C. Recrystallization solvent: ethanol-diethylether

NMR (DMSO) δ: 2.73 (3H, s), 4.20 (2H, s), 7.12–7.18 (2H, m), 7.35–7.39 (2H, m), 7.38 (1H, d, J=8.9 Hz), 7.87 (1H, d, J=8.9 Hz), 8.15 (1H, d, J=2.1 Hz), 8.87 (1H, d, J=1.8 Hz).

Example 67

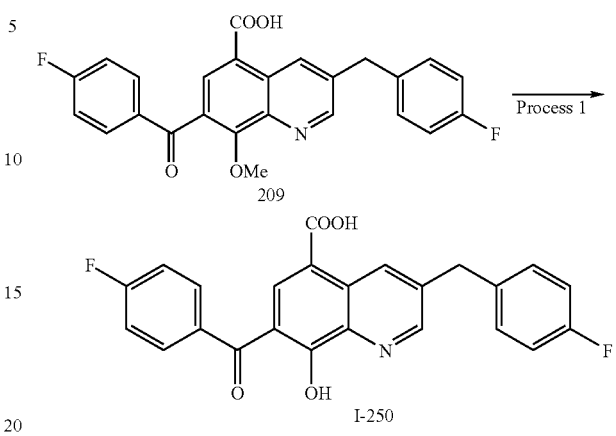

Process 1

Compound 209 (77.0 mg, 0.178 mmol) prepared in a same manner similar to process 1 to 3 of Example 64 was reacted with a same manner similar to process 6 of Example 18 to give a title compound I-250 (34.0 mg, 0.08 mmol, 46.0%) as yellow crystals.

M.p.: 255–256° C. Recrystallization solvent: ethyl acetate

NMR (d₆-DMSO) δ: 4.28 (2H, s), 7.14–7.20 (2H, m), 7.32–7.39 (4H, m), 7.85–7.89 (2H, m), 8.29 (1H, s), 8.90 (1H, d, J=2.1 Hz), 9.32 (1H, d, J=2.1 Hz).

Compound I-251 was prepared in a same manner similar to Example 67.

Compound I-251

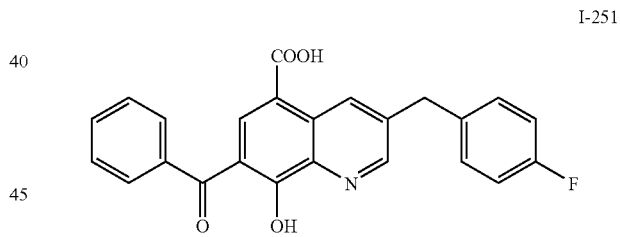

M.p.: 220–223° C. Recrystallization solvent: methanol-chloroform

NMR (DMSO-d₆) δ: 4.28 (2H, s), 7.17 (2H, m), 7.37 (2H, m), 7.53 (2H, m), 7.67 (1H, m), 7.79 (2H, m), 8.30 (1H, s), 8.92 (1H, m), 9.31 (1H, m).

Example 68

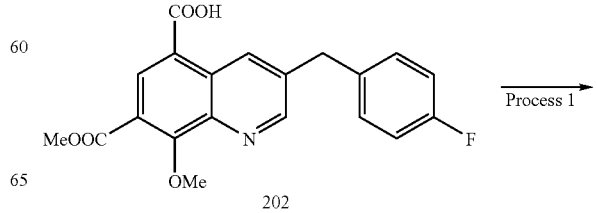

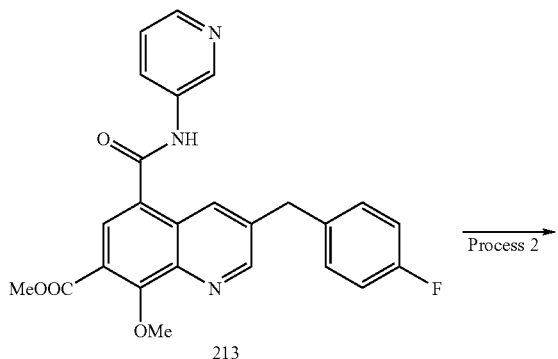

213

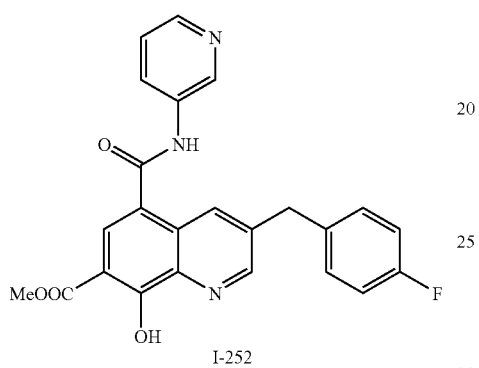

I-252

Process 1

To a solution of compound 202 (200 mg, 0.542 mmol) synthesized by process 7 of Example 62 in methylene chloride (2 ml) were added oxalyl chloride (0.9 ml, 1.1 mmol) and cat. DMF at room temperature, and the mixture was stirred at room temperature for 1 hour. The reaction mixture was concentrated under reduced pressure and dissolved in acetonitrile (2 ml). Subsequently, to a solution of 3-amino pyridine (46 mg, 0.49 mmol) in acetonitrile (1 ml) was added lithium bis(trimethylsilyl) acetamide (0.24 ml, 0.97 mmol) at room temperature, and the mixture was stirred at 40–45° C. for 20 minutes. The reaction mixture was cooled to room temperature, and a solution of the above acid chloride in acetonitrile was added to the reaction mixture, and the mixture was stirred for 30 minutes at room temperature. The reaction mixture was concentrated under reduced pressure, extracted with ethyl acetate, washed twice with saturated sodium hydrogen carbonate solution, brine and dried over sodium sulfate. A crude product obtained by evaporation under reduced pressure was crystallized with ether-ethyl acetate and washed to give compound 213 (60 mg, 0.13 mmol, 24.0%) as gray crystals.

Process 2

Compound 213 (60 mg, 0.13 mmol) obtained process 1 was reacted with a same manner similar to process 3 of Example 45 to give a title compound I-252 (40 mg, 0.093 mmol, 72.0%) as yellow crystals.

NMR (d$_6$-DMSO) δ: 3.92 (3H, s), 4.26 (2H, s), 7.13–7.21 (3H, m), 7.33–7.41 (3H, m), 8.63(1H, s), 8.88 (1H, d, J=1.8 Hz), 8.92 (1H, d, J=2.1 Hz), 9.26 (1H, brs), 9.74 (1H, brs), 12.82 (1H, brs).

Example 69

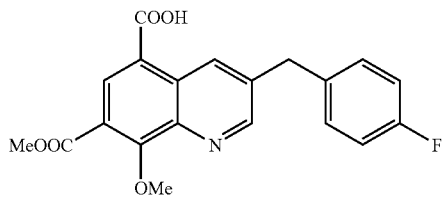

202

214

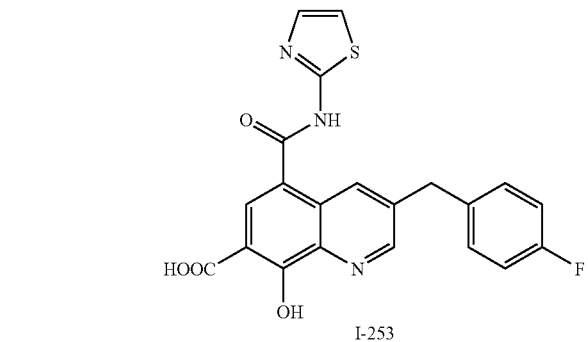

I-253

Process 1

Compound 202 (200 mg, 0.542 mmol, 86.7%) synthesized by process 7 of Example 62 was reacted with a same manner similar to process 8 of Example 62 to give compound 214 (212 mg, 0.470 mmol) as gray crystals.

Process 2

Compound 214 (10 mg, 0.022 mmol) obtained by process 1 was reacted with a same manner similar to process 2 of Example 68 to give a title compound I-253 (5 mg, 0.012 mmol, 55.0%) as yellow-green crystals.

NMR (d$_6$-DMSO) δ: 4.33 (2H, s), 7.13–7.19(2H, m), 7.27 (1H, d, J=3.3 Hz), 7.36–7.41 (2H, m), 7.56 (1H, d, J=3.3 Hz), 8.56(1H, s), 8.90 (1H, d, J=1.8 Hz), 9.30 (1H, d, J=1.8 Hz), 12.73 (1H, brs).

Example 70

Compound I-254 was prepared in a same manner similar to Example 62.

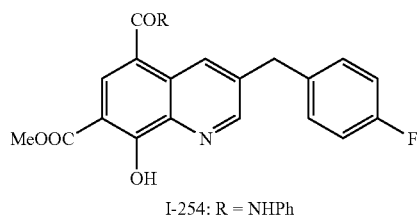

I-254: R = NHPh

M.p.: 212–213° C. Recrystallization solvent: acetone-acetonitrile

NMR (CDCl$_3$) δ: 4.01 (3H, s), 4.09 (2H, s), 6.96 (2H, t, J=8.4 Hz), 7.10–7.26 (3H, m), 7.42 (2H, d, J=7.8 Hz), 7.68 (2H, d, J=7.8 Hz), 8.06 (1H, br.s), 8.13 (1H, s), 8.64 (1H, br.s), 8.78 (1H, br.s), 11.89 (1H, br.s).

Example 71

Compound I-255 was prepared in a same manner similar to Example 62.

Compound I-255

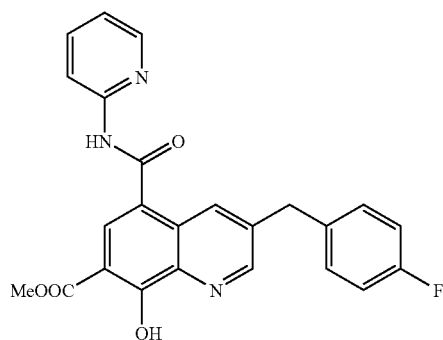

M.p.: 190–194° C. Recrystallization solvent: acetone-acetonitrile

NMR (CDCl$_3$) δ: 4.05 (3H, s), 4.18 (2H, s), 6.99 (2H, t, J=8.4 Hz), 7.11–7.20 (3H, m), 7.79–7.86 (1H, m), 8.30–8.33 (1H, m), 8.35 (1H, s), 8.41 (2H, d, J=8.1 Hz), 8.74 (1H, br.s), 8.79 (1H, d, J=2.1 Hz), 8.87 (1H, d, J=2.1 Hz), 12.13 (1H, br.s).

The compounds of the present invention include the following compounds. The following compounds are synthesized with a same manner similar to the above examples.

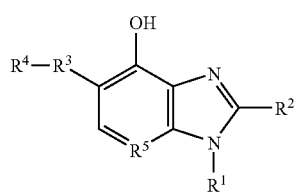

I

The substituents of R$^1$, R$^2$, R$^3$, R$^4$ and R$^5$ of above compound I include the following substitution group.

R$^1$=H (1A), Me (1B), Et (1C), i-Pr (1D), i-Bu (1E)

R$^2$=H (2A), Me (2B), Et (2C), n-Pr (2D), OMe (2E)

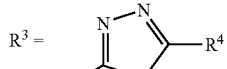  (3A)

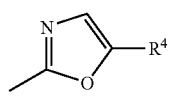  (3B)

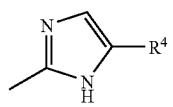  (3C)

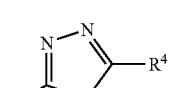  (3D)

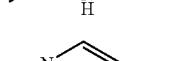  (3E)

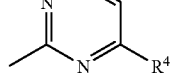  (3F)

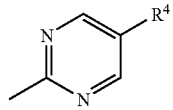  (4A)

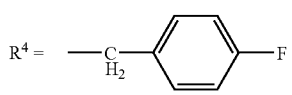  (4B)

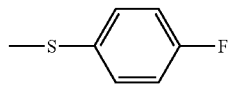  (4C)

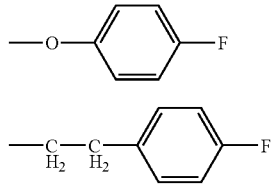  (4D)

R$^5$=N (5A), CH (5B), CMe (5C), CF (5D)

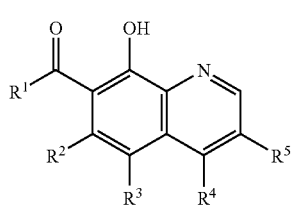

II

The substituents of R$^1$, R$^2$, R$^3$, R$^4$ and R$^5$ of above compound II include the following substitution group.

R$^1$=OH (1A), OMe (1B), OEt (1C), Oi-Pr (1D), Et(1E)

R²=—CONH₂ (2A), —CH₂—CONH₂(2B), —CH₂—CH₂—CONH₂(2C), —CONHMe(2D), —CH₂CH₂OMe (2E)

R³=—CONH₂ (3A), —CH₂—CONH₂(3B), —CH₂—CH₂—CONH₂(3C), —CONHMe(3D), —CH₂CH₂OMe (3E), —CH₂CH₂OH(3F)

R⁴=—CONH₂ (4A), —CH₂—CONH₂(4B), —CH₂—CH₂—CONH₂(4C), —CONHMe(4D)

R⁵ =

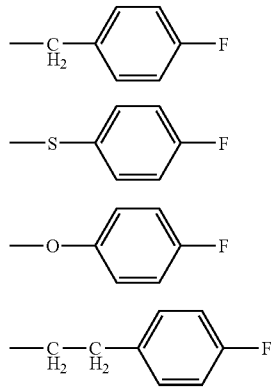

The preferable combinations (R¹,R²,R³,R⁴,R⁵) of the substituents of above compound I and II include the followings.

(1A,2A,3A,4A,5A),(1A,2A,3A,4A,5B),(1A,2A,3A,4A,5C),(1A,2A,3A,4A,5D),(1A,2A,3A,4B, 5A), (1A,2A,3A,4B,5B), (1A,2A,3A,4B,5C), (1A,2A,3A,4B,5D),(1A,2A,3A,4C,5A),(1A,2A,3A, 4C,5B),(1A,2A,3A,4C,5C),(1A,2A,3A, 4C,5D),(1A,2A,3A,4D,5A),(1A,2A,3A,4D,5B),(1A,2A,3A,4D,5C),(1A,2A,3A,4D,5D),(1A,2A,3B,4A,5A),(1A,2A,3B,4A,5B),(1A,2A,3B,4A,5C),(1A, 2A,3B,4A,5D),(1A,2A,3B,4B,5A),(1A,2A,3B,4B,5B),(1A,2A,3B,4B,5C),(1A,2A,3B,4B, 5D),(1A,2A,3B,4C,5A),(1A,2A,3B,4C,5B),(1A,2A,3B,4C,5C),(1A,2A,3B,4C,5D),(1A,2A,3B, 4D,5A),(1A,2A,3B,4D,5B),(1A,2A,3B,4D,5C),(1A,2A,3B,4D,5D),(1A,2A,3C,4A,5A),(1A, 2A,3C,4A,5B),(1A,2A,3C,4A,5C),(1A,2A,3C,4A,5D),(1A,2A,3C,4B,5A),(1A,2A,3C,4B,5B), (1A,2A,3C,4B,5C),(1A,2A,3C,4B,5D),(1A,2A,3C,4C,5A),(1A,2A,3C,4C,5B),(1A,2A,3C,4C, 5C),(1A,2A,3C,4C,5D),(1A,2A,3C,4D,5A),(1A,2A,3C,4D,5B),(1A,2A,3C,4D,5C),(1A,2A,3C, 4D,5D),(1A,2A,3D,4A,5A),(1A,2A,3D,4A,5B),(1A, 2A,3D,4A,5C),(1A,2A,3D,4A,5D),(1A, 2A,3D,4B,5A), (1A,2A,3D,4B,5B),(1A,2A,3D,4B,5C),(1A,2A,3D,4B,5D), (1A,2A,3D,4C,5A), (1A,2A,3D,4C,5B),(1A,2A,3D,4C,5C),(1A,2A,3D,4C,5D),(1A,2A,3D,4D,5A),(1A,2A,3D,4D, 5B),(1A,2A,3D,4D,5C),(1A,2A,3D,4D,5D),(1A,2A,3E,4A, 5A),(1A,2A,3E,4A,5B),(1A,2A, 3E,4A,5C),(1A,2A,3E,4A, 5D),(1A,2A,3E,4B,5A),(1A,2A,3E,4B,5B),(1A,2A,3E,4B, 5C),(1A, 2A,3E,4B,5D),(1A,2A,3E,4C,5A),(1A,2A,3E,4C, 5B),(1A,2A,3E,4C,5C),(1A,2A,3E,4C,5D), (1A,2A,3E,4D, 5A),(1A,2A,3E,4D,5B),(1A,2A,3E,4D,5C),(1A,2A,3E,4D, 5D),(1A,2A,3F,4A, 5A),(1A,2A,3F,4A,5B),(1A,2A,3F,4A, 5C),(1A,2A,3F,4A,5D),(1A,2A,3F,4B,5A),(1A,2A,3F,4B, 5B),(1A,2A,3F,4B,5C),(1A,2A,3F,4B,5D),(1A,2A,3F,4C, 5A),(1A,2A,3F,4C,5B),(1A,2A,3F, 4C,5C),(1A,2A,3F,4C, 5D),(1A,2A,3F,4D,5A),(1A,2A,3F,4D,5B),(1A,2A,3F,4D, 5C),(1A,2A, 3F,4D,5D),(1A,2B,3A,4A,5A),(1A,2B,3A,4A, 5C),(1A,2B,3A,4A,5D),(1A,2B,3A,4B,5A),(1A, 2B,3A,4B, 5B),(1A,2B,3A,4B,5C),(1A,2B,3A,4B,5D),(1A,2B,3A,4C, 5A),(1A,2B,3A,4C, 5B),(1A,2B,3A,4C,5C),(1A,2B,3A,4C, 5D),(1A,2B,3A,4D,5A),(1A,2B,3A,4D,5B),(1A,2B,3A, 4D,5C),(1A,2B,3A,4D,5D),(1A,2B,3B,4A,5A),(1A,2B,3B, 4A,5C),(1A,2B,3B,4A,5D),(1A, 2B,3B,4B,5A),(1A,2B,3B, 4B,5B),(1A,2B,3B,4B,5C),(1A,2B,3B,4B,5D),(1A,2B,3B, 4C,5A), (1A,2B,3B,4C,5B),(1A,2B,3B,4C,5C),(1A,2B,3B, 4C,5D),(1A,2B,3B,4D,5A),(1A,2B,3B,4D, 5B),(1A,2B,3B, 4D,5C),(1A,2B,3B,4D,5D),(1A,2B,3C,4A,5A),(1A,2B,3C, 4A,5B),(1A,2B,3C, 4A,5C),(1A,2B,3C,4A,5D),(1A,2B,3C, 4B,5A),(1A,2B,3C,4B,5B),(1A,2B,3C,4B,5C),(1A, 2B,3C, 4B,5D),(1A,2B,3C,4C,5A),(1A,2B,3C,4C,5B),(1A,2B,3C, 4C,5C),(1A,2B,3C,4C,5D), (1A,2B,3C,4D,5A),(1A,2B,3C, 4D,5B),(1A,2B,3C,4D,5C),(1A,2B,3C,4D,5D),(1A,2B,3D, 4A, 5A),(1A,2B,3D,4A,5B),(1A,2B,3D,4A,5C),(1A,2B,3D, 4A,5D),(1A,2B,3D,4B,5A),(1A,2B,3D, 4B,5B),(1A,2B,3D, 4B,5C),(1A,2B,3D,4B,5D),(1A,2B,3D,4C,5A),(1A,2B,3D, 4C,5B),(1A, 2B,3D,4C,5C),(1A,2B,3D,4C,5D),(1A,2B,3D, 4D,5A),(1A,2B,3D,4D,5B),(1A,2B,3D,4D,5C), (1A,2B,3D, 4D,5D),(1A,2B,3E,4A,5A),(1A,2B,3E,4A,5B),(1A,2B,3E, 4A,5C),(1A,2B,3E,4A, 5D),(1A,2B,3E,4B,5A),(1A,2B,3E, 4B,5B),(1A,2B,3E,4B,5C),(1A,2B,3E,4B,5D),(1A,2B, 3E,4C,5A),(1A,2B,3E,4C,5B),(1A,2B,3E,4C,5C),(1A,2B, 3E,4C,5D),(1A,2B,3E,4D,5A),(1A, 2B,3E,4D,5B),(1A,2B, 3E,4D,5C),(1A,2B,3E,4D,5D),(1A,2B,3F,4A,5A),(1A,2B, 3F,4A,5B), (1A,2B,3F,4A,5C),(1A,2B,3F,4A,5D),(1A,2B, 3F,4B,5A),(1A,2B,3F,4B,5B),(1A,2B,3F,4B, 5C),(1A,2B, 3F,4B,5D),(1A,2B,3F,4C,5A),(1A,2B,3F,4C,5B),(1A,2B, 3F,4C,5C),(1A,2B,3F, 4C,5D),(1A,2B,3F,4D,5A),(1A,2B, 3F,4D,5B),(1A,2B,3F,4D,5C),(1A,2B,3F,4D,5D),(1A,2C, 3A,4A,5A),(1A,2C,3A,4A,5B),(1A,2C,3A,4A,5C),(1A,2C, 3A,4A,5D),(1A,2C,3A,4B,5A),(1A, 2C,3A,4B,5B),(1A,2C, 3A,4B,5C),(1A,2C,3A,4B,5D),(1A,2C,3A,4C,5A),(1A,2C, 3A,4C, 5B),(1A,2C,3A,4C,5C),(1A,2C,3A,4C,5D),(1A,2C, 3A,4D,5A),(1A,2C,3A,4D,5B),(1A,2C,3A, 4D,5C),(1A,2C, 3A,4D,5D),(1A,2C,3B,4A,5A),(1A,2C,3B,4A,5B),(1A,2C, 3B,4A,5C),(1A, 2C,3B,4A,5D),(1A,2C,3B,4B,5A),(1A,2C, 3B,4B,5B),(1A,2C,3B,4B,5C),(1A,2C,3B,4B,5D), (1A,2C, 3B,4C,5A),(1A,2C,3B,4C,5B),(1A,2C,3B,4C,5C),(1A,2C, 3B,4C,5D),(1A,2C,3B,4D, 5A),(1A,2C,3B,4D,5B),(1A,2C, 3B,4D,5C),(1A,2C,3B,4D,5D),(1A,2C,3C,4A,5A),(1A,2C, 3C, 4A,5B),(1A,2C,3C,4A,5C),(1A,2C,3C,4A,5D),(1A,2C, 3C,4B,5A),(1A,2C,3C,4B,5B),(1A, 2C,3C,4B,5C),(1A,2C, 3C,4B,5D),(1A,2C,3C,4C,5A),(1A,2C,3C,4C,5B),(1A,2C, 3C,4C,5C), (1A,2C,3C,4C,5D),(1A,2C,3C,4D,5A),(1A,2C, 3C,4D,5B),(1A,2C,3C,4D,5C),(1A,2C,3C,4D, 5D),(1A,2C, 3D,4A,5A),(1A,2C,3D,4A,5B),(1A,2C,3D,4A,5C),(1A,2C, 3D,4A,5D),(1A,2C, 3D, 4B,5A),(1A,2C,3D,4B,5B),(1A,2C, 3D,4B,5C),(1A,2C,3D,4B,5D),(1A,2C,3D,4C,5A),(1A, 2C,3D,4C,5B),(1A,2C,3D,4C,5C),(1A,2C,3D,4C,5D),(1A, 2C,3D,4D,5A),(1A,2C,3D,4D,5B), (1A,2C,3D,4D,5C),(1A, 2C,3D,4D,5D),(1A,2C,3E,4A,5A),(1A,2C,3E,4A,5B),(1A, 2C,3E,4A, 5C),(1A,2C,3E,4A,5D),(1A,2C,3E,4B,5A),(1A, 2C,3E,4B,5B),(1A,2C,3E,4B,5C),(1A,2C, 3E,4B,5D),(1A, 2C,3E,4C,5A),(1A,2C,3E,4C,5B),(1A,2C,3E,4C,5C),(1A, 2C,3E,4C,5D),(1A, 2C,3E,4D,5A),(1A,2C,3E,4D,5B),(1A, 2C,3E,4D,5C),(1A,2C,3E,4D,5D),(1A,2C,3F,4A,5A), (1A, 2C,3F,4A,5B),(1A,2C,3F,4A,5C),(1A,2C,3F,4A,5D),(1A, 2C,3F,4B,5A),(1A,2C,3F,4B, 5B),(1A,2C,3F,4B,5C),(1A, 2C,3F,4B,5D),(1A,2C,3F,4C,5A),(1A,2C,3F,4C,5B),(1A, 2C,3F, 4C,5C),(1A,2C,3F,4C,5D),(1A,2C,3F,4D,5A),(1A, 2C,3F,4D,5B),(1A,2C,3F,4D,5D),(1A,2C, 3F,4D,5D),(1A, 2D,3A,4A,5A),(1A,2D,3A,4A,5B),(1A,2D,3A,4A,5C),(1A, 2D,3A,4A,5D),(1A, 2D,3A,4B,5A),(1A,2D,3A,4B,5B), (1A,2D,3A,4B,5C),(1A,2D,3A,4B,5D),(1A,2D,3A,4C, 5A),(1A,2D,3A,4C,5B),(1A,2D,3A,4C,5C),(1A,2D,3A,4C, 5D),(1A,2D,3A,4D,5A),(1A,2D,3A, 4D,5B),(1A,2D,3A, 4D,5C),(1A,2D,3A,4D,5D),(1A,2D,3B,4A,5A),(1A,2D,3B, 4A,5B),(1A, 2D,3B,4A,5C),(1A,2D,3B,4A,5D),(1A,2D,3B, 4B,5A),(1A,2D,3B,4B,5B),(1A,2D,3B,4B,5C), (1A,2D,3B, 4B,5D),(1A,2D,3B,4C,5A),(1A,2D,3B,4C,5B),(1A,2D,3B, 4C,5C),(1A,2D,3B,4C, 5D),(1A,2D,3B,4D,5A),(1A,2D,3B, 4D,5B),(1A,2D,3B,4D,5C),(1A,2D,3B,4D,5D),(1A,2D,3C, 4A,5A),(1A,2D,3C,4A,5B),(1A,2D,3C,4A,5C),(1A,2D,3C, 4A,5D),(1A,2D,3C,4B,5A),(1A, 2D,3C,4B,5B),(1A,2D,3C, 4B,5C),(1A,2D,3C,4B,5D),(1A,2D,3C,4C,5A),(1A,2D,3C, 4C,5B), (1A,2D,3C,4C,5C),(1A,2D,3C,4C,5D),(1A,2D,3C, 4D,5A),(1A,2D,3C,4D,5B),(1A,2D,3C,4D, 5C),(1A,2D,3C, 4D,5D),(1A,2D,3D,4A,5A),(1A,2D,3D,4A,5B),(1A,2D, 3D,4A,5C),(1A,2D, 3D,4A,5D),(1A,2D,3D,4B,5A),(1A, 2D,3D,4B,5B),(1A,2D,3D,4B,5C),(1A,2D,3D,4B,5D),(1A, 2D,3D,4C,5A),(1A,2D,3D,4C,5B),(1A,2D,3D,4C,5C),(1A, 2D,3D,4C,5D),(1A,2D,3D,4D, 5A),(1A,2D,3D,4D,5B), (1A,2D,3D,4D,5C),(1A,2D,3D,4D,5D),(1A,2D,3E,4A,5A), (1A,2D,3E, 4A,5B),(1A,2D,3E,4A,5C),(1A,2D,3E,4A,5D), (1A,2D,3E,4B,5A),(1A,2D,3E,4B,5B),(1A, 2D,3E,4B,5C), (1A,2D,3E,4B,5D),(1A,2D,3E,4C,5A),(1A,2D,3E,4C,5B), (1A,2D,3E,4C,5C), (1A,2D,3E,4C,5D),(1A,2D,3E,4D,5A), (1A,2D,3E,4D,5B),(1A,2D,3E,4D,5C),(1A,2D,3E,4D, 5D), (1A,2D,3F,4A,5A),(1A,2D,3F,4A,5B),(1A,2D,3F,4A,5C), (1A,2D,3F,4A,5D),(1A,2D,3F, 4B,5A),(1A,2D,3F,4B,5B), (1A,2D,3F,4B,5C),(1A,2D,3F,4B,5D),(1A,2D,3F,4C,5A), (1A,2D, 3F,4C,5B),(1A,2D,3F,4C,5C),(1A,2D,3F,4C,5D), (1A,2D,3F,4D,5A),(1A,2D,3F,4D,5B),(1A, 2D,3F,4D,5C), (1A,2D,3F,4D,5D),(1A,2E,3A,4A,5A),(1A,2E,3A,4A,5B), (1A,2E,3A,4A,5C), (1A,2E,3A,4A,5D),(1A,2E,3A,4B,5A), (1A,2E,3A,4B,5B),(1A,2E,3A,4B,5C),(1A,2E,3A, 4B,5D), (1A,2E,3A,4C,5A),(1A,2E,3A,4C,5B),(1A,2E,3A,4C,5C), (1A,2E,3A,4C,5D),(1A,2E, 3A,4D,5A),(1A,2E,3A,4D,5B), (1A,2E,3A,4D,5C),(1A,2E,3A,4D,5D),(1A,2E,3B,4A,5A), (1A, 2E,3B,4A,5B),(1A,2E,3B,4A,5C),(1A,2E,3B,4A,5D), (1A,2E,3B,4B,5A),(1A,2E,3B,4B, 5B),(1A,2E,3B,4B,5C), (1A,2E,3B,4B,5D),(1A,2E,3B,4C,5A),(1A,2E,3B,4C,5B), (1A,2E,3B, 4C,5C),(1A,2E,3B,4C,5D),(1A,2E,3B,4D,5A), (1A,2E,3B,4D,5B),(1A,2E,3B,4D,5C),(1A,2E, 3B,4D,5D), (1A,2E,3C,4A,5A),(1A,2E,3C,4A,5B),(1A,2E,3C,4A, 5C), (1A,2E,3C,4A,5D),(1A, 2E,3C,4B,5A),(1A,2E,3C,4B,5B), (1A,2E,3C,4B,5C),(1A,2E,3C,4B,5D),(1A,2E,3C,4C, 5A), (1A,2E,3C,4C,5B),(1A,2E,3C,4C,5C),(1A,2E,3C,4C,5D), (1A,2E,3C,4D,5A),(1A,2E,3C, 4D,5B),(1A,2E,3C,4D,5C), (1A,2E,3C,4D,5D),(1A,2E,3D,4A,5A),(1A,2E,3D,4A,5B), (1A, 2E,3D,4A,5C),(1A,2E,3D,4A,5D),(1A,2E,3D,4B,5A), (1A,2E,3D,4B,5B),(1A,2E,3D,4B,5C), (1A,2E,3D,4B,5D), (1A,2E,3D,4C,5A),(1A,2E,3D,4C,5B),(1A,2E,3D,4C,5C), (1A,2E,3D,4C, 5D),(1A,2E,3D,4D,5A),(1A,2E,3D,4D,5B), (1A,2E,3D,4D,5C),(1A,2E,3D,4D,5D),(1A,2E,3E, 4A,5A), (1A,2E,3E,4A,5B),(1A,2E,3E,4A,5C),(1A,2E,3E,4A,5D), (1A,2E,3E,4B,5A),(1A, 2E,3E,4B,5B),(1A,2E,3E,4B,5C), (1A,2E,3E,4B,5D),(1A,2E,3E,4C,5A),(1A,2E,3E,4C,5B), (1A,2E,3E,4C,5C),(1A,2E,3E,4C,5D),(1A,2E,3E,4D,5A), (1A,2E,3E,4D,5B),(1A,2E,3E,4D, 5C),(1A,2E,3E,4D,5D), (1A,2E,3F,4A,5A),(1A,2E,3F,4A,5B),(1A,2E,3F,4A,5C), (1A,2E,3F, 4A,5D),(1A,2E,3F,4B,5A),(1A,2E,3F,4B,5B), (1A,2E,3F,4B,5C),(1A,2E,3F,4B,5D),(1A,2E, 3F,4C,5A), (1A,2E,3F,4C,5B),(1A,2E,3F,4C,5C),(1A,2E,3F,4C,5D), (1A,2E,3F,4D,5A),(1A, 2E,3F,4D,5B),(1A,2E,3F,4D,5C), (1A,2E,3F,4D,5D),(1B,2A,3A,4A,5A),(1B,2A,3A,4A,5B), (1B, 2A,3A,4A,5C),(1B,2A,3A,4A,5D),(1B,2A,3A,4B,5A), (1B,2A,3A,4B,5B),(1B,2A,3A,4B, 5C),(1B,2A,3A,4B,5D), (1B,2A,3A,4C,5A),(1B,2A,3A,4C,5B),(1B,2A,3A,4C,5C), (1B,2A,3A, 4C,5D),(1B,2A,3A,4D,5A),(1B,2A,3A,4D,5B), (1B,2A,3A,4D,5C),(1B,2A,3A,4D,5D),(1B,2A, 3B,4A,5A), (1B,2A,3B,4A,5B),(1B,2A,3B,4A,5C),(1B,2A,3B,4A,5D), (1B,2A,3B,4B,5A),(1B, 1B,2A,3B,4B,5B),(1B,2A,3B,4B, 5C),(1B,2A,3B,4B,5D),(1B,2A,3B,4C,5A),(1B,2A,3B,4C, 5B),(1B,2A,3B,4C,5C),(1B,2A,3B,4C,5D),(1B,2A,3B,4D, 5A),(1B,2A,3B,4D,5B),(1B,2A,3B, 4D,5C),(1B,2A,3B, 4D,5D),(1B,2A,3C,4A,5A),(1B,2A,3C,4A,5B),(1B,2A,3C,4A, 5C),(1B, 2A,3C,4A,5D),(1B,2A,3C,4B,5A),(1B,2A,3C,4B, 5B),(1B,2A,3C,4B,5C),(1B,2A,3C,4B,5D), (1B,2A,3C,4C, 5A),(1B,2A,3C,4C,5B),(1B,2A,3C,4C,5C),(1B,2A,3C,4C, 5D),(1B,2A,3C,4D, 5A),(1B,2A,3C,4D,5B),(1B,2A,3C,4D, 5C),(1B,2A,3C,4D,5D),(1B,2A,3D,4A,5A),(1B,2A,3D, 4A,5B),(1B,2A,3D,4A,5C),(1B,2A,3D,4A,5D),(1B,2A,3D, 4B,5A),(1B,2A,3D,4B,5B),(1B, 2A,3D,4B,5C),(1B,2A,3D, 4B,5D),(1B,2A,3D,4C,5A),(1B,2A,3D,4C,5B),(1B,2A,3D, 4C,5C), (1B,2A,3D,4C,5D),(1B,2A,3D,4D,5A),(1B,2A,3D, 4D,5B),(1B,2A,3D,4D,5C),(1B,2A,3D,4D, 5D),(1B,2A,3E, 4A,5A),(1B,2A,3E,4A,5B),(1B,2A,3E,4A,5C),(1B,2A,3E, 4A,5D),(1B,2A, 3E,4B,5A),(1B,2A,3E,4B,5B),(1B,2A,3E, 4B,5C),(1B,2A,3E,4B,5D),(1B,2A,3E,4C,5A),(1B, 2A,3E, 4C,5B),(1B,2A,3E,4C,5C),(1B,2A,3E,4C,5D),(1B,2A,3E, 4D,5A),(1B,2A,3E,4D,5B), (1B,2A,3E,4D,5C),(1B,2A,3E, 4D,5D),(1B,2A,3F,4A,5A),(1B,2A,3F,4A,5B),(1B,2A,3F, 4A, 5C),(1B,2A,3F,4A,5D),(1B,2A,3F,4B,5A),(1B,2A,3F, 4B,5B),(1B,2A,3F,4B,5C),(1B,2A,3F,4B, 5D),(1B,2A,3F, 4C,5A),(1B,2A,3F,4C,5B),(1B,2A,3F,4C,5C),(1B,2A,3F, 4C,5D),(1B,2A,3F, 4D,5A),(1B,2A,3F,4D,5B),(1B,2A,3F, 4D,5C),(1B,2A,3F,4D,5D),(1B,2B,3A,4A,5B),(1B,2B, 3A,4A,5C),(1B,2B,3A,4A,5D),(1B,2B,3A,4B,5A),(1B,2B, 3A,4B,5B),(1B,2B,3A,4B,5C),(1B, 2B,3A,4B,5D),(1B,2B, 3A,4C,5A),(1B,2B,3A,4C,5B),(1B,2B,3A,4C,5C),(1B,2B, 3A,4C, 5D),(1B,2B,3A,4D,5A),(1B,2B,3A,4D,5B),(1B,2B, 3A,4D,5C),(1B,2B,3A,4D,5D),(1B,2B,3B, 4A,5A),(1B,2B, 3B,4A,5B),(1B,2B,3B,4A,5C),(1B,2B,3B,4A,5D),(1B,2B, 3B,4B,5A),(1B, 2B,3B,4B,5B),(1B,2B,3B,4B,5C),(1B,2B, 3B,4B,5D),(1B,2B,3B,4C,5A),(1B,2B,3B,4C,5B), (1B,2B, 3B,4C,5C),(1B,2B,3B,4C,5D),(1B,2B,3B,4D,5A),(1B,2B, 3B,4D,5B),(1B,2B,3B,4D, 5C),(1B,2B,3B,4D,5D),(1B,2B, 3C,4A,5A),(1B,2B,3C,4A,5B),(1B,2B,3C,4A,5C),(1B,2B, 3C, 4A,5D),(1B,2B,3C,4B,5A),(1B,2B,3C,4B,5B),(1B,2B, 3C,4B,5C),(1B,2B,3C,4B,5D),(1B, 2B,3C,4C,5A),(1B,2B, 3C,4C,5B),(1B,2B,3C,4C,5C),(1B,2B,3C,4C,5D),(1B,2B, 3C,4D,5A), (1B,2B,3C,4D,5B),(1B,2B,3C,4D,5C),(1B,2B, 3C,4D,5D),(1B,2B,3D,4A,5A),(1B,2B,3D,4A, 5B),(1B,2B, 3D,4A,5C),(1B,2B,3D,4A,5D),(1B,2B,3D,4B,5A),(1B,2B, 3D,4B,5B),(1B,2B,3D, 4B,5C),(1B,2B,3D,4B,5D),(1B,2B, 3D,4C,5A),(1B,2B,3D,4C,5B),(1B,2B,3D,4C,5C),(1B, 2B,3D,4C,5D),(1B,2B,3D,4D,5A),(1B,2B,3D,4D,5B),(1B, 2B,3D,4D,5C),(1B,2B,3D,4D, 5D), (1B,2B,3E,4A,5A),(1B, 2B,3E,4A,5B),(1B,2B,3E,4A,5C),(1B,2B,3E,4A,5D),(1B, 2B,3E,4B, 5A),(1B,2B,3E,4B,5B),(1B,2B,3E,4B,5C),(1B, 2B,3E,4B,5D),(1B,2B,3E,4C,5A),(1B,2B, 3E,4C,5B),(1B, 2B,3E,4C,5C),(1B,2B,3E,4C,5D),(1B,2B,3E,4D,5A),(1B, 2B,3E,4D,5B),(1B, 2B,3E,4D,5C),(1B,2B,3E,4D,5D),(1B, 2B,3F,4A,5A),(1B,2B,3F,4A,5B),(1B,2B,3F,4A,5C), (1B, 2B,3F,4A,5D),(1B,2B,3F,4B,5A),(1B,2B,3F,4B,5B),(1B, 2B,3F,4B,5C),(1B,2B,3F,4B, 5D),(1B,2B,3F,4C,5A),(1B, 2B,3F,4C,5B),(1B,2B,3F,4C,5C),(1B,2B,3F,4C,5D),(1B, 2B,3F, 4D,5A),(1B,2B,3F,4D,5B),(1B,2B,3F,4D,5C),(1B, 2B,3F,4D,5D),(1B,2C,3A,4A,5A),(1B,2C, 3A,4A,5B),(1B, 2C,3A,4A,5C),(1B,2C,3A,4A,5D),(1B,2C,3A,4B,5A),(1B, 2C,3A,4B,5B),(1B, 2C,3A,4B,5C),(1B,2C,3A,4B,5D),(1B, 2C,3A,4C,5A),(1B,2C,3A,4C,5B),(1B,2C,3A,4C,5C), (1B, 2C,3A,4C,5D),(1B,2C,3A,4D,5A),(1B,2C,3A,4D,5B),(1B, 2C,3A,4D,5C),(1B,2C,3A,4D, 5D),(1B,2C,3B,4A,5A),(1B, 2C,3B,4A,5B),(1B,2C,3B,4A,5C),(1B,2C,3B,4A,5D),(1B, 2C,3B, 4B,5A),(1B,2C,3B,4B,5B),(1B,2C,3B,4B,5C),(1B, 2C,3B,4B,5D),(1B,2C,3B,4C,5A),(1B, 2C,3B,4C,5B),(1B, 2C,3B,4C,5C),(1B,2C,3B,4C,5D),(1B,2C,3B,4D,5A),(1B, 2C,3B,4D,5B), (1B,2C,3B,4D,5C),(1B,2C,3B,4D,5D),(1B, 2C,3C,4A,5A),(1B,2C,3C,4A,5B),(1B,2C,3C,4A, 5C),(1B, 2C,3C,4A,5D),(1B,2C,3C,4B,5A),(1B,2C,3C,4B,5B),(1B, 2C,3C,4B,5C),(1B,2C,3C, 4B,5D),(1B,2C,3C,4C,5A),(1B,
2C,3C,4C,5B),(1B,2C,3C,4C,5C),(1B,2C,3C,4C,5D),(1B,
2C, 3C,4D,5A),(1B,2C,3C,4D,5B),(1B,2C,3C,4D,5C),(1B,
2C,3C,4D,5D),(1B,2C,3D,4A,5A),(1B, 1B,2C,3D,4A,5B),
(1B,2C,3D,4A,5C),(1B,2C,3D,4A,5D),(1B,2C,3D,4B,5A),
(1B,2C,3D,4B, 5B),(1B,2C,3D,4B,5C),(1B,2C,3D,4B,5D),
(1B,2C,3D,4C,5A),(1B,2C,3D,4C,5B),(1B,2C,3D, 4C,5C),
(1B,2C,3D,4C,5D),(1B,2C,3D,4D,5A),(1B,2C,3D,4D,5B),
(1B,2C,3D,4D,5C),(1B, 2C,3D,4D,5D),(1B,2C,3E,4A,5A),
(1B,2C,3E,4A,5B),(1B,2C,3E,4A,5C),(1B,2C,3E,4A,5D),
(1B,2C,3E,4B,5A),(1B,2C,3E,4B,5B),(1B,2C,3E,4B,5C),
(1B,2C,3E,4B,5D),(1B,2C,3E,4C, 5A),(1B,2C,3E,4C,5B),
(1B,2C,3E,4C,5C),(1B,2C,3E,4C,5D),(1B,2C,3E,4D,5A),
(1B,2C,3E, 4D,5B),(1B,2C,3E,4D,5C),(1B,2C,3E,4D,5D),
(1B,2C,3F,4A,5A),(1B,2C,3F,4A,5B),(1B, 2C,3F,4A,5C),
(1B,2C,3F,4A,5D),(1B,2C,3F,4B,5A),(1B,2C,3F,4B,5B),
(1B,2C,3F,4B,5C),(1B, 2C,3F,4B,5D),(1B,2C,3F,4C,5A),
(1B,2C,3F,4C,5B),(1B,2C,3F,4C,5C),(1B,2C,3F,4C,5D),
(1B,2C,3F,4D,5A),(1B,2C,3F,4D,5B),(1B,2C,3F,4D,5C),
(1B,2C,3F,4D,5D),(1B,2D,3A,4A, 5A),(1B,2D,3A,4A,5B),
(1B,2D,3A,4A,5C),(1B,2D,3A,4A,5D),(1B,2D,3A,4B,5A),
(1B,2D,3A, 4B,5B),(1B,2D,3A,4B,5C),(1B,2D,3A,4B,5D),
(1B,2D,3A,4C,5A),(1B,2D,3A,4C,5B),(1B, 2D,3A,4C,5C),
(1B,2D,3A,4C,5D),(1B,2D,3A,4D,5A),(1B,2D,3A,4D,5B),
(1B,2D,3A,4D,5C), (1B,2D,3A,4D,5D),(1B,2D,3B,4A,5A),
(1B,2D,3B,4A,5B),(1B,2D,3B,4A,5C),(1B,2D,3B,4A, 5D),
(1B,2D,3B,4B,5A),(1B,2D,3B,4B,5B),(1B,2D,3B,4B,5C),
(1B,2D,3B,4B,5D),(1B,2D, 3B,4C,5A),(1B,2D,3B,4C,5B),
(1B,2D,3B,4C,5C),(1B,1B,2D,3B,4C,5D),(1B,2D,3B,4D,
5A),(1B, 2D,3B,4D,5B),(1B,2D,3B,4D,5C),(1B,2D,3B,4D,
5D),(1B,2D,3C,4A,5A),(1B,2D,3C,4A, 5B),(1B,2D,3C,4A,
5C),(1B,2D,3C,4A,5D),(1B,2D,3C,4B,5A),(1B,2D,3C,4B,
5B),(1B,2D,3C, 4B,5C),(1B,2D,3C,4B,5D),(1B,2D,3C,4C,
5A),(1B,2D,3C,4C,5B),(1B,2D,3C,4C,5C),(1B, 2D,3C,4C,
5D),(1B,2D,3C,4D,5A),(1B,2D,3C,4D,5B),(1B,2D,3C,4D,
5C),(1B,2D,3C,4D,5D), (1B,2D,3D,4A,5A),(1B,2D,3D,4A,
5B),(1B,2D,3D,4A,5C),(1B,2D,3D,4A,5D),(1B,2D,3D,
4B,5A),(1B,2D,3D,4B,5B),(1B,2D,3D,4B,5C),(1B,2D,3D,
4B,5D),(1B,2D,3D,4C,5A),(1B,2D, 3D,4C,5B),(1B,2D,3D,
4C,5C),(1B,2D,3D,4C,5D),(1B,2D,3D,4D,5A),(1B,2D,3D,
4D,5B), (1B,2D,3D,4D,5C),(1B,2D,3D,4D,5D),(1B,2D,3E,
4A,5A),(1B,2D,3E,4A,5B),(1B,2D,3E,4A, 5C),(1B,2D,3E,
4A,5D),(1B,2D,3E,4B,5A),(1B,2D,3E,4B,5B),(1B,2D,3E,
4B,5C),(1B,2D, 3E,4B,5D),(1B,2D,3E,4C,5A),(1B,2D,3E,
4C,5B),(1B,2D,3E,4C,5C),(1B,2D,3E,4C,5D),(1B, 2D,3E,
4D,5A),(1B,2D,3E,4D,5B),(1B,2D,3E,4D,5C),(1B,2D,3E,
4D,5D),(1B,2D,3F,4A,5A), (1B,2D,3F,4A,5B),(1B,2D,3F,
4A,5C),(1B,2D,3F,4A,5D),(1B,2D,3F,4B,5A),(1B,2D,3F,
4B, 5B),(1B,2D,3F,4B,5C),(1B,2D,3F,4B,5D),(1B,2D,3F,
4C,5A),(1B,2D,3F,4C,5B),(1B,2D,3F, 4C,5C),(1B,2D,3F,
4C,5D),(1B,2D,3F,4D,5A),(1B,2D,3F,4D,5B),(1B,2D,3F,
4D,5C),(1B,2D, 3F,4D,5D),(1B,2E,3A,4A,5A),(1B,2E,3A,
4A,5B),(1B,2E,3A,4A,5C),(1B,2E,3A,4A,5D),(1B, 2E,3A,
4B,5A),(1B,2E,3A,4B,5B),(1B,2E,3A,4B,5C),(1B,2E,3A,
4B,5D),(1B,2E,3A,4C, 5A),(1B,2E,3A,4C,5B),(1B,2E,3A,
4C,5C),(1B,2E,3A,4C,5D),(1B,2E,3A,4D,5A),(1B,2E,3A,
4D,5B),(1B,2E,3A,4D,5C),(1B,2E,3A,4D,5D),(1B,2E,3B,
4A,5A),(1B,2E,3B,4A,5B),(1B, 2E,3B,4A,5C),(1B,2E,3B,
4A,5D),(1B,2E,3B,4B,5A),(1B,2E,3B,4B,5B),(1B,2E,3B,
4B,5C), (1B,2E,3B,4B,5D),(1B,2E,3B,4C,5A),(1B,2E,3B,
4C,5B),(1B,2E,3B,4C,5C),(1B,2E,3B,4C, 5D),(1B,2E,3B,
4D,5A),(1B,2E,3B,4D,5B),(1B,2E,3B,4D,5C),(1B,2E,3B,
4D,5D),(1B,2E,3C, 4A,5A),(1B,2E,3C,4A,5B),(1B,2E,3C,
4A,5C),(1B,2E,3C,4B,5A),(1B, 2E,3C,4B,5B),(1B,2E,3C,
4B,5B),(1B,2E,3C,4B,5C),(1B,2E,3C,4B,5D),(1B,2E,3C,
4C,5A),(1B,2E,3C,4C,5B), (1B,2E,3C,4C,5C),(1B,2E,3C,
4C,5D),(1B,2E,3C,4D,5A),(1B,2E,3C,4D,5B),(1B,2E,3C,
4D, 5C),(1B,2E,3C,4D,5D),(1B,2E,3D,4A,5A),(1B,2E,3D,
4A,5B),(1B,2E,3D,4A,5C),(1B,2E,3D, 4A,5D),(1B,2E,3D,
4B,5A),(1B,2E,3D,4B,5B),(1B,2E,3D,4B,5C),(1B,2E,3D,
4C,5A),(1B, 2E,3D,4C,5B),(1B,2E,3D,4C,5C),(1B,2E,3D,
4C,5C),(1B,2E,3D,4C,5D),(1B,2E,3D,4D,5A), (1B,2E,3D,
4D,5B),(1B,2E,3D,4D,5C),(1B,2E,3D,4D,5D),(1B,2E,3E,
4A,5A),(1B,2E,3E,4A, 5B),(1B,2E,3E,4A,5C),(1B,2E,3E,
4A,5D),(1B,2E,3E,4B,5A),(1B,2E,3E,4B,5B),(1B,2E,3E,
4B,5C),(1B,2E,3E,4B,5D),(1B,2E,3E,4C,5A),(1B,2E,3E,
4C,5B),(1B,2E,3E,4C,5C),(1B,2E, 3E,4C,5D),(1B,2E,3E,
4D,5A),(1B,2E,3E,4D,5B),(1B,2E,3E,4D,5C),(1B,2E,3E,
4D,5D),(1B, 2E,3F,4A,5A),(1B,2E,3F,4A,5B),(1B,2E,3F,
4A,5C),(1B,2E,3F,4A,5D),(1B,2E,3F,4B,5A), (1B,2E,3F,
4B,5B),(1B,2E,3F,4B,5C),(1B,2E,3F,4B,5D),(1B,2E,3F,4C,
5A),(1B,2E,3F,4C,5B), (1B,2E,3F,4C,5C),(1B,2E,3F,4C,
5D),(1B,2E,3F,4D,5A),(1B,2E,3F,4D,5B),(1B,2E,3F,4D,
5C),(1B,2E,3F,4D,5D),(1C,2A,3A,4A,5A),(1C,2A,3A,4A,
5B),(1C,2A,3A,4A,5C),(1C,2A, 3A,4A,5D),(1C,2A,3A,4B,
5A),(1C,2A,3A,4B,5B),(1C,2A,3A,4B,5C),(1C,2A,3A,4B,
5D),(1C, 2A,3A,4C,5A),(1C,2A,3A,4C,5B),(1C,2A,3A,4C,
5C),(1C,2A,3A,4C,5D),(1C,2A,3A,4D,5A), (1C,2A,3A,4D,
5B),(1C,2A,3A,4D,5C),(1C,2A,3A,4D,5D),(1C,2A,3B,4A,
5A),(1C,2A,3B, 4A,5B),(1C,2A,3B,4A,5C),(1C,2A,3B,4A,
5D),(1C,2A,3B,4B,5A),(1C,2A,3B,4B,5B),(1C,2A, 3B,4B,
5C),(1C,2A,3B,4B,5D),(1C,2A,3B,4C,5A),(1C,2A,3B,4C,
5B),(1C,2A,3B,4C,5C),(1C, 2A,3B,4C,5D),(1C,2A,3B,4D,
5A),(1C,2A,3B,4D,5B),(1C,2A,3B,4D,5C),(1C,2A,3B,4D,
5D), (1C,2A,3C,4A,5A),(1C,2A,3C,4A,5B),(1C,2A,3C,4A,
5C),(1C,2A,3C,4A,5D),(1C,2A,3C,4B, 5A),(1C,2A,3C,4B,
5B),(1C,2A,3C,4B,5C),(1C,2A,3C,4B,5D),(1C,2A,3C,4C,
5A),(1C,2A,3C, 4C,5B),(1C,2A,3C,4C,5C),(1C,2A,3C,4C,
5D),(1C,2A,3C,4D,5A),(1C,2A,3C,4D,5B),(1C,2A, 3C,4D,
5C),(1C,2A,3C,4D,5D),(1C,2A,3D,4A,5A),(1C,2A,3D,4A,
5B),(1C,2A,3D,4A,5A),(1C, 1C,2A,3D,4A,5D),(1C,2A,3D,
4B,5A),(1C,2A,3D,4B,5B),(1C,2A,3D,4B,5C),(1C,2A,3D,
4B, 5D),(1C,2A,3D,4C,5A),(1C,2A,3D,4C,5B),(1C,2A,3D,
4C,5C),(1C,2A,3D,4C,5D),(1C,2A,3D, 4D,5A),(1C,2A,3D,
4D,5B),(1C,2A,3D,4D,5C),(1C,2A,3D,4D,5D),(1C,2A,3E,
4A,5A),(1C, 2A,3E,4A,5B),(1C,2A,3E,4A,5C),(1C,2A,3E,
4A,5D),(1C,2A,3E,4B,5A),(1C,2A,3E,4B,5B), (1C,2A,3E,
4B,5C),(1C,2A,3E,4B,5D),(1C,2A,3E,4C,5A),(1C,2A,3E,
4C,5B),(1C,2A,3E,4C, 5C),(1C,2A,3E,4C,5D),(1C,2A,3E,
4D,5A),(1C,2A,3E,4D,5B),(1C,2A,3E,4D,5C),(1C,2A,3E,
4D,5D),(1C,2A,3F,4A,5A),(1C,2A,3F,4A,5B),(1C,2A,3F,
4A,5C),(1C,2A,3F,4A,5D),(1C,2A, 3F,4B,5A),(1C,2A,3F,
4B,5B),(1C,2A,3F,4B,5C),(1C,2A,3F,4B,5D),(1C,2A,3F,
4C,5A),(1C, 2A,3F,4C,5B),(1C,2A,3F,4C,5C),(1C,2A,3F,
4C,5D),(1C,2A,3F,4D,5A),(1C,2A,3F,4D,5B), (1C,2A,3F,
4D,5C),(1C,2A,3F,4D,5D),(1C,2B,3A,4A,5A),(1C,2B,3A,
4A,5C),(1C,2B,3A,4A, 5D),(1C,2B,3A,4B,5A),(1C,2B,3A,
4B,5B),(1C,2B,3A,4B,5C),(1C,2B,3A,4B,5D),(1C,2B,3A,
4C,5A),(1C,2B,3A,4C,5B),(1C,2B,3A,4C,5C),(1C,2B,3A,
4C,5D),(1C,2B,3A,4D,5A),(1C, 2B,3A,4D,5B),(1C,2B,3A,
4D,5C),(1C,2B,3A,4D,5D),(1C,2B,3B,4A,5A),(1C,2B,3B,
4A,5C), (1C,2B,3B,4A,5D),(1C,2B,3B,4B,5A),(1C,2B,3B,
4B,5B),(1C,2B,3B,4B,5C),(1C,2B,3B,4B, 5D),(1C,2B,3B,
4C,5A),(1C,2B,3B,4C,5B),(1C,2B,3B,4C,5C),(1C,2B,3B,
4C,5D),(1C,2B,3B, 4D,5A),(1C,2B,3B,4D,5B),(1C,2B,3B,
4D,5C),(1C,2B,3B,4D,5D),(1C,2B,3C,4A,5A),(1C, 2B,3C,
4A,5B),(1C,2B,3C,4A,5C),(1C,2B,3C,4A,5D),(1C,2B,3C,
4B,5A),(1C,2B,3C,4B,5B), (1C,2B,3C,4B,5C),(1C,2B,3C,
4B,5D),(1C,2B,3C,4C,5A),(1C,2B,3C,4C,5B),(1C,2B,3C,
4C, 5C),(1C,2B,3C,4C,5D),(1C,2B,3C,4D,5A),(1C,2B,3C,
4D,5B),(1C,2B,3C,4D,5C),(1C,2B,3C, 4D,5D),(1C,2B,3D,
4A,5A),(1C,2B,3D,4A,5B),(1C,2B,3D,4A,5C),(1C,2B,3D,
4A,5D),(1C, 2B,3D,4B,5A),(1C,2B,3D,4B,5B),(1C,2B,3D,
4B,5C),(1C,2B,3D,4B,5D),(1C,2B,3D,4C,5A), (1C,2B,3D, 4C,5B),(1C,2B,3D,4C,5C),(1C,2B,3D,4C,5D),(1C,2B,3D,
4D,5A),(1C,2B,3D,4D, 5B),(1C,2B,3D,4D,5C),(1C,2B,3D,
4D,5D),(1C,2B,3E,4A,5A,(1C,2B,3E,4A,5B),(1C,2B,
3E,4A,5C),(1C,2B,3E,4A,5D),(1C,2B,3E,4A,5A),(1C,2B,
3E,4B,5B),(1C,2B,3E,4B,5C),(1C, 2B,3E,4B,5D),(1C,2B,
3E,4C,5A),(1C,2B,3E,4C,5B),(1C,2B,3E,4C,5C),(1C,2B,
3E,4C,5D), (1C,2B,3E,4D,5A),(1C,2B,3E,4D,5B),(1C,2B,
3E,4D,5C),(1C,2B,3E,4D,5D),(1C,2B,3F,4A, 5A),(1C,2B,
3F,4A,5B),(1C,2B,3F,4A,5C),(1C,2B,3F,4A,5D),(1C,2B,
3F,4B,5A),(1C,2B,3F,4A, 5B),(1C,2B,3F,4B,5C),(1C,2B,
3F,4B,5D),(1C,2B,3F,4C,5A),(1C,2B,3F,4C,5B),(1C,2B,
3F, 4C,5C),(1C,2B,3F,4C,5D),(1C,2B,3F,4D,5A),(1C,2B,
3F,4D,5B),(1C,2B,3F,4D,5C),(1C,2B, 3F,4D,5D),(1C,2C,
3A,4A,5A),(1C,2C,3A,4A,5B),(1C,2C,3A,4A,5C),(1C,2C,
3A,4A,5D),(1C, 1C,2C,3A,4B,5A),(1C,2C,3A,4B,5B),(1C,
2C,3A,4B,5C),(1C,2C,3A,4B,5D),(1C,2C,3A,4C, 5A),(1C,
2C,3A,4C,5B),(1C,2C,3A,4C,5C),(1C,2C,3A,4C,5D),(1C,
2C,3A,4D,5A),(1C,2C,3A, 4D,5B),(1C,2C,3A,4D,5C),(1C,
2C,3A,4D,5D),(1C,2C,3B,4A,5A),(1C,2C,3B,4A,5B),(1C,
2C,3B,4A,5C),(1C,2C,3B,4A,5D),(1C,2C,3B,4B,5A),(1C,
2C,3B,4B,5B),(1C,2C,3B,4B,5C), (1C,2C,3B,4B,5D),(1C,
2C,3B,4C,5A),(1C,2C,3B,4C,5B),(1C,2C,3B,4C,5C),(1C,
2C,3B,4C, 5D),(1C,2C,3B,4D,5A),(1C,2C,3B,4D,5B),(1C,
2C,3B,4D,5D),(1C,2C,3B,4D,5D),(1C,2C,3C, 4A,5A),(1C,
2C,3C,4A,5B),(1C,2C,3C,4A,5C),(1C,2C,3C,4A,5D),(1C,
2C,3C,4B,5A),(1C, 2C,3C,4B,5B),(1C,2C,3C,4B,5C),(1C,
2C,3C,4B,5D),(1C,2C,3C,4C,5A),(1C,2C,3C,4C,5B), (1C,
2C,3C,4C,5C),(1C,2C,3C,4C,5D),(1C,2C,3C,4D,5A),(1C,
2C,3C,4D,5B),(1C,2C,3C,4D, 5C),(1C,2C,3C,4D,5D),(1C,
2C,3D,4A,5A),(1C,2C,3D,4A,5B),(1C,2C,3D,4A,5C),(1C,
2C,3D, 4A,5D),(1C,2C,3D,4B,5A),(1C,2C,3D,4B,5B),(1C,
2C,3D,4B,5C),(1C,2C,3D,4B,5D),(1C, 2C,3D,4C,5A),(1C,
2C,3D,4C,5B),(1C,2C,3D,4C,5C),(1C,2C,3D,4C,5D),(1C,
2C,3D,4D,5A), (1C,2C,3D,4D,5B),(1C,2C,3D,4D,5C),(1C,
2C,3D,4D,5D),(1C,2C,3E,4A,5A),(1C,2C,3E,4A, 5B),(1C,
2C,3E,4A,5C),(1C,2C,3E,4A,5D),(1C,2C,3E,4B,5A),(1C,
2C,3E,4B,5B),(1C,2C,3E, 4B,5C),(1C,2C,3E,4B,5D),(1C,
2C,3E,4C,5A),(1C,2C,3E,4C,5B),(1C,2C,3E,4C,5C),(1C,
2C, 3E,4C,5D),(1C,2C,3E,4D,5A),(1C,2C,3E,4D,5B),(1C,
2C,3E,4D,5C),(1C,2C,3E,4D,5D),(1C, 2C,3F,4A,5A),(1C,
2C,3F,4A,5B),(1C,2C,3F,4A,5C),(1C,2C,3F,4A,5D),(1C,
2C,3F,4B,5A), (1C,2C,3F,4B,5B),(1C,2C,3F,4B,5C),(1C,
2C,3F,4B,5D),(1C,2C,3F,4C,5A),(1C,2C,3F,4C,5B), (1C,
2C,3F,4C,5C),(1C,2C,3F,4C,5D),(1C,2C,3F,4D,5A),(1C,
2C,3F,4D,5B),(1C,2C,3F,4D, 5C),(1C,2C,3F,4D,5D),(1C,
2D,3A,4A,5A),(1C,2D,3A,4A,5B),(1C,2D,3A,4A,5C),(1C,
2D, 3A,4A,5D),(1C,2D,3A,4B,5A),(1C,2D,3A,4B,5B),(1C,
2D,3A,4B,5C),(1C,2D,3A,4B,5D),(1C, 2D,3A,4C,5A),(1C,
2D,3A,4C,5B),(1C,2D,3A,4C,5C),(1C,2D,3A,4C,5D),(1C,
2D,3A,4D,5A), (1C,2D,3A,4D,5B),(1C,2D,3A,4D,5C),(1C,
2D,3A,4D,5D),(1C,2D,3B,4A,5A),(1C,2D,3B, 4A,5B),(1C,
2D,3B,4A,5C),(1C,2D,3B,4A,5D),(1C,2D,3B,4B,5A),(1C,
2D,3B,4B,5B),(1C,2D, 3B,4B,5C),(1C,2D,3B,4B,5D),(1C,
2D,3B,4C,5A),(1C,2D,3B,4C,5B),(1C,2D,3B,4C,5C),(1C,
2D,3B,4C,5D),(1C,2D,3B,4D,5A),(1C,2D,3B,4D,5B),(1C,
2D,3B,4D,5C),(1C,2D,3B,4D, 5D),(1C,2D,3C,4A,5A),(1C,
2D,3C,4A,5B),(1C,2D,3C,4A,5C),(1C,2D,3C,4A,5D),(1C,
2D,3C, 4B,5A),(1C,2D,3C,4B,5B),(1C,2D,3C,4B,5C),(1C,
2D,3C,4B,5D),(1C,2D,3C,4C,5A),(1C, 2D,3C,4C,5B),(1C,
2D,3C,4C,5C),(1C,2D,3C,4C,5D),(1C,2D,3C,4D,5A),(1C,
2D,3C,4D,5B), (1C,2D,3C,4D,5C),(1C,2D,3C,4D,5D),(1C,
2D,3D,4A,5A),(1C,2D,3D,4A,5B),(1C,2D,3D, 4A,5C),(1C,
2D,3D,4A,5D),(1C,2D,3D,4B,5A),(1C,2D,3D,4B,5B),(1C,
2D, 3D,4B,5C),(1C,2D,3D,4C,5A),(1C,
2D,3D,4C,5B),(1C,2D,3D,4C,5C),(1C,2D,3D,4C,5D), (1C,
2D,3D,4D,5A),(1C,2D,3D,4D,5B),(1C,2D,3D,4D,5C),(1C,
2D,3D, 4D,5D),(1C,2D,3E,4A, 5A),(1C,2D,3E,4A,5B),
(1C,2D,3E,4A,5C),(1C,2D,3E,4A,5D),(1C,2D,3E,4A,5A),
(1C,2D, 3E,4B,5B),(1C,2D,3E,4B,5C),(1C,2D,3E,4B,5D),
(1C,2D,3E,4C,5A),(1C,2D,3E,4C,5B),(1C, 2D,3E,4C,5C),
(1C,2D,3E,4C,5D),(1C,2D,3E,4D,5A),(1C,2D,3E,4D,5B),
(1C,2D,3E,4D, 5C),(1C,2D,3E,4D,5D),(1C,2D,3F,4A,5A),
(1C,2D,3F,4A,5B),(1C,2D,3F,4A,5C),(1C,2D,3F, 4A,5D),
(1C,2D,3F,4B,5A),(1C,2D,3F,4B,5B),(1C,2D,3F,4B,5C),
(1C,2D,3F,4B,5D),(1C,2D, 3F,4C,5A),(1C,2D,3F,4C,5B),
(1C,2D,3F,4C,5C),(1C,2D,3F,4C,5D),(1C,2D,3F,4D,5A),
(1C, 2D,3F,4D,5B),(1C,2D,3F,4D,5C),(1C,2D,3F,4D,5D),
(1C,2E,3A,4A,5A),(1C,2E,3A,4A,5B), (1C,2E,3A,4A,5C),
(1C,2E,3A,4A,5D),(1C,2E,3A,4B,5A),(1C,2E,3A,4B,5B),
(1C,2E,3A,4B, 5C),(1C,2E,3A,4B,5D),(1C,2E,3A,4C,5A),
(1C,2E,3A,4C,5B),(1C,2E,3A,4C,5C),(1C,2E,3A, 4C,5D),
(1C,2E,3A,4D,5A),(1C,2E,3A,4D,5B),(1C,2E,3A,4D,5C),
(1C,2E,3A,4D,5D),(1C,2E, 3B,4A,5A),(1C,2E,3B,4A,5B),
(1C,2E,3B,4A,5C),(1C,2E,3B,4A,5D),(1C,2E,3B,4B,5A),
(1C, 2E,3B,4B,5B),(1C,2E,3B,4B,5C),(1C,2E,3B,4B,5D),
(1C,2E,3B,4C,5A),(1C,2E,3B,4C, 5B),(1C,2E,3B,4C,5C),
(1C,2E,3B,4C,5D),(1C,2E,3B,4D,5A),(1C,2E,3B,4D,5B),
(1C,2E,3B, 4D,5C),(1C,2E,3B,4D,5D),(1C,2E,3C,4A,5A),
(1C,2E,3C,4A,5B),(1C,2E,3C,4A,5C),(1C, 2E,3C,4A,5D),
(1C,2E,3C,4B,5A),(1C,2E,3C,4B,5B),(1C,2E,3C,4B,5C),
(1C,2E,3C,4B,5D), (1C,2E,3C,4C,5A),(1C,2E,3C,4C,5B),
(1C,2E,3C,4C,5C),(1C,2E,3C,4C,5D),(1C,2E,3C,4D, 5A),
(1C,2E,3C,4D,5B),(1C,2E,3C,4D,5C),(1C,2E,3C,4D,5D),
(1C,2E,3D,4A,5A),(1C,2E,3D, 4A,5B),(1C,2E,3D,4A,5C),
(1C,2E,3D,4A,5D),(1C,2E,3D,4B,5A),(1C,2E,3D,4B,5B),
(1C, 2E,3D,4B,5C),(1C,2E,3D,4B,5D),(1C,2E,3D,4C,5A),
(1C,2E,3D,4C,5B),(1C,2E,3D,4C,5C), (1C,2E,3D,4C,5D),
(1C,2E,3D,4D,5A),(1C,2E,3D,4D,5B),(1C,2E,3D,4D,5C),
(1C,2E,3D,4D, 5D),(1C,2E,3E,4A,5A),(1C,2E,3E,4A,5B),
(1C,2E,3E,4A,5C),(1C,2E,3E,4A,5D),(1C,2E, 3E,4B,5A),
(1C,2E,3E,4B,5B),(1C,2E,3E,4B,5C),(1C,2E,3E,4B,5D),
(1C,2E,3E,4C,5A),(1C, 2E,3E,4C,5B),(1C,2E,3E,4C,5C),
(1C,2E,3E,4C,5D),(1C,2E,3E,4D,5A),(1C,2E,3E,4D,5B),
(1C,2E,3E,4D,5C),(1C,2E,3E,4D,5D),(1C,2E,3F,4A,5A),
(1C,2E,3F,4A,5B),(1C,2E,3F,4A, 5C),(1C,2E,3F,4A,5D),
(1C,2E,3F,4B,5A),(1C,2E,3F,5B),(1C,2E,3F,4B,5C),(1C,
2E,3F,4B, 5D),(1C,2E,3F,4C,5A),(1C,2E,3F,4C,5B),(1C,
2E,3F,4C,5C),(1C,2E,3F,4C,5D),(1C,2E,3F, 4D,5A),(1C,
2E,3F,4D,5B),(1C,2E,3F,4D,5C),(1C,2E,3F,4D,5D),(1D,
2A,3A,4A,5A),(1D,2A, 3A,4A,5B),(1D,2A,3A,4A,6C),
(1D,2A,3A,4A,5D),(1D,2A,3A,4B,5A),(1D,2A,3A,4B,5B),
(1D, 2A,3A,4B,5C),(1D,2A,3A,4B,5D),(1D,2A,3A,4C,
5A),(1D,2A,3A,4C,5B),(1D,2A,3A,4C,(1D,2A,3A,4A,5A),
5C),(1D,2A,3A,4C,5D),(1D,2A,3A,4D,5A),(1D,2A,3A,4D,
5B),(1D,2A,3A,4D,5C),(1D,2A,3A, 4D,5D),(1D,2A,3B,
4A,5A),(1D,2A,3B,4A,5B),(1D,2A,3B,4A,5C),(1D,2A,3B,
4A,5D),(1D, 2A,3B,4B,5A),(1D,2A,3B,4B,5B),(1D,2A,3B,
4B,5C),(1D,2A,3B,4B,5D),(1D,2A,3B,4C,5A), (1D,2A,3B,
4C,5B),(1D,2A,3B,4C,5C),(1D,2A,3B,4C,5D),(1D,2A,3B,
4D,5A),(1D,2A,3B,4D, 5B),(1D,2A,3B,4D,5C),(1D,2A,3B,
4D,5D),(1D,2A,3C,4A,5A),(1D,2A,3C,4A,5B),(1D,2A,
3C,4A,5C),(1D,2A,3C,4A,5D),(1D,2A,3C,4B,5A),(1D,2A,
3C,4B,5B),(1D,2A,3C,4B,5C),(1D, 2A,3C,4B,5D),(1D,2A,
3C,4C,5A),(1D,2A,3C,4C,5B),(1D,2A,3C,4C,5C),(1D,2A,
3C,4C,5D), (1D,2A,3C,4D,5A),(1D,2A,3C,4D,5B),(1D,2A,
3C,4D,5C),(1D,2A,3C,4D,5D),(1D,2A,3D, 4A,5A),(1D,
2A,3D,4A,5B),(1D,2A,3D,4A,5C),(1D,2A,3D,4A,5D),(1D,
2A,3D,4B,5A),(1D, 2A,3D,4B,5B),(1D,2A,3D,4B,5C),(1D,
2A,3D,4B,5D),(1D,2A,3D,4C,5A),(1D,2A,3D,4C,5B),
(1D,2A,3D,4C,5C),(1D,2A,3D,4C,5D),(1D,2A,3D,4D,5A),
(1D,2A,3D,4D,5B),(1D,2A,3D, 4D,5C),(1D,2A,3E,4A,5A),(1D,2A,3E,4A,5B),(1D,2A,3E,4A,
5D),(1D,2A,3E,4A,5B),(1D,2A,3E,4A, 5C),(1D,2A, 3E,4A,5D),(1D,2A,3E,4B,5A),(1D,2A,3E,4B,
5B),(1D,2A,3E,4B,5C),(1D,2A,3E,4B,5D),(1D, 1D,2A,3E, 4C,5A),(1D,2A,3E,4C,5B),(1D,2A,3E,4C,5C),(1D,2A,3E, 4C,5D),(1D,2A,3E,4D, 5A),(1D,2A,3E,4D,5B),(1D,2A,3E, 4D,5C),(1D,2A,3E,4D,5D),(1D,2A,3F,4A,5A),(1D,2A,3F, 4A,5B),(1D,2A,3F,4A,5C),(1D,2A,3F,4A,5D),(1D,2A,3F, 4B,5A),(1D,2A,3F,4B,5B),(1D,2A, 3F,4B,5C),(1D,2A,3F, 4B,5D),(1D,2A,3F,4C,5A),(1D,2A,3F,4C,5B),(1D,2A,3F, 4C,5C),(1D, 2A,3F,4C,5D),(1D,2A,3F,4D,5A),(1D,2A,3F, 4D,5B),(1D,2A,3F,4D,5C),(1D,2A,3F,4D,5D), (1D,2B,3A, 4A,5A),(1D,2B,3A,4A,5B),(1D,2B,3A,4A,5C),(1D,2B,3A, 4A,5D),(1D,2B,3A, 4B,5A),(1D,2B,3A,4B,5B),(1D,2B,3A, 4B,5C),(1D,2B,3A,4B,5D),(1D,2B,3A,4C,5A),(1D,2B, 3A,4C,5B),(1D,2B,3A,4C,5C),(1D,2B,3A,4C,5D),(1D,2B, 3A,4D,5A),(1D,2B,3A,4D,5B), (1D,2B,3A,4D,5C),(1D,2B, 3A,4D,5D),(1D,2B,3B,4A,5A),(1D,2B,3B,4A,5B),(1D,2B, 3B,4A, 5C),(1D,2B,3B,4A,5D),(1D,2B,3B,4B,5A),(1D,2B, 3B,4B,5B),(1D,2B,3B,4B,5C),(1D,2B, 3B,4B,5D),(1D,2B, 3B,4C,5A),(1D,2B,3B,4C,5B),(1D,2B,3B,4C,5C),(1D,2B, 3B,4C,5D),(1D, 2B,3B,4D,5A),(1D,2B,3B,4D,5B),(1D,2B, 3B,4D,5C),(1D,2B,3B,4D,5D),(1D,2B,3C,4A, 5A),(1D,2B, 3C,4A,5B),(1D,2B,3C,4A,5C),(1D,2B,3C,4A,5D),(1D,2B, 3C,4B,5A),(1D,2B,3C, 4B,5B),(1D,2B,3C,4B,5C),(1D,2B, 3C,4B,5D),(1D,2B,3C,4C,5A),(1D,2B,3C,4C,5B),(1D, 2B,3C,4C,5C),(1D,2B,3C,4C,5D),(1D,2B,3C,4D,5A),(1D, 2B,3C,4D,5B),(1D,2B,3C,4D,5C), (1D,2B,3C,4D,5D),(1D, 2B,3D,4A,5A),(1D,2B,3D,4A,5B),(1D,2B,3D,4A,5C),(1D, 2B,3D, 4A,5D),(1D,2B,3D,4B,5A),(1D,2B,3D,4B,5B),(1D, 2B,3D,4B,5C),(1D,2B,3D,4B,5D),(1D,2B, 3D,4C,5A),(1D, 2B,3D,4C,5B),(1D,2B,3D,4C,5C),(1D,2B,3D,4C,5D),(1D, 2B,3D,4D,5A), (1D,2B,3D,4D,5B),(1D,2B,3D,4D,5C),(1D, 2B,3D,4D,5D),(1D,2B,3E,4A,5A),(1D,2B,3E,4A, 5B),(1D, 2B,3E,4A,5C),(1D,2B,3E,4A,5D),(1D,2B,3E,4B,5A),(1D, 2B,3E,4B,5B),(1D,2B, 3E,4B,5C),(1D,2B,3E,4B,5D),(1D, 2B,3E,4C,5A),(1D,2B,3E,4C,5B),(1D,2B,3E,4C,5C),(1D, 2B,3E,4C,5D),(1D,2B,3E,4D,5A),(1D,2B,3E,4D,5B),(1D, 2B,3E,4D,5C),(1D,2B,3E,4D, 5D),(1D,2B,3F,4A,5A),(1D, 2B,3F,4A,5B),(1D,2B,3F,4A,5C),(1D,2B,3F,4A,5D),(1D, 2B,3F, 4B,5A),(1D,2B,3F,4B,5B),(1D,2B,3F,4B,5C),(1D, 2B,3F,4B,5D),(1D,2B,3F,4C,5A),(1D,2B, 3F,4C,5B),(1D, 2B,3F,4C,5C),(1D,2B,3F,4C,5D),(1D,2B,3F,4D,5A),(1D, 2B,3F,4D,5B),(1D, 2B,3F,4D,5C),(1D,2B,3F,4D,5D),(1D, 2C,3A,4A,5A),(1D,2C,3A,4A,5B),(1D,2C,3A,4A,5C), (1D, 2C,3A,4A,5D),(1D,2C,3A,4B,5A),(1D,2C,3A,4B,5B),(1D, 2C,3A,4B,5C),(1D,2C,3A,4B, 5D),(1D,2C,3A,4C,5A),(1D, 2C,3A,4C,5B),(1D,2C,3A,4C,5C),(1D,2C,3A,4C,5D),(1D, 2C,3A, 4D,5A),(1D,2C,3A,4D,5B),(1D,2C,3A,4D,5C),(1D, 2C,3A,4D,5D),(1D,2C,3B,4A,5A),(1D, 2C,3B,4A,5B),(1D, 2C,3B,4A,5C),(1D,2C,3B,4A,5D),(1D,2C,3B,4B,5A),(1D, 2C,3B,4B,5B), (1D,2C,3B,4B,5C),(1D,2C,3B,4B,5D),(1D, 2C,3B,4C,5A),(1D,2C,3B,4C,5B),(1D,2C,3B,4C, 5C),(1D, 2C,3B,4C,5D),(1D,2C,3B,4D,5A),(1D,2C,3B,4D,5B),(1D, 2C,3B,4D,5C),(1D,2C,3B, 4D,5D),(1D,2C,3C,4A,5A),(1D, 2C,3C,4A,5B),(1D,2C,3C,4A,5C),(1D,2C,3C,4A,5D),(1D, 2C,3C,4B,5A),(1D,2C,3C,4B,5B),(1D,2C,3C,4B,5C),(1D, 2C,3C,4B,5D),(1D,2C,3C,4C,5A), (1D,2C,3C,4C,5B),(1D, 2C,3C,4C,5C),(1D,2C,3C,4C,5D),(1D,2C,3C,4D,5A),(1D, 2C,3C,4D, 5B),(1D,2C,3C,4D,5C),(1D,2C,3C,4D,5D),(1D, 2C,3D,4A,5A),(1D,2C,3D,4A,5B),(1D,2C, 3D,4A,5C),(1D, 2C,3D,4A,5D),(1D,2C,3D,4B,5A),(1D,2C,3D,4B,5B),(1D, 2C,3D,4B,5C),(1D, 2C,3D,4B,5D),(1D,2C,3D,4C,5A),(1D, 2C,3D,4C,5B),(1D,2C,3D,4C,5C),(1D,2C,3D,4C, 5D),(1D, 2C,3D,4D,5A),(1D,2C,3D,4D,5B),(1D,2C,3D,4D,5C),(1D, 2C,3D,4D,5D),(1D,2C, 3E,4A,5A),(1D,2C,3E,4A,5B),(1D, 2C,3E,4A,5C),(1D,2C,3E,4A,5D),(1D,2C,3E,4B,5A),(1D, 2C,3E,4B,5B),(1D,2C,3E,4B,5C),(1D,2C,3E,4B,5D),(1D, 2C,3E,4C,5A),(1D,2C,3E,4A,5B), (1D,2C,3E,4C,5C),(1D, 2C,3E,4C,5D),(1D,2C,3E,4D,5A),(1D,2C,3E,4D,5B),(1D, 2C,3E, 4D,5C),(1D,2C,3E,4D,5D),(1D,2C,3F,4A,5A),(1D, 2C,3F,4A,5B),(1D,2C,3F,4A,5C),(1D,2C, 3F,4A,5D),(1D, 2C,3F,4B,5A),(1D,2C,3F,4B,5B),(1D,2C,3F,4B,5C),(1D, 2C,3F,4B,5D),(1D, 2C,3F,4C,5A),(1D,2C,3F,4C,5B),(1D, 2C,3F,4C,5C),(1D,2C,3F,4C,5D),(1D,2C,3F,4D,5A),(1D, 1D,2C,3F,4D,5B),(1D,2C,3F,4D,5C),(1D,2C,3F,4D,5D), (1D,2D,3A,4A,5A),(1D,2D,3A,4A, 5B),(1D,2D,3A,4A, 5C),(1D,2D,3A,4A,5D),(1D,2D,3A,4B,5A),(1D,2D,3A,4B, 5B),(1D,2D,3A, 4B,5C),(1D,2D,3A,4B,5D),(1D,2D,3A,4C, 5A),(1D,2D,3A,4C,5B),(1D,2D,3A,4C,5C),(1D, 2D,3A,4C, 5D),(1D,2D,3A,4D,5A),(1D,2D,3A,4D,5B),(1D,2D,3A, 4D,5C),(1D,2D,3A,4D,5D), (1D,2D,3B,4A,5A),(1D,2D, 3B,4A,5B),(1D,2D,3B,4A,5C),(1D,2D,3B,4A,5D),(1D,2D, 3B, 4B,5A),(1D,2D,3B,4B,5B),(1D,2D,3B,4B,5C),(1D,2D, 3B,4B,5D),(1D,2D,3B,4C,5A),(1D, 2D,3B,4C,5B),(1D,2D, 3B,4C,5C),(1D,2D,3B,4C,5D),(1D,2D,3B,4D,5A),(1D,2D, 3B,4D,5B), (1D,2D,3B,4D,5C),(1D,2D,3B,4D,5D),(1D,2D, 3C,4A,5A),(1D,2D,3C,4A,5B),(1D,2D,3C, 4A,5C),(1D,2D, 3C,4A,5D),(1D,2D,3C,4B,5A),(1D,2D,3C,4B,5B),(1D,2D, 3C,4B,5C),(1D, 2D,3C,4B,5D),(1D,2D,3C,4C,5A),(1D,2D, 3C,4C,5B),(1D,2D,3C,4C,5C),(1D,2D,3C,4C,5D), (1D,2D, 3C,4D,5A),(1D,2D,3C,4D,5B),(1D,2D,3C,4D,5C),(1D,2D, 3C,4D,5D),(1D,2D,3D,4A, 5A),(1D,2D,3D,4A,5B),(1D, 2D,3D,4A,5C),(1D,2D,3D,4A,5D),(1D,2D,3D,4B,5A),(1D, 2D, 3D,4B,5B),(1D,2D,3D,4B,5C),(1D,2D,3D,4B,5D),(1D, 2D,3D,4C,5A),(1D,2D,3D,4C,5B), (1D,2D,3D,4C,5C),(1D, 2D,3D,4C,5D),(1D,2D,3D,4D,5A),(1D,2D,3D,4D,5B),(1D, 2D,3D,4D, 5C),(1D,2D,3D,4D,5D),(1D,2D,3E,4A,5A), (1D,2D,3E,4A,5B),(1D,2D,3E,4A,5C),(1D,2D, 3E,4A,5D), (1D,2D,3E,4B,5A),(1D,2D,3E,4B,5B),(1D,2D,3E,4B,5C), (1D,2D,3E,4B,5D), (1D,2D,3E,4C,5A),(1D,2D,3E,4C,5B), (1D,2D,3E,4C,5C),(1D,2D,3E,4C,5D),(1D,2D,3E,4D, 5A), (1D,2D,3E,4D,5B),(1D,2D,3E,4D,5C),(1D,2D,3E,4D,5D), (1D,2D,3F,4A,5A),(1D,2D, 3F,4A,5B),(1D,2D,3F,4A,5C), (1D,2D,3F,4A,5D),(1D,2D,3F,4B,5A),(1D,2D,3F,4B,5B), (1D, 2D,3F,4B,5C),(1D,2D,3F,4B,5D),(1D,2D,3F,4C,5A), (1D,2D,3F,4C,5B),(1D,2D,3F,4C,5C), (1D,2D,3F,4C,5D), (1D,2D,3F,4D,5A),(1D,2D,3F,4D,5B),(1D,2D,3F,4D,5C), (1D,2D,3F, 4D,5D),(1D,2E,3A,4A,5A),(1D,2E,3A,4A,5B), (1D,2E,3A,4A,5C),(1D,2E,3A,4A,5D),(1D,2E, 3A,4B,5A), (1D,2E,3A,4B,5B),(1D,2E,3A,4B,5C),(1D,2E,3A,4B,5D), (1D,2E,3A,4C,5A),(1D, 2E,3A,4C,5B),(1D,2E,3A,4C,5C), (1D,2E,3A,4C,5D),(1D,2E,3A,4D,5A),(1D,2E,3A,4D, 5B), (1D,2E,3A,4D,5C),(1D,2E,3A,4D,5D),(1D,2E,3B,4A,5A), (1D,2E,3B,4A,5B),(1D,2E,3B, 4A,5C),(1D,2E,3B,4A,5D), (1D,2E,3B,4B,5A),(1D,2E,3B,4B,5B),(1D,2E,3B,4B,5C), (1D, 2E,3B,4B,5D),(1D,2E,3B,4C,5A),(1D,2E,3B,4C,5B), (1D,2E,3B,4C,5C),(1D,2E,3B,4C,5D), (1D,2E,3B,4D,5A), (1D,2E,3B,4D,5B),(1D,2E,3B,4D,5C),(1D,2E,3B,4D,5D), (1D,2E,3C,4A, 5A),(1D,2E,3C,4A,5B),(1D,2E,3C,4A,5C), (1D,2E,3C,4A,5D),(1D,2E,3C,4B,5A),(1D,2E, 3C,4B,5B), (1D,2E,3C,4B,5C),(1D,2E,3C,4B,5D),(1D,2E,3C,4C,5A), (1D,2E,3C,4C,5B),(1D, 2E,3C,4C,5C),(1D,2E,3C,4C,5D), (1D,2E,3C,4D,5A),(1D,2E,3C,4D,5B),(1D,2E,3C,4D, 5C), (1D,2E,3C,4D,5D),(1D,2E,3D,4A,5A),(1D,2E,3D,4A,5B), (1D,2E,3D,4A,5C),(1D,2E,3D, 4A,5D),(1D,2E,3D,4B,5A), (1D,2E,3D,4B,5B),(1D,2E,3D,4B,5C),(1D,2E,3D,4B,5D), (1D, 2E,3D,4C,5A),(1D,2E,3D,4C,5B),(1D,2E,3D,4C,5C), (1D,2E,3D,4C,5D),(1D,2E,3D,4D, 5A),(1D,2E,3D,4D,5B), (1D,2E,3D,4D,5C),(1D,2E,3D,4D,5D),(1D,2E,3E,4A,5A), (1D,2E,3E, 4A,5B),(1D,2E,3E,4A,5C),(1D,2E,3E,4A,5D), (1D,2E,3E,4B,5A),(1D,2E,3E,4B,5B),(1D, 2E,3E,4B,5C), (1D,2E,3E,4B,5D),(1D,2E,3E,4C,5A),(1D,2E,3E,4C,5B), (1D,2E,3E,4C,5C), (1D,2E,3E,4C,5D),(1D,2E,3E,4D,5A), (1D,2E,3E,4D,5B),(1D,2E,3E,4D,5C),(1D,2E,3E,4D, 5D), (1D,2E,3F,4A,5A),(1D,2E,3F,4A,5B),(1D,2E,3F,4A,5C), (1D,2E,3F,4A,5D),(1D,2E,3F, 4B,5A),(1D,2E,3F,4B,5B), (1D,2E,3F,4B,5C),(1D,2E,3F,4B,5D),(1D,2E,3F,4C,5A), (1D,2E, 3F,4C,5B),(1D,2E,3F,4C,5C),(1D,2E,3F,4C,5D),
(1D,2E,3F,4D,5A),(1D,2E,3F,4D,5B),(1D, 2E,3F,4D,5C),
(1D,2E,3F,4D,5D),(1E,2A,3A,4A,5A),(1E,2A,3A,4A,5B),
(1E,2A,3A,4A,5C), (1E,2A,3A,4A,5D),(1E,2A,3A,4B,5A),
(1E,2A,3A,4B,5B),(1E,2A,3A,4B,5C),(1E,2A,3A, 4B,5D),
(1E,2A,3A,4C,5A),(1E,2A,3A,4C,5B),(1E,2A,3A,4C,5C),
(1E,2A,3A,4C,5D),(1E,2A, 3A,4D,5A),(1E,2A,3A,4D,5B),
(1E,2A,3A,4D,5C),(1E,2A,3A,4D,5D),(1E,2A,3B,4A,5A),
(1E, 2A,3B,4A,5B),(1E,2A,3B,4A,5C),(1E,2A,3B,4A,5D),
(1E,2A,3B,4B,5A),(1E,2A,3B,4B, 5B),(1E,2A,3B,4B,5C),
(1E,2A,3B,4B,5D),(1E,2A,3B,4C,5A),(1E,2A,3B,4C,5B),
(1E,2A,3B, 4C,5C),(1E,2A,3B,4C,5D),(1E,2A,3B,4D,5A),
(1E,2A,3B,4D,5B),(1E,2A,3B,4D,5C),(1E,2A, 3B,4D,5D),
(1E,2A,3C,4A,5A),(1E,2A,3C,4A,5B),(1E,2A,3C,4A,5C),
(1E,2A,3C,4A,5D),(1E, 2A,3C,4B,5A),(1E,2A,3C,4B,5B),
(1E,2A,3C,4B,5C),(1E,2A,3C,4B,5D),(1E,2A,3C,4C, 5A),
(1E,2A,3C,4C,5B),(1E,2A,3C,4C,5C),(1E,2A,3C,4C,5D),
(1E,2A,3C,4D,5A),(1E,2A,3C, 4D,5B),(1E,2A,3C,4D,5C),
(1E,2A,3C,4D,5D),(1E,2A,3D,4A,5A),(1E,2A,3D,4A,5B),
(1E, 2A,3D,4A,5C),(1E,2A,3D,4A,5D),(1E,2A,3D,4B,5A),
(1E,2A,3D,4B,5B),(1E,2A,3D,4B,5C), (1E,2A,3D,4B,5D),
(1E,2A,3D,4C,5A),(1E,2A,3D,4C,5B),(1E,2A,3D,4C,5C),
(1E,2A,3D,4C, 5D),(1E,2A,3D,4D,5A),(1E,2A,3D,4D,5B),
(1E,2A,3D,4D,5C),(1E,2A,3D,4D,5D),(1E,2A,3E, 4A,5A),
(1E,2A,3E,4A,5B),(1E,2A,3E,4A,5C),(1E,2A,3E,4A,5D),
(1E,2A,3E,4B,5A),(1E, 2A,3E,4B,5B),(1E,2A,3E,4B,5C),
(1E,2A,3E,4B,5D),(1E,2A,3E,4C,5A),(1E,2A,3E,4C,5B),
(1E,2A,3E,4C,5C),(1E,2A,3E,4C,5D),(1E,2A,3E,4D,5A),
(1E,2A,3E,4D,5B),(1E,2A,3E,4D, 5C),(1E,2A,3E,4D,5D),
(1E,2A,3F,4A,5A),(1E,2A,3F,4A,5B),(1E,2A,3F,4A,5C),
(1E,2A,3F, 4A,5D),(1E,2A,3F,4B,5A),(1E,2A,3F,4B,5B),
(1E,2A,3F,4B,5C),(1E,2A,3F,4B,5D),(1E,2A, 3F,4C,5A),
(1E,2A,3F,4C,5B),(1E,2A,3F,4C,5C),(1E,2A,3F,4C,5D),
(1E,2A,3F,4D,5A),(1E, 2A,3F,4D,5B),(1E,2A,3F,4D,5C),
(1E,2A,3F,4D,5D),(1E,2B,3A,4A,5A),(1E,2B,3A,4A,5B),
(1E, 2B,3A,4A,5C),(1E,2B,3A,4A,5D),(1E,2B,3A,4B,5A),
(1E,2B,3A,4B,5B),(1E,2B,3A,4B, 5C),(1E,2B,3A,4B,5D),
(1E,2B,3A,4C,5A),(1E,2B,3A,4C,5B),(1E,2B,3A,4C,5C),
(1E,2B,3A, 4C,5D),(1E,2B,3A,4D,5A),(1E,2B,3A,4D,5B),
(1E,2B,3A,4D,5C),(1E,2B,3A,4D,5D),(1E,2B, 3B,4A,5A),
(1E,2B,3B,4A,5B),(1E,2B,3B,4A,5C),(1E,2B,3B,4A,5D),
(1E,2B,3B,4B,5A),(1E, 2B,3B,4B,5B),(1E,2B,3B,4B,5C),
(1E,2B,3B,4B,5D),(1E,2B,3B,4C,5A),(1E,2B,3B,4C, 5B),
(1E,2B,3B,4C,5C),(1E,2B,3B,4C,5D),(1E,2B,3B,4D,5A),
(1E,2B,3B,4D,5B),(1E,2B,3B, 4D,5C),(1E,2B,3B,4D,5D),
(1E,2B,3C,4A,5A),(1E,2B,3C,4A,5B),(1E,2B,3C,4A,5C),
(1E, 2B,3C,4A,5D),(1E,2B,3C,4B,5A),(1E,2B,3C,4B,5B),
(1E,2B,3C,4B,5C),(1E,2B,3C,4B,5D), (1E,2B,3C,4C,5A),
(1E,2B,3C,4C,5B),(1E,2B,3C,4C,5C),(1E,2B,3C,4C,5D),
(1E,2B,3C,4D, 5A),(1E,2B,3C,4D,5B),(1E,2B,3C,4D,5C),
(1E,2B,3C,4D,5D),(1E,2B,3D,4A,5A),(1E,2B,3D, 4A,5B),
(1E,2B,3D,4A,5C),(1E,2B,3D,4A,5D),(1E,2B,3D,4B,5A),
(1E,2B,3D,4B,5B),(1E, 2B,3D,4B,5C),(1E,2B,3D,4B,5D),
(1E,2B,3D,4C,5A),(1E,2B,3D,4C,5B),(1E,2B,3D,4C,5C),
(1E,2B,3D,4C,5D),(1E,2B,3D,4D,5A),(1E,2B,3D,4D,5B),
(1E,2B,3D,4D,5C),(1E,2B,3D,4D, 5D),(1E,2B,3E,4A,5A),
(1E,2B,3E,4A,5B),(1E,2B,3E,4A,5C),(1E,2B,3E,4A,5D),
(1E,2B, 3E,4B,5A),(1E,2B,3E,4B,5B),(1E,2B,3E,4B,5C),
(1E,2B,3E,4B,5D),(1E,2B,3E,4C,5A),(1E, 2B,3E,4C,5B),
(1E,2B,3E,4C,5C),(1E,2B,3E,4C,5D),(1E,2B,3E,4D,5A),
(1E,2B,3E,4D,5B), (1E,2B,3E,4D,5C),(1E,2B,3E,4D,5D),
(1E,2B,3F,4A,5A),(1E,2B,3F,4A,5B),(1E,2B,3F,4A, 5C),
(1E,2B,3F,4A,5D),(1E,2B,3F,4B,5A),(1E,2B,3F,4B,5B),
(1E,2B,3F,4B,5C),(1E,2B,3F,4B, 5D),(1E,2B,3F,4C,5A),
(1E,2B,3F,4C,5B),(1E,2B,3F,4C,5C),(1E,2B,3F,4C,5D),
(1E,2B,3F, 4D,5A),(1E,2B,3F,4D,5B),(1E,2B,3F,4D,5C),
(1E,2B,3F,4D,5D),(1E,2C,3A,4A,5A),(1E,2C, 3A,4A,5B),
(1E,2C,3A,4A,5C),(1E,2C,3A,4A,5D),(1E,2C,3A,4B,5A),
(1E,2C,3A,4B,5B),(1E, 2C,3A,4B,5C),(1E,2C,3A,4B,5D),
(1E,2C,3A,4C,5A),(1E,2C,3A,4C,5B),(1E,2C,3A,4C, 5C),
(1E,2C,3A,4C,5D),(1E,2C,3A,4D,5A),(1E,2C,3A,4D,5B),
(1E,2C,3A,4D,5C),(1E,2C,3A, 4D,5D),(1E,2C,3B,4A,5A),
(1E,2C,3B,4A,5B),(1E,2C,3B,4A,5C),(1E,2C,3B,4A,5D),
(1E, 2C,3B,4B,5A),(1E,2C,3B,4B,5B),(1E,2C,3B,4B,5C),
(1E,2C,3B,4B,5D),(1E,2C,3B,4C,5A), (1E,2C,3B,4C,5B),
(1E,2C,3B,4C,5C),(1E,2C,3B,4C,5D),(1E,2C,3B,4D,5A),
(1E,2C,3B,4D, 5B),(1E,2C,3B,4D,5C),(1E,2C,3B,4D,5D),
(1E,2C,3C,4A,5A),(1E,2C,3C,4A,5B),(1E,2C,3C, 4A,5C),
(1E,2C,3C,4A,5D),(1E,2C,3C,4B,5A),(1E,2C,3C,4B,5B),
(1E,2C,3C,4B,5C),(1E, 2C,3C,4B,5D),(1E,2C,3C,4C,5A),
(1E,2C,3C,4C,5B),(1E,2C,3C,4C,5C),(1E,2C,3C,4C,5D),
(1E,2C,3C,4D,5A),(1E,2C,3C,4D,5B),(1E,2C,3C,4D,5C),
(1E,2C,3C,4D,5D),(1E,2C,3D,4A, 5A),(1E,2C,3D,4A,5B),
(1E,2C,3D,4A,5C),(1E,2C,3D,4A,5D),(1E,2C,3D,4B,5A),
(1E,2C,3D, 4B,5B),(1E,2C,3D,4B,5C),(1E,2C,3D,4B,5D),
(1E,2C,3D,4C,5A),(1E,2C,3D,4C,5B),(1E, 2C,3D,4C,5C),
(1E,2C,3D,4C,5D),(1E,2C,3D,4D,5A),(1E,2C,3D,4D,5B),
(1E,2C,3D,4D,5C), (1E,2C,3D,4D,5D),(1E,2C,3E,4A,5A),
(1E,2C,3E,4A,5B),(1E,2C,3E,4A,5C),(1E,2C,3E,4A, 5D),
(1E,2C,3E,4B,5A),(1E,2C,3E,4B,5B),(1E,2C,3E,4B,5C),
(1E,2C,3E,4B,5D),(1E,2C, 3E,4C,5A),(1E,2C,3E,4C,5B),
(1E,2C,3E,4C,5C),(1E,2C,3E,4C,5D),(1E,2C,3E,4D,5A),
(1E, 2C,3E,4D,5B),(1E,2C,3E,4D,5C),(1E,2C,3E,4D,5D),
(1E,2C,3F,4A,5A),(1E,2C,3F,4A,5B), (1E,2C,3F,4A,5C),
(1E,2C,3F,4A,5D),(1E,2C,3F,4B,5A),(1E,2C,3F,4B,5B),
(1E,2C,3F,4B, 5C),(1E,2C,3F,4B,5D),(1E,2C,3F,4C,5A),
(1E,2C,3F,4C,5B),(1E,2C,3F,4C,5C),(1E,2C,3F, 4C,5D),
(1E,2C,3F,4D,5A),(1E,2C,3F,4D,5B),(1E,2C,3F,4D,5C),
(1E,2C,3F,4D,5D),(1E,2D, 3A,4A,5A),(1E,2D,3A,4A,5B),
(1E,2D,3A,4A,5C),(1E,2D,3A,4A,5D),(1E,2D,3A,4B,5A),
(1E, 2D,3A,4B,5B),(1E,2D,3A,4B,5C),(1E,2D,3A,4B,5D),
(1E,2D,3A,4C,5A),(1E,2D,3A,4C, 5B),(1E,2D,3A,4C,5C),
(1E,2D,3A,4C,5D),(1E,2D,3A,4D,5A),(1E,2D,3A,4D,5B),
(1E,2D,3A, 4D,5C),(1E,2D,3A,4D,5D),(1E,2D,3B,4A,5A),
(1E,2D,3B,4A,5B),(1E,2D,3B,4A,5C),(1E, 2D,3B,4A,5D),
(1E,2D,3B,4B,5A),(1E,2D,3B,4B,5B),(1E,2D,3B,4B,5C),
(1E,2D,3B,4B,5D), (1E,2D,3B,4C,5A),(1E,2D,3B,4C,5B),
(1E,2D,3B,4C,5C),(1E,2D,3B,4C,5D),(1E,2D,3B,4D, 5A),
(1E,2D,3B,4D,5B),(1E,2D,3B,4D,5C),(1E,2D,3B,4D,5D),
(1E,2D,3C,4A,5A),(1E,2D,3C, 4A,5B),(1E,2D,3C,4A,5C),
(1E,2D,3C,4A,5D),(1E,2D,3C,4B,5A),(1E,2D,3C,4B,5B),
(1E, 2D,3C,4B,5C),(1E,2D,3C,4B,5D),(1E,2D,3C,4C,5A),
(1E,2D,3C,4C,5B),(1E,2D,3C,4C,5C), (1E,2D,3C,4C,5D),
(1E,2D,3C,4D,5A),(1E,2D,3C,4D,5B),(1E,2D,3C,4D,5C),
(1E,2D,3C,4D, 5D),(1E,2D,3D,4A,5A),(1E,2D,3D,4A,5B),
(1E,2D,3D,4A,5C),(1E,2D,3D,4A,5D),(1E,2D, 3D,4B,5A),
(1E,2D,3D,4B,5B),(1E,2D,3D,4B,5C),(1E,2D,3D,4B,5D),
(1E,2D,3D,4C,5A), (1E,2D,3D,4C,5B),(1E,2D,3D,4C,5C),
(1E,2D,3D,4C,5D),(1E,2D,3D,4D,5A),(1E,2D,3D,4D, 5B),
(1E,2D,3D,4D,5C),(1E,2D,3D,4D,5D),(1E,2D,3E,4A,5A),
(1E,2D,3E,4A,5B),(1E,2D, 3E,4A,5C),(1E,2D,3E,4A,5D),
(1E,2D,3E,4B,5A),(1E,2D,3E,4B,5B),(1E,2D,3E,4B,5C),
(1E, 2D,3E,4B,5D),(1E,2D,3E,4C,5A),(1E,2D,3E,4C,5B),
(1E,2D,3E,4C,5C),(1E,2D,3E,4A,5D), (1E,2D,3E,4D,5A),
(1E,2D,3E,4D,5B),(1E,2D,3E,4D,5C),(1E,2D,3E,4D,5D),
(1E,2D,3F, 4A,5A),(1E,2D,3F,4A,5B),(1E,2D,3F,4A,5C),
(1E,2D,3F,4A,5D),(1E,2D,3F,4B,5A),(1E,2D, 3F,4B,5B),
(1E,2D,3F,4B,5C),(1E,2D,3F,4B,5D),(1E,2D,3F,4C,5A),
(1E,2D,3F,4C,5B),(1E, 2D,3F,4C,5C),(1E,2D,3F,4C,5D),
(1E,2D,3F,4D,5A),(1E,2D,3F,4D,5B),(1E,2D,3F,4D,5C),
(1E, 2D,3F,4D,5D),(1E,2E,3A,4A,5A),(1E,2E,3A,4A,5B),
(1E,2E,3A,4A,5C),(1E,2E,3A,4A, 5D),(1E,2E,3A,4B,5A),
(1E,2E,3A,4B,5B),(1E,2E,3A,4B,5C),(1E,2E,3A,4B,5D),
(1E,2E,3A, 4C,5A),(1E,2E,3A,4C,5B),(1E,2E,3A,4C,5C), (1E,2E,3A,4C,5D),(1E,2E,3A,4D,5A),(1E, 2E,3A,4D,5B), (1E,2E,3A,4D,5C),(1E,2E,3A,4D,5D),(1E,2E,3B,4A,5A), (1E,2E,3B,4A,5B), (1E,2E,3B,4A,5C),(1E,2E,3B,4A,5D), (1E,2E,3B,4B,5A),(1E,2E,3B,4B,5B),(1E,2E,3B,4B, 5C), (1E,2E,3B,4B,5D),(1E,2E,3B,4C,5A),(1E,2E,3B,4C,5B), (1E,2E,3B,4C,5C),(1E,2E,3B, 4C,5D),(1E,2E,3B,4D,5A), (1E,2E,3B,4D,5B),(1E,2E,3B,4D,5C),(1E,2E,3B,4D,5D), (1E,2E, 3C,4A,5A),(1E,2E,3C,4A,5B),(1E,2E,3C,4A,5C), (1E,2E,3C,4A,5D),(1E,2E,3C,4B,5A),(1E, 2E,3C,4B,5B), (1E,2E,3C,4B,5C),(1E,2E,3C,4B,5D),(1E,2E,3C,4C,5A), (1E,2E,3C,4C, 5B),(1E,2E,3C,4C,5C),(1E,2E,3C,4C,5D), (1E,2E,3C,4D,5A),(1E,2E,3C,4D,5B),(1E,2E,3C, 4D,5C), (1E,2E,3C,4D,5D),(1E,2E,3D,4A,5A),(1E,2E,3D,4A,5B), (1E,2E,3D,4A,5C),1E, 2E,3D,4A,5D),(1E,2E,3D,4B,5A), (1E,2E,3D,4B,5B),(1E,2E,3D,4B,5C),(1E,2E,3D,4B,5D), (1E,2E,3D,4C,5A),(1E,2E,3D,4C,5B),(1E,2E,3D,4C,5C), (1E,2E,3D,4C,5D),(1E,2E,3D,4D, 5A),(1E,2E,3D,4D,5B), (1E,2E,3D,4D,5C),(1E,2E,3D,4D,5D),(1E,2E,3E,4A,5A), (1E,2E,3E, 4A,5B),(1E,2E,3E,4A,5C),(1E,2E,3E,4A,5D), (1E,2E,3E,4B,5A),(1E,2E,3E,4B,5B),(1E, 2E,3E,4B,5C), (1E,2E,3E,4B,5D),(1E,2E,3E,4C,5A),(1E,2E,3E,4C,5B), (1E,2E,3E,4C,5C), (1E,2E,3E,4C,5D),(1E,2E,3E,4D,5A), (1E,2E,3E,4D,5B),(1E,2E,3E,4D,5C),(1E,2E,3E,4D, 5D), (1E,2E,3F,4A,5A),(1E,2E,3F,4A,5B),(1E,2E,3F,4A,5C), (1E,2E,3F,4A,5D),(1E,2E,3F, 4B,5A),(1E,2E,3F,4B,5B), (1E,2E,3F,4B,5C),(1E,2E,3F,4B,5D),(1E,2E,3F,4C,5A), (1E,2E, 3F,4C,5B),(1E,2E,3F,4C,5C),(1E,2E,3F,4C,5D), (1E,2E,3F,4D,5A),(1E,2E,3F,4D,5B),(1E, 2E,3F,4D,5C), (1E,2E,3F,4D,5D)

And $(R^1,R^2,R^3,R^4,R^5)=(1A,2A,3A,4A,5A)$ is the compound which $R^1$ is 1A, $R^2$ is 2A $R^3$ is 3A, $R^4$ is 4A and $R^5$ is 5A. The other combinations are the same.

Experimental Example 1

The inhibitory activities against integrase of the compounds in the present invention have been determined by the assay described below.

(1) Preparation of DNA Solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/µl and 5 pmol/µl, respectively. The DNA solutions were annealed with each complement by slowly cooling after heating.

$KH_2PO_4$) and blocked with 300 µL of 1% skim milk in PBS for 30 min. Additionally, each well was washed twice with PBS and added 50 µl of substrate DNA solution (2 pmol/µl). The microtiter plates were kept at room temperature for 30 min. Then, each well was washed twice with PBS and once with $H_2O$.

Subsequently, in the each well prepared above were added 45 µl of the reaction buffer prepared from 12 µl of the buffer (composition: 150 mM MOPS (pH 7.2), 75 mM $MnCl_2$, 50 mM 2-mercaptoethanol, 25% glycerol, 500 µg/ml bovine serum albumin-fraction V), 1 µl of target DNA (5 pmol/µl), and 32 µl of the distilled water. Additionally, 6 µl of either a test compound in DMSO or DMSO for positive control (PC) was mixed with the above reaction buffer, then 9 µl of an integrase solution (30 pmol) was added and mixed well. In the well of negative control (NC) was added 9 µl of the integrase dilution buffer (composition: 20 mM MOPS (pH7.2), 400 mM potassium glutamate, 1 mM EDTA, 0.1% NP-40, 20% glycerol, 1 mM DTT, 4 M urea).

The microtiter plates were incubated at 30° C. for 1 hour. The reaction solution was removed and each well was washed twice with PBS. Subsequently, each well of the microtiter plates was filled with 100 µl of anti-digoxigenin antibody labeled with alkaline phosphatase (Sheep Fab fragment: obtained from Boehringer) and incubated at 30° C. for 1 hour. Then, each well was washed twice with 0.05% Tween20 in PBS and once with PBS. Next, 150 µl of the Alkaline phosphatase reaction buffer (composition: 10 mM p-Nitrophenylphosphate (obtained from Vector Laboratories), 5 mM $MgCl_2$, 100 mM NaCl, 100 mM Tris-HCl (pH 9.5)) was added in each well. The microtiter plates were incubated at 30° C. for 2 hours and the reaction was terminated by the addition of 50 µl of 1 N NaOH solution. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the
NC abs.: the OD of the negative control (NC)
PC abs.: the OD of the positive control (PC)

When the percent inhibition (%) is X % at the concentration of x µg/ml and the percent inhibition (%) is Y % at the concentration of y µg/ml, one of which is more than 50% and the other is less than 50%, $IC_{50}$ can be determined by the following expression.

```
(Substrate DNA)
5'-Biotin-ACC CTT TTA GTC AGT GTG AAA AAT CTC TAG CAG T-3'    (SEQ ID NO: 1)

3'-GAA AAT CAG TCA CAC CTT TTA GAG ATC GTC A-5'               (SEQ ID NO: 2)

(Target DNA)
5'-TGA CCA AGG GCT AAT TCA CT-Dig-3'                          (SEQ ID NO: 3)

3'-Dig-ACT GGT TCC CGA TTA AGT GA-5'                          (SEQ ID NO: 4)
```

(2) Calculations of the Percent Inhibitions (the $IC_{50}$ Values of Test Compounds)

Streptavidin, obtained from Vector Laboratories, was dissolved in 0.1 M carbonate buffer (composition: 90 mM $Na_2CO_3$, 10 mM $NaHCO_3$) at concentration of 40 µg/ml. After coating each well of microtiter plates (obtained from NUNC) with 50 µl of the above solution at 4° C. over night, each well was washed twice with PBS (composition: 13.7 mM NaCl, 0.27 mM KCl, 0.43 mM $Na_2HPO_4$, 0.14 mM $IC_{50}(µg/ml)=x-\{(X-50)(x-y)/(X-Y)\}$ The $IC_{50}$ values, the concentration of the compounds at percent inhibition 50%, are shown in the following Table 1. Compound No. in the Table 1 is the same as compound No. of the above example.

TABLE 1

| compound No. | $IC_{50}$ (μg/ml) |
|---|---|
| I-1 | 0.540 |
| I-6 | 0.444 |
| I-20 | 0.760 |
| I-27 | 0.190 |
| I-35 | 0.240 |
| I-37 | 0.550 |
| I-63 | 0.420 |
| I-65 | 0.11 |
| I-67 | 0.22 |

The compounds of the present invention except the above compounds had the same or more integrase inhibitory activities.

And the compounds of the present invention have high stability against metabolism and they are superior inhibitory agents against integrase.

Formulation Example

It is to be noted that the following Formulation Examples 1 to 8 are mere illustration, but not intended to limit the scope of the invention. The term "active ingredient" means the compounds of the present invention, the tautomers, the prodrugs thereof, their pharmaceutical acceptable salts, or their solvate.

Formulation Example 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| Active ingredient | 100 mg |
|---|---|
| Isotonic saline | 1000 ml |

The solution of the above ingredients is generally administered intravenously to a subject at a rate of 1 ml per minute.

INDUSTRIAL APPLICABILITY

The compounds of the present invention have inhibitory activities against integrase and efficient for treatment of AIDS as an antiviral agent and an anti-HIV agent.

What is claimed is:

1. A compound of the formula:

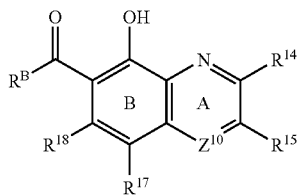

wherein $R^B$ is hydroxy, alkoxy, optionally substituted alkyl, wherein the substituent is alkoxy and/or optionally substituted amino, or optionally substituted amino, wherein the substituent is alkyl and/or alkoxy, $Z^{10}$ is —C(—$R^{16}$)=, $R^{15}$ is a group of the formula: -$Z^1$-$Z^2$-$Z^3$-$R^1$ wherein $Z^1$ and $Z^3$ each is a bond, $Z^2$ is $C_1$–$C_4$ alkylene, $C_2$–$C_3$ alkenylene, —S—, or —O—; $R^1$ is optionally substituted phenyl, $R^{14}$, $R^{16}$ and $R^{18}$ each is independently hydrogen, lower alkyl, or halogen, $R^{17}$ is hydrogen, halogen, alkoxycarbonyl, carboxy, optionally substituted alkyl, optionally substituted alkenyl, optionally substituted amino, cyano, optionally substituted carbamoyl, formyl, aryl, or aralkyl optionally substituted with halogen, or a pharmaceutically acceptable salt or a solvate thereof.

2. A compound according to claim 1, wherein $R^{15}$ is a group of the formula:

-$Z^1$-$Z^2$-$Z^3$-$R^1$ wherein $Z^1$ and $Z^3$ are bonds, $Z^2$ is $C_1$–$C_4$ alkylene, $R^1$ is optionally substituted phenyl, wherein the substituent is alkyl, halogen, alkoxy, haloalkyl and/or azide, $R^{17}$ is selected from hydrogen, halogen, optionally substituted alkyl, optionally substituted alkenyl, aryl, aralkyl optionally substituted with halogen, optionally substituted carbamoyl, cyano, alkoxycarbonyl, carboxy, optionally substituted amino, or formyl, or a pharmaceutically acceptable salt or a solvate thereof.

3. A compound according to claim 1, wherein $Z^{10}$ is —C(—R )= wherein $R^{16}$ is hydrogen, or a pharmaceutically acceptable salt or a solvate thereof.

4. A compound according to claim 1, wherein $Z^{10}$ is —C(—$R^{16}$)= wherein $R^{16}$ is hydrogen, and $R^{14}$ is hydrogen, or a pharmaceutically acceptable salt or a solvate thereof.

5. A compound according to claim 1, wherein $Z^{10}$ is —C(—$R^{16}$)= wherein $R^{16}$ is hydrogen, and $R^{14}$ and $R^{18}$ are hydrogen, or a pharmaceutically acceptable salt or a solvate thereof.

6. A compound according to claim 1, wherein $Z^{10}$ is —C(—$R^{16}$)= wherein $R^{16}$ is hydrogen, $R^{14}$ and $R^{18}$ are hydrogen, $R^{15}$ is —$CH_2$—$R^1$ wherein $R^1$ is phenyl optionally substituted with halogen, $R^{17}$ is hydrogen, halogen, optionally substituted alkyl, optionally substituted alkenyl, aryl, aralkyl optionally substituted with halogen, optionally substituted carbamoyl, cyano, alkoxycarbonyl, carboxy, optionally substituted amino, or formyl, or a pharmaceutically acceptable salt or a solvate thereof.

7. A compound according to claim 1, wherein $Z^{10}$ is —C(—$R^{16}$)= wherein $R^{16}$ is hydrogen, $R^{14}$ and $R^{18}$ are hydrogen, $R^{15}$ is —$CH_2$—$R^1$ wherein $R^1$ is phenyl optionally substituted with halogen, $R^{17}$ is hydrogen, halogen, optionally substituted alkyl, optionally substituted alkenyl, aryl, aralkyl optionally substituted with halogen, optionally substituted carbamoyl, cyano, alkoxycarbonyl, carboxy, optionally substituted amino, or formyl, and $R^B$ is alkoxy, or a pharmaceutically acceptable salt or a solvate thereof.

8. A compound according to claim 1, wherein $Z^{10}$ is —C(—$R^{16}$)= wherein $R^{16}$ is hydrogen, $R^{14}$ and $R^{18}$ hydrogen, $R^{15}$ is —$CH_2$—$R^1$ wherein $R^1$ is phenyl optionally substituted with halogen, $R^{17}$ is alkoxycarbonyl, carboxy, or optionally substituted carbamoyl, and $R^B$ is alkoxy, or a pharmaceutically acceptable salt or a solvate thereof.

9. A compound of the formula:

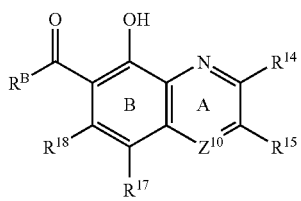

wherein $R^B$ is hydroxy, alkoxy, optionally substituted alkyl, wherein the substituent is alkoxy and/or optionally substituted amino, or optionally substituted amino, wherein the substituent is alkyl and/or alkoxy, $Z^{10}$ is —C(—$R^{16}$)=, $R^{14}$ is hydrogen, alkyl, alkenyl, halogen, haloalkyl, alkoxy, haloalkoxy or optionally substituted amino, one of $R^{15}$ and $R^{16}$ is a group of the formula: -$Z^1$-$Z^2$-$Z^3$-$R^1$ wherein $Z^1$ and $Z^3$ each is independently a bond, optionally substituted alkylene or optionally substituted alkenylene; $Z^2$ is a bond, optionally substituted alkylene, optionally substituted alkenylene, CH(OH)—, —S—, —SO—, —SO$_2$—, —SO$_2$NR$^2$—, —NR$^2$SO$_2$—, —O—, —NR$^2$—, —NR$^2$CO—, —CONR$^2$—, —C(=O)—O—, —O—C(=O)— or —CO; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle, and the other of $R^{15}$ and $R^{16}$, and $R^{18}$, are selected from hydrogen and the substitution group A, wherein the substitution group A is halogen, alkoxycarbonyl, carboxy, optionally substituted alkyl, alkoxy, alkoxyalkyl, nitro, hydroxy, optionally substituted alkenyl, alkynyl, alkylsulfonyl, optionally substituted amino, alkylthio, alkylthioalkyl, haloalkyl, haloalkoxy, haloalkoxyalkyl, cycloalkyl, cycloalkenyl, oxo, thioxo, alkylenedioxy, alkylene, alkenylene, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted heterocycle, optionally substituted aralkyl, optionally substituted heteroaralkyl, optionally substituted aryloxy, optionally substituted heteroaryloxy, optionally substituted arylthio, optionally substituted heteroarylthio, optionally substituted aralkyloxy, optionally substituted heteroaralkyloxy, optionally substituted aralkylthio, optionally substituted heteroaralkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl and optionally substituted heteroaralkylsulfonyl, $R^{17}$ is optionally substituted carbamoyl, alkoxycarbonyl, or carboxy, or a pharmaceutically acceptable salt or a solvate thereof.

10. A compound according to claim 9, wherein one of $R^{15}$ and $R^{16}$ is a group of the formula: -$Z^1$-$Z^2$-$Z^3$-$R^1$ wherein $Z^1$ and $Z^3$ are bonds, $Z^2$ is $C_1$–$C_4$ alkylene, $R^1$ is optionally substituted phenyl, wherein the substituent is alkyl, halogen, alkoxy, haloalkyl and/or azide, the other of $R^{15}$ and $R^{16}$ is hydrogen, lower alkyl or halogen, $R^{17}$ is optionally substituted carbamoyl wherein the substituent is alkyl, alkylene, alkoxyalkyl, aralkyl, aryl and/or heteroaryl; alkoxycarbonyl or carboxy, $R^{18}$ hydrogen, lower alkyl or halogen, or a pharmaceutically acceptable salt or a solvate thereof.

11. A compound according to claim 9, wherein $R^{15}$ is a group of the formula: -$Z^1$-$Z^2$-$Z^3$-$R^1$ wherein $Z^1$ and $Z^3$ are bonds, $Z^2$ is $C_1$–$C_4$ alkylene, $R^1$ is optionally substituted phenyl wherein the substituent is alkyl, halogen, alkoxy, haloalkyl and/or azide, $R^{16}$ and $R^{18}$ each is independently hydrogen, lower alkyl or halogen, and $R^{17}$ is optionally substituted carbamoyl wherein the substituent is alkyl, alkylene, alkoxyalkyl, aralkyl, aryl and/or heteroaryl; alkoxycarbonyl, or carboxy, or a pharmaceutically acceptable salt or a solvate thereof.

12. A compound according to claim 9, wherein $R^B$ is hydroxy or alkoxy, $R^{14}$ is hydrogen, lower alkyl, or halogen, one of $R^{15}$ and $R^{16}$ is a group of the formula: -$Z^1$-$Z^2$-$Z^3$-$R^1$ wherein $Z^1$ and $Z^3$ are bonds, $Z^2$ is $C_1$–$C_4$ alkylene, $R^1$ is optionally substituted phenyl wherein the substituent is alkyl, halogen, alkoxy, haloalkyl and/or azide, the other of $R^{15}$ and $R^{16}$ is hydrogen, lower alkyl or halogen, $R^{17}$ is optionally substituted carbamoyl, alkoxycarbonyl or carboxy, $R^{18}$ is hydrogen, lower alkyl or halogen, or a pharmaceutically acceptable salt or a solvate thereof.

13. A pharmaceutical composition comprising the compound according to claim 1 or 9, or a pharmaceutically acceptable salt or a solvate thereof as an active ingredient together with a pharmaceutically acceptable carrier or diluent.

14. An anti-HIV mixture which comprises a pharmaceutical composition according to claim 13 in combination with a reverse transcriptase inhibitor and/or a protease inhibitor.

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: n= biotin-a

<400> SEQUENCE: 1 nccctttag tcagtgtgga aaatctctag cagt                    34

<210> SEQ ID NO 2
<211> LENGTH: 31
<212> TYPE: DNA
<213> ORGANISM: Artificial
<220> FEATURE:
<223> OTHER INFORMATION: Synthetic Construct

<400> SEQUENCE: 2
actgctagag attttccaca ctgactaaaa g                      31

<210> SEQ ID NO 3
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: modified_base
```

```
<222> LOCATION: (20)..(20)
<223> OTHER INFORMATION: n= t-Dig

<400> SEQUENCE: 3
tgaccaaggg ctaattcacn                                          20

<210> SEQ ID NO 4
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: modified_base
<222> LOCATION: (20)..(20)
<223> OTHER INFORMATION: n= a-Dig

<400> SEQUENCE: 4
agtgaattag cccttggtcn                                          20
```